(12) United States Patent
Campbell

(10) Patent No.: US 11,498,899 B2
(45) Date of Patent: Nov. 15, 2022

(54) NITRONE HERBICIDES

(71) Applicant: FMC Corporation, Philadelphia, PA (US)

(72) Inventor: Matthew James Campbell, Flemington, NJ (US)

(73) Assignee: FMC Corporation, Philadelphia, PA (US)

( * ) Notice: Subject to any disclaimer, the term of this patent is extended or adjusted under 35 U.S.C. 154(b) by 136 days.

(21) Appl. No.: 16/471,248

(22) PCT Filed: Dec. 1, 2017

(86) PCT No.: PCT/US20/17064
§ 371 (c)(1),
(2) Date: Jun. 19, 2019

(87) PCT Pub. No.: WO2018/118384
PCT Pub. Date: Jun. 28, 2018

(65) Prior Publication Data
US 2020/0115337 A1  Apr. 16, 2020

Related U.S. Application Data

(60) Provisional application No. 62/437,248, filed on Dec. 21, 2016.

(51) Int. Cl.
| | | |
|---|---|---|
| *A01N 25/02* | (2006.01) | |
| *C07D 207/46* | (2006.01) | |
| *A01N 25/08* | (2006.01) | |
| *A01N 43/36* | (2006.01) | |
| *C07D 207/22* | (2006.01) | |

(52) U.S. Cl.
CPC ........... *C07D 207/46* (2013.01); *A01N 25/02* (2013.01); *A01N 25/08* (2013.01); *A01N 43/36* (2013.01); *C07D 207/22* (2013.01)

(58) Field of Classification Search
CPC .... C07D 207/46; C07D 207/22; A01N 43/36; A01N 25/08; A01N 25/02
See application file for complete search history.

(56) References Cited

U.S. PATENT DOCUMENTS

| | | |
|---|---|---|
| 3,741,989 A | 6/1973 | Zaugg |
| 3,959,481 A | 5/1976 | Davis et al. |
| 4,594,094 A | 6/1986 | Kollmeyer |
| 4,874,422 A | 10/1989 | Woolard |
| 5,196,534 A | 3/1993 | Whitehead et al. |
| 5,856,273 A | 1/1999 | Kay et al. |
| 7,205,318 B2 | 4/2007 | Qiao et al. |
| 7,355,053 B2 | 4/2008 | Reinhard et al. |
| 7,375,232 B2 | 5/2008 | Clark et al. |
| 8,293,926 B2 | 10/2012 | Yasuoka et al. |
| 8,461,202 B2 | 6/2013 | Sancho Sanz et al. |
| 8,575,154 B2 | 11/2013 | Kori et al. |
| 8,946,216 B2 | 2/2015 | Deng et al. |
| 9,119,397 B2 | 9/2015 | Yerkes et al. |
| 9,446,995 B2 | 9/2016 | Chong |
| 9,737,073 B2 | 8/2017 | Gifford et al. |
| 9,944,602 B2 | 4/2018 | Satterfield et al. |
| 9,969,728 B2 | 5/2018 | Defays et al. |
| 10,227,286 B2 | 3/2019 | Satterfield |
| 10,294,202 B2 | 5/2019 | Satterfield et al. |
| 10,405,547 B2 | 9/2019 | Satterfield et al. |
| 10,442,807 B2 | 10/2019 | Campbell et al. |
| 10,875,838 B2 | 12/2020 | Chen et al. |
| 11,178,873 B2 | 11/2021 | Satterfield et al. |
| 2004/0242671 A1 | 12/2004 | Grimee et al. |
| 2007/0123508 A1 | 5/2007 | Olsson et al. |

(Continued)

FOREIGN PATENT DOCUMENTS

| | | |
|---|---|---|
| CN | 102531918 | 10/2013 |
| DE | 1262277 | 3/1968 |

(Continued)

OTHER PUBLICATIONS

Campaigne et el.; Synthesis of Some Ureidodihydrofurans and Related Pyrimidones as Potential Antimalarials; J. Med. Chem.; 1969; 339-342. (XP002278920).
Cauliez et al.; "Studies on Pyrrolidinones. On the Carbamoylation of Some Pyroglutamic Derivatives"; J. Het. Chem.; 33; 1996; 1233-1237. (XP055297107).
Hwang et al.; "Diastereoselective Synthesis of Oxazolidinone Derivatives and Their Antifungal Activities"; Korean J. of Med. Chem.; vol. 4, No. 1; 1994; 52-56. (XP009191451).
IPCOM000241978D; Jun. 11, 2015.
Murata et al.; "Oxidation of N-Acyl-Pyrrolidines and -Piperidines with Iron(II)-Hydrogen Peroxide and an Iron Complex-Molecular Oxygen"; J. Chem. Soc. Perkin Trans.; 1987; 1259-1262. (XP055297105).

(Continued)

*Primary Examiner* — Robert A Wax
*Assistant Examiner* — Danielle Sullivan
(74) *Attorney, Agent, or Firm* — Reed A Coats; FMC Corporation

(57) ABSTRACT

Disclosed are compounds of Formula 1, including all stereoisomers, N-oxides, and salts thereof, wherein $R^1$, $R^2$, $R^3$, $R^4$, $R^5$, $R^6$, $J^2$, $Q^1$, $Q^2$, T and Y are as defined in the disclosure. Also disclosed are compositions containing the compounds, N-oxides and salts, and methods for controlling undesired vegetation comprising contacting the undesired vegetation or its environment with an effective amount of a compound, N-oxide, salt or composition.

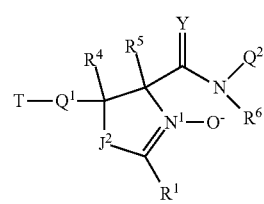

13 Claims, No Drawings

(56) References Cited

U.S. PATENT DOCUMENTS

| | | | |
|---|---|---|---|
| 2009/0062366 A1 | 3/2009 | Hachiya et al. |
| 2009/0203694 A1 | 8/2009 | Hurley et al. |
| 2011/0218199 A1 | 9/2011 | Georges et al. |
| 2015/0173371 A1 | 6/2015 | Mann et al. |
| 2016/0137639 A1 | 5/2016 | Kotoku et al. |
| 2016/0297756 A1 | 10/2016 | Satterfield et al. |
| 2018/0049437 A1 | 2/2018 | Satterfield et al. |
| 2018/0057442 A1 | 3/2018 | Satterfield |
| 2018/0077931 A1 | 3/2018 | Stevenson et al. |
| 2018/0099935 A1 | 4/2018 | Satterfield et al. |
| 2018/0141904 A1 | 5/2018 | Campbell et al. |
| 2018/0213788 A1 | 8/2018 | Satterfield et al. |
| 2018/0215760 A1 | 8/2018 | Campbell et al. |
| 2020/0095202 A1 | 3/2020 | Puri |
| 2020/0154709 A1 | 5/2020 | McMahon |

FOREIGN PATENT DOCUMENTS

| | | |
|---|---|---|
| EP | 2336104 | 6/2011 |
| IN | 1462DEL08 | 6/2008 |
| JP | 53-056288 | 5/1978 |
| JP | 54-088114 | 7/1979 |
| JP | 08-269145 | 10/1996 |
| KR | 20130142477 | 12/2013 |
| RU | 2555370 | 7/2015 |
| WO | 2000/09481 | 2/2000 |
| WO | 2002/006512 | 1/2002 |
| WO | 2003024222 | 3/2003 |
| WO | 2004/046081 | 6/2004 |
| WO | 2006/081562 | 8/2006 |
| WO | 2006/127396 | 11/2006 |
| WO | 2009/062371 | 5/2009 |
| WO | 2010/072781 | 7/2010 |
| WO | 20120034957 | 3/2012 |
| WO | 2015/084796 | 6/2015 |
| WO | 2016/003997 | 1/2016 |
| WO | 2016/094117 | 6/2016 |
| WO | 2016/164201 | 10/2016 |
| WO | 2016/176082 | 11/2016 |
| WO | 2016/182780 | 11/2016 |
| WO | 2016/196019 | 12/2016 |
| WO | 2016/196593 | 12/2016 |
| WO | 20170023515 | 2/2017 |
| WO | 2017075559 | 5/2017 |
| WO | 2018/065311 | 4/2018 |
| WO | 2018/175226 | 9/2018 |
| WO | 2018/175231 | 9/2018 |
| WO | 2018222646 | 12/2018 |
| WO | 2018222647 | 12/2018 |

OTHER PUBLICATIONS

PubChem Entry CID 29937915 (4S)-4[3-(trifluoromethyl)phenyl]pyrrolidin-2-one: May 28, 2009.
XP002734980; Jan. 20, 2002.
XP002734981; WO0009481; Feb. 24, 2000.
XP002759805; Jan. 20, 2002.
XP002759806; Mar. 23, 2009.
International Search Report of corresponding application No. PCT/US2017/064213 dated Jun. 28, 2018.
Chemical Protection of Plants, Edited by Professor G. S. Gruzdev, 3rd ed., Rev. and suppl., Moscow: Agropromizdat, 1987, Chapter 2, pp. 12-16, Chapter 8, pp. 297-305, 415.
CN Decision, "Invalidation Request Examination Decision," in CN Appln. No. 201480074726.8, dated Apr. 20, 2021, 23 pages.
CN Opposition, "Request for Invalitation of a Patent Right," in CN Appln. No 201480074726.8, dated Sep. 9, 2020, 49 pages (English Translation).
CN Support, "Declaration of Aman Chandi," in CN Appln. No 201480074726.8, dated Dec. 18, 2020, 9 pages.
CN Support, "Declaration of Steven Gutteridge," in CN Appln. No. 201480074726.8, dated Dec. 18, 2020, 5 pages.
CN Support, "Declaration of Steven Gutteridge," in CN Appln. No. 201480074726.8, dated Feb. 10, 2021, 5 pages.
EP Opposition Response, "Auxiliary Request 1—marked up," in EP Appln No. 14815174.9, from response dated Jun. 25, 2021, 10 pages.
EP Opposition Response, "Auxiliary Request 1," in EP Appln No. 14815174.9, from response dated Jun. 25, 2021, 10 pages.
EP Opposition Response, "Auxiliary Request 2—marked up," in EP Appln No. 14815174.9, from response dated Jun. 25, 2021, 10 pages.
EP Opposition Response, "Auxiliary Request 2," in EP Appln No. 14815174.9, from response dated Jun. 25, 2021, 10 pages.
EP Opposition Response, "Auxiliary Request 3—marked up," in EP Appln No. 14815174.9, from response dated Jun. 25, 2021, 10 pages.
EP Opposition Response, "Auxiliary Request 3," in EP Appln No. 14815174.9, from response dated Jun. 25, 2021, 9 pages.
EP Opposition Response, "Auxiliary Request 4—marked up," in EP Appln No. 14815174.9, from response dated Jun. 25, 2021, 10 pages.
EP Opposition Response, "Auxiliary Request 4," in EP Appln No. 14815174.9, from response dated Jun. 25, 2021, 9 pages.
EP Opposition Response, "Auxiliary Request 5—marked up," in EP Appln No. 14815174.9, from response dated Jun. 25, 2021, 11 pages.
EP Opposition Response, "Auxiliary Request 5," in EP Appln No. 14815174.9, from response dated Jun. 25, 2021, 7 pages.
EP Opposition Response, "Data testing herbicidal activity of compounds IC1*, IC3* andIC6 against plants," Exhibit D16 in EP Appln No. 14815174.9, from response dated Jun. 25, 2021, 5 pages.
EP Opposition Response, "Experimental data for further compounds," Exhibit D19 in EP Appln. No. 14815174.9, from response dated Jun. 25, 2021, 9 pages.
EP Opposition Response, "HRAC Mode of Action Classification 2021," Exhibit D21 in EP Appln. No. 14815174.9, from response dated Jun. 25, 2021, 2 pages.
EP Opposition Response, "Press Release—Novel herbicide tetflupyrolimet from FMC Corporation granted a new mode of action classification," Exhibit D20 in EP Appln. No 14815174.9, dated Apr. 8, 2021, 3 pages.
EP Opposition Response, "Submission In Opposition Proceedings—FMC," in EP Appln. No. 14815174 9, dated Jun. 25, 2021, 43 pages.
EP Opposition, "Cudney—Why Herbicides Are Selective," Exhibit D22 in EP Appln. No. 14815174.9, 1996 Symposium Proceedings, 3 pages.
EP Opposition, "Notice of Opposition to a European Patent," in EP Appln. No. 14815174.9, dated Aug. 31, 2020, 55 pages.
EP Opposition, "English translation of the second amendments based on granted claims in CNIPA Decision," Exhibit D28 in EP Appln. No 14815174 9, dated Apr. 15, 2021, 3 pages.
EP Opposition, "Smith—Organic Chemistry, An Acid-Base Approach," Exhibit D25 in EP Appln. No. 14815174.9, CRC Press, Taylor & Francis Group, LLC, 2011, pp. 24-32, 23 pages.
EP Opposition, "Submission In Opposition Proceedings—Syngenta," in EP Appln. No. 14815174.9, dated Nov. 5, 2020, 68 pages.
EP Opposition, "Summons to Attend Oral Proceedings Pursuant to Rule 115(1) EPC," in EP Appln. No 14815174.9, dated Jul. 16, 2021, 14 pages.
EP Opposition, "TechLine Invasive Plant News—Factors Affecting Herbicide Performance," Exhibit D23 in EP Appln. No 14815174.9, dated Jun. 2019, 9 pages.
EP Opposition, "US-PTAB Decision in relation to U.S. Pat. No. 10,294,202 B2," Exhibit D30 in EP Appln. No. 14815174.9, dated Aug. 31, 2021, 66 pages.
EP Opposition, "Walsh—Enzymatic Reaction Mechanisms," Exhibit D26 in EP Appln. No. 14815174.9, W. H. Freeman and Company, 1979, Chapter 2, pp. 24-48, 27 pages.
EP Opposition, "Williams—Opportunities for Chiral Agrochemicals," Exhibit D24 in EP Appln. No. 14815174.9, Pestic Sci., 1996, 46:3-9.
EP Opposition, "Written Submission," in EP Appln. No. 14815174. 9, dated Dec. 14, 2021, 3 pages.
EP Opposition, "Written Submission," in EP Appln. No. 14815174. 9, dated Dec. 7, 2021, 2 pages.

(56) References Cited

OTHER PUBLICATIONS

EP Opposition, "Written Submission," in EP Appln. No. 14815174.9, dated Nov. 25, 2021, 32 pages.
EP Opposition, "Written Submission," in EP Appln. No. 14815174.9, dated Nov. 30, 2021, 6 pages.
IN Opposition, "Declaration of Dhaval Dayabhai Diyora," in IN Appln. No. 201617018886, dated Jun. 1, 2016, 60 pages.
Banerjee et al., "A Stereoselective Cyclization Strategy for the Preparation of gamma-Lactams and Their Use in the Synthesis of alpha-Methyl-beta-Proline", J. Org. Chem. 2012, vol. 77, pp. 10925-10930.
Wang et al., "Asymmetric Cyanation of Activated Olefins with Ethyl Cyanoformate Catalyzed by a Modular Titanium Catalyst", Org. Lett., 2010, vol. 12(6), pp. 1280-1283.
Hajra et al., "Organocatalytic enantioselective conjugate addition of nitromethane to alkylidenemalonates: asymmetric synthesis of pyrrolidine-3-carboxylic acid derivatives", RSC Advances, vol. 3, No. 26, Jan. 1, 2013, pp. 10185-10188 (XP055665141).

NITRONE HERBICIDES

FIELD OF THE DISCLOSURE

This disclosure relates to certain nitrone compounds, N-oxides thereof, and salts of the nitrones and N-oxides; compositions comprising such nitrones, N-oxides and salts; processes for making such nitrones, N-oxides, salts and compositions; and methods for using such nitrones, N-oxides, salts and compositions to control undesirable vegetation.

BACKGROUND

The control of undesired vegetation is extremely important in achieving high crop efficiency. Achievement of selective control of the growth of weeds especially in such useful crops as rice, soybean, sugar beet, maize, potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds that are more effective, less costly, less toxic, environmentally safer or have different sites of action.

SUMMARY

This disclosure relates, in part, to compounds of Formula 1 (including all stereoisomers), N-oxides of such compounds, and salts of such compounds and N-oxides:

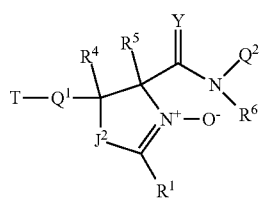

1 wherein
- $Q^1$ is a phenyl ring or a naphthalenyl ring system, each ring or ring system optionally substituted with up to 4 substituents independently selected from $R^7$; or a 4- to 7-membered heterocyclic ring; or an 8- to 10-membered bicyclic ring system, each ring or ring system containing ring members selected from carbon atoms and 1 to 5 heteroatoms independently selected from up to 2 O, up to 2 S and up to 5 N atoms, wherein up to 3 carbon ring members are independently selected from $C(=O)$ and $C(=S)$, and the sulfur atom ring members are independently selected from $S(=O)_u(=NR^8)_v$, each ring or ring system optionally substituted with up to 5 substituents independently selected from $R^7$ on carbon atom ring members and selected from $R^9$ on nitrogen atom ring members; or
- $Q^1$ is $C_2$-$C_{10}$ alkenylene, $C_2$-$C_{10}$ alkynylene, $C_2$-$C_{10}$ haloalkenylene, $C_2$-$C_{10}$ haloalkynylene, $C_4$-$C_{10}$ cycloalkenylene, $C_4$-$C_{10}$ halocycloalkenylene, $C_2$-$C_8$ alkylenecarbonyl or $C_2$-$C_8$ alkoxyalkylene;
- T is H; or
- T is $J^1$-A-, wherein the free bond projecting to the right next to A indicates the connecting point of $J^1$-A- to $Q^1$; or
- T is $R^{17}ON=CR^{17a}$—, $(R^{18})_2C=NO$—, $(R^{19})_2NN=CR^{17a}$—, $(R^{18})_2C=NNR^{21}$, $R^{20}N=CR^{17a}$—, $(R^{18})_2C=N$—, $R^{17}ON=CR^{17a}C(R^{22})_2$— or $(R^{18})_2C=NOC(R^{23})_2$—, wherein the free bond projecting to the right indicates the connecting point to $Q^1$;
- T is $R^7$, provided T is bonded to a carbon ring member of $Q^1$; or
- T is $R^9$, provided T is bonded to a nitrogen ring member of $Q^1$;
- A is a saturated, partially unsaturated or fully unsaturated chain containing 1 to 3 atoms selected from up to 3 carbon, up to 1 O, up to 1 S and up to 2 N atoms, the chain optionally substituted with up to 2 substituents independently selected from $R^{15}$ on carbon atoms and $R^{16}$ on nitrogen atoms;
- $Q^2$ is a phenyl ring or a naphthalenyl ring system, each ring or ring system optionally substituted with up to 5 substituents independently selected from $R^{10}$; or a 4- to 7-membered heterocyclic ring or an 8- to 10-membered bicyclic ring system, each ring or ring system containing ring members selected from carbon atoms and 1 to 4 heteroatoms independently selected from up to 2 O, up to 2 S and up to 5 N atoms, wherein up to 3 carbon ring members are independently selected from $C(=O)$ and $C(=S)$, and the sulfur atom ring members are independently selected from $S(=O)_u(=NR^8)_v$, each ring or ring system optionally substituted with up to 5 substituents independently selected from $R^{10}$ on carbon atom ring members and selected from $R^{11}$ on nitrogen atom ring members; or
- $Q^2$ is $C_2$-$C_{10}$ alkenyl, $C_2$-$C_{10}$ alkynyl, $C_2$-$C_{10}$ haloalkenyl, $C_2$-$C_{10}$ haloalkynyl, $C_4$-$C_{10}$ cycloalkenyl, $C_4$-$C_{10}$ halocycloalkenyl, $C_2$-$C_8$ alkylcarbonyl or $C_2$-$C_8$ alkoxyalkyl;
- $J^1$ is a phenyl ring or a naphthalenyl ring system, each ring or ring system optionally substituted with up to 5 substituents independently selected from $R^{7a}$; or a 4- to 6-membered heterocyclic ring or an 8- to 10-membered bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from $C(=O)$ and $C(=S)$, and the sulfur atom ring members are independently selected from $S(=O)_u(=NR^8)_v$, each ring or ring system optionally substituted with up to 5 substituents independently selected from $R^{7a}$ on carbon atom ring members and selected from $R^9$ on nitrogen atom ring members; or
- $J^1$ is $C_4$-$C_{10}$ cycloalkylalkoxy, $C_4$-$C_{10}$ cycloalkylalkyl, $C_2$-$C_8$ alkenyloxy, $C_2$-$C_8$ haloalkenyloxy, $C_2$-$C_8$ alkoxyalkoxy, $C_2$-$C_8$ alkylthioalkyl, $C_2$-$C_8$ alkylsulfinylalkyl, $C_2$-$C_8$ alkylsulfonylalkyl, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_2$-$C_8$ alkynyl, $C_2$-$C_8$ haloalkynyl, $C_2$-$C_8$ alkoxyalkyl, $C_2$-$C_8$ haloalkoxyalkyl, $C_3$-$C_8$ haloalkoxyalkoxy, $C_2$-$C_8$ haloalkoxyhaloalkyl, $C_1$-$C_8$ haloalkyl, $C_3$-$C_8$ halocycloalkyl, $C_2$-$C_8$ alkylcarbonyloxy or $C_2$-$C_8$ haloalkylcarbonyloxy;
- $J^2$ is (—$CR^2R^3$—)$_z$, —$NR^{2b}$— or —O—;
- Y is O, S or $NR^{12}$;

$R^1$ is H, hydroxy, amino, cyano, formyl, $C_3$-$C_8$ alkylcarbonylalkyl, —C($C_1$-$C_4$ alkyl)=N—O($C_1$-$C_4$ alkyl), —C(O)NH$_2$, $C_1$-$C_6$ alkyl, $C_1$-$C_6$ haloalkyl, $C_2$-$C_6$ alkenyl, $C_3$-$C_6$ alkynyl, $C_2$-$C_6$ cyanoalkyl, $C_3$-$C_6$ cycloalkyl, $C_3$-$C_8$ cycloalkenyl, $C_4$-$C_8$ cycloalkylalkyl, $C_2$-$C_8$ alkoxyalkyl, $C_3$-$C_8$ alkoxyalkoxyalkyl, $C_2$-$C_8$ haloalkoxyalkyl, $C_2$-$C_8$ haloalkenylalkyl, $C_2$-$C_8$ alkylthioalkyl, $C_2$-$C_8$ alkylsulfinylalkyl, $C_2$-$C_8$ alkylsulfonylalkyl, $C_5$-$C_{10}$ cycloalkylcarbonylalkyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl; or —CPh=N—O($C_1$-$C_4$ alkyl), each optionally substituted on ring members with up to 5 substituents independently selected from $R^{13}$; or $G^1$; or $W^1G^1$;

$R^{2b}$ is $C_1$-$C_6$ alkyl, $C_2$-$C_6$ alkenyl, $C_3$-$C_6$ alkynyl or $C_1$-$C_6$ alkoxy; or $R^1$ and $R^{2b}$ are taken together as $C_3$-$C_6$ alkylene or —CH$_2$OCH$_2$—; each $R^2$ and $R^3$, bonded to the same carbon atom, is independently H, halogen, hydroxy, $C_1$-$C_4$ alkyl, $C_1$-$C_4$ haloalkyl or $C_1$-$C_4$ alkoxy; or $R^2$ and $R^3$, together with the carbon atom to which they are both bonded, form a $C_3$-$C_7$ cycloalkyl ring;

each $R^2$ and $R^3$ bonded to the same carbon atom is defined independent of any $R^2$ and $R^3$ bonded to a different carbon atom;

$R^4$ and $R^5$ are each independently H, halogen, hydroxy, $C_1$-$C_4$ alkoxy, $C_1$-$C_4$ haloalkyl or $C_1$-$C_4$ alkyl;

$R^6$ is H, hydroxy, amino, $C_1$-$C_6$ alkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl or $C_3$-$C_{10}$ trialkylsilyl or $G^1$; or $R^6$ and $Q^2$ are taken together with the nitrogen atom to which they are both bonded to form an 8- to 10-membered bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from S(=O)$_u$(=NR$^8$)$_v$, each ring or ring system optionally substituted with up to 5 substituents independently selected from $R^7$ on carbon atom ring members and selected from $R^{11}$ on nitrogen atom ring members;

each $R^7$ is independently halogen, hydroxy, cyano, nitro, amino, $C_1$-$C_8$ alkyl, $C_1$-$C_8$ cyanoalkyl, $C_1$-$C_8$ cyanoalkoxy, $C_1$-$C_8$ haloalkyl, $C_1$-$C_8$ nitroalkyl, $C_2$-$C_8$ alkenyl, $C_2$-$C_8$ haloalkenyl, $C_2$-$C_8$ nitroalkenyl, $C_2$-$C_8$ alkynyl, $C_2$-$C_8$ haloalkynyl, $C_2$-$C_8$ alkoxyalkyl, $C_3$-$C_8$ alkoxyalkoxyalkyl, $C_2$-$C_8$ haloalkoxyalkyl, $C_2$-$C_8$ haloalkoxyhaloalkoxy, $C_3$-$C_6$ cycloalkyl, cyclopropylmethyl, 1-methylcyclopropyl, 2-methylcyclopropyl, $C_4$-$C_{10}$ cycloalkylalkyl, $C_4$-$C_{10}$ halocycloalkylalkyl, $C_5$-$C_{12}$ alkylcycloalkylalkyl, $C_5$-$C_{12}$ cycloalkylalkenyl, $C_5$-$C_{12}$ cycloalkylalkynyl, $C_3$-$C_8$ cycloalkyl, $C_3$-$C_8$ halocycloalkyl, $C_4$-$C_{10}$ alkylcycloalkyl, $C_6$-$C_{12}$ cycloalkylcycloalkyl, $C_3$-$C_8$ cycloalkenyl, $C_3$-$C_8$ halocycloalkenyl, $C_2$-$C_8$ haloalkoxyalkoxy, $C_2$-$C_8$ alkoxyalkoxy, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_8$ alkylamino, $C_2$-$C_8$ dialkylamino, $C_2$-$C_8$ halodialkylamino, $C_2$-$C_8$ alkylaminoalkyl, $C_2$-$C_8$ haloalkylaminoalkyl, $C_4$-$C_{10}$ cycloalkylaminoalkyl, $C_3$-$C_{10}$ dialkylaminoalkyl, —CHO, $C_2$-$C_8$ alkylcarbonyl, $C_2$-$C_8$ haloalkylcarbonyl, $C_4$-$C_{10}$ cycloalkylcarbonyl, —C(=O)OH, $C_2$-$C_8$ alkoxycarbonyl, $C_2$-$C_8$ haloalkoxycarbonyl, $C_4$-$C_{10}$ cycloalkoxycarbonyl, $C_5$-$C_{12}$ cycloalkylalkoxycarbonyl, —C(=O)NH$_2$, $C_2$-$C_8$ alkylaminocarbonyl, $C_4$-$C_{10}$ cycloalkylaminocarbonyl, $C_3$-$C_{10}$ dialkylaminocarbonyl, $C_1$-$C_8$ alkoxy, $C_1$-$C_8$ haloalkoxy, $C_2$-$C_8$ alkoxyalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_3$-$C_8$ cycloalkylsulfonyl, formylamino, $C_2$-$C_8$ alkylcarbonylamino, $C_2$-$C_8$ haloalkylcarbonylamino, $C_3$-$C_8$ cycloalkylamino, $C_2$-$C_8$ alkoxycarbonylamino, $C_1$-$C_6$ alkylsulfonylamino, $C_1$-$C_6$ haloalkylsulfonylamino, —SF$_5$, —SCN, SO$_2$NH$_2$, $C_3$-$C_{12}$ trialkylsilyl, $C_4$-$C_{12}$ trialkylsilylalkyl, $C_4$-$C_{12}$ trialkylsilylalkoxy or $C_1$-$C_6$ haloalkylamino; or $G^2$; or each $R^7$ is independently $R^{26}$S(=O)=N—, $R^{26}$S(=O)$_2$NR$^{25}$—C(=O)—, $R^{26}$(R$^{25}$N=)$_q$S(=O)$_p$—, wherein the free bond projecting to the right indicates the connecting point to $Q^1$; or two adjacent $R^7$, are taken together with the carbon atoms to which they are bonded to form a $C_3$-$C_7$ cycloalkyl ring;

each $R^{7a}$ is independently halogen, hydroxy, cyano, nitro, $C_1$-$C_8$ alkyl, $C_2$-$C_4$ alkoxyalkyl, $C_3$-$C_8$ alkoxyalkoxyalkyl, $C_1$-$C_4$ cyanoalkyl, $C_1$-$C_4$ cyanoalkoxy, $C_1$-$C_8$ haloalkyl, $C_1$-$C_8$ nitroalkyl, $C_2$-$C_8$ alkenyl, $C_2$-$C_8$ haloalkenyl, $C_2$-$C_8$ nitroalkenyl, $C_2$-$C_8$ alkynyl, $C_2$-$C_8$ haloalkynyl, $C_4$-$C_{10}$ cycloalkylalkyl, $C_4$-$C_{10}$ halocycloalkylalkyl, $C_5$-$C_{12}$ alkylcycloalkylalkyl, $C_5$-$C_{12}$ cycloalkylalkenyl, $C_5$-$C_{12}$ cycloalkylalkynyl, $C_3$-$C_8$ cycloalkyl, $C_3$-$C_8$ halocycloalkyl, $C_4$-$C_{10}$ alkylcycloalkyl, $C_6$-$C_{12}$ cycloalkylcycloalkyl, $C_3$-$C_8$ cycloalkenyl, $C_3$-$C_8$ halocycloalkenyl, $C_2$-$C_8$ alkoxyalkyl, $C_2$-$C_8$ haloalkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_2$-$C_8$ haloalkylaminoalkyl, $C_4$-$C_{10}$ cycloalkylaminoalkyl, $C_3$-$C_{10}$ dialkylaminoalkyl, —CHO, $C_2$-$C_8$ alkylcarbonyl, $C_2$-$C_8$ haloalkylcarbonyl, $C_4$-$C_{10}$ cycloalkylcarbonyl, —C(=O)OH, $C_2$-$C_8$ alkoxycarbonyl, $C_2$-$C_8$ haloalkoxycarbonyl, $C_4$-$C_{10}$ cycloalkoxycarbonyl, $C_5$-$C_{12}$ cycloalkylalkoxycarbonyl, —C(=O)NH$_2$, $C_2$-$C_8$ alkylaminocarbonyl, $C_4$-$C_{10}$ cycloalkylaminocarbonyl, $C_3$-$C_{10}$ dialkylaminocarbonyl, $C_1$-$C_8$ alkoxy, $C_1$-$C_8$ haloalkoxy, $C_2$-$C_8$ alkoxyalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_3$-$C_8$ cycloalkylsulfonyl, amino, $C_1$-$C_8$ alkylamino, $C_1$-$C_6$ haloalkylamino, $C_3$-$C_8$ cycloalkylamino, $C_2$-$C_8$ dialkylamino, $C_2$-$C_8$ halodialkylamino, formylamino, $C_2$-$C_8$ alkylcarbonylamino, $C_2$-$C_8$ haloalkylcarbonylamino, $C_1$-$C_6$ alkylsulfonylamino, $C_1$-$C_6$ haloalkylsulfonylamino, —$SF_5$, —SCN, $C_3$-$C_{12}$ trialkylsilyl, $C_4$-$C_{12}$ trialkylsilylalkyl, $C_4$-$C_{12}$ trialkylsilylalkoxy; or two adjacent $R^{7a}$, are taken together with the carbon atoms to which they are bonded to form a $C_3$-$C_7$ cycloalkyl ring;

each $R^8$ is independently H, cyano, $C_2$-$C_3$ alkylcarbonyl or $C_2$-$C_3$ haloalkylcarbonyl; each $R^9$ and $R^{11}$ are independently cyano, $C_1$-$C_3$ alkyl, $C_2$-$C_3$ alkenyl, $C_2$-$C_3$ alkynyl, $C_3$-$C_6$ cycloalkyl, $C_2$-$C_3$ alkoxyalkyl, $C_1$-$C_3$ alkoxy, $C_2$-$C_3$ alkylcarbonyl, $C_2$-$C_3$ alkoxycarbonyl, $C_2$-$C_3$ alkylaminoalkyl or $C_3$-$C_4$ dialkylaminoalkyl;

each $R^{10}$ is independently halogen, hydroxy, cyano, nitro, amino, $C_1$-$C_8$ alkyl, $C_1$-$C_8$ cyanoalkyl, $C_1$-$C_8$ cyanoalkoxy, $C_1$-$C_8$ haloalkyl, $C_1$-$C_8$ nitroalkyl, $C_2$-$C_8$ alkenyl, $C_2$-$C_8$ haloalkenyl, $C_2$-$C_8$ nitroalkenyl, $C_2$-$C_8$ alkynyl, $C_2$-$C_8$ haloalkynyl, $C_2$-$C_8$ alkoxyalkyl, $C_3$-$C_8$ alkoxyalkoxyalkyl, $C_2$-$C_8$ haloalkoxyalkyl, $C_2$-$C_8$ haloalkoxyhaloalkoxy, $C_3$-$C_6$ cycloalkyl, cyclopropylmethyl, 1-methylcyclopropyl, 2-methylcyclopropyl, $C_4$-$C_{10}$ cycloalkylalkyl, $C_4$-$C_{10}$ halocycloalkylalkyl, $C_5$-$C_{12}$ alkylcycloalkylalkyl, $C_5$-$C_{12}$ cycloalkylalkenyl, $C_5$-$C_{12}$ cycloalkylalkynyl, $C_3$-$C_8$ cycloalkyl, $C_3$-$C_8$ halocycloalkyl, $C_4$-$C_{10}$ alkylcycloalkyl, $C_6$-$C_{12}$ cycloalkylcycloalkyl, $C_3$-$C_8$ cycloalkenyl, $C_3$-$C_8$ halocycloalkenyl, $C_2$-$C_8$ haloalkoxyalkoxy, $C_2$-$C_8$ alkoxyalkoxy, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_8$ alkylamino, $C_2$-$C_8$ dialkylamino, $C_2$-$C_8$ halodialkylamino, $C_2$-$C_8$ alkylaminoalkyl, $C_2$-$C_8$ haloalkylaminoalkyl, $C_3$-$C_{10}$ cycloalkylaminoalkyl, $C_3$-$C_{10}$ dialkylaminoalkyl, —CHO, $C_2$-$C_8$ alkylcarbonyl, $C_2$-$C_8$ haloalkylcarbonyl, $C_4$-$C_{10}$ cycloalkylcarbonyl, —C(=O)OH, $C_2$-$C_8$ alkoxycarbonyl, $C_2$-$C_8$ haloalkoxycarbonyl, $C_4$-$C_{10}$ cycloalkoxycarbonyl, $C_5$-$C_{12}$ cycloalkylalkoxycarbonyl, —C(=O)$NH_2$, $C_2$-$C_8$ alkylaminocarbonyl, $C_4$-$C_{10}$ cycloalkylaminocarbonyl, $C_3$-$C_{10}$ dialkylaminocarbonyl, $C_1$-$C_8$ alkoxy, $C_1$-$C_8$ haloalkoxy, $C_2$-$C_8$ alkoxyalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_3$-$C_8$ cycloalkylsulfonyl, formylamino, $C_2$-$C_8$ alkylcarbonylamino, $C_2$-$C_8$ haloalkylcarbonylamino, $C_3$-$C_8$ cycloalkylcarbonylamino, $C_2$-$C_8$ alkoxycarbonylamino, $C_1$-$C_6$ alkylsulfonylamino, $C_1$-$C_6$ haloalkylsulfonylamino, —$SF_5$, —SCN, $SO_2NH_2$, $C_3$-$C_{12}$ trialkylsilyl, $C_4$-$C_{12}$ trialkylsilylalkyl, $C_4$-$C_{12}$ trialkylsilylalkoxy, $C_1$-$C_6$ haloalkylamino, $C_1$-$C_8$ hydroxyalkyl or $G^2$; or each $R^{10}$ is independently $R^{17}ON=CR^{17a}$—, $(R^{18})_2C=NO$—, $(R^{19})_2NN=CR^{17a}$, $(R^{18})_2C=NNR^{21}$—, $R^{20}N=CR^{17a}$—, $(R^{18})_2C=N$—, $R^{17}ON=CR^{17a}C(R^{22})_2$—, $(R^{18})_2C=NOC(R^{23})_2$—, $R^{26}S(=O)=N$—, $R^{26}S(=O)_2NR^{25}$—C(=O)— or $R^{26}(R^{25}N=)_qS(=O)_p$—, wherein the free bond projecting to the right of any such substituent indicates the connecting point to $Q^2$; or two adjacent $R^{10}$, are taken together with the carbon atoms to which they are bonded form a $C_3$-$C_7$ cycloalkyl ring;

each $R^{12}$ is independently H, cyano, hydroxy, CHO, $C_1$-$C_4$ alkyl, $C_1$-$C_4$ haloalkyl, $C_1$-$C_4$ alkoxy, $C_1$-$C_4$ haloalkoxy, $C_2$-$C_6$ alkylcarbonyl, $C_2$-$C_6$ haloalkylcarbonyl, —(C=O)$CH_3$ or —(C=O)$CF_3$;

each $G^1$ is independently phenyl, phenylmethyl (i.e. benzyl), pyridinylmethyl, phenylcarbonyl (i.e. benzoyl), phenylcarbonylalkyl, phenoxy, phenylethynyl, phenylsulfonyl or a 5- or 6-membered heterocyclic ring, each optionally substituted on ring members with up to 5 substituents independently selected from $R^{13}$;

each $G^2$ is independently phenyl, phenylmethyl (i.e. benzyl), pyridinylmethyl, phenylcarbonyl (i.e. benzoyl), phenylcarbonylalkyl, phenoxy, phenylethynyl, phenylsulfonyl or a 5- or 6-membered heterocyclic ring, each optionally substituted on ring members with up to 5 substituents independently selected from $R^{13}$;

$W^1$ is $C_1$-$C_3$ alkylene, $C_2$-$C_4$ alkenylene, $C_2$-$C_4$ alkynylene, —($C_1$-$C_2$ alkylene)C(=O)—, —C(=O)($C_1$-$C_2$ alkylene)-, —$CH_2O$—, —$CH_2NH$—, —$OCH_2$—, —$NCH_2$—, —N—, —O—, —S—, —SO— or —$SO_2$— wherein the free bond projecting to the left indicates the connecting point of $W^1$ to N and the free bond projecting to the right indicates the connecting point of $W^1$ to $G^1$;

each $R^{13}$ is independently halogen, cyano, hydroxy, amino, nitro, —CHO, —C(=O)OH, —C(=O)$NH_2$, —$SO_2NH_2$, $C_1$-$C_6$ alkyl, $C_1$-$C_6$ haloalkyl, $C_2$-$C_6$ alkenyl, $C_2$-$C_6$ alkynyl, $C_2$-$C_8$ alkylcarbonyl, $C_2$-$C_8$ haloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_1$-$C_6$ alkoxy, $C_1$-$C_6$ haloalkoxy, $C_2$-$C_8$ alkylcarbonyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylaminosulfonyl, $C_2$-$C_8$ dialkylaminosulfonyl, $C_3$-$C_{10}$ trialkylsilyl, $C_1$-$C_6$ alkylamino, $C_2$-$C_8$ dialkylamino, $C_2$-$C_8$ alkylcarbonylamino, $C_1$-$C_6$ alkylsulfonylamino, phenyl, pyridinyl or thienyl;

each $R^{15}$ is independently halogen, cyano, hydroxy, $C_1$-$C_4$ alkyl, $C_1$-$C_4$ haloalkyl, $C_1$-$C_4$ alkoxy, $C_1$-$C_4$ haloalkoxy, $C_2$-$C_4$ alkoxyalkyl, $C_2$-$C_4$ alkylcarbonyl, $C_2$-$C_4$ alkoxycarbonyl or $C_3$-$C_6$ cycloalkyl;

each $R^{16}$ is independently H, cyano, $C_1$-$C_4$ alkyl, $C_1$-$C_4$ haloalkyl, $C_1$-$C_4$ alkoxy, $C_2$-$C_4$ alkylcarbonyl, $C_2$-$C_4$ alkoxycarbonyl or $C_3$-$C_6$ cycloalkyl; each $R^{17}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$;

each $R^{17a}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_6$ alkoxy, $C_1$-$C_6$ alkylthio, $C_1$-$C_6$ haloalkylthio, $C_3$-$C_8$ cycloalkylthio, $C_3$-$C_{10}$ trialkylsilyl or $G^1$;

each $R^{18}$ is independently H, hydroxy, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$;

each $R^{19}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$; each $R^{20}$ is independently H, hydroxy, amino, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$;

each $R^{21}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_6$ alkoxy, $C_3$-$C_{10}$ trialkylsilyl or $G^1$;

each $R^{22}$ is independently H, halogen, cyano, hydroxy, $C_1$-$C_4$ alkyl, $C_3$-$C_8$ cycloalkyl, $C_4$-$C_8$ cycloalkylalkyl, $C_1$-$C_4$ haloalkyl, $C_1$-$C_4$ alkoxy, $C_1$-$C_4$ haloalkoxy, $C_2$-$C_4$ alkoxyalkyl, $C_2$-$C_4$ alkylcarbonyl, $C_2$-$C_4$ alkoxycarbonyl or $C_3$-$C_6$ cycloalkyl;

each $R^{23}$ is independently H, $C_1$-$C_4$ alkyl, $C_3$-$C_8$ cycloalkyl, $C_4$-$C_8$ cycloalkylalkyl, $C_1$-$C_4$ haloalkyl, $C_1$-$C_4$ alkoxy, $C_1$-$C_4$ haloalkoxy, $C_2$-$C_4$ alkoxyalkyl, $C_2$-$C_4$ alkylcarbonyl, $C_2$-$C_4$ alkoxycarbonyl or $C_3$-$C_6$ cycloalkyl;

each $R^{25}$ is independently H, cyano, $C_2$-$C_3$ alkylcarbonyl or $C_2$-$C_3$ haloalkylcarbonyl;

each $R^{26}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_6$ alkoxy, $C_3$-$C_{10}$ trialkylsilyl or $G^1$;

each u and v are independently 0, 1 or 2 in each instance of $S(=O)_u(=NR^8)_v$, provided that the sum of u and v is 0, 1 or 2;

each p and q are independently 0, 1 or 2 in each instance of $R^{26}(R^{25}N=)_q S(=O)_p-$, provided that the sum of p and q is 0, 1 or 2; and z is 1, 2 or 3.

This disclosure also relates, in part, to an agricultural composition (generally herbicidal) comprising such a compound, N-oxide or salt in a herbicidally effective amount and at least one component selected from the group consisting of surfactants, solid diluents and liquid diluents, the composition optionally further comprising at least one additional active ingredient selected from the group consisting of other herbicides and herbicide safeners.

This disclosure also relates, in part, to a herbicidal mixture comprising (a) a compound selected from Formula 1, N-oxides, and salts thereof, and (b) at least one additional active ingredient selected from (b1) through (b16); and salts of compounds of (b1) through (b16), as described below.

This disclosure also relates, in part, to processes for making the above-identified compounds, N-oxides, salts and compositions.

This disclosure also relates, in part, to methods for controlling the growth of undesired vegetation comprising contacting the vegetation or its environment with a herbicidally effective amount of an above-identified compound, N-oxide, salt or composition.

DETAILED DESCRIPTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process, method, article, or apparatus that comprises a list of elements is not necessarily limited to only those elements but may include other elements not expressly listed or inherent to such composition, mixture, process, method, article, or apparatus.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, method or apparatus that includes materials, steps, features, components, or elements, in addition to those literally disclosed, provided that these additional materials, steps, features, components, or elements do not materially affect the basic and novel characteristic(s) of the claimed disclosure. The term "consisting essentially of" occupies a middle ground between "comprising" and "consisting of".

Where applicants have defined an disclosure or a portion thereof with an open-ended term such as "comprising," it should be readily understood that (unless otherwise stated) the description should be interpreted to also describe such an disclosure using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the disclosure are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to herein, the term "seedling", used either alone or in a combination of words means a young plant developing from the embryo of a seed.

As referred to herein, the term "broadleaf" used either alone or in words such as "broadleaf weed" means dicot or dicotyledon, a term used to describe a group of angiosperms characterized by embryos having two cotyledons.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkylene" denotes a straight-chain or branched alkanediyl. Examples of "alkylene" include $CH_2$, $CH_2CH_2$, $CH(CH_3)$, $CH_2CH_2CH_2$, $CH_2CH(CH_3)$ and the different butylene isomers. "Alkenylene" denotes a straight-chain or branched alkenediyl containing one olefinic bond. Examples of "alkenylene" include $CH=CH$, $CH_2CH=CH$ and $CH=C(CH_3)$. "Alkynylene" denotes a straight-chain or branched alkynediyl containing one triple bond. Examples of "alkynylene" include $C\equiv C$, $CH_2C\equiv C$, $C\equiv CCH_2$ and the different butynylene isomers.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$—, $CH_3OCH_2CH_2$—, $CH_3CH_2OCH_2$—, $CH_3CH_2CH_2CH_2OCH_2$— and $CH_3CH_2OCH_2CH_2$—. "Aloxyalkoxyalkyl" denotes alkoxy substitution on the alkoxy moiety of an alkoxyalkyl moiety. Examples of "alkoxyalkoxyalkyl" include $CH_3OCH_2OCH_2$—, $CH_3CH_2O(CH_3)CHOCH_2$— and $(CH_3O)_2CHOCH_2$—. "Alkoxyalkoxy" denotes alkoxy substitution on alkoxy. Examples of "alkoxyalkoxy" include $CH_3OCH_2O$—, $CH_3OCH_2(CH_3O)CHCH_2O$— and $(CH_3)_2CHOCH_2CH_2O$—. "Alkenyloxy" includes straight-chain or branched alkenyloxy moieties. Examples of "alkenyloxy" include $H_2C=CHCH_2O$—, $(CH_3)_2C=CHCH_2O$—, $(CH_3)CH=CHCH_2O$—, $(CH_3)CH=C(CH_3)CH_2O$— and $CH_2=CHCH_2CH_2O$—. "Alkynyloxy" includes straight-chain or branched alkynyloxy moieties. Examples of "alkynyloxy" include $HC\equiv CCH_2O$—, $CH_3C\equiv CCH_2O$— and $CH_3C\equiv CCH_2CH_2O$—. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)$—, $CH_3CH_2S(O)$—, $CH_3CH_2CH_2S(O)$—, $(CH_3)_2CHS(O)$— and the different butylsulfinyl, pentylsulfinyl and hexylsulfinyl isomers. Examples of "alkylsulfonyl" include $CH_3S(O)_2$—, $CH_3CH_2S(O)_2$—, $CH_3CH_2CH_2S(O)_2$—, $(CH_3)_2CHS(O)_2$—, and the different butylsulfonyl, pentylsulfonyl and hexylsulfonyl isomers. "Alkylthioalkyl" denotes alkylthio substitution on alkyl. Examples of "alkylthioalkyl" include $CH_3SCH_2$—, $CH_3SCH_2CH_2$—, $CH_3CH_2SCH_2$—, $CH_3CH_2CH_2CH_2SCH_2$— and $CH_3CH_2SCH_2CH_2$—. "Alkylsulfinylalkyl" denotes alkylsulfinyl substitution on alkyl. Examples of "alylsulfinylalkyl" include $CH_3S(=O)CH_2$—, $CH_3S(=O)CH_2CH_2$—, $CH_3CH_2S(=O)CH_2$— and $CH_3CH_2S(=O)CH_2CH_2$—. "Alkylamino" "dialkylamino", and the like, are defined analogously to the above examples. "Alkylaminoalkyl" denotes a straight-chain or branched alkyl moieties bonded to a nitrogen atom of amino(straight-chain or branched)alkyl moiety. Examples of "alkylaminoalkyl" include $CH_3NHCH_2$—, $(CH_3)_2CHNHCH_2$— and $CH_3NHCH(CH_3)$—. "Haloalkylaminoalkyl" denotes an halogen group substituted with alkylaminoalkyl group. "Haloalkylaminoalkyl" includes halogen group attached any alkyl groups as well as nitrogen. Examples of "haloalkylaminoalkyl" include $CH_3NHCHCl$—, $(CH_3)_2CClNHCH_2$— and $CH_3NClCH(CH_3)$—. "Dialkylaminoalkyl" denotes two independent straight-chain or branched alkyl moieties bonded to a nitrogen atom of amino(straight-chain or branched)alkyl moiety. Examples of "dialkylaminoalkyl" include $(CH_3)_2NCH_2$—, $(CH_3)_2NC(CH_3)H$— and $(CH_3)(CH_3)NCH_2$—. "Cyanoalkyl" denotes an alkyl group substituted with one cyano group. Examples of "cyanoalkyl" include $NCCH_2$—, $NCCH_2CH_2$— and $CH_3CH(CN)CH_2$—. "Cyanoalkoxy" denotes an alkoxy group substituted with one cyano group. Examples of "cyanoalkoxy" include $NCCH_2O$—, $NCCH_2CH_2O$— and $CH_3CH(CN)CH_2O$—. "Alkenylthio", "alkenylsulfinyl", "alkenylsulfonyl", "alkynylthio", "alkynylsulfinyl", "alkynylsulfonyl", and the like, are defined analogously to the above examples.

"Alkylcarbonyl" denotes a straight-chain or branched alkyl moieties bonded to a $C(=O)$ moiety. Examples of "alkylcarbonyl" include $CH_3C(=O)$—, $CH_3CH_2CH_2C(=O)$— and $(CH_3)_2CHC(=O)$—. An example of "cycloalkylcarbonyl" is cyclopentyl-$C(=O)$—. Examples of "haloalkylcarbonyl" include $C(O)CF_3$, $C(O)CCl_3$, $C(O)CH_2CF_3$ and $C(O)CF_2CF_3$. Examples of "alkylcarbonylalkoxy" include $CH_3C(=O)CH_2O$—, $CH_3CH_2CH_2C(=O)CH_2O$— and $(CH_3)_2CHC(=O)CH_2O$—. "Alkylcarbonyloxy" denotes an alkylcarbonyl moiety linked through an oxygen atom attached to the carbonyl. Examples of "alkylcarbonyloxy" include $CH_3C(=O)O$—, $CH_3CH_2CH_2C(=O)O$— and $(CH_3)_2CHC(=O)O$—. Examples of "cycloalkylcarbonyloxy" include cyclopentyl-$C(=O)O$—. Examples of "alkoxycarbonyl" include $CH_3OC(=O)$—, $CH_3CH_2OC(=O)$—, $CH_3CH_2CH_2OC(=O)$—, $(CH_3)_2CHOC(=O)$— and the different butoxy- or pentoxycarbonyl isomers. Examples of "alkylaminocarbonyl" include $CH_3NHC(O)$—, $(CH_3)_2CHNHC(O)$— and $CH_3CH_2NHC(O)$—. Examples of "dialkylaminocarbonyl" include $(CH_3)_2NC(=O)$—, $(CH_3CH_2)_2NC(=O)$—, $CH_3CH_2(CH_3)NC(=O)$—, $(CH_3)_2CHN(CH_3)C(=O)$— and $CH_3CH_2CH_2(CH_3)NC(=O)$—. "Cycloalkylalkoxycarbonyl" denotes a cycloalkylalkyl moiety bonded to a oxygen atom of alkoxycarbonyl moiety. Examples of "cycloalkylalkoxycarbonyl" include cyclopropyl-$CH_2OC(=O)$—, cyclopropyl-$CH(CH_3)OC(=O)$— and cyclopentyl-$CH_2OC(=O)$—. An example of "alkylcarbonylamino" includes $NHC(O)CH_3$. The terms "alkoxycarbonylamino" denotes a straight-chain or branched alkoxy moieties bonded to a $C(=O)$ moiety of carbonylamino group. Examples of "alkoxycarbonylamino" include $CH_3OC(=O)NH$— and $CH_3CH_2OC(=O)NH$—. Examples of "alkylsulfonylamino" include $CH_3S(O)_2NH$—, $CH_3CH_2S(O)_2NH$—, $CH_3CH_2CH_2S(O)_2NH$—, $(CH_3)_2CH_2(O)_2NH$—, and the different butylsulfonylamino, pentylsulfonylamino and hexylsulfonylamino isomers. Examples of "alkylsulfonyloxy" include $CH_3S(O)_2O$—, $CH_3CH_2S(O)_2O$—, $CH_3CH_2CH_2S(O)_2O$—, $(CH_3)_2CHS(O)_2O$—, and the different butylsulfonyloxy, pentylsulfonyloxy and hexylsulfonyloxy isomers. "Alkylsulfonylalkyl" denotes alkylsulfonyl substitution on alkyl.

Examples of "alkylsulfonylalkyl" include $CH_3S(=O)_2CH_2$—, $CH_3S(=O)_2CH_2CH_2$—, $CH_3CH_2S(=O)_2CH_2$— and $CH_3CH_2S(=O)_2CH_2CH_2$—. An example of "alkylaminosulfonyl" is $CH_3NHS(O)_2$—. An example of "dialkylaminosulfonyl" is $(CH_3)_2NS(O)_2$—.

"Cycloalkyl" includes, for example, cyclopropyl, cyclobutyl, cyclopentyl and cyclohexyl. The term "alkylcycloalkyl" denotes alkyl substitution on a cycloalkyl moiety and includes, for example, methylcyclopropyl, ethylcyclopropyl, i-propylcyclobutyl, 3-methylcyclopentyl and 4-methylcyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. "Halocycloalkylalkyl" denotes halogen substitution on cycloalkyl group, alkyl group or both of cycloalkylalkyl moiety. Examples of "halocycloalkylalkyl" include 2-chlorocyclopropylmethyl, cyclopentyl-1-chloroethyl, and 3-chlorocyclopentyl-1-chloroethyl. The term "cycloalkoxy" denotes cycloalkyl linked through an oxygen atom such as cyclopentyloxy and cyclohexyloxy. "Cycloalkylalkoxy" denotes cycloalkylalkyl linked through an oxygen atom attached to the alkyl chain. Examples of "cycloalkylalkoxy" include cyclopropylmethoxy, cyclopentylethoxy, and other cycloalkyl moieties bonded to straight-chain or branched alkoxy groups. "Cycloalkoxyalkyl" denotes cycloalkoxy substitution on an alkyl moiety. Examples of "cycloalkoxyalkyl" include cyclopropoxymethyl, cyclopentoxyethyl, and other cycloalkoxy moieties bonded to straight-chain or branched alkyl groups. "Cycloalkenyl" includes groups such as cyclopentenyl and cyclohexenyl as well as groups with more than one double bond such as 1,3- and 1,4-cyclohexadienyl. "Cycloalkylalkenyl" denotes cycloalkyl substitution on an alkenyl moiety. An example of "cycloalkylalkenyl" is cyclopropylethenyl. "Cycloalkylalkynyl" denotes cycloalkyl substitution on an alkynyl moiety. An example of "cycloalkylalkynyl" is cyclopropylethynyl. "Cycloalkylamino" denotes an NH radical substituted with cycloalkyl. Examples of "cycloalkylamino" include groups such as cyclopropylamino, cyclobutylamino, cyclopentylamino and cyclohexylamino. Examples of "alkoxycarbonylamino" include $CH_3OC(=O)NH$— and $CH_3CH_2OC(=O)NH$—. The term "cycloalkylaminoalkyl" denotes cycloalkylamino substitution on an alkyl group. Examples of "cycloalkylaminoalkyl" include cyclopropylaminomethyl, cyclopentylaminoethyl, and other cycloalkylamino moieties bonded to straight-chain or branched alkyl groups. "Cycloalkylalkoxycarbonyl" denotes a cycloalkylalkyl moiety bonded to an oxygen atom of an alkoxycarbonyl moiety. Examples of "cycloalkylalkoxycarbonyl" include cyclopropyl-$CH_2OC(=O)$—, cyclopropyl-$CH(CH_3)OC(=O)$— and cyclopentyl-$CH_2OC(=O)$—. "Cycloalkoxycarbonyl" denotes cycloalkoxy bonded to a $C(=O)$ moiety. Examples of "cycloalkoxycarbonyl" include cyclopentyl-$OC(=O)$—. "Alkylcycloalkylalkyl" denotes an alkyl group substituted with alkylcycloalkyl. Examples of "alkylcycloalkylalkyl" include 1-, 2-, 3- or 4-methyl or -ethyl cylohexylmethyl. The term "cycloalkylcycloalkyl" denotes cycloalkyl substitution on another cycloalkyl ring, wherein each cycloalkyl ring independently has from 3 to 7 carbon atom ring members. Examples of "cycloalkylcycloalkyl" include cyclopropylcyclopropyl (such as 1,1'-bicyclopropyl-1-yl, 1,1'-bicyclopropyl-2-yl), cyclohexylcyclopentyl (such as 4-cyclopentylcyclohexyl) and cyclohexylcyclohexyl (such as 1,1-bicyclohexyl-1-yl), and the different cis- and trans-cycloalkylcycloalkyl isomers, (such as (1R,2S)-1,1'-bicyclopropyl-2-yl and (1R,2R)-1,1'-bicyclopropyl-2-yl). An example of "cycloalkylthio" is cyclopentyl-$S$—. An example of "cycloalkylsufinyl" is cyclopentyl-$S(=O)$—. An example of "cycloalkylsulfonyl" is cyclopentyl-$S(O)_2$—.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$—, $ClCH_2$—, $CF_3CH_2$— and $CF_3CCl_2$—. The terms "haloalkenyl", "haloalkynyl", "halocycloalkyl", "halocycloalkenyl", "haloalkylcarbonyl", "haloalkylcarbonyloxy", "haloalkoxy", "halocycloalkoxy", "haloalkoxyalkyl", "haloalkoxyhaloalkyl", "haloalkoxyalkoxy", "haloalkoxycarbonyl", "haloalkoxylhaloalkoxy", "haloalkenyloxy", "haloalkynyloxy", "haloalkylthio", "haloalkylsulfinyl", "haloalkylsulfonyl", "haloalkylsulfonyloxy", "halodialkylamino", "haloalkylaminoalkyl", "haloalkylcarbonylamino", "haloalkylsulfonylamino" and the like, are defined analogously to the term "haloalkyl". Examples of "haloalkenyl" include $(Cl)_2C=CHCH_2$— and $CF_3CH_2CH=CHCH_2$—. Examples of "haloalkynyl" include $HC\equiv CCHCl$—, $CF_3C\equiv C$—, $CCl_3C\equiv C$— and $FCH_2C\equiv CCH_2$—. Examples of "haloalkoxy" include $CF_3O$—, $CCl_3CH_2O$—, $HCF_2CH_2CH_2O$— and $CF_3CH_2O$—. "Haloalkoxyalkyl" denotes at least one halogen group substituted with alkoxy moiety of alkoxyalkyl group. Examples of "haloalkoxyalkyl" include $CH_2ClOCH_2$—, $CHCl_2OCH_2$—, $CF_3OCH_2$—, $ClCH_2CH_2OCH_2CH_2$—, $Cl_3CCH_2OCH_2$— as well as branched alkyl derivatives. "Haloalkoxyhaloalkyl" denotes at least two halogen groups independently substituted with both alkoxy moiety and alkyl moiety of alkoxyalkyl group. Examples of "haloalkoxyhaloalkyl" include $CH_2ClOCHCl$— and $CH_2FCH_2OCl_2C$—. The term "haloalkoxyalkoxy" denotes halogen group substituted with first alkoxy moiety of alkoxyalkoxy group. Examples of "haloalkoxyalkoxy" include $CF_3OCH_2O$—, $ClCH_2CH_2OCH_2CH_2O$—, $Cl_3CCH_2OCH_2O$— as well as branched alkyl derivatives. Examples of "haloalkoxycarbonyl" include $CF_3OC(O)$—, $ClCH_2CH_2OCH_2CH_2$—, $Cl_3CCH_2OCH_2OC(O)$— as well as branched alkyl derivatives. The term "haloalkoxyhaloalkoxy" denotes halogen group independently substituted with both alkoxy moiety of alkoxyalkoxy group. Examples of "haloalkoxyhaloalkoxy" include $CF_3OCHClO$—, $ClCH_2CH_2OCHClCH_2O$—, $Cl_3CCH_2OCHClO$— as well as branched alkyl derivatives. Examples of "haloalkylthio" include $CCl_3S$—, $CF_3S$—, $CCl_3CH_2S$— and $ClCH_2CH_2CH_2S$—. Examples of "haloalkylsulfinyl" include $CF_3S(O)$—, $CCl_3S(O)$—, $CF_3CH_2S(O)$— and $CF_3CF_2S(O)$—. Examples of "haloalkylsulfonyl" include $CF_3S(O)_2$—, $CCl_3S(O)_2$—, $CF_3CH_2S(O)_2$— and $CF_3CF_2S(O)_2$—. An example of "haloalkylamino" is $CH_2ClHN$—. The term "halodialkylamino" denotes at least one halogen group substituted with any alkyl moiety of dialkylamino group. Examples of "halodialkylamino" include $CF_3(CH_3)N$—, $(CF_3)_2N$— and $CH_2C_1(CH_3)N$—. "Haloalkylaminoalkyl" denotes a halogen group substituted with alkylaminoalkyl group. "Haloalkylaminoalkyl" includes halogen group attached to an alkyl group as well as nitrogen. Examples of "haloalkylaminoalkyl" include $CH_3NHCHCl$—, $(CH_3)_2CClNHCH_2$— and $CH_3NClCH(CH_3)$—. An example of "haloalkylcarbonylamino" is $NHC(O)CF_3$.

"Trialkylsilyl" includes 3 branched and/or straight-chain alkyl radicals attached to and linked through a silicon atom, such as trimethylsilyl, triethylsilyl and tert-butyldimethylsilyl.

"—CHO" means formyl.

When a compound is substituted with a substituent bearing a subscript that indicates the number of said substituents can exceed 1, said substituents (when they exceed 1) are independently selected from the group of defined substituents, e.g., ($[(R^7)_n]$, n is 1, 2, 3, 4 or 5). Further, when the subscript indicates a range, e.g. $(R)_{i-j}$, then the number of substituents may be selected from the integers between i and j inclusive. When a group contains a substituent which can be hydrogen, for example ($R^1$ or $R^2$), then when this substituent is taken as hydrogen, it is recognized that this is equivalent to said group being unsubstituted. When a variable group is shown to be optionally attached to a position, for example $[(R^7)_n]$ wherein n may be 0, then hydrogen may be at the position even if not recited in the variable group definition. When one or more positions on a group are said to be "not substituted" or "unsubstituted", then hydrogen atoms are attached to take up any free valency.

The expression "fully saturated" in relation to a ring of atoms means that the bonds between the atoms of the ring are all single. The expression "fully unsaturated" in relation to a ring means that the bonds between the atoms in the ring are single or double bonds according to valence bond theory and furthermore the bonds between the atoms in the ring include as many double bonds as possible without double bonds being cumulative (i.e. no C=C=C, N=C=C, etc.). The term "partially unsaturated" in relation to a ring denotes a ring comprising at least one ring member bonded to an adjacent ring member though a double bond and which conceptually potentially accommodates a number of non-cumulated double bonds through adjacent ring members (i.e. in its fully unsaturated counterpart form) greater than the number of double bonds present (i.e. in its partially unsaturated form). When a fully unsaturated ring satisfies Hückel's rule then it can also be described as aromatic.

Unless otherwise indicated, a "ring" or "ring system" as a component of Formula 1 (e.g., substituent $Q^1$) is carbocyclic or heterocyclic. The term "ring system" denotes two or more fused rings. The terms "bicyclic ring system" and "fused bicyclic ring system" denote a ring system consisting of two fused rings, in which either ring can be saturated, partially unsaturated, or fully unsaturated unless otherwise indicated. The term "fused heterobicyclic ring system" denotes a fused bicyclic ring system in which at least one ring atom is not carbon. A "bridged bicyclic ring system" is formed by bonding a segment of one or more atoms to nonadjacent ring members of a ring. The term "ring member" refers to an atom or other moiety (e.g., C(=O), C(=S), S(O) or $S(O)_2$) forming the backbone of a ring or ring system.

The terms "carbocyclic ring", "carbocycle" or "carbocyclic ring system" denote a ring or ring system wherein the atoms forming the ring backbone are selected only from carbon. Unless otherwise indicated, a carbocyclic ring can be a saturated, partially unsaturated, or fully unsaturated ring. When a fully unsaturated carbocyclic ring satisfies Hückel's rule, then said ring is also called an "aromatic ring". "Saturated carbocyclic" refers to a ring having a backbone consisting of carbon atoms linked to one another by single bonds; unless otherwise specified, the remaining carbon valences are occupied by hydrogen atoms.

The terms "heterocyclic ring", "heterocycle" or "heterocyclic ring system" denote a ring or ring system in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring" or "aromatic heterocyclic ring". Unless otherwise indicated, heterocyclic rings and ring systems can be attached through any available carbon or nitrogen by replacement of a hydrogen on said carbon or nitrogen.

"Aromatic" indicates that each of the ring atoms is essentially in the same plane and has a p-orbital perpendicular to the ring plane, and that (4n+2) π electrons, where n is a positive integer, are associated with the ring to comply with Hückel's rule. The term "aromatic ring system" denotes a carbocyclic or heterocyclic ring system in which at least one ring of the ring system is aromatic. The term "aryl" can be used alone or in compound words such as "arylcarbonyl". "Arylcarbonyl" denotes an aryl group bonded to a C(=O) moiety. The terms "arylalkenylalkyl" is defined similarly. The term "aromatic carbocyclic ring system" denotes a carbocyclic ring system in which at least one ring of the ring system is aromatic. The term "aromatic heterocyclic ring system" denotes a heterocyclic ring system in which at least one ring of the ring system is aromatic. The term "nonaromatic ring system" denotes a carbocyclic or heterocyclic ring system that may be fully saturated, as well as partially or fully unsaturated, provided that none of the rings in the ring system are aromatic. The term "nonaromatic carbocyclic ring system" in which no ring in the ring system is aromatic. The term "nonaromatic heterocyclic ring system" denotes a heterocyclic ring system in which no ring in the ring system is aromatic.

The term "optionally substituted" in connection with the heterocyclic rings refers to groups which are unsubstituted or have at least one non-hydrogen substituent that does not extinguish the biological activity possessed by the unsubstituted analog. As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

When $Q^1$ or $Q^2$ is a 5- or 6-membered nitrogen-containing heterocyclic ring, it may be attached to the remainder of Formula 1 though any available carbon or nitrogen ring atom, unless otherwise described. As noted above, $Q^1$ or $Q^2$ can be (among others) phenyl optionally substituted with one or more substituents selected from a group of substituents as defined in the Summary. An example of phenyl optionally substituted with one to five substituents is the ring illustrated as U-1 in Exhibit 1, wherein $R^v$ is $R^7$ as defined in the Summary for $Q^1$ or $R^v$ is $R^{10}$ as defined in the Summary for $Q^2$, and r is an integer (from 0 to 5).

As noted above, $Q^1$ or $Q^2$ can be (among others) 5- or 6-membered heterocyclic ring, which may be saturated or unsaturated, optionally substituted with one or more substituents selected from a group of substituents as defined in the Summary. Examples of a 5- or 6-membered unsaturated aromatic heterocyclic ring optionally substituted with from one or more substituents include the rings U-2 through U-61 illustrated in Exhibit 1 wherein $R^v$ is any substituent as defined in the Summary for $Q^1$ or $Q^2$ and r is an integer from 0 to 5, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^v)_r$.

Exhibit 1

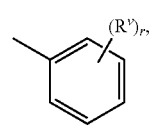
U-1

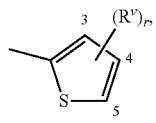
U-2

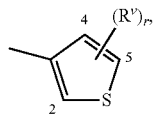
U-3

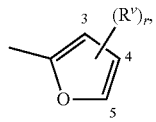
U-4

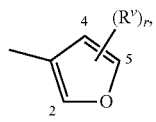
U-5

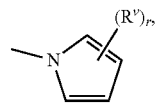
U-6

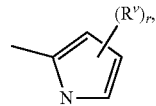
U-7

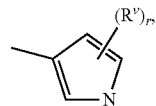
U-8

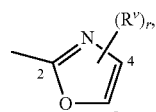
U-9

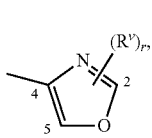
U-10

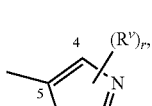
U-11

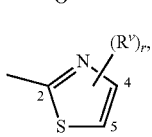
U-12

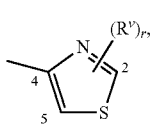
U-13

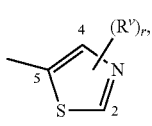
U-14

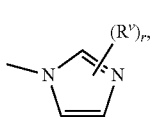
U-15

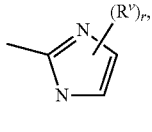
U-16

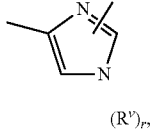
U-17

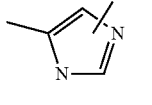
U-18

| | |
|---|---|
| U-19 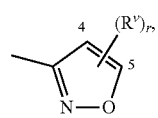 | U-31 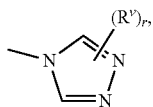 |
| U-20 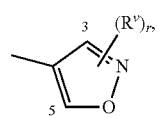 | U-32 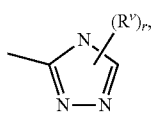 |
| U-21 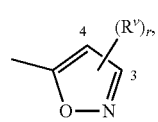 | U-33 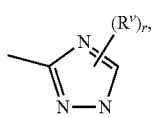 |
| U-22 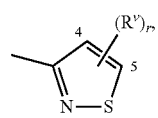 | U-34 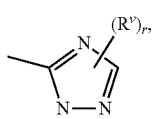 |
| U-23 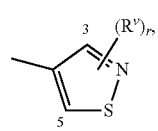 | U-35 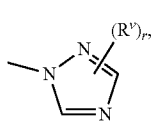 |
| U-24 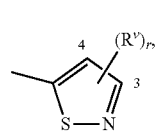 | U-36 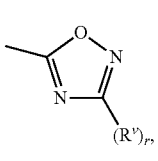 |
| U-25 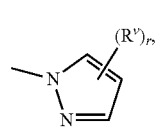 | U-37 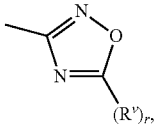 |
| U-26 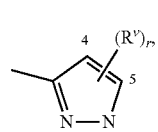 | U-38 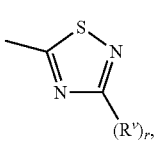 |
| U-27 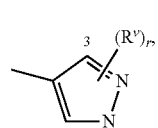 | U-39 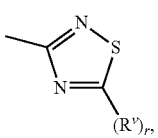 |
| U-28 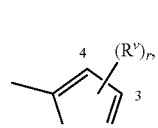 | U-40 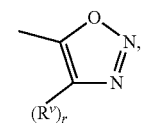 |
| U-29 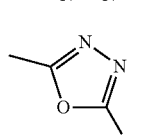 | U-41 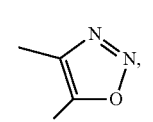 |
| U-30 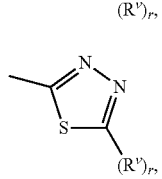 | U-42 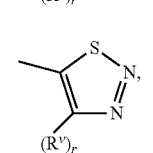 |

-continued

U-43 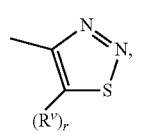

U-44 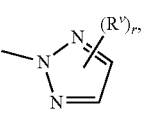

U-45 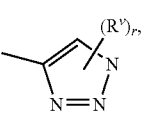

U-46 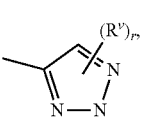

U-47 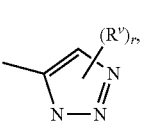

U-48 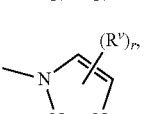

U-49 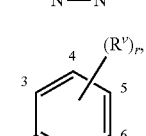

U-50 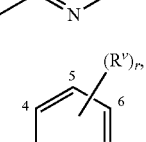

U-51 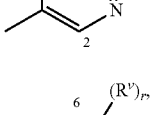

U-52 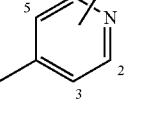

U-53 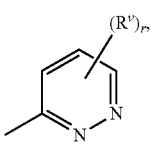

U-54 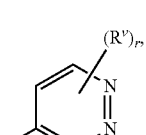

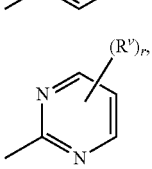

-continued

U-55 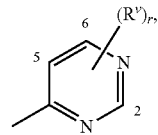

U-56 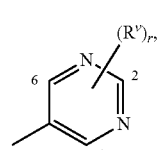

U-57 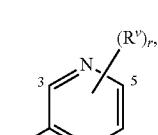

U-58 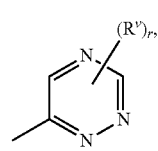

U-59 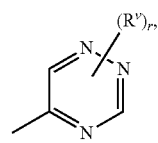

U-60 and 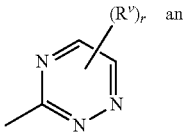

U-61 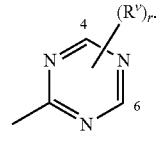

As noted above, $Q^1$ and $Q^2$ can be an 8- to 10-membered heterocyclic ring system optionally substituted with one or more substituents selected from a group of substituents as defined in the Summary for $Q^1$ and $Q^2$. Examples of 8- to 10-membered heterocyclic ring system optionally substituted with from one or more substituents include the rings U-62 through U-102 illustrated in Exhibit 2 wherein $R^v$ is any substituent as defined in the Summary for $Q^1$ or $Q^2$, and r is typically an integer from 0 to 5. The free bond denoted by a straight line can be located on either ring irregardless of where they are drawn. The free bond connected to $(R^v)_r$ can be located on either ring irregardless of where they are drawn.

Exhibit 2

U-62 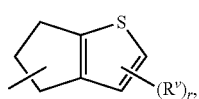

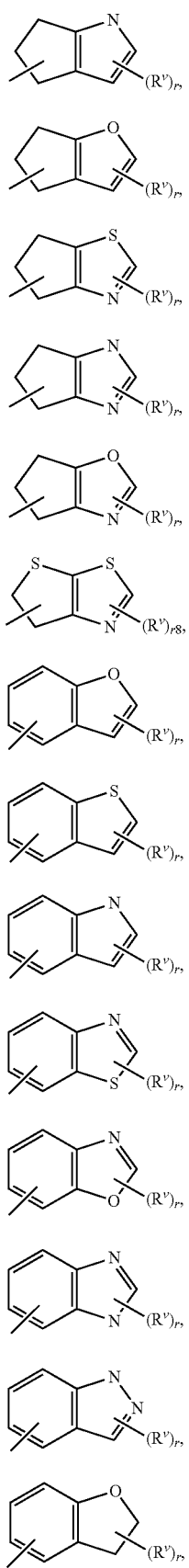
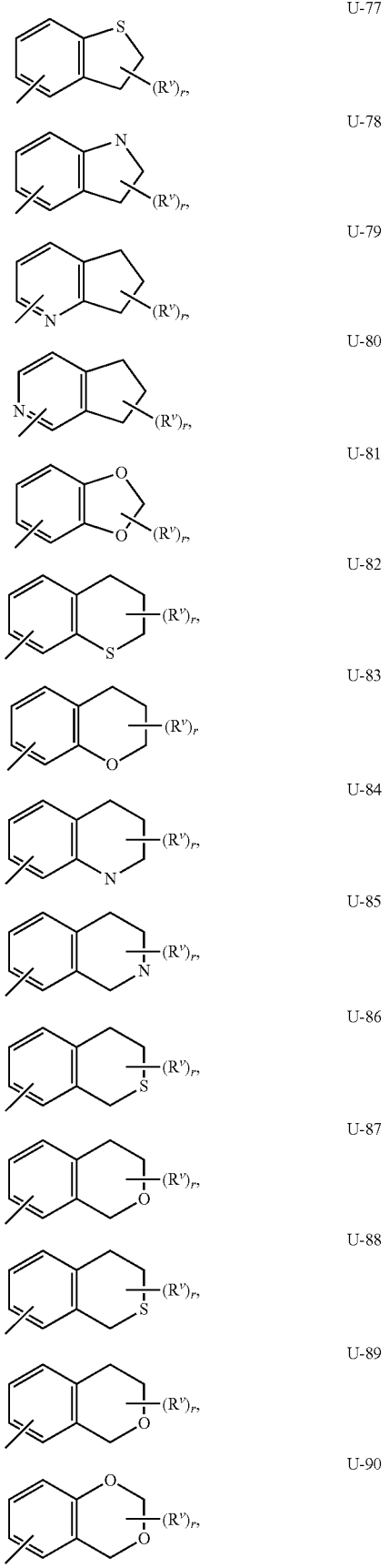

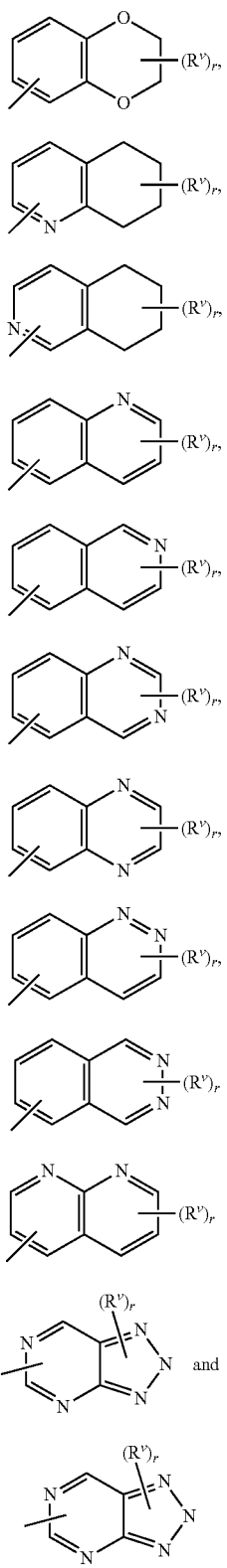

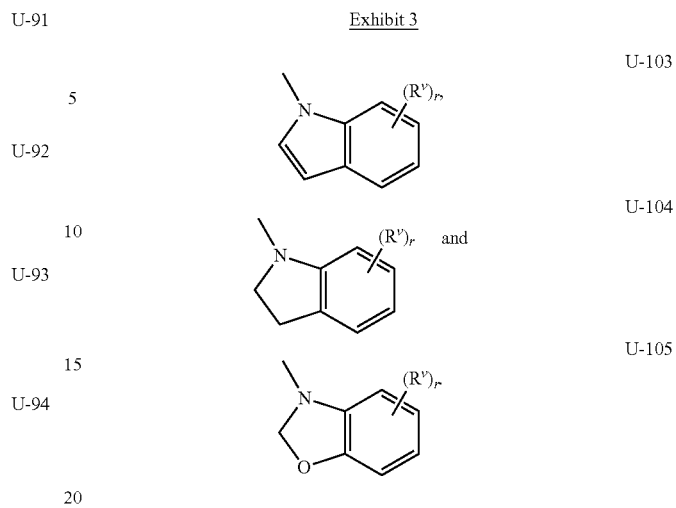

Some examples of a 4- to 6-membered saturated heterocyclic ring optionally substituted with one or more substituents include but not limited to the rings U-106 through U-110 illustrated in Exhibit 3 wherein $R^v$ is any substituent as defined in the Summary for $Q^1$ or $Q^2$, and r is typically an integer from 0 to 4 or 5.

Exhibit 4

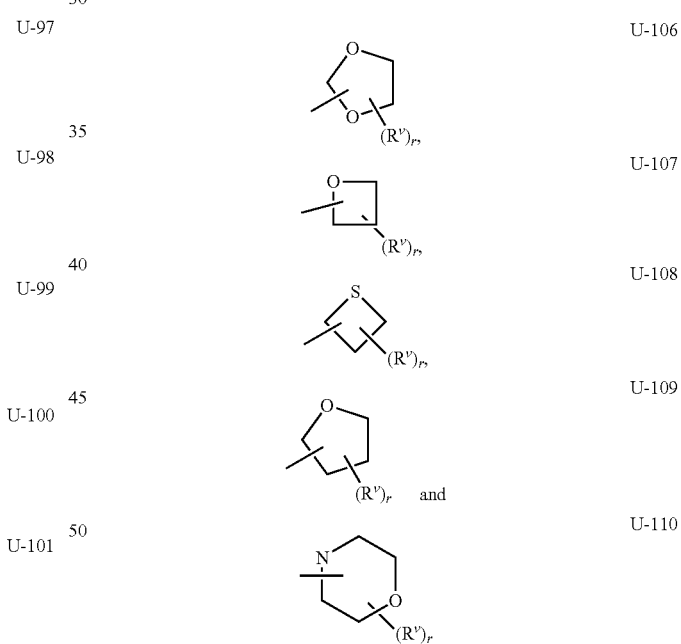

As noted above, $R^6$ and $Q^2$ can be taken together with the nitrogen atom to which they are both bonded to form an 8- to 10-membered bicyclic ring system. Examples of $R^6$ and $Q^2$ taken together are shown in Exhibit 3.

Although $R^v$ groups are shown in the structures U-1 through U-110, it is noted that they do not need to be present since they are optional substituents. Note that when $R^v$ is H when attached to an atom, this is the same as if said atom is unsubstituted. The nitrogen atoms that require substitution to fill their valence are substituted with H or $R^v$. Note that when the attachment point between $(R^v)_r$ and the U group is illustrated as floating, $(R^v)_r$ can be attached to any available carbon atom or nitrogen atom of the U group. Note that when the attachment point on the U group is illustrated as floating, the U group can be attached to the remainder of Formula 1 through any available carbon or nitrogen of the U group by replacement of a hydrogen atom. In some embodiments, for greater herbicidal activity, the U group is attached to the remainder of Formula 1 through an available carbon or nitrogen on a fully unsaturated ring of the U group. Note that some U groups can only be substituted with less than 4 $R^v$ groups (e.g., U-2 through U-5, U-7 through U-48, and U-52 through U-61).

In the present disclosure, the term "nitrone" refers to the presence of an oxidized nitrogen species carrying a formal charge either as a substituent or as part of the ring.

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this disclosure can exist as one or more stereoisomers. The various stereoisomers include enantiomers, diastereomers, atropisomers and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the disclosure may be present as a mixture of stereoisomers, individual stereoisomers or as an optically active form. Particularly when $R^4$ and $R^5$ are each H, the $C(O)N(Q^2)(R^6)$ and $Q^1$ substituents are typically mostly in the thermodynamically preferred trans configuration on the nitrone ring.

For example the $C(Y)N(Q^2)(R^6)$ moiety (bonded to the carbon at the 2-position of the nitrone ring wherein Y is oxygen and $J^2$ is —$CR^2R^3$— and both $R^2$ and $R^3$ are H) and $Q^1$ (bonded to the carbon at the 3-position of the nitrone ring) are generally found in the trans configuration. These two carbon atoms (i.e. at the 2- and 3-positions of the central ring of Formula 1) both possess a chiral center. The two most prevelant pairs of enantiomers are depicted as Formula 1' and Formula 1" where the chiral centers are identified (i.e. as 2S,3R or as 2R,3S). The skilled artisan will understand that in some Embodiments of the disclosure, the R or S designation is determined relative to other substituents around the same carbon and therefore a compound of the disclosure could also be given the 2S,3S or 2R,3R designation. In Synthesis Example 1, the compound trans-3-(4-chlorophenyl)-N-(2,3-difluorophenyl)-3,4-dihydro-5-methyl-2H-pyrrole-2-carboxamide 1-oxide may also be referred to as rel-(2S,3R)-3-(4-chlorophenyl)-N-(2,3-difluorophenyl)-3,4-dihydro-5-methyl-2H-pyrrole-2-carboxamide 1-oxide, and the compounds prepared in Synthesis Examples 2, 3 and 4 may also be named in a similar manner. For a comprehensive discussion of all aspects of stereoisomerism, see Ernest L. Eliel and Samuel H. Wilen, *Stereochemistry of Organic Compounds*, John Wiley & Sons, 1994.

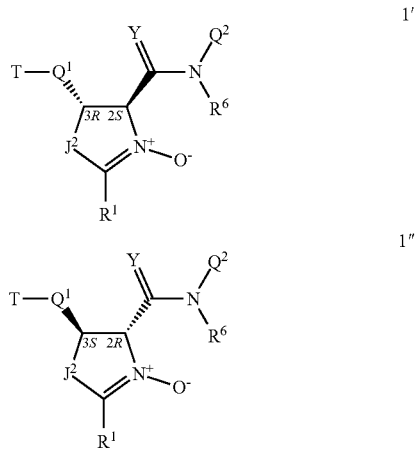

Molecular depictions drawn herein follow standard conventions for depicting stereochemistry. To indicate stereoconfiguration, bonds rising from the plane of the drawing and towards the viewer are denoted by solid wedges wherein the broad end of the wedge is attached to the atom rising from the plane of the drawing towards the viewer. Bonds going below the plane of the drawing and away from the viewer are denoted by dashed wedges wherein the narrow end of the wedge is attached to the atom further away from the viewer. Constant width lines indicate bonds with a direction opposite or neutral relative to bonds shown with solid or dashed wedges; constant width lines also depict bonds in molecules or parts of molecules in which no particular stereoconfiguration is intended to be specified.

This disclosure comprises racemic mixtures, for example, equal amounts of the enantiomers of Formulae 1' and 1". In addition, this disclosure includes compounds that are enriched compared to the racemic mixture in an enantiomer of Formula 1. Also included are the essentially pure enantiomers of compounds of Formula 1, for example, Formula 1' and Formula 1".

When enantiomerically enriched (i.e. enantio-enriched), one enantiomer is present in greater amounts than the other, and the extent of enrichment can be defined by an expression of enantiomeric excess ("ee"), which is defined as (2x−1) ·100%, where x is the mole fraction of the dominant enantiomer in the mixture (e.g., an ee of 20% corresponds to a 60:40 ratio of enantiomers). The compounds of the disclosure can be prepared entantiomerically enriched (i.e. enantio-enriched) by utilizing a corresponding enantiomerically enriched intermediate during the course of synthesis. In these instances, the enantiomeric excess is not measured in the final product but is presumed to be "enantiomerically enriched" based on equivalent known chemical transformations in the literature.

Preferably the compositions of this disclosure have at least a 50% enantiomeric excess; more preferably at least a 75% enantiomeric excess; still more preferably at least a 90% enantiomeric excess; and the most preferably at least a 94% enantiomeric excess of the more active isomer. Of particular note are enantiomerically pure embodiments of the more active isomer.

Compounds of Formula 1 can comprise additional chiral centers. For example, substituents and other molecular constituents such as $R^2$ and $R^3$ may themselves contain chiral centers. This disclosure comprises racemic mixtures as well as enriched and essentially pure stereoconfigurations at these additional chiral centers.

Compounds of this disclosure can exist as one or more conformational isomers due to restricted rotation about the amide bond (e.g., C(Y)N(Q$^2$)(R$^6$)) in Formula 1. This disclosure comprises mixtures of conformational isomers. In addition, this disclosure includes compounds that are enriched in one conformer relative to others.

Compounds of Formula 1 typically exist in more than one form, and Formula 1 thus include all crystalline and noncrystalline forms of the compounds they represent. Noncrystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of Formula 1 can exhibit beneficial effects (e.g., suitability for preparation of useful formulations, improved biological performance) relative to another polymorph or a mixture of polymorphs of the same compound of Formula 1. Preparation and isolation of a particular polymorph of a compound of Formula 1 can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of a compound of Formula 1 are useful for control of undesired vegetation (i.e. are agriculturally suitable). The salts of a compound of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present disclosure comprises compounds selected from Formula 1, N-oxides and agriculturally suitable salts thereof.

Embodiments of the present disclosure as described in the Summary include (where Formula 1 as used in the following Embodiments includes N-oxides and salts thereof):

Embodiment 1

A compound of Formula 1 wherein when Q$^1$ is a phenyl ring optionally substituted with up to 4 substituents selected from R$^7$; or an 8- to 10-membered heteroaromatic bicyclic ring system optionally substituted with up to 5 substituents independently selected from R$^7$ on carbon atom ring members and selected from R$^9$ on nitrogen atom ring members.

Embodiment 2

A compound of Formula 1 or Embodiment 1 wherein Q$^1$ is a phenyl ring or a benzodioxolane (i.e. U-81) ring optionally substituted with up to 4 substituents independently selected from R$^7$.

Embodiment 3

A compound of Embodiment 2 wherein Q$^1$ is a phenyl ring optionally substituted with 1 to 3 substituents or a benzodioxolane ring substituted with 1 to 3 substituents independently selected from R$^7$.

Embodiment 4

A compound of Embodiment 3 wherein Q$^1$ is a phenyl ring or a benzodioxolane ring substituted with 1 to 2 substituents independently selected from R$^7$.

Embodiment 5

A compound of Formula 1 or any one of Embodiments 1 through 4 wherein Q$^1$ is a phenyl ring having at least one substituent selected from R$^7$ at the para (4-) position (and optionally other substituents).

Embodiment 6

A compound of Formula 1 or any one of Embodiments 1 through 4 wherein Q$^1$ is a phenyl ring having at least one substituent selected from R$^7$ at the meta (3-) position (and optionally other substituents).

Embodiment 7

A compound of Formula 1 or any one of Embodiments 1 through 6 wherein when Q$^1$ is a phenyl ring substituted with at least two substituents independently selected from $R^7$, then one substituent is at the meta (3-) position and at least one other substituent is at a para position (of the phenyl ring).

Embodiment 8

A compound of Formula 1 or any one of Embodiments 1 through 7 wherein $Q^2$ is a phenyl ring, a 5- to 6-membered heteroaromatic ring or an 8- to 10-membered heteroaromatic bicyclic ring system, each ring or ring system optionally substituted with up to 5 substituents independently selected from $R^{10}$ on carbon atom ring members and selected from $R^{11}$ on nitrogen atom ring members.

Embodiment 9

A compound of Formula 1 or any one of Embodiments 1 through 8 wherein $Q^2$ is a phenyl, pyridinyl or thiophenyl ring optionally substituted with 1 to 5 substituents independently selected from $R^{10}$.

Embodiment 10

A compound of Embodiment 9 wherein $Q^2$ is a phenyl, pyridinyl or thiophenyl ring substituted with 1 to 3 substituents independently selected from $R^{10}$.

Embodiment 11

A compound of Embodiment 10 wherein $Q^2$ is a phenyl, 2-pyridinyl, 3-pyridinyl or 3-thiophenyl ring substituted with 1 to 2 substituents independently selected from $R^{10}$.

Embodiment 12

A compound of Formula 1 or any one of Embodiments 1 through 11 wherein $Q^2$ is a phenyl ring having at least one substituent selected from $R^{10}$ at an ortho (e.g., 2-) position (and optionally other substituents).

Embodiment 13

A compound of Formula 1 or any one of Embodiments 1 through 11 wherein when $Q^2$ is a phenyl ring substituted with at least two substituents independently selected from $R^{10}$, then at least one substituent is at an ortho (e.g., 2-) position and at least one substituent is at an adjacent meta (e.g., 3-) position (of the phenyl ring).

Embodiment 14

A compound of Formula 1 or any one of Embodiments 1 through 13 wherein, each $R^7$ and $R^{10}$ is independently halogen, cyano, nitro, $C_1$-$C_4$ alkyl, $C_1$-$C_4$ haloalkyl, $C_2$-$C_4$ alkenyl, $C_2$-$C_4$ haloalkenyl $C_2$-$C_4$ alkynyl, $C_2$-$C_4$ haloalkynyl, $C_1$-$C_4$ nitroalkyl, $C_2$-$C_4$ nitroalkenyl, $C_2$-$C_4$ alkoxyalkyl, $C_2$-$C_4$ haloalkoxyalkyl, $C_3$-$C_4$ cycloalkyl, $C_3$-$C_4$ halocycloalkyl, cyclopropylmethyl, methylcyclopropyl, $C_1$-$C_4$ alkoxy, $C_1$-$C_4$ haloalkoxy, $C_2$-$C_4$ alkenyloxy, $C_2$-$C_4$ haloalkenyloxy, $C_3$-$C_4$ alkynyloxy, $C_3$-$C_4$ haloalkynyloxy, $C_3$-$C_4$ cycloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, hydroxy, formyl, $C_2$-$C_4$ alkylcarbonyl, $C_2$-$C_4$ alkylcarbonyloxy, $C_1$-$C_4$ alkylsulfonyloxy, $C_1$-$C_4$ haloalkylsulfonyloxy, amino, $C_1$-$C_4$ alkylamino, $C_2$-$C_4$ dialkylamino, formylamino, $C_2$-$C_4$ alkylcarbonylamino, —$SF_5$, —SCN, $C_3$-$C_4$ trialkylsilyl, trimethylsilylmethyl or trimethylsilylmethoxy.

Embodiment 15

A compound of Embodiment 14 wherein each $R^7$ is independently halogen, cyano, $C_1$-$C_2$ alkyl, $C_1$-$C_3$ haloalkyl or $C_1$-$C_3$ haloalkoxy.

Embodiment 16

A compound of Embodiment 15 wherein each $R^7$ is independently halogen, $C_1$-$C_2$ alkyl or $C_1$-$C_2$ haloalkyl.

Embodiment 17

A compound of Embodiment 16 wherein each $R^7$ is independently halogen, $C_1$ alkyl or $C_1$ haloalkyl.

Embodiment 18

A compound of Embodiment 17 wherein each $R^7$ is independently halogen, $C_1$ alkyl or $C_1$ fluoroalkyl.

Embodiment 19

A compound of Embodiment 18 wherein each $R^7$ is independently halogen, $CH_3$ or $CF_3$.

Embodiment 20

A compound of Embodiment 19 wherein each $R^7$ is independently F, Cl, Br, $CH_3$ or $CF_3$.

Embodiment 21

A compound of Embodiment 20 wherein each $R^7$ is independently F, $CH_3$ or $CF_3$.

Embodiment 22

A compound of Embodiment 20 or 21 wherein when $Q^1$ is phenyl at most only one $CF_3$ substituent is present and is at the para position of the $Q^1$ phenyl ring.

Embodiment 23

A compound of any one of Embodiments 14 through 22 wherein each $R^{10}$ is independently halogen, cyano, $C_1$-$C_2$ alkyl, $C_1$-$C_3$ haloalkyl, $C_1$-$C_3$ alkylthio, $C_1$-$C_3$ alkylsulfinyl or $C_1$-$C_3$ alkylsulfonyl.

Embodiment 24

A compound of Embodiment 23 wherein each $R^{10}$ is independently halogen or $C_1$-$C_2$ haloalkyl.

Embodiment 25

A compound of Embodiment 24 wherein each $R^{10}$ is independently halogen or $C_1$ haloalkyl.

Embodiment 26

A compound of Embodiment 25 wherein each $R^{10}$ is independently halogen or $C_1$ fluoroalkyl.

Embodiment 27

A compound of Embodiment 26 wherein each $R^{10}$ is independently halogen or $CF_3$.

Embodiment 28

A compound of Embodiment 27 wherein each $R^{10}$ is independently F, Cl, Br or $CF_3$.

Embodiment 29

A compound of Embodiment 28 wherein each $R^{10}$ is independently F or $CF_3$.

Embodiment 30

A compound of Embodiment 29 wherein each $R^{10}$ is F.

Embodiment 31

A compound of Formula 1 or any one of Embodiments 1 through 30 wherein, each $R^9$ and $R^{11}$ is independently $C_1$-$C_2$ alkyl.

Embodiment 32

A compound of Embodiment 31 wherein, each $R^9$ and $R^{11}$ is independently $CH_3$.

Embodiment 33

A compound of Formula 1 or any one of Embodiments 1 through 32 wherein Y is O.

Embodiment 34

A compound of Formula 1 or any one of Embodiments 1 through 33 wherein T is H.

Embodiment 35

A compound of Formula 1 or any one of Embodiments 1 through 34 wherein $R^1$ is H, $CH_3$ or $CF_3$.

Embodiment 36

A compound of Embodiment 35 wherein $R^1$ is $CH_3$.

Embodiment 37

A compound of Formula 1 or any one of Embodiments 1 through 36 wherein each $R^2$ is independently H or $CH_3$.

Embodiment 38

A compound of Embodiment 37 wherein each $R^2$ is H.

Embodiment 39

A compound of Formula 1 or any one of Embodiments 1 through 38 wherein each $R^3$ is independently H or $CH_3$.

Embodiment 40

A compound of Embodiment 39 wherein each $R^3$ is H.

Embodiment 41

A compound of Formula 1 or any one of Embodiments 1 through 40 wherein $R^4$ is H or $CH_3$.

Embodiment 42

A compound of Embodiment 41 wherein $R^4$ is H.

Embodiment 43

A compound of Formula 1 or any one of Embodiments 1 through 42 wherein $R^5$ is H, F or $CH_3$.

Embodiment 44

A compound of Embodiment 43 wherein $R^5$ is H.

Embodiment 45

A compound of Embodiment 44 wherein $R^6$ is H.

Embodiment 46

A compound of Formula 1 or any one of Embodiments 1-45 wherein $J^2$ is $(-CR_2R^3-)_z$ and z is 1.

Embodiment 47

A compound of Formula 1 or any one of Embodiments 1 through 46 wherein $Q^1$ is a benzodioxolane ring substituted with two $R^7$ both being F:

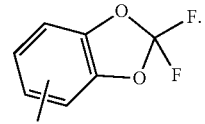

Embodiments of this disclosure, including Embodiments 1-47 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this disclosure, including Embodiments 1-45 above as well as any other embodiments described herein, and any combination thereof, pertain to the compositions and methods of the present disclosure.

Combinations of Embodiments 1-45 are illustrated by:

Embodiment A

A compound of Formula 1 wherein
each $R^7$ and $R^{10}$ is independently halogen, cyano, nitro, $C_1$-$C_4$ alkyl, $C_1$-$C_4$ haloalkyl, $C_2$-$C_4$ alkenyl, $C_2$-$C_4$ haloalkenyl $C_2$-$C_4$ alkynyl, $C_2$-$C_4$ haloalkynyl, $C_1$-$C_4$ nitroalkyl, $C_2$-$C_4$ nitroalkenyl, $C_2$-$C_4$ alkoxyalkyl, $C_2$-$C_4$ haloalkoxyalkyl, $C_3$-$C_4$ cycloalkyl, $C_3$-$C_4$ halocycloalkyl, cyclopropylmethyl, methylcyclopropyl, $C_1$-$C_4$ alkoxy, $C_1$-$C_4$ haloalkoxy, $C_2$-$C_4$ alkenyloxy, $C_2$-$C_4$ haloalkenyloxy, $C_3$-$C_4$ alkynyloxy, $C_3$-$C_4$ haloalkynyloxy, $C_3$-$C_4$ cycloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, hydroxy, formyl, $C_2$-$C_4$ alkylcarbonyl, $C_2$-$C_4$ alkylcarbonyloxy, $C_1$-$C_4$ alkylsulfonyloxy, $C_1$-$C_4$ haloalkylsulfonyloxy, amino, $C_1$-$C_4$ alkylamino, $C_2$-$C_4$ dialkylamino, formylamino, $C_2$-$C_4$ alkylcarbonylamino, —$SF_5$, —SCN, $C_3$-$C_4$ trialkylsilyl, trimethylsilylmethyl or trimethylsilylmethoxy; and each $R^9$ and $R^{11}$ is $C_1$-$C_2$ alkyl.

Embodiment B

A compound of Embodiment A wherein
Y is O;
$R^1$ is $CH_3$; and
T, $R^2$, $R^3$, $R^4$, $R^5$ and $R^6$ are each H.

Embodiment C

A compound of Embodiment B wherein
wherein $Q^1$ is a phenyl ring optionally substituted with 1 to 3 substituents or a benzodioxolane ring substituted with 1 to 3 substituents independently selected from $R^7$; and
$Q^2$ is a phenyl, pyridinyl or thiophenyl ring substituted with 1 to 3 substituents independently selected from $R^{10}$.

Embodiment D

A compound of Embodiment C wherein
each $R^7$ is independently halogen, cyano, $C_1$-$C_2$ alkyl, $C_1$-$C_3$ haloalkyl or $C_1$-$C_3$ haloalkoxy; and
each $R^{10}$ is independently halogen, cyano, $C_1$-$C_2$ alkyl, $C_1$-$C_3$ haloalkyl, $C_1$-$C_3$ alkylthio, $C_1$-$C_3$ alkylsulfinyl or $C_1$-$C_3$ alkylsulfonyl.

Embodiment E

A compound of Embodiment D wherein
$Q^1$ is a phenyl ring having at least one substituent selected from $R^7$ at the meta (3-) or the para (4-) position or substituted with at least two substituents independently selected from $R^7$ wherein one substituent is at the-meta position and at least one other substituent is at a para position; and
$Q^2$ is a phenyl, 2-pyridinyl, 3-pyridinyl or 3-thiophene ring substituted with 1 to 2 substituents independently selected from $R^{10}$.

Embodiment F

A compound of Embodiment E wherein
each $R^7$ is independently F, $CH_3$ or $CF_3$; and
each $R^{10}$ is F.

Specific embodiments include compounds of Formula 1 selected from the group consisting of a compound of Formula 1 wherein $Q^1$ is Ph(4-$CF_3$), $Q^2$ if Ph(2,3-di-F), $R^1$ is $CH_3$, $J^2$ is $CH_2CH_2$ and T, $R^4$, $R^5$ and $R^6$ are H; a compound of Formula 1 wherein $Q^1$ is Ph(4-$CH_3$), $Q^2$ if Ph(2,3-di-F), $R^1$ is $CH_3$, $J^2$ is $CH_2CH_2$ and T, $R^4$, $R^5$ and $R^6$ are H, and a compound of Formula 1 wherein $Q^1$ is Ph(4-$C_1$), $Q^2$ is Ph(2,3-di-F), $R^1$ is $CH_3$, $J^2$ is $CH_2CH_2$ and T, $R^4$, $R^5$ and $R^6$ are H.

Specific embodiments include compounds of Formula 1 selected from the group consisting of:
rel-(2S,3R)-3-(4-chlorophenyl)-N-(2,3-difluorophenyl)-3,4-dihydro-5-methyl-2H-pyrrole-2-carboxamide 1-oxide (Compound 5; Example 1);

rel-(2S,3R)—N-(2,3-difluorophenyl)-3,4-dihydro-5-methyl-3-[4-(trifluoromethyl)phenyl]-2H-pyrrole-2-carboxamide 1-oxide (Compound 2; Example 2);

rel-(2S,3R)—N-(2-fluorophenyl)-3,4-dihydro-5-methyl-3-[4-(trifluoromethyl)phenyl]-2H-pyrrole-2-carboxamide 1-oxide (Compound 26; Example 3);

rel-(2S,3R)—N-(2,3-Difluorophenyl)-3,4-dihydro-5-methyl-3-(4-methylphenyl)-2H-pyrrole-2-carboxamide 1-oxide (Compound 6);

rel-(2S,3R)-3-(2,2-Difluoro-1,3-benzodioxol-5-yl)-N-(2,3-difluorophenyl)-3,4-dihydro-5-methyl-2H-pyrrole-2-carboxamide 1-oxide (Compound 25);

rel-(2S,3R)-3-(4-Difluoromethyl)phenyl)-N-(2,3-difluorophenyl) 3,4-dihydro-5-methyl-2H-pyrrole-2-carboxamide 1-oxide (Compound 93);

(2S,3R)—N-(2,3-Difluorophenyl)-3-[4-fluoro-3-(1,1,2,2-tetrafluoroethyoxy)phenyl]-3,4-dihydro-5-methyl-2H-pyrrole-2-carboxamide 1-oxide (Compound 54);

rel-(2S,3R)—N-(2,6-Difluoro-3-pyridinyl)-3,4-dihydro-5-methyl-3-[4-(trifluoromethyl)phenyl]-2H-pyrrole-2-carboxamide 1-oxide (Compound 37);

rel-(2S,3R)—N-(2,3-Difluorophenyl)-3-[3-fluoro-4-(trifluoromethyl)phenyl]-3,4-dihydro-5-methyl-2H-pyrrole-2-carboxamide 1-oxide (Compound 61);

(2S,3R)-3-(4-chlorophenyl)-N-(2,3-difluorophenyl)-3,4-dihydro-5-methyl-2H-pyrrole-2-carboxamide 1-oxide (Compound 40);

(2S,3R)—N-(2,3-difluorophenyl)-3,4-dihydro-5-methyl-3-[4-(trifluoromethyl)phenyl]-2H-pyrrole-2-carboxamide 1-oxide (Compound 30); and (2S,3R)—N-(2,3-Difluorophenyl)-3,4-dihydro-5-methyl-3-(4-methylphenyl)-2H-pyrrole-2-carboxamide 1-oxide (Compound 42).

This disclosure also relates to a method for controlling undesired vegetation comprising applying to the locus of the vegetation herbicidally effective amounts of the compounds of the disclosure (e.g., as a composition described herein). Of note as embodiments relating to methods of use are those involving the compounds of embodiments described above.

Compounds of the disclosure are particularly useful for selective control of weeds in crops such as wheat, barley, maize, soybean, sunflower, cotton, oilseed rape and rice, and specialty crops such as sugarcane, citrus, fruit and nut crops.

Also noteworthy as embodiments are herbicidal compositions of the present disclosure comprising the compounds of embodiments described above.

This disclosure also includes a herbicidal mixture comprising (a) a compound selected from Formula 1, N-oxides, and salts thereof, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, hydantocidin, metam, methyldymron, oleic acid, oxaziclomefone, pelargonic acid and pyributicarb, and (b16) herbicide safeners; and salts of compounds of (b1) through (b16).

"Photosystem II inhibitors" (b1) are chemical compounds that bind to the D-1 protein at the $Q_B$-binding niche and thus block electron transport from $Q_A$ to $Q_B$ in the chloroplast thylakoid membranes. The electrons blocked from passing through photosystem II are transferred through a series of reactions to form toxic compounds that disrupt cell membranes and cause chloroplast swelling, membrane leakage, and ultimately cellular destruction. The $Q_B$-binding niche has three different binding sites: binding site A binds the triazines such as atrazine, triazinones such as hexazinone, and uracils such as bromacil, binding site B binds the phenylureas such as diuron, and binding site C binds benzothiadiazoles such as bentazon, nitriles such as bromoxynil and phenyl-pyridazines such as pyridate. Examples of photosystem II inhibitors include ametryn, amicarbazone, atrazine, bentazon, bromacil, bromofenoxim, bromoxynil, chlorbromuron, chloridazon, chlorotoluron, chloroxuron, cumyluron, cyanazine, daimuron, desmedipham, desmetryn, dimefuron, dimethametryn, diuron, ethidimuron, fenuron, fluometuron, hexazinone, ioxynil, isoproturon, isouron, lenacil, linuron, metamitron, methabenzthiazuron, metobromuron, metoxuron, metribuzin, monolinuron, neburon, pentanochlor, phenmedipham, prometon, prometryn, propanil, propazine, pyridafol, pyridate, siduron, simazine, simetryn, tebuthiuron, terbacil, terbumeton, terbuthylazine, terbutryn and trietazine.

"AHAS inhibitors" (b2) are chemical compounds that inhibit acetohydroxy acid synthase (AHAS), also known as acetolactate synthase (ALS), and thus kill plants by inhibiting the production of the branched-chain aliphatic amino acids such as valine, leucine and isoleucine, which are required for protein synthesis and cell growth. Examples of AHAS inhibitors include amidosulfuron, azimsulfuron, bensulfuron-methyl, bispyribac-sodium, cloransulam-methyl, chlorimuron-ethyl, chlorsulfuron, cinosulfuron, cyclosulfamuron, diclosulam, ethametsulfuron-methyl, ethoxysulfuron, flazasulfuron, florasulam, flucarbazone-sodium, flumetsulam, flupyrsulfuron-methyl, flupyrsulfuron-sodium, foramsulfuron, halosulfuron-methyl, imazamethabenzmethyl, imazamox, imazapic, imazapyr, imazaquin, imazethapyr, imazosulfuron, iodosulfuron-methyl (including sodium salt), iofensulfuron (2-iodo-N-[[(4-methoxy-6-methyl-1,3,5-triazin-2-yl)amino]carbonyl]benzenesulfonamide), mesosulfuron-methyl, metazosulfuron (3-chloro-4-(5,6-dihydro-5-methyl-1,4,2-dioxazin-3-yl)-N-[[(4,6-dimethoxy-2-pyrimidinyl)amino]carbonyl]-1-methyl-1H-pyrazole-5-sulfonamide), metosulam, metsulfuron-methyl, nicosulfuron, oxasulfuron, penoxsulam, primisulfuronmethyl, propoxycarbazone-sodium, propyrisulfuron (2-chloro-N-[[(4,6-dimethoxy-2-pyrimidinyl)amino]carbonyl]-6-propylimidazo[1,2-b]pyridazine-3-sulfonamide), prosulfuron, pyrazosulfuron-ethyl, pyribenzoxim, pyriftalid, pyriminobac-methyl, pyrithiobac-sodium, rimsulfuron, sulfometuron-methyl, sulfosulfuron, thiencarbazone, thifensulfuron-methyl, triafamone (N-[2-[(4,6-dimethoxy-1,3,5-triazin-2-yl)carbonyl]-6-fluorophenyl]-1,1-difluoro-N-methylmethanesulfonamide), triasulfuron, tribenuronmethyl, trifloxysulfuron (including sodium salt), triflusulfuron-methyl and tritosulfuron.

"ACCase inhibitors" (b3) are chemical compounds that inhibit the acetyl-CoA carboxylase enzyme, which is responsible for catalyzing an early step in lipid and fatty acid synthesis in plants. Lipids are essential components of cell membranes, and without them, new cells cannot be produced. The inhibition of acetyl CoA carboxylase and the subsequent lack of lipid production leads to losses in cell membrane integrity, especially in regions of active growth such as meristems. Eventually shoot and rhizome growth ceases, and shoot meristems and rhizome buds begin to die back. Examples of ACCase inhibitors include alloxydim, butroxydim, clethodim, clodinafop, cycloxydim, cyhalofop, diclofop, fenoxaprop, fluazifop, haloxyfop, pinoxaden, profoxydim, propaquizafop, quizalofop, sethoxydim, tepraloxydim and tralkoxydim, including resolved forms such as fenoxaprop-P, fluazifop-P, haloxyfop-P and quizalofop-P and ester forms such as clodinafop-propargyl, cyhalofop-butyl, diclofop-methyl and fenoxaprop-P-ethyl.

Auxin is a plant hormone that regulates growth in many plant tissues. "Auxin mimics" (b4) are chemical compounds mimicking the plant growth hormone auxin, thus causing uncontrolled and disorganized growth leading to plant death in susceptible species. Examples of auxin mimics include aminocyclopyrachlor (6-amino-5-chloro-2-cyclopropyl-4-pyrimidinecarboxylic acid) and its methyl and ethyl esters and its sodium and potassium salts, aminopyralid, benazolin-ethyl, chloramben, clacyfos, clomeprop, clopyralid, dicamba, 2,4-D, 2,4-DB, dichlorprop, fluroxypyr, halauxifen (4-amino-3-chloro-6-(4-chloro-2-fluoro-3-methoxyphenyl)-2-pyridinecarboxylic acid), halauxifen-methyl (methyl 4-amino-3-chloro-6-(4-chloro-2-fluoro-3-methoxyphenyl)-2-pyridinecarboxylate), MCPA, MCPB, mecoprop, picloram, quinclorac, quinmerac, 2,3,6-TBA, triclopyr, and methyl 4-amino-3-chloro-6-(4-chloro-2-fluoro-3-methoxyphenyl)-5-fluoro-2-pyridinecarboxylate.

"EPSP synthase inhibitors" (b5) are chemical compounds that inhibit the enzyme, 5-enol-pyruvylshikimate-3-phosphate synthase, which is involved in the synthesis of aromatic amino acids such as tyrosine, tryptophan and phenylalanine. EPSP inhibitor herbicides are readily absorbed through plant foliage and translocated in the phloem to the growing points. Glyphosate is a relatively nonselective postemergence herbicide that belongs to this group. Glyphosate includes esters and salts such as ammonium, isopropylammonium, potassium, sodium (including sesquisodium) and trimesium (alternatively named sulfosate).

"Photosystem I electron diverters" (b6) are chemical compounds that accept electrons from Photosystem I, and after several cycles, generate hydroxyl radicals. These radicals are extremely reactive and readily destroy unsaturated lipids, including membrane fatty acids and chlorophyll. This destroys cell membrane integrity, so that cells and organelles "leak", leading to rapid leaf wilting and desiccation, and eventually to plant death. Examples of this second type of photosynthesis inhibitor include diquat and paraquat.

"PPO inhibitors" (b7) are chemical compounds that inhibit the enzyme protoporphyrinogen oxidase, quickly resulting in formation of highly reactive compounds in plants that rupture cell membranes, causing cell fluids to leak out. Examples of PPO inhibitors include acifluorfen-sodium, azafenidin, benzfendizone, bifenox, butafenacil, carfentrazone, carfentrazone-ethyl, chlomethoxyfen, cinidon-ethyl, fluazolate, flufenpyr-ethyl, flumiclorac-pentyl, flumioxazin, fluoroglycofen-ethyl, fluthiacet-methyl, fomesafen, halosafen, lactofen, oxadiargyl, oxadiazon, oxyfluorfen, pentoxazone, profluazol, pyraclonil, pyraflufen-ethyl, saflufenacil, sulfentrazone, thidiazimin, trifludimoxazin (dihydro-1,5-dimehyl-6-thioxo-3-[2,2,7-trifluoro-3,4-dihydro-3-oxo-4-(2-propyn-1-yl)-2H-1,4-benzoxazin-6-yl]-1,3,5-triazine-2,4(1H,3H)-dione) and tiafenacil (methyl N-[2-[[2- chloro-5-[3,6-dihydro-3-methyl-2,6-dioxo-4-(trifluoromethyl)-1(2H)-pyrimidinyl]-4-fluorophenyl]thio]-1-oxopropyl]-(β-alaninate).

"GS inhibitors" (b8) are chemical compounds that inhibit the activity of the glutamine synthetase enzyme, which plants use to convert ammonia into glutamine. Consequently, ammonia accumulates and glutamine levels decrease. Plant damage probably occurs due to the combined effects of ammonia toxicity and deficiency of amino acids required for other metabolic processes. The GS inhibitors include glufosinate and its esters and salts such as glufosinate-ammonium and other phosphinothricin derivatives, glufosinate-P ((2S)-2-amino-4-(hydroxymethylphosphinyl)butanoic acid) and bilanaphos.

"VLCFA elongase inhibitors" (b9) are herbicides having a wide variety of chemical structures, which inhibit the elongase. Elongase is one of the enzymes located in or near chloroplasts which are involved in biosynthesis of VLCFAs. In plants, very-long-chain fatty acids are the main constituents of hydrophobic polymers that prevent desiccation at the leaf surface and provide stability to pollen grains. Such herbicides include acetochlor, alachlor, anilofos, butachlor, cafenstrole, dimethachlor, dimethenamid, diphenamid, fenoxasulfone (3-[[(2,5-dichloro-4-ethoxyphenyl)methyl]sulfonyl]-4,5-dihydro-5,5-dimethylisoxazole), fentrazamide, flufenacet, indanofan, mefenacet, metazachlor, metolachlor, naproanilide, napropamide, napropamide-M ((2R)—N,N-diethyl-2-(1-naphthalenyloxy)propanamide), pethoxamid, piperophos, pretilachlor, propachlor, propisochlor, pyroxasulfone, and thenylchlor, including resolved forms such as S-metolachlor and chloroacetamides and oxyacetamides.

"Auxin transport inhibitors" (b10) are chemical substances that inhibit auxin transport in plants, such as by binding with an auxin-carrier protein. Examples of auxin transport inhibitors include diflufenzopyr, naptalam (also known as N-(1-naphthyl)phthalamic acid and 2-[(1-naphthalenylamino)carbonyl]benzoic acid).

"PDS inhibitors" (b11) are chemical compounds that inhibit carotenoid biosynthesis pathway at the phytoene desaturase step. Examples of PDS inhibitors include beflubutamid, diflufenican, fluridone, flurochloridone, flurtamone norflurzon and picolinafen.

"HPPD inhibitors" (b12) are chemical substances that inhibit the biosynthesis of synthesis of 4-hydroxyphenyl-pyruvate dioxygenase. Examples of HPPD inhibitors include benzobicyclon, benzofenap, bicyclopyrone (4-hydroxy-3-[[2-[(2-methoxyethoxy)methyl]-6-(trifluoromethyl)-3-pyridinyl]carbonyl]bicyclo[3.2.1]oct-3-en-2-one), fenquinotrione (2-[[8-chloro-3,4-dihydro-4-(4-methoxyphenyl)-3-oxo-2-quinoxalinyl]carbonyl]-1,3-cyclohexanedione), isoxachlortole, isoxaflutole, mesotrione, pyrasulfotole, pyrazolynate, pyrazoxyfen, sulcotrione, tefuryltrione, tembotrione, tolpyralate (1-[[1-ethyl-4-[3-(2-methoxyethoxy)-2-methyl-4-(methylsulfonyl)benzoyl]-1H-pyrazol-5-yl]oxy]ethyl methyl carbonate), topramezone, 5-chloro-3-[(2-hydroxy-6-oxo-1-cyclohexen-1-yl)carbonyl]-1-(4-methoxyphenyl)-2(1H)-quinoxalinone, 4-(2,6-diethyl-4-methylphenyl)-5-hydroxy-2,6-dimethyl-3(2H)-pyridazinone, 4-(4-fluorophenyl)-6-[(2-hydroxy-6-oxo-1-cyclohexen-1-yl)carbonyl]-2-methyl-1,2,4-triazine-3,5(2H,4H)-dione, 5-[(2-hydroxy-6-oxo-1-cyclohexen-1-yl)carbonyl]-2-(3-methoxyphenyl)-3-(3-methoxypropyl)-4(3H)-pyrimidinone, 2-methyl-N-(4-methyl-1,2,5-oxadiazol-3-yl)-3-(methylsulfinyl)-4-(trifluoromethyl)benzamide and 2-methyl-3-(methylsulfonyl)-N-(1-methyl-1H-tetrazol-5-yl)-4-(trifluoromethyl)benzamide.

"HST inhibitors" (b13) disrupt a plant's ability to convert homogentisate to 2-methyl-6-solanyl-1,4-benzoquinone, thereby disrupting carotenoid biosynthesis. Examples of HST inhibitors include haloxydine, pyriclor, 3-(2-chloro-3,6-difluorophenyl)-4-hydroxy-1-methyl-1,5-naphthyridin-2(1H)-one, 7-(3,5-dichloro-4-pyridinyl)-5-(2,2-difluoroethyl)-8-hydroxypyrido[2,3-b]pyrazin-6(5H)-one and 4-(2,6-diethyl-4-methylphenyl)-5-hydroxy-2,6-dimethyl-3(2H)-pyridazinone.

HST inhibitors also include compounds of Formulae A and B.

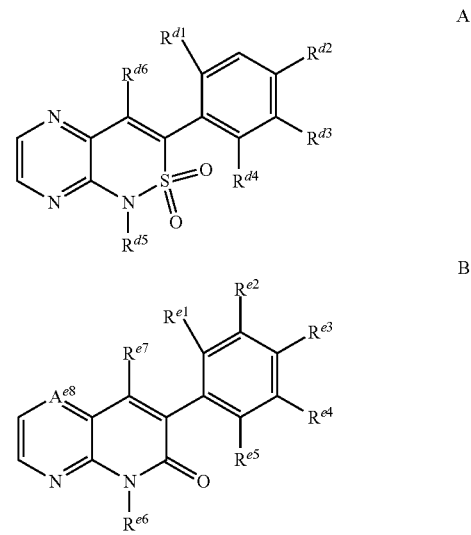

wherein $R^{d1}$ is H, Cl or $CF_3$; $R^{d2}$ is H, Cl or Br; $R^{d3}$ is H or Cl; $R^{d4}$ is H, Cl or $CF_3$; $R^{d5}$ is $CH_3$, $CH_2CH_3$ or $CH_2CHF_2$; and $R^{d6}$ is OH, or —OC(=O)-i-Pr; and $R^{e1}$ is H, F, Cl, $CH_3$ or $CH_2CH_3$; $R^{e2}$ is H or $CF_3$; $R^{e3}$ is H, $CH_3$ or $CH_2CH_3$; $R^{e4}$ is H, F or Br; $R^{e5}$ is Cl, $CH_3$, $CF_3$, $OCF_3$ or $CH_2CH_3$; $R^{e6}$ is H, $CH_3$, $CH_2CHF_2$ or C≡CH; $R^{e7}$ is OH, —OC(=O)Et, —OC(=O)-i-Pr or —OC(=O)-t-Bu; and $A^{e8}$ is N or CH.

"Cellulose biosynthesis inhibitors" (b14) inhibit the biosynthesis of cellulose in certain plants. They are most effective when applied preemergence or early postemergence on young or rapidly growing plants. Examples of cellulose biosynthesis inhibitors include chlorthiamid, dichlobenil, flupoxam, indaziflam ($N^2$-[(1R,2S)-2,3-dihydro-2,6-dimethyl-1H-inden-1-yl]-6-(1-fluoroethyl)-1,3,5-triazine-2,4-diamine), isoxaben and triaziflam.

"Other herbicides" (b15) include herbicides that act through a variety of different modes of action such as mitotic disruptors (e.g., flamprop-M-methyl and flamprop-M-isopropyl), organic arsenicals (e.g., DSMA, and MSMA), 7,8-dihydropteroate synthase inhibitors, chloroplast isoprenoid synthesis inhibitors and cell-wall biosynthesis inhibitors. Other herbicides include those herbicides having unknown modes of action or do not fall into a specific category listed in (b1) through (b14) or act through a combination of modes of action listed above. Examples of other herbicides include aclonifen, asulam, amitrole, bromobutide, cinmethylin, clomazone, cumyluron, cyclopyrimorate (6-chloro-3-(2-cyclopropyl-6-methylphenoxy)-4-pyridazinyl 4-morpholinecarboxylate), daimuron, difenzoquat, etobenzanid, fluometuron, flurenol, fosamine, fosamine-ammonium, dazomet, dymron, ipfencarbazone (1-(2,4-dichlorophenyl)-

N-(2,4-difluorophenyl)-1,5-dihydro-N-(1-methylethyl)-5-oxo-4H-1,2,4-triazole-4-carboxamide), metam, methyldymron, oleic acid, oxaziclomefone, pelargonic acid, pyributicarb and 5-[[(2,6-difluorophenyl)methoxy]methyl]-4,5-dihydro-5-methyl-3-(3-methyl-2-thienyl)isoxazole.

"Herbicide safeners" (b16) are substances added to a herbicide formulation to eliminate or reduce phytotoxic effects of the herbicide to certain crops. These compounds protect crops from injury by herbicides but typically do not prevent the herbicide from controlling undesired vegetation. Examples of herbicide safeners include but are not limited to benoxacor, cloquintocet-mexyl, cumyluron, cyometrinil, cyprosulfamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone, naphthalic anhydride, oxabetrinil, N-(aminocarbonyl)-2-methylbenzenesulfonamide and N-(aminocarbonyl)-2-fluorobenzenesulfonamide, 1-bromo-4-[(chloromethyl)sulfonyl]benzene, 2-(dichloromethyl)-2-methyl-1,3-dioxolane (MG 191), 4-(dichloroacetyl)-1-oxa-4-azospiro[4.5]decane (MON 4660), 2,2-dichloro-1-(2,2,5-trimethyl-3-oxazolidinyl)-ethanone and 2-methoxy-N-[[4-[[(methylamnino)carbonyl]amino]phenyl]sulfonyl]-benzamide.

The compounds of Formula 1 can be prepared by general methods known in the art of synthetic organic chemistry. Of note are the following methods described in Schemes 1-15 and variations thereof. The definitions of $R^1$, $R^2$, $R^{2b}$, $R^3$, $R^4$, $R^5$, $R^6$, $R^{20}$, $R^{21}$, $Q^1$, $Q^2$, T, Y and $J^2$ in the compounds of Formulae 1 through 22 below are as defined above in the Summary unless otherwise noted. Formulae 1a-1d are various subsets of a compound of Formula 1. Substituents for each subset formula are as defined above for its parent formula unless otherwise noted.

As shown in Scheme 1 compounds of Formula 1a (i.e. Formula 1 wherein Y is O) can be prepared by reaction of acids of Formula 2 with amines of Formula 3 in the presence of a dehydrative coupling reagent such as propylphosphonic anhydride, dicyclohexylcarbodiimide, N-(3-dimethylaminopropyl)-N'-ethylcarbodiimide, N,N'-carbonyldiimidazole, 2-chloro-1,3-dimethylimidazolium chloride or 2-chloro-1-methylpyridinium iodide. Polymer-supported reagents, such as polymer-supported cyclohexylcarbodiimide, are also suitable. These reactions are typically run at temperatures ranging from 0-60° C. in a solvent such as dichloromethane, acetonitrile, N,N-dimethylformamide or ethyl acetate in the presence of a base such as triethylamine, N,N-diisopropylamine, or 1,8-diazabicyclo[5.4.0]undec-7-ene. See *Organic Process Research & Development* 2009, 13, 900-906 for coupling conditions employing propylphosphonic anhydride. The method of Scheme 1 utilizing propylphosphonic anhydride is illustrated by Step D of Synthesis Example 2. Substituents in the 2- and 3-positions of the dihydropyrrolium oxide ring of compounds of Formula 1a, i.e. $C(O)N(Q^2)(R^6)$ and $Q^1T$, respectively, are predominantly in the trans configuration. In some instances, the presence of minor amounts of the cis isomer can be detected by NMR.

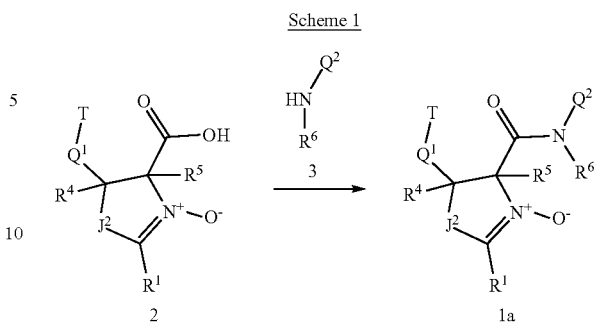

Scheme 1

As shown in Scheme 2 compounds of Formula 1a can be prepared by reaction of alkyl esters of Formula 4 with amines of Formula 3 in the presence of an organometallic compound. Suitable organometallic compounds for the reaction include, but are not limited to, trialkylaluminum reagents such as trimethylaluminum, diorganoaluminum hydrides such as diisobutylaluminum hydride and organomagnesium halides such as methylmagnesium bromide. A wide variety of solvents are suitable for the reaction including, but not limited to, toluene, benzene, dichloromethane, 1,2-dichloroethane, diethyl ether and tetrahydrofuran. The reaction is conducted at temperatures ranging from –20° C. to the boiling point of the solvent, and typically from 0 to 120° C. See *Journal of the American Chemical Society* 2010, 132, 1740-1740 for coupling conditions employing trimethylaluminum and *Journal of the American Chemical Society* 2015, 137, 13492-13495 for coupling conditions employing methylmagnesium bromide. The method of Scheme 2 is illustrated by Step A of Synthesis Example 3.

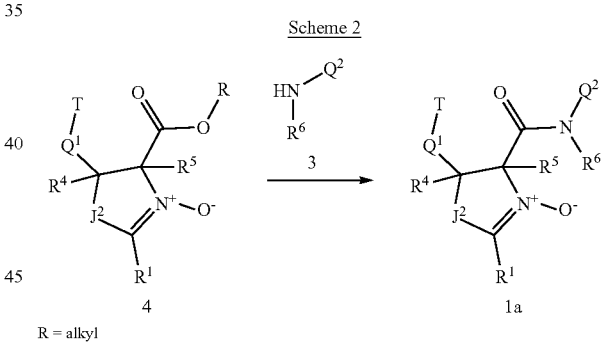

Scheme 2

R = alkyl

As shown in Scheme 3 compounds of Formula 1 can be prepared by oxidation of dihydropyrroles of Formula 5 by methods well known to those skilled in the art. Oxidation is carried out with an oxidant, optionally in the presence of a catalyst and typically in the presence of a co-solvent. Suitable oxidants for the reaction include, but are not limited to, urea hydrogen peroxide, hydrogen peroxide, peracids such as m-chloroperbenzoic acid and dioxiranes such as dimethyldioxirane. Suitable catalysts for the reaction include, but are not limited to, sodium tungstate and methyltrioxorhenium. A wide variety of co-solvents are suitable for the reaction including, but not limited to, water, ethanol, methanol, acetone, chloroform and dichloromethane. The reaction is conducted at temperatures ranging from –20° C. to the boiling point of the solvent, and typically from 0 to 50° C. See *Organic Letters* 2007, 9, 473-476 for oxidation conditions using methyltrioxorhenium and urea hydrogen peroxide.

Scheme 3

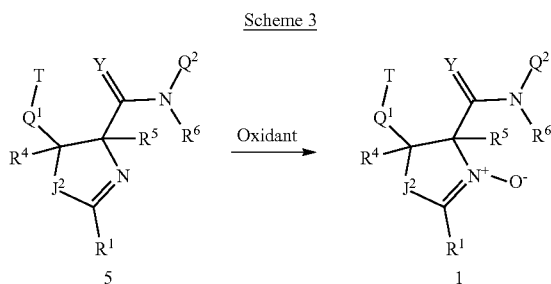

Scheme 5

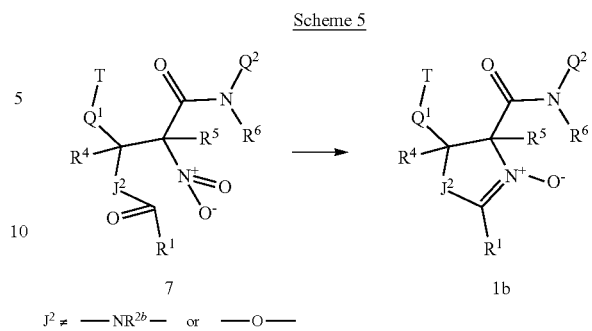

$J^2 \neq$ —$NR^{2b}$— or —O—

As shown in Scheme 4 compounds of Formula 1 can be prepared by oxidation of dihydropyrroles of Formula 6 by methods well known to those skilled in the art. Oxidation is carried out with an oxidant, optionally in the presence of a catalyst and typically in the presence of a co-solvent. Suitable oxidants for the reaction include, but are not limited to, urea hydrogen peroxide, hydrogen peroxide, oxone, peracids such as m-chloroperbenzoic acid, oxaziridines such as 3-phenyl-2-(phenylsulfonyl)oxaziridine and dioxiranes such as dimethyldioxirane. Suitable catalysts for the reaction include, but are not limited to, sodium tungstate, selenium dioxide and methyltrioxorhenium. A wide variety of co-solvents are suitable for the reaction including, but not limited to, water, ethanol, methanol, acetone, acetonitrile, tetrahydrofuran, chloroform and dichloromethane. The reaction is conducted at temperatures ranging from −20° C. to the boiling point of the solvent, and typically from 0 to 50° C. See *Organic Letters* 2013, 15, 326-329 for oxidation conditions using sodium tungstate and urea hydrogen peroxide.

Compounds of Formula 5a (i.e. a compound of Formula 5 wherein $R^1$ is OR, NHR, $NH_2R$, SR or CN) can be synthesized from a compound of Formula 8 by the reaction shown in Scheme 6. The substitution reaction is carried out with an appropriate nucleophile, optionally in the presence of a base and typically in the presence of a co-solvent. Suitable nucleophiles for the reaction include, but are not limited to, alkyl alcohols, amines, alkyl thiols and cyanide salts. Suitable bases for the reaction include, but are not limited to, sodium hydride, sodium methoxide, sodium ethoxide, cesium carbonate, potassium carbonate or potassium tert-butoxide are employed. Typically the reaction is conducted in a solvent such as water, methanol, ethanol, tetrahydrofuran, dimethylsulfoxide, N,N-dimethylformamide, N,N-dimethylacetamide, N-methylpyrrolidinone and acetonitrile or a mixture thereof at temperatures ranging from ambient temperature to the reflux temperature of the solvent.

Scheme 4

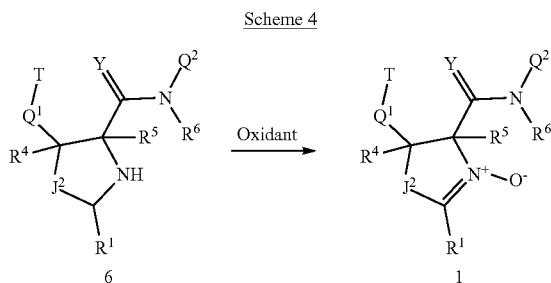

Scheme 6

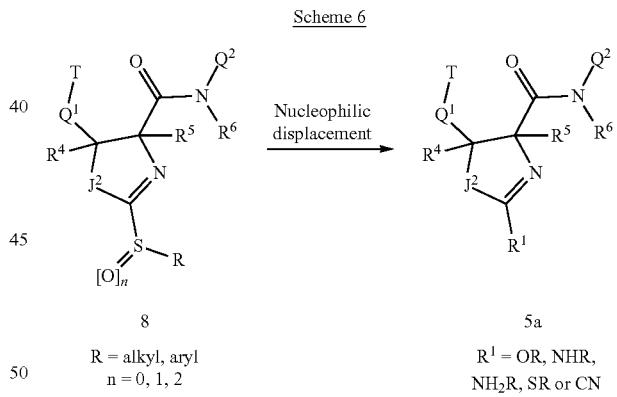

R = alkyl, aryl
n = 0, 1, 2

$R^1$ = OR, NHR,
$NH_2R$, SR or CN

As shown in Scheme 5, compounds of Formula 1b (i.e. a compound of Formula 1 wherein $J^2$ is other than —$NR^{2b}$— or —O— and Y is O) can be obtained by reduction of compounds of Formula 7 and subsequent in situ cyclization of the resulting intermediate amine. A wide variety of methods for reduction of the aliphatic nitro group in compounds of Formula 7 are known in the literature. Methods include catalytic hydrogenation in the presence of palladium on carbon or Raney nickel and iron or zinc metal in acidic medium (see, for an example using iron metal, *Synlett*, 2015, 26, 846-850 and for an example using zinc metal, *Tetrahedron*, 2000, 56, 1889-1897). Alternatively sodium borohydride in the presence of a nickel catalyst such as nickel(II) acetate or nickel(II) chloride can be used (see for example, *Angewandte Chemie, International Edition*, 2013, 52, 5575-5579). The method of Scheme 5 utilizing zinc metal in the presence of ammonium chloride is illustrated by Step E of Synthesis Example 1.

As shown in Scheme 7, compounds of Formula 5b (i.e. a compound of Formula 5 wherein $R^1$ is $C_1$-$C_6$ alkylthio, $C_1$-$C_6$ haloalkylthio, $C_3$-$C_8$ cycloalkylthio; and Y is O) can be prepared by alkylation of compounds of Formula 9 with an appropriate alkylating agent optionally in the presence of a base. Suitable alkylating agents include, but are not limited to, trialkyloxonium tetrafluoroborates such as trimethyloxonium tetrafluoroborate and triethyloxonium tetrafluoroborate, alkyliodides, alkylbromides, and alkyl sulfonates. Suitable bases for the reaction include, but are not limited to, carbonates such as sodium and potassium carbonate and neutral nitrogen-containing bases such as triethylamine and 1,8-diazabicyclo[5.4.0]undec-7-ene. A wide variety of co-solvents are suitable for the reaction including, but not limited to, dimethylsulfoxide, N,N-dimethylformamide, N,N-dimethylacetamide, N-methylpyrrolidinone, acetonitrile, acetone and tetrahydrofuran. The reaction is conducted at temperatures ranging from −20° C. to the boiling point of the solvent, and typically from 0-150° C.

Scheme 7

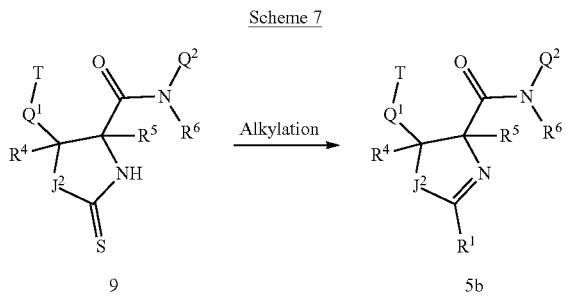

$R^1$ = $C_1$-$C_6$ alkylthio, $C_1$-$C_6$ haloalkylthio, or $C_3$-$C_8$ cycloalkylthio As shown in Scheme 8, thiolactams of Formula 9 can be prepared by thiocarbonyl transfer to nitrones of Formula 10. The reaction is carried out with a thiocarbonyl transfer reagent, optionally in the presence of a co-solvent. Suitable thiocarbonyl transfer reagents for the reaction include, but are not limited to, 1,1'-thiocarbonyl-di-(1,2,4)-triazole, chlorodiphenylphosphine sulfide, phenylthiophosphoryl dichloride ($Cl_2P(=S)Ph$ and thiophosphoryl chloride ($Cl_3PS$). A variety of co-solvents are suitable for the reaction including, but not limited to, benzene, toluene and tetrahydrofuran. The reaction is conducted at temperatures ranging from −20° C. to the boiling point of the solvent, and typically from 0 to 100° C. See *Canadian Journal of Chemistry*, 1985, 63, 951-957 for conditions using 1,1'-thiocarbonyl-di-(1,2,4)-triazole.

Scheme 8

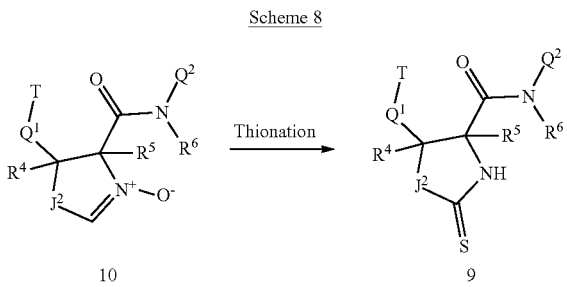

As shown in Scheme 9, compounds of Formula 5c can be obtained by reduction of a compound of Formula 7 and subsequent in situ cyclization of the resulting intermediate amine. A wide variety of methods for reduction of the aliphatic nitro group in compounds of Formula 7 are known in the literature. Methods include catalytic hydrogenation in the presence of palladium on carbon or Raney nickel, iron or zinc metal in acidic medium (see, for an example using iron metal, *Angewandte Chemie, International Edition*, 2013, 52, 5575-5579 and for an example using zinc metal, *Tetrahedron*, 2000, 56, 1889-1897) and titanium(III) trichloride.

Scheme 9

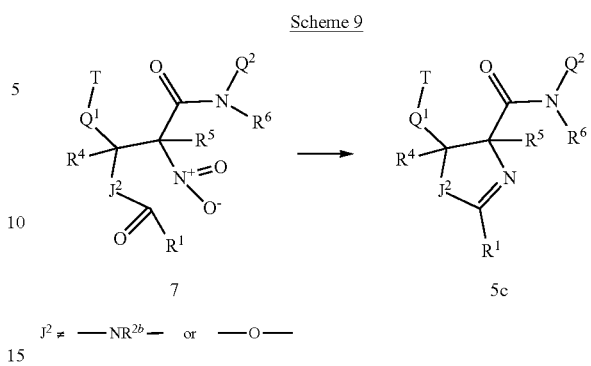

$J^2 \neq$ —$NR^{2b}$— or —O—

As shown in Scheme 10 a compound of Formula 2 can be prepared by hydrolysis of esters of Formula 11. Hydrolysis is carried out with aqueous base or aqueous acid, typically in the presence of a co-solvent. Suitable bases for the reaction include, but are not limited to, hydroxides such as sodium and potassium hydroxide and carbonates such as sodium and potassium carbonate. Suitable acids for the reaction include, but are not limited to, inorganic acids such as hydrochloric acid, hydrobromic acid and sulfuric acid, and organic acids such as acetic acid and trifluoroacetic acid. A wide variety of co-solvents are suitable for the reaction including, but not limited to, methanol, ethanol and tetrahydrofuran. The reaction is conducted at temperatures ranging from −20° C. to the boiling point of the solvent, and typically from 0-100° C. The method of Scheme 10 is illustrated by Step A of Synthesis Example 3

Scheme 10

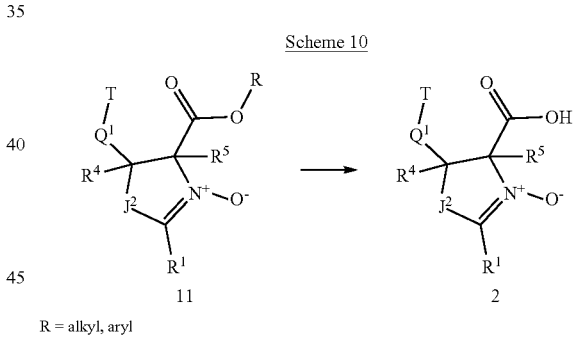

R = alkyl, aryl

As shown in Scheme 11, a compound of Formula 12 can be obtained by reduction of compounds of Formula 13 and subsequent in situ cyclization of the resulting intermediate amine. A wide variety of methods for reduction of the aliphatic nitro group in compounds of Formula 13 are known in the literature. Methods well known to those skilled in the art include catalytic hydrogenation in the presence of palladium on carbon or Raney nickel and iron or zinc metal in acidic medium (see, for an example using iron metal, *Synlett*, 2015, 26, 846-850 and for an example using zinc metal, *Tetrahedron*, 2000, 56, 1889-1897). Alternatively sodium borohydride in the presence of a nickel catalyst such as nickel(II) acetate or nickel(II) chloride can be used (see for example, *Angewandte Chemie, International Edition*, 2013, 52, 5575-5579). The method of Scheme 11 utilizing zinc metal in the presence of ammonium chloride is illustrated by Step B of Synthesis Example 2.

Scheme 11

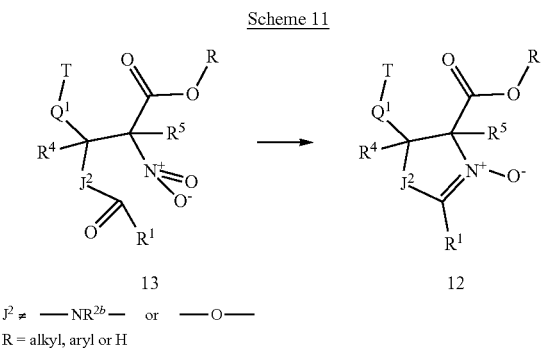

$J^2 \neq$ —$NR^{2b}$— or —O—
R = alkyl, aryl or H

As shown in Scheme 12, compounds of Formula 14 can be obtained by reduction of compounds of Formula 13 and subsequent in situ cyclization of the resulting intermediate amine. A wide variety of methods for reduction of the aliphatic nitro group in compounds of Formula 13 are known in the literature. Methods include catalytic hydrogenation in the presence of palladium on carbon or Raney nickel, iron or zinc metal in acidic medium (see, for an example using iron metal, *Angewandte Chemie, International Edition*, 2013, 52, 5575-5579 and for an example using zinc metal, *Tetrahedron*, 2000, 56, 1889-1897) and titanium(III) trichloride.

Scheme 12

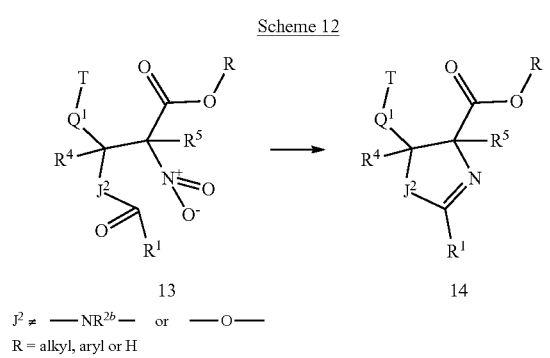

$J^2 \neq$ —$NR^{2b}$— or —O—
R = alkyl, aryl or H

As shown in Scheme 13, a compound of Formula 15 can be obtained by the conjugate addition of nitro-containing compounds of Formula 16 to an α,β-unsaturated carbonyl compound of Formula 17. The reaction can be conducted under base-promoted conditions, optionally in the presence of a co-solvent and a carboxylic acid. Suitable bases for the reaction include, but are not limited to, fluorides such as potassium fluoride, carbonates such as sodium and potassium carbonate, amines such as triethylamine and diethylamine, and phosphazenes such as 2-tert-butylimino-2-diethylamino-1,3-dimethylperhydro-1,3,2-diazaphosphorine. A wide variety of co-solvents are suitable for the reaction including, but not limited to, methanol, ethanol, tetrahydrofuran and dichloromethane. The reaction is conducted at temperatures ranging from −20° C. to the boiling point of the solvent, and typically from 0-100° C. The method of Scheme 13 is illustrated by Step D of Synthesis Example 1 and Step A of Synthesis Example 2. The method of Scheme 13 utilizing zinc metal in the presence of ammonium chloride is illustrated by Step B of Synthesis Example 2. The conjugate addition can also be conducted using a suitable catalyst. Typically, these catalysts contain stereocenters and can be synthesized in high optical purity. The use of enantioenriched catalysts can result in the formation of enantioenriched compounds of Formula 15. A variety of suitable catalysts are well known in the literature: see *Chemistry—A European Journal*, 2014, 20, 979-982 for conditions using copper/ligand complexes, see *Tetrahedron*, 2014, 70, 8168-8173 for conditions using squaramides and see *Chemistry—A European Journal*, 2011, 17, 5931-5938 for conditions using thioureas. Compounds of Formula 16 and compounds of Formula 17 are commercially available or their preparation is known in the art.

Scheme 13

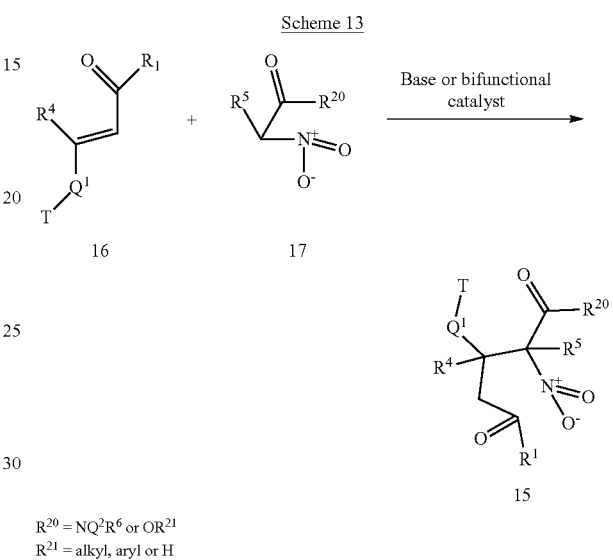

$R^{20} = NQ^2R^6$ or $OR^{21}$
$R^{21}$ = alkyl, aryl or H

As shown in Scheme 14, compounds of Formula 18 can be obtained by the ring expansion of a compound of Formula 19 using an appropriate promoter in an appropriate solvent. Suitable promoters include, but are not limited to, boron trifluoride etherate, iron(III) nitrate, sodium iodide and trimethylsilyl iodide. A variety of co-solvents are suitable for the reaction including, but not limited to, dimethylsulfoxide, N,N-dimethylformamide, N,N-dimethylacetamide, N-methylpyrrolidinone N,N-dimethylformamide, acetonitrile, acetone and tetrahydrofuran. The reaction is conducted at temperatures ranging from −20° C. to the boiling point of the solvent, and typically from 0-100° C. See *Recueil des Travaux Chimiques des Pays-Bas*, 1992, 111, 16-21 for ring expansion conditions using boron trifluoride etherate. N-Acyl aziridines of Formula 19 can readily be prepared by literature methods.

Scheme 14

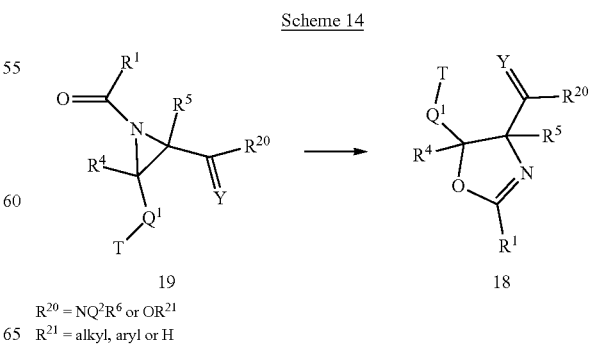

$R^{20} = NQ^2R^6$ or $OR^{21}$
$R^{21}$ = alkyl, aryl or H

As shown in Scheme 15, compounds of Formula 20 can be obtained by the reaction of aziridines of Formula 21 with imidoyl chlorides of Formula 22 and subsequent ring expansion. The reaction is typically conducted in the presence of a base with the optional use of a co-solvent. Suitable bases include, but are not limited to, alkylamines such as triethylamine and diethylamine, arylamines such as N,N-dimethylaniline, and pyridines such as 2,6-lutidine. A variety of co-solvents are suitable for the reaction including, but not limited to, dimethylsulfoxide, N,N-dimethylformamide, N,N-dimethylacetamide, N-methylpyrrolidinone N,N-dimethylformamide, acetonitrile, acetone and tetrahydrofuran. The reaction is conducted at temperatures ranging from −20° C. to the boiling point of the solvent, and typically from 0-100° C. See *Journal of Organic Chemistry*, 2011, 76, 2913-2919 for conditions using 2,6-lutidine in N,N-dimethylformamide. Imidoyl chlorides of Formula 22 can readily be prepared from amides by literature methods. Aziridines of Formula 21 can readily be prepared by literature methods.

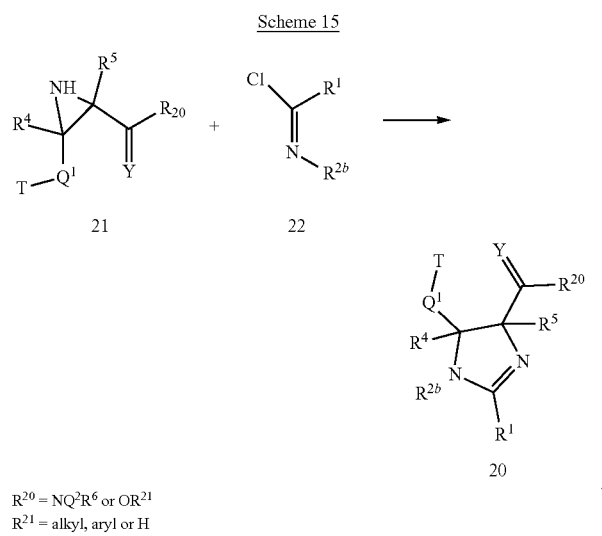

Scheme 15

21     22

20

$R^{20}$ = NQ$^2$R$^6$ or OR$^{21}$
$R^{21}$ = alkyl, aryl or H

It is recognized by one skilled in the art that various functional groups can be converted into others to provide different compounds of Formula 1. For a valuable resource that illustrates the interconversion of functional groups in a simple and straightforward fashion, see Larock, R. C., *Comprehensive Organic Transformations: A Guide to Functional Group Preparations*, 2nd Ed., Wiley-VCH, New York, 1999. For example, intermediates for the preparation of compounds of Formula 1 may contain aromatic nitro groups, which can be reduced to amino groups, and then be converted via reactions well known in the art such as the Sandmeyer reaction, to various halides, providing compounds of Formula 1. The above reactions can also in many cases be performed in alternate order.

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present disclosure to its fullest extent. The following non-limiting Examples are illustrative of the disclosure. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "q" means quartet, "m" means multiplet, "dd" means doublet of doublets, "dt" means doublet of triplets, and "br s" means broad singlet.

Synthesis Example 1

Preparation of trans-3-(4-chlorophenyl)-N-(2,3-difluorophenyl)-3,4-dihydro-5-methyl-2H-pyrrole-2-carboxamide 1-oxide (Compound 5)

Step A: Preparation of Dipotassium Nitroacetate

A solution of potassium hydroxide (44.9 g, 0.68 mol) in water (22 mL) was heated to 70° C. Nitromethane (12.2 g, 0.20 mol) was added dropwise over the course of 15 minutes, during which the internal temperature increased to 105° C. The reaction mixture was heated in a 180° C. sand bath and held at a slow reflux for 1 h. The reaction was cooled to 23° C. and then filtered. The filter cake was washed with methanol (3×40 mL) and dried under vacuum to afford the title compound (13.2 g) as a beige solid.

Step B: Preparation of Nitroacetic Acid

A solution of (L)-tartaric acid (80.4 g, 0.54 mol) in water (150 mL) was cooled to 0° C. A solution of dipotassium nitroacetate (i.e. the product of Step A, 11.3 g, 62 mmol) in water (40 mL) was cooled to −5° C. The tartartic acid solution was added slowly to the dipotassium nitroacetate solution, keeping the internal temperature between −5° C. and 0° C. The reaction mixture was stirred at 0° C. for 30 min. The mixture was filtered, and the filtrate was extracted with ice cold diethyl ether (3×100 mL). The organic layer was dried over MgSO$_4$ and concentrated under reduced pressure in an ice bath to afford the title compound (6.0 g) as a pale yellow solid that was used immediately in the next step.

Step C: Preparation of N-(2,3-difluorophenyl)-2-nitroacetamide

A solution of nitroacetic acid (i.e. the product of Step B, 6.0 g, 57 mmol) and 2,3-difluoroaniline (5.8 mL, 57 mmol) in tetrahydrofuran (150 mL) was cooled to 0° C. N,N'-Dicyclohexylcarbodiimide (13.0 g, 63 mmol) was added portionwise, keeping the temperature under 15° C. The reaction mixture was stirred for 45 min at 0° C. The reaction mixture was filtered, and the filtrate was concentrated to afford the crude product. The crude product was purified by column chromatography, eluting with 0% to 50% ethyl acetate in hexanes, to afford the title compound (3.0 g) as a pale yellow solid. Additional product (6.0-g, 45% pure by weight) was isolated as a mixture with N,N'-dicyclohexylurea.

$^1$H NMR δ 8.59 (br s, 1H), 8.02-7.96 (m, 1H), 7.15-7.08 (m, 1H), 7.06-6.96 (m, 1H), 5.30 (s, 2H).

Step D: Preparation of 3-(4-chlorophenyl)-N-(2,3-difluorophenyl)-2-nitro-5-oxo-hexanamide A mixture of N-(2,3-difluorophenyl)-2-nitroacetamide (i.e. the product of Step C, 0.20 □g, 0.93 mmol), (E)-4-(4-chlorophenyl)but-3-en-2-one (0.18 g, 1.02 mmol) and triethylamine (0.38 mL, 2.78 mmol) in tetrahydrofuran (0.9 mL) was refluxed for 1 h. The reaction mixture was cooled to 23° C. and diluted with ethyl acetate (50 mL). The organic layer was washed with 1 M hydrochloric acid (2×15 mL), dried over MgSO$_4$, and concentrated to afford the crude product. The crude product was purified by column chromatography, eluting with 0% to 100% ethyl acetate in hexanes, to afford the title compound (0.20 g, 1:1 mixture of diastereomers) as a yellow oil.

$^1$H NMR (2 diastereomers) δ 8.69 (br s, 1H), 8.26 (br s, 1H), 7.91-7.86 (m, 1H), 7.73-7.68 (m, 1H), 7.35-7.26 (m, 4H), 7.23-7.18 (m, 4H), 7.13-6.93 (m, 4H), 5.67 (d, J=10.9 Hz, 1H), 5.57 (d, J=8.8 Hz, 1H), 4.29-4.23 (m, 2H), 3.13-2.98 (m, 3H), 2.94-2.88 (m, 1H), 2.12 (s, 3H), 2.08 (s, 3H).

Step E: Preparation of trans-3-(4-chlorophenyl)-N-(2,3-difluorophenyl)-3,4-dihydro-5-methyl-2H-pyrrole-2-carboxamide 1-oxide To a solution of 3-(4-chlorophenyl)-N-(2,3-difluorophenyl)-2-nitro-5-oxo-hexanamide (i.e. the product of Step D, 0.20 g, 0.50 mmol) in tetrahydrofuran (2.5 mL) was added saturated ammonium chloride solution (2.5 mL). The mixture was cooled to 0° C. Zinc dust (0.10 g, 1.50 mmol) was added, and the reaction was stirred vigorously at 0° C. for 30 min. The reaction mixture was filtered through Celite® diatomaceous filter aid, washing the filter cake with ethyl acetate (30 mL). The organic layer was separated, washed with saturated NaCl (10 mL), dried over MgSO$_4$, and concentrated to afford the crude product. The crude product was purified by column chromatography, eluting with 0% to 100% ethyl acetate in hexanes, to afford the title compound, a compound of the present disclosure, as a colorless solid (0.072 g).

$^1$H NMR δ 11.66 (br s, 1H), 8.06-8.00 (m, 1H), 7.38-7.33 (m, 2H), 7.29-7.24 (m, 2H), 7.07-7.00 (m, 1H), 6.94-6.87 (m, 1H), 4.78-4.71 (m, 1H), 4.20-4.14 (m, 1H), 3.32-3.22 (m, 1H), 2.87-2.78 (m, 1H), 2.25-2.21 (m, 3H).

Synthesis Example 2

Preparation of trans-N-(2,3-difluorophenyl)-3,4-dihydro-5-methyl-3-[4-(trifluoromethyl)phenyl]-2H-pyrrole-2-carboxamide 1-oxide (Compound 2)

Step A: Preparation of ethyl 2-nitro-5-oxo-3-[4-(trifluoromethyl)phenyl]hexanoate To a solution of ethyl nitroacetate (11.0 mL, 95 mmol) and (E)-4-[4-(trifluoromethyl)phenyl]but-3-en-2-one (17.0 g, 79 mmol) in tetrahydrofuran (36 mL) was added triethylamine (33.0 mL, 237 mmol) dropwise over 15 min. The reaction mixture was then refluxed for 3 h. The reaction mixture was cooled to 23° C. and diluted with ethyl acetate (300 mL). The organic layer was washed with 1 M hydrochloric acid (100 mL) and saturated sodium chloride (100 mL). The organic layer was dried over MgSO$_4$ and concentrated to afford the crude product (28.9 g). The crude product was stirred in a 3:1 mixture of hexanes/1-chlorobutane (50 mL) for 45 min. The mixture was filtered to afford the title compound (19.4 g, 2.5:1 mixture of diastereomers) as a colorless solid. The filtrate was concentrated and triturated with hexanes (25 mL) to afford the title compound (4.7 g, minor diastereomer) as an orange solid.

$^1$H NMR (major diastereomer) δ 7.60-7.55 (m, 2H), 7.43-7.38 (m, 2H), 5.44 (d, J=8.5 Hz, 1H), 4.37-4.28 (m, 1H), 4.15-4.04 (m, 2H), 3.17-3.09 (m, 1H), 3.05-2.98 (m, 1H), 2.10 (s, 3H), 1.11-1.07 (m, 3H); (minor diastereomer) δ 7.60-7.55 (m, 2H), 7.43-7.38 (m, 2H), 5.51 (d, J=9.6 Hz, 1H), 4.37-4.22 (m, 3H), 4.15-4.04 (m, 2H), 3.13-3.06 (m, 1H), 3.01-2.94 (m, 1H), 2.10 (s, 3H), 1.32-1.27 (m, 3H).

Step B: Preparation of ethyl 5-methyl-1-oxido-3-[4-(trifluoromethyl)phenyl]-3,4-dihydro-2H-pyrrol-1-ium-2-carboxylate To a solution of ethyl 2-nitro-5-oxo-3-[4-(trifluoromethyl)phenyl]hexanoate (i.e. the product of Step A, 24.1 g, 69.4 mmol, 1.35:1 mixture of diastereomers) in tetrahydrofuran (115 mL) was added saturated ammonium chloride solution (115 mL). The mixture was cooled to 0° C. Zinc dust (13.6 g, 208 mmol) was added portionwise keeping the temperature under 5° C. After the addition, the reaction was stirred vigorously at 0° C. for 60 min. The reaction mixture was filtered through Celite® diatomaceous filter aid, and the filter cake was washed with ethyl acetate (150 mL). Ethyl acetate (150 mL) and water (150 mL) were added to the reaction mixture. The organic layer was separated, dried over MgSO$_4$, and concentrated to afford the crude product. The crude product was purified by column chromatography, eluting with 0% to 25% methanol in ethyl acetate, to afford the cis diastereomer of the title compound as a colorless solid (2.05 g) and the trans diastereomer of the title compound as a yellow oil (7.07 g).

$^1$H NMR (major diastereomer, trans) δ 7.66-7.60 (m, 2H), 7.36-7.31 (m, 2H), 4.77-4.71 (m, 1H), 4.39-4.25 (m, 2H), 3.83-3.75 (m, 1H), 3.43-3.33 (m, 1H), 2.84-2.75 (m, 1H), 2.20-2.16 (m, 3H), 1.35-1.29 (m, 3H); (minor diastereomer, cis) δ 7.64-7.57 (m, 2H), 7.44-7.38 (m, 2H), 4.95-4.89 (m, 1H), 4.19-4.10 (m, 1H), 3.93-3.84 (m, 1H), 3.82-3.73 (m, 1H), 3.41-3.31 (m, 1H), 3.10-3.01 (m, 1H), 2.27-2.21 (m, 3H), 0.85-0.78 (m, 3H).

Step C: Preparation of trans-5-methyl-1-oxido-3-[4-(trifluoromethyl)phenyl]-3,4-dihydro-2H-pyrrol-1-ium-2-carboxylic acid To a solution of ethyl 5-methyl-1-oxido-3-[4-(trifluoromethyl)phenyl]-3,4-dihydro-2H-pyrrol-1-ium-2-carboxylate (i.e. the product of Step B, 0.070 g, 0.22 mmol, trans diastereomer) in methanol (1.1 mL) was added 1M NaOH (0.44 mL, 0.44 mmol). The mixture was stirred vigorously at 23° C. for 2 h. The mixture was diluted with 1 M NaOH (3 mL) and washed with diethyl ether (10 mL). The organic layer was back extracted with 1M NaOH (2 mL). The combined aqueous layers were acidified to pH 1 with 1 M HCl, extracted with ethyl acetate (2×10 mL), dried over MgSO$_4$, and concentrated to afford to afford the trans diastereomer of the title compound as an orange oil (0.058 g).
$^1$H NMR δ 7.68-7.62 (m, 2H), 7.51-7.44 (m, 2H), 4.69-4.62 (m, 1H), 4.10-4.01 (m, 1H), 3.33-3.22 (m, 1H), 3.01-2.90 (m, 1H), 2.29-2.22 (m, 3H), —CO$_2$H signal not observed.

Step D: Preparation of trans-N-(2,3-difluorophenyl)-3,4-dihydro-5-methyl-3-[4-(trifluoromethyl)phenyl]-2H-pyrrole-2-carboxamide 1-oxide To a solution of trans-5-methyl-1-oxido-3-[4-(trifluoromethyl)phenyl]-3,4-dihydro-2H-pyrrol-1-ium-2-carboxylic acid (i.e. the product of Step C, 0.058 g, 0.20 mmol) in tetrahydrofuran (2.0 mL) was added 2,3-difluoroaniline (0.090 mL, 0.44 mmol), triethylamine (0.084 mL, 0.61 mmol), and propylphosphonic anhydride solution (50 wt. % in ethyl acetate, 0.072 mL, 0.24 mmol). The mixture allowed to stand at 23° C. for 35 min. The reaction mixture was directly purified by column chromatography, eluting with 0% to 100% ethyl acetate in hexanes, to afford the title compound, a compound of the present disclosure, as a colorless solid (0.025 g).
$^1$H NMR δ 11.69 (br s, 1H), 8.06-8.00 (m, 1H), 7.68-7.63 (m, 2H), 7.50-7.42 (m, 2H), 7.08-7.00 (m, 1H), 6.96-6.88 (m, 1H), 4.82-4.76 (m, 1H), 4.30-4.23 (m, 1H), 3.36-3.26 (m, 1H), 2.91-2.82 (m, 1H), 2.27-2.23 (m, 3H).

Synthesis Example 3

Preparation of trans-N-(2-fluorophenyl)-3,4-dihydro-5-methyl-3-[4-(trifluoromethyl)phenyl]-2H-pyrrole-2-carboxamide 1-oxide (Compound 26)

Step A: trans-N-(2-fluorophenyl)-3,4-dihydro-5-methyl-3-[4-(trifluoromethyl)phenyl]-2H-pyrrole-2-carboxamide 1-oxide Ethyl 5-methyl-1-oxido-3-[4-(trifluoromethyl)phenyl]-3,4-dihydro-2H-pyrrol-1-ium-2-carboxylate (i.e. the product of Example 2, Step B, 0.250 g, 0.79 mmol, trans diastereomer) was dissolved in anhydrous toluene (2.0 mL). In a separate vessel, trimethylaluminum solution (2.0 M in toluene, 0.44 mL, 0.87 mmol) was added dropwise over 10 min to a solution of 2-fluoroaniline (0.084 mL, 0.87 mmol) in anhydrous toluene (2.0 mL). The solution was stirred for 5 min at 23° C. The solution of the ester was added to the aluminum amide solution. The resulting solution was stirred for 1 h at 100° C. The reaction was cooled to 23° C. and carefully quenched with the addition of 1 M HCl. The mixture was diluted with water (50 mL) and extracted with ethyl acetate (100 mL). The organic layer was washed with saturated NaCl (50 mL) and adsorbed onto silica gel. This mixture was purified by column chromatography, eluting with 60% to 100% ethyl acetate in hexanes and then with 0-10% methanol in ethyl acetate, to afford the title compound, a compound of the present disclosure, as a colorless solid (0.160 g).

$^1$H NMR δ 11.47 (br s, 1H), 8.30-8.22 (m, 1H), 7.60-7.62 (m, 2H), 7.52-7.43 (m, 2H), 7.17-7.03 (m, 3H), 4.82-4.75 (m, 1H), 4.32-4.24 (m, 1H), 3.36-3.25 (m, 1H), 2.89-2.81 (m, 1H), 2.27-2.21 (m, 3H).

Synthesis Example 4

Preparation of trans-N-(2,3-difluorophenyl)-3-(4,6-dimethoxypyrimidin-2-yl)-5-methyl-1-oxido-3,4-dihydro-2H-pyrrol-1-ium-2-carboxamide (Compound 59)

Step A: Preparation of (E)-4-(4,6-dimethoxypyrimidin-2-yl)but-3-en-2-one

A mixture of 2-chloro-4,6-dimethoxy-pyrimidine (0.50 g, 2.9 mmol), methyl vinyl ketone (0.61 g, 8.7 mmol), tetrabutylammonium acetate (1.72 g, 5.7 mmol) and bis(tri-tert-butylphosphine)palladium(0) (0.11 g, 0.21 mmol) in 1,4-dioxane (2.0 mL) was heated to 100° C. in a microwave reactor for 30 minutes. The reaction mixture was cooled to 23° C. and then directly purified by column chromatography, eluting with 0% to 40% ethyl acetate in hexanes to afford the title compound as a colorless solid (0.20 g).
$^1$H NMR δ 7.35-7.20 (m, 2H), 6.46 (s, 1H), 4.03 (s, 3H), 4.00 (s, 3H), 2.40 (s, 3H).

Step B: Preparation of trans-N-(2,3-difluorophenyl)-3-(4,6-dimethoxypyrimidin-2-yl)-5-methyl-1-oxido-3,4-dihydro-2H-pyrrol-1-ium-2-carboxamide A mixture of N-(2,3-difluorophenyl)-2-nitroacetamide (i.e. the product of Example 1, Step C, 0.46 g, 2.1 mmol), (E)-4-(4,6-dimethoxypyrimidin-2-yl)but-3-en-2-one (0.44 g, 2.1 mmol) and triethylamine (0.89 mL, 6.3 mmol) in tetrahydrofuran (8.0 mL) was refluxed for 2 h. The mixture was cooled to 0° C. and diluted with addition tetrahydrofuran (5 mL). Concentrated hydrochloric acid was added until the pH was adjusted to 6. Zinc dust (0.44 g, 6.3 mmol) was added, and the reaction was stirred vigorously at 0° C. for 1 h. A solution of 50% aqueous sodium hydroxide was added to adjust the pH to 13, and the reaction was stirred vigorously for 20 min. The reaction mixture was extracted with ethyl acetate (3×20 mL). The organic layer was washed with saturated NaCl (10 mL), dried over MgSO$_4$, and concentrated to afford the crude product. The crude product was twice purified by column chromatography, eluting with 0% to 100% ethyl acetate in hexanes to afford a colorless solid. The solid was triturated with diethyl ether to afford the title compound, a compound of the present disclosure, as a colorless solid (0.12 g).
$^1$H NMR δ 11.93 (br s, 1H), 8.05-7.99 (m, 1H), 7.06-6.99 (m, 1H), 6.94-6.87 (m, 1H), 6.51 (s, 1H), 5.19-5.13 (m, 1H), 4.11-4.03 (m, 1H), 3.98 (s, 3H), 3.98 (s, 3H), 3.09-3.03 (m, 2H), 2.19 (m, 3H).

By the procedures described herein together with methods known in the art, the following compounds of Tables 1 to (960) can be prepared. The following abbreviations are used in the Tables which follow: t means tertiary, s means secondary, n means normal, i means iso, c means cyclo, Me means methyl, Et means ethyl, Pr means propyl, Bu means butyl, i-Pr means isopropyl, c-Pr cyclopropyl, t-Bu means tertiary butyl, Ph means phenyl, OMe means methoxy, OEt means ethoxy, SMe means methylthio, —CN means cyano, —NO$_2$ means nitro, TMS means trimethylsilyl, SOMe means methylsulfinyl, C$_2$F$_5$ means CF$_2$CF$_3$ and SO$_2$Me means methylsulfonyl.

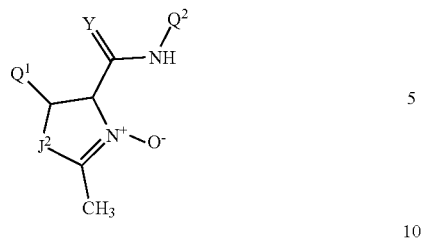

Y is O; J² is —CH₂—; Q² is Ph(2-F); and Q¹ is

| Q¹ | Q¹ | Q¹ |
|---|---|---|
| Ph(3-Cl) | Ph(3-CN) | 1H-Imidazol-2-yl(1-Me,5-F) |
| Ph(3-F) | Ph(3-NO₂) | 2-Thienyl |
| Ph(3-Br) | Ph(3-Ph) | 2-Thienyl(4-F) |
| Ph(3-Me) | Ph(3-COMe) | 2-Thienyl(4-Cl) |
| Ph(3-Et) | Ph(3-OCOMe) | 2-Thienyl(4-CF₃) |
| Ph(3-t-Bu) | Ph(3-CO₂Me) | 2-Thienyl(5-F) |
| Ph(3-i-Pr) | Ph(3-OCO₂Me) | 2-Thienyl(5-Cl) |
| Ph(3-c-Pr) | Ph(3-TMS) | 2-Thienyl(5-CF₃) |
| Ph(3-cyclohexyl) | Ph(3-SF₅) | Ph(4-Cl) |
| Ph(3-CH=CH₂) | Ph[3-(1H-pyrazol-1-yl)] | Ph(4-F) |
| Ph(3-CF₃) | Ph[3-(2H-1,2,3-triazol-2-yl)] | Ph(4-Br) |
| Ph(3-CH₂CF₃) | Ph[3-(1H-imidazol-1-yl)] | Ph(4-Me) |
| Ph(3-CHF₂) | Ph[3-(3-pyridinyl)] | Ph(4-Et) |
| Ph(3-CH₂F) | Ph[3-(4-pyridinyl)] | Ph(4-t-Bu) |
| Ph(3-OCF₃) | Ph[3-(2-pyridinyl)] | Ph(4-i-Pr) |
| Ph(3-OCH₂F) | 4-Pyridinyl(2-CF₃) | Ph(4-c-Pr) |
| Ph(3-SCF₃) | 4-Pyridinyl(2-Cl) | Ph(4-cyclohexyl) |
| Ph(3-SMe) | 4-Pyridinyl(2-F) | Ph(4-CH=CH₂) |
| Ph(3-SOMe) | 4-Pyridinyl(2-OCF₃) | Ph(4-CF₃) |
| 3-SO₂Me | 4-Pyridinyl(2-Me) | Ph(4-CH₂CF₃) |
| Ph(3-OSO₂Me) | 4-Pyridinyl(2-Br) | Ph(4-CHF₂) |
| Ph(3-C≡CH) | 4-Pyridinyl | Ph(4-CH₂F) |
| Ph(3-OMe) | 1H-Pyrazol-4-yl(1-Me) | Ph(4-OCF₃) |
| Ph(3-OEt) | 1H-Pyrazol-4-yl(1-CH₂CF₃) | Ph(4-OCH₂F) |
| Ph(3-NHCO₂-t-Bu) | 1H-Imidazol-2-yl(1-Me) | Ph(4-SCF₃) |
| Ph(3-NHCOMe) | 1H-Imidazol-2-yl(1-CH₂CF₃) | Ph(4-SMe) |
| Ph(3-NHCOCF₃) | 1H-Imidazol-2-yl(1-Me,5-Cl) | Ph(4-SOMe) |
| Ph(4-SO₂Me) | 1H-Pyrazol-3-yl(1-Me) | Ph(3-F,4-CN) |
| Ph(4-OSO₂Me) | 1H-Pyrazol-3-yl(1-CH₂CF₃) | Ph(3-F,4-SF₅) |
| Ph(4-C≡CH) | 1H-Pyrazol-3-yl(1-Me,4-F) | Ph(3-Br,4-Cl) |
| Ph(4-OMe) | 1H-Pyrazol-3-yl(1-Me,4-Cl) | Ph(3-Br,4-F) |
| Ph(4-OEt) | 1H-Imidazol-5-yl(1-Me) | Ph(3,4-di-Br) |
| Ph(4-NHCO₂-t-Bu) | 1H-Imidazol-5-yl(1-CH₂CF₃) | Ph(3-Br,4-Me) |
| Ph(4-NHCOMe) | 1H-Imidazol-4-yl(1-Me) | Ph(3-Br,4-c-Pr) |
| Ph(4-NHCOCF₃) | 1H-Imidazol-4-yl(1-CH₂CF₃) | Ph(3-Br,4-CF₃) |
| Ph(4-CN) | 3-Thienyl | Ph(3-Br,4-CHF₂) |
| Ph(4-NO₂) | 3-Thienyl(5-F) | Ph(3-Br,4-OCF₃) |
| Ph(4-Ph) | 3-Thienyl(5-Cl) | Ph(3-Br,4-OCHF₂) |
| Ph(4-COMe) | 3-Thienyl(5-CF₃) | Ph(3-Br,4-SO₂Me) |
| Ph(4-OCOMe) | Ph(3,4-di-Cl) | Ph(3-Br,4-TMS) |
| Ph(4-CO₂Me) | Ph(3-Cl,4-F) | Ph(3-Br,4-CN) |
| Ph(4-OCO₂Me) | Ph(3-Cl,4-Br) | Ph(3-Me,4-Cl) |
| Ph(4-TMS) | Ph(3-Cl,4-Me) | Ph(3-Me,4-F) |
| Ph(4-SF₅) | Ph(3-Cl,4-t-Bu) | Ph(3-Me,4-Br) |
| Ph(1H-pyrazol-1-yl) | Ph(3-Cl,4-c-Pr) | Ph(3,4-di-Me) |
| Ph(2H-1,2,3-triazol-2-yl) | Ph(3-Cl,4-CF₃) | Ph(3-Me,4-t-Bu) |
| Ph(1H-imidazol-1-yl) | Ph(3-Cl,4-CHF₂) | Ph(3-Me,4-c-Pr) |
| Ph[4-(3-pyridinyl)] | Ph(3-Cl,4-OCF₃) | Ph(3-Me,4-CF₃) |
| Ph[4-(4-pyridinyl)] | Ph(3-Cl,4-OCHF₂) | Ph(3-Me,4-OCF₃) |
| Ph[4-(2-pyridinyl)] | Ph(3-Cl,4-SO₂Me) | Ph(3-Me,4-OCHF₂) |
| 3-Pyridinyl(5-CF₃) | Ph(3-Cl,4-TMS) | Ph(3-Me,4-SO₂Me) |
| 3-Pyridinyl(5-Cl) | Ph(3-Cl,4-CN) | Ph(3-Me,4-TMS) |
| 3-Pyridinyl(5-F) | Ph(3-F,4-Cl) | Ph(3-Me,4-CN) |
| 3-Pyridinyl(5-OCF₃) | Ph(3,4-di-F)* | Ph(3-t-Bu,4-Cl) |
| 3-Pyridinyl(5-Me) | Ph(3-F,4-Br) | Ph(3-t-Bu,4-F) |
| 3-Pyridinyl(5-Br) | Ph(3-F,4-Me) | Ph(3-t-Bu,4-Br) |
| 3-Pyridinyl(4-CF₃) | Ph(3-F,4-t-Bu) | Ph(3-t-Bu,4-Me) |
| 3-Pyridinyl(4-CHF₂) | Ph(3-F,4-c-Pr) | Ph(3,4-di-t-Bu) |
| 3-Pyridinyl(4-CH₂F) | Ph(3-F,4-CF₃) | Ph(3-t-Bu,4-c-Pr) |
| 3-Pyridinyl(4-Me) | Ph(3-F,4-CHF₂) | Ph(3-t-Bu,4-CF₃) |
| 3-Pyridinyl(4-Cl) | Ph(3-F,4-OCF₃) | Ph(3-t-Bu,4-CHF₂) |
| 3-Pyridinyl(4-Br) | Ph(3-F,4-OCHF₂) | Ph(3-t-Bu,4-OCF₃) |
| 3-Pyridinyl(4-F) | Ph(3-F,4-SO₂Me) | Ph(3-t-Bu,4-OCHF₂) |

-continued

| Q¹ | Q¹ | Q¹ |
| --- | --- | --- |
| 3-Pyridinyl | Ph(3-F,4-TMS) | Ph(3-t-Bu,4-SO₂Me) |
| Ph(3-t-Bu,4-TMS) | Ph(3-OCF₃,4-OCHF₂) | Ph(3-CN,4-CHF₂) |
| Ph(3-t-Bu,4-CN) | Ph(3-OCF₃,4-SO₂Me) | Ph(3-CN,4-OCF₃) |
| Ph(3-c-Pr,4-Cl) | Ph(3-OCF₃,4-TMS) | Ph(3-CN,4-OCHF₂) |
| Ph(3-c-Pr,4-F) | Ph(3-OCF₃,4-CN) | Ph(3-CN,4-SO₂Me) |
| Ph(3-c-Pr,4-Br) | Ph(3-SO₂Me,4-Cl) | Ph(3-CN,4-TMS) |
| Ph(3-c-Pr,4-Me) | Ph(3-SO₂Me,4-F) | Ph(3,4-di-CN) |
| Ph(3-c-Pr,4-t-Bu) | Ph(3-SO₂Me,4-Br) | Ph(3-SF₅,4-F) |
| Ph(3,4-di-c-Pr) | Ph(3-SO₂Me,4-Me) | Ph(2-F,3-Cl,4-Cl) |
| Ph(3-c-Pr,4-CF₃) | Ph(3-SO₂Me,4-t-Bu) | Ph(2-F,3-Cl,4-F) |
| Ph(3-c-Pr,4-CHF₂) | Ph(3-SO₂Me,4-c-Pr) | Ph(2-F,3-Cl,4-Br) |
| Ph(3-c-Pr,4-OCF₃) | Ph(3-SO₂Me,4-CF₃) | Ph(2-F,3-Cl,4-Me) |
| Ph(3-c-Pr,4-OCHF₂) | Ph(3-SO₂Me,4-CHF₂) | Ph(2-F,3-Cl,4-t-Bu) |
| Ph(3-c-Pr,4-SO₂Me) | Ph(3-SO₂Me,4-OCF₃) | Ph(2-F,3-Cl,4-c-Pr) |
| Ph(3-c-Pr,4-TMS) | Ph(3-SO₂Me,4-OCHF₂) | Ph(2-F,3-Cl,4-CF₃) |
| Ph(3-c-Pr,4-CN) | Ph(3,4-di-SO₂Me) | Ph(2-F,3-Cl,4-CHF₂) |
| Ph(3-CF₃,4-Cl) | Ph(3-SO₂Me,4-TMS) | Ph(2-F,3-Cl,4-OCF₃) |
| Ph(3-CF₃,4-F) | Ph(3-SO₂Me,4-CN) | Ph(2-F,3-Cl,4-OCHF₂) |
| Ph(3-CF₃,4-Br) | Ph(3-CHF₂,4-Cl) | Ph(2-F,3-Cl,4-SO₂Me) |
| Ph(3-CF₃,4-Me) | Ph(3-CHF₂,4-F) | Ph(2-F,3-Cl,4-TMS) |
| Ph(3-CF₃,4-t-Bu) | Ph(3-CHF₂,4-Br) | Ph(2-F,3-Cl,4-CN) |
| Ph(3-CF₃,4-c-Pr) | Ph(3-CHF₂,4-Me) | Ph(2-F,3-F,4-Cl) |
| Ph(3,4-di-CF₃) | Ph(3-CHF₂,4-t-Bu) | Ph(2-F,3-F,4-F) |
| Ph(3-CF₃,4-CHF₂) | Ph(3-CHF₂,4-c-Pr) | Ph(2-F,3-F,4-Br) |
| Ph(3-CF₃,4-OCF₃) | Ph(3-CHF₂,4-CF₃) | Ph(2-F,3-F,4-Me) |
| Ph(3-CF₃,4-OCHF₂) | Ph(3-CHF₂,4-CHF₂) | Ph(2-F,3-F,4-t-Bu) |
| Ph(3-CF₃,4-SO₂Me) | Ph(3-CHF₂,4-OCF₃) | Ph(2-F,3-F,4-c-Pr) |
| Ph(3-CF₃,4-TMS) | Ph(3-CHF₂,4-OCHF₂) | Ph(2-F,3-F,4-CF₃) |
| Ph(3-CF₃,4-CN) | Ph(3-CHF₂,4-SO₂Me) | Ph(2-F,3-F,4-CHF₂) |
| Ph(3-OCF₃,4-Cl) | Ph(3-CHF₂,4-TMS) | Ph(2-F,3-F,4-OCF₃) |
| Ph(3-OCF₃,4-F) | Ph(3-CHF₂,4-CN) | Ph(2-F,3-F,4-OCHF₂) |
| Ph(3-OCF₃,4-Br) | Ph(3-CN,4-Cl) | Ph(2-F,3-F,4-SO₂Me) |
| Ph(3-OCF₃,4-Me) | Ph(3-CN,4-F) | Ph(2-F,3-F,4-TMS) |
| Ph(3-OCF₃,4-t-Bu) | Ph(3-CN,4-Br) | Ph(2-F,3-F,4-CN) |
| Ph(3-OCF₃,4-c-Pr) | Ph(3-CN,4-Me) | Ph(2-F,3-Br,4-Cl) |
| Ph(3-OCF₃-4-CF₃) | Ph(3-CN,4-t-Bu) | Ph(2-F,3-Br,4-F) |
| Ph(3-OCF₃,4-CHF₂) | Ph(3-CN,4-c-Pr) | Ph(2-F,3-Br,4-Br) |
| Ph(3,4-di-OCF₃) | Ph(3-CN,4-CF₃) | Ph(2-F,3-Br,4-Me) |
| Ph(2-F,3-Br,4-t-Bu) | Ph(2-F,3-c-Pr,4-Me) | Ph(2-F,3-SO₂Me,4-F) |
| Ph(2-F,3-Br,4-c-Pr) | Ph(2-F,3-c-Pr,4-t-Bu) | Ph(2-F,3-SO₂Me,4-Br) |
| Ph(2-F,3-Br,4-CF₃) | Ph(2-F,3,4-di-c-Pr) | Ph(2-F,3-SO₂Me,4-Me) |
| Ph(2-F,3-Br,4-CHF₂) | Ph(2-F,3-c-Pr,4-CF₃) | Ph(2-F,3-SO₂Me,4-t-Bu) |
| Ph(2-F,3-Br,4-OCF₃) | Ph(2-F,3-c-Pr,4-CHF₂ | Ph(2-F,3-SO₂Me,4-c-Pr) |
| Ph(2-F,3-Br,4-OCHF₂) | Ph(2-F,3-c-Pr,4-OCF₃) | Ph(2-F,3-SO₂Me,4-CF₃) |
| Ph(2-F,3-Br,4-SO₂Me) | Ph(2-F,3-c-Pr,4-OCHF₂) | Ph(2-F,3-SO₂Me,4-CHF₂) |
| Ph(2-F,3-Br,4-TMS) | Ph(2-F,3-c-Pr,4-SO₂Me) | Ph(2-F,3-SO₂Me,4-OCF₃) |
| Ph(2-F,3-Br,4-CN) | Ph(2-F,3-c-Pr,4-TMS) | Ph(2-F,3-SO₂Me,4-OCHF₂) |
| Ph(2-F,3-Me,4-Cl) | Ph(2-F,3-c-Pr,4-CN) | Ph(2-F,3,4-di-SO₂Me) |
| Ph(2-F,3-Me,4-F) | Ph(2-F,3-CF₃,4-Cl) | Ph(2-F,3-SO₂Me,4-TMS) |
| Ph(2-F,3-Me,4-Br) | Ph(2-F,3-CF₃,4-F) | Ph(2-F,3-SO₂Me,4-CN) |
| Ph(2-F,3-Me,4-Me) | Ph(2-F,3-CF₃,4-Br) | Ph(2-F,3-CHF₂,4-Cl) |
| Ph(2-F,3-Me,4-t-Bu) | Ph(2-F,3-CF₃,4-Me) | Ph(2-F,3-CHF₂,4-F) |
| Ph(2-F,3-Me,4-CF₃) | Ph(2-F,3-CF₃,4-t-Bu) | Ph(2-F,3-CHF₂,4-Br) |
| Ph(2-F,3-Me,4-CHF₂) | Ph(2-F,3-CF₃,4-c-Pr) | Ph(2-F,3-CHF₂,4-Me) |
| Ph(2-F,3-Me,4-OCF₃) | Ph(2-F,3-CF₃,4-CF₃) | Ph(2-F,3-CHF₂,4-t-Bu) |
| Ph(2-F,3-Me,4-OCHF₂) | Ph(2-F,3-CF₃,4-CHF₂) | Ph(2-F,3-CHF₂,4-c-Pr) |
| Ph(2-F,3-Me,4-SO₂Me) | Ph(2-F,3-CF₃,4-OCF₃) | Ph(2-F,3-CHF₂,4-CF₃) |
| Ph(2-F,3-Me,4-TMS) | Ph(2-F,3-CF₃,4-OCHF₂) | Ph(2-F,3-CHF₂,4-CHF₂) |
| Ph(2-F,3-Me,4-CN) | Ph(2-F,3-CF₃,4-SO₂Me) | Ph(2-F,3-CHF₂,4-OCF₃) |
| Ph(2-F,3-t-Bu,4-Cl) | Ph(2-F,3-CF₃,4-TMS) | Ph(2-F,3-CHF₂,4-OCHF₂) |
| Ph(2-F,3-t-Bu,4-F) | Ph(2-F,3-CF₃,4-CN) | Ph(2-F,3-CHF₂,4-SO₂Me) |
| Ph(2-F,3-t-Bu,4-Br) | Ph(2-F,3-OCF₃,4-Cl) | Ph(2-F,3-CHF₂,4-TMS) |
| Ph(2-F,3-t-Bu,4-Me) | Ph(2-F,3-OCF₃,4-F) | Ph(2-F,3-CHF₂,4-CN) |
| Ph(2-F,3-t-Bu,4-t-Bu) | Ph(2-F,3-OCF₃,4-Br) | Ph(2-F,3-CN,4-Cl) |
| Ph(2-F,3-t-Bu,4-c-Pr) | Ph(2-F,3-OCF₃,4-Me) | Ph(2-F,3-CN,4-F) |
| Ph(2-F,3-t-Bu,4-CF₃) | Ph(2-F,3-OCF₃,4-t-Bu) | Ph(2-F,3-CN,4-Br) |
| Ph(2-F,3-t-Bu,4-CHF₂) | Ph(2-F,3-OCF₃,4-c-Pr) | Ph(2-F,3-CN,4-Me) |
| Ph(2-F,3-t-Bu,4-OCF₃) | Ph(2-F,3-OCF₃,4-CF₃) | Ph(2-F,3-CN,4-t-Bu) |
| Ph(2-F,3-t-Bu,4-OCHF₂) | Ph(2-F,3-OCF₃,4-CHF₂) | Ph(2-F,3-CN,4-c-Pr) |
| Ph(2-F,3-t-Bu,4-SO₂Me) | Ph(2-F,3-OCF₃,4-OCF₃) | Ph(2-F,3-CN,4-CF₃) |
| Ph(2-F,3-t-Bu,4-TMS) | Ph(2-F,3-OCF₃,4-OCHF₂) | Ph(2-F,3-CN,4-CHF₂) |
| Ph(2-F,3-t-Bu,4-CN) | Ph(2-F,3-OCF₃,4-SO₂Me) | Ph(2-F,3-CN,4-OCF₃) |
| Ph(2-F,3-c-Pr,4-Cl) | Ph(2-F,3-OCF₃,4-TMS) | Ph(2-F,3-CN,4-OCHF₂) |
| Ph(2-F,3-c-Pr,4-F) | Ph(2-F,3-OCF₃,4-CN) | Ph(2-F,3-CN,4-SO₂Me) |
| Ph(2-F,3-c-Pr,4-Br) | Ph(2-F,3-SO₂Me,4-Cl) | Ph(2-F,3-CN,4-TMS) |
| Ph(2-F,3-CN,4-CN) | Ph(2-cyclohexyl) | Ph(2-OC₂F₅) |
| Ph(2-F,4-Cl) | Ph(2-CH=CH₂) | Ph(2-OCH₂CF₃) |

-continued

| $Q^1$ | $Q^1$ | $Q^1$ |
|---|---|---|
| Ph(2-F,4-F) | Ph(2-CF$_3$) | Ph(2-OCH$_2$C≡CH) |
| Ph(2-F,4-Br) | Ph(2-CH$_2$CF$_3$) | Ph(2-OCH$_2$C≡CCF$_3$) |
| Ph(2-F,4-Me) | Ph(2-CF$_2$H) | Ph(2-OCH$_2$C≡CCF$_2$H) |
| Ph(2-F,4-t-Bu) | Ph(2-CH$_2$F) | Ph(2-OCH$_2$C≡CCH$_3$) |
| Ph(2-F,4-c-Pr) | Ph(2-OCF$_3$) | Ph(2-OCH$_2$C≡C-c-Pr) |
| Ph(2-F,4-CF$_3$) | Ph(2-OCH$_2$F) | Ph(2-C≡CCF$_2$H) |
| Ph(2-F,4-CHF$_2$) | Ph(2-OCF$_2$H) | Ph(2-C≡CCH$_3$) |
| Ph(2-F,4-OCF$_3$) | Ph(2-SCF$_3$) | Ph(2-C≡C-c-Pr) |
| Ph(2-F,4-OCHF$_2$) | Ph(2-SMe) | Ph(2-OPh) |
| Ph(2-F,4-SO$_2$Me) | Ph(2-SOMe) | Ph(2-C≡CCF$_3$) |
| Ph(2-F,4-TMS) | Ph(2-SO$_2$Me) | Ph(2-CH═CF$_2$) |
| Ph(2-F,4-CN) | Ph(2-OSO$_2$Me) | Ph(2-CH═CCl$_2$) |
| Ph(2-F,3-Cl) | Ph(2-C≡CH) | Ph(2-CH═CBr$_2$) |
| Ph(2-F,3-F) | Ph(2-OMe) | Ph(2-OCH═CH$_2$) |
| Ph(2-F,3-Br) | Ph(2-OEt) | Ph(2-OCH═CF$_2$) |
| Ph(2-F,3-Me) | Ph(2-NHCO$_2$-t-Bu) | Ph(2-OCH═CCl$_2$) |
| Ph(2-F,3-t-Bu) | Ph(2-NHCOMe) | Ph(2-OCH═CBr$_2$) |
| Ph(2-F,3-c-Pr) | Ph(2-NHCOCF$_3$) | Ph(2-CH$_2$CH═CH$_2$) |
| Ph(2-F,3-CF$_3$) | Ph(2-CN) | Ph(2-CH$_2$CH═CF$_2$) |
| Ph(2-F,3-CHF$_2$) | Ph(2-NO$_2$) | Ph(2-CH$_2$CH═CCl$_2$) |
| Ph(2-F,3-OCF$_3$) | Ph(2-Ph) | Ph(2-CH$_2$CH═CBr$_2$) |
| Ph(2-F,3-OCHF$_2$) | Ph(2-COMe) | Ph(2-OCH$_2$CH═CH$_2$) |
| Ph(2-F,3-SO$_2$Me) | Ph(2-OCOMe) | Ph(2-OCH$_2$CH═CF$_2$) |
| Ph(2-F,3-TMS) | Ph(2-CO$_2$Me) | Ph(2-OCH$_2$CH═CCl$_2$) |
| Ph(2-F,3-CN) | Ph(2-OCO$_2$Me) | Ph(2-OCH$_2$CH═CBr$_2$) |
| Ph(2-Cl) | Ph(2-TMS) | Ph(2-SCF$_2$H) |
| Ph(2-F) | Ph[2-(1H-pyrazol-1-yl)] | Ph(2-SCF$_2$CF$_2$H) |
| Ph(2-Br) | Ph[2-(2H-1,2,3-triazol-2-yl)] | Ph(3-I) |
| Ph(2-I) | Ph[2-(1H-imidazol-1-yl)] | Ph(3-n-Pr) |
| Ph(2-Me) | Ph[2-(3-pyridinyl)] | Ph(3-CF$_2$H) |
| Ph(2-Et) | Ph[2-(4-pyridinyl)] | Ph(3-OCF$_2$H) |
| Ph(2-n-Pr) | Ph[2-(2-pyridinyl)] | Ph(3-SO$_2$Me) |
| Ph(2-t-Bu) | Ph(2-C$_2$F$_5$) | Ph(3-C$_2$F$_5$) |
| Ph(2-i-Pr) | Ph(2-CF$_2$CF$_2$H) | Ph(3-CF$_2$CF$_2$H) |
| Ph(2-c-Pr) | Ph(2-OCF$_2$CF$_2$H) | Ph(3-OCF$_2$CF$_2$H) |
| Ph(3-OC$_2$F$_5$) | Ph(2-Cl,3-i-Pr) | Ph(2-Cl,3-C$_2$F$_5$) |
| Ph(3-OCH$_2$CF$_3$) | Ph(2-Cl,3-c-Pr) | Ph(2-Cl,3-CF$_2$CF$_2$H) |
| Ph(3-OCH$_2$C≡CH) | Ph(2-Cl,3-cyclohexyl) | Ph(2-Cl,3-OCF$_2$CF$_2$H) |
| Ph(3-OCH$_2$C≡CCF$_3$) | Ph(2-Cl,3-CH═CH$_2$) | Ph(2-Cl,3-OC$_2$F$_5$) |
| Ph(3-OCH$_2$C≡CCF$_2$H) | Ph(2-Cl,3-CF$_3$) | Ph(2-Cl,3-OCH$_2$CF$_3$) |
| Ph(3-OCH$_2$C≡CCH$_3$) | Ph(2-Cl,3-CH$_2$CF$_3$) | Ph(2-Cl,3-OCH$_2$C≡CH) |
| Ph(3-OCH$_2$C≡C-c-Pr) | Ph(2-Cl,3-CF$_2$H) | Ph(2-Cl,3-OCH$_2$C≡CCF$_3$) |
| Ph(3-C≡CCF$_2$H) | Ph(2-Cl,3-CH$_2$F) | Ph(2-Cl,3-OCH$_2$C≡CCF$_2$H) |
| Ph(3-C≡CCH$_3$) | Ph(2-Cl,3-OCF$_3$) | Ph(2-Cl,3-OCH$_2$C≡CCH$_3$) |
| Ph(3-C≡C-c-Pr) | Ph(2-Cl,3-OCH$_2$F) | Ph(2-Cl,3-OCH$_2$C≡C-c-Pr) |
| Ph(3-OPh) | Ph(2-Cl,3-OCF$_2$H) | Ph(2-Cl,3-C≡CCF$_2$H) |
| Ph(3-C≡CCF$_3$) | Ph(2-Cl,3-SCF$_3$) | Ph(2-Cl,3-C≡CCH$_3$) |
| Ph(3-CH═CF$_2$) | Ph(2-Cl,3-SMe) | Ph(2-Cl,3-C≡C-c-Pr) |
| Ph(3-CH═CCl$_2$) | Ph(2-Cl,3-SOMe) | Ph(2-Cl,3-OPh) |
| Ph(3-CH═CBr$_2$) | Ph(2-Cl,3-SO$_2$Me) | Ph(2-Cl,3-C≡CCF$_3$) |
| Ph(3-OCH═CH$_2$) | Ph(2-Cl,3-OSO$_2$Me) | Ph(2-Cl,3-CH═CF$_2$) |
| Ph(3-OCH═CF$_2$) | Ph(2-Cl,3-C≡CH) | Ph(2-Cl,3-CH═CCl$_2$) |
| Ph(3-OCH═CCl$_2$) | Ph(2-Cl,3-OMe) | Ph(2-Cl,3-CH═CBr$_2$) |
| Ph(3-OCH═CBr$_2$) | Ph(2-Cl,3-OEt) | Ph(2-Cl,3-OCH═CH$_2$) |
| Ph(3-CH$_2$CH═CH$_2$) | Ph(2-Cl,3-NHCO$_2$-t-Bu) | Ph(2-Cl,3-OCH═CF$_2$) |
| Ph(3-CH$_2$CH═CF$_2$) | Ph(2-Cl,3-NHCOMe) | Ph(2-Cl,3-OCH═CCl$_2$) |
| Ph(3-CH$_2$CH═CCl$_2$) | Ph(2-Cl,3-NHCOCF$_3$) | Ph(2-Cl,3-OCH═CBr$_2$) |
| Ph(3-CH$_2$CH═CBr$_2$) | Ph(2-Cl,3-CN) | Ph(2-Cl,3-CH$_2$CH═CH$_2$) |
| Ph(3-OCH$_2$CH═CH$_2$) | Ph(2-Cl,3-NO$_2$) | Ph(2-Cl,3-CH$_2$CH═CF$_2$) |
| Ph(3-OCH$_2$CH═CF$_2$) | Ph(2-Cl,3-Ph) | Ph(2-Cl,3-CH$_2$CH═CCl$_2$) |
| Ph(3-OCH$_2$CH═CCl$_2$) | Ph(2-Cl,3-COMe) | Ph(2-Cl,3-CH$_2$CH═CBr$_2$) |
| Ph(3-OCH$_2$CH═CBr$_2$) | Ph(2-Cl,3-OCOMe) | Ph(2-Cl,3-OCH$_2$CH═CH$_2$) |
| Ph(3-SCF$_2$H) | Ph(2-Cl,3-CO$_2$Me) | Ph(2-Cl,3-OCH$_2$CH═CF$_2$) |
| Ph(3-SCF$_2$CF$_2$H) | Ph(2-Cl,3-OCO$_2$Me) | Ph(2-Cl,3-OCH$_2$CH═CCl$_2$) |
| Ph(2-Cl,3-Cl) | Ph(2-Cl,3-TMS) | Ph(2-Cl,3-OCH$_2$CH═CBr$_2$) |
| Ph(2-Cl,3-F) | Ph[3-(2-Cl,1H-pyrazol-1-yl)] | Ph(2-Cl,3-SCF$_2$H) |
| Ph(2-Cl,3-Br) | Ph[3-(2-Cl,2H-1,2,3-triazol-2-yl)] | Ph(2-Cl,3-SCF$_2$CF$_2$H) |
| Ph(2-Cl,3-I) | Ph[3-(2-Cl,1H-imidazol-1-yl)] | Ph(2-F,3-F) |
| Ph(2-Cl,3-Me) | Ph[3-(2-Cl,3-pyridinyl)] | Ph(2-F,3-Br) |
| Ph(2-Cl,3-Et) | Ph[3-(2-Cl,4-pyridinyl)] | Ph(2-F,3-I) |
| Ph(2-Cl,3-n-Pr) | Ph[3-(2-Cl,2-pyridinyl)] | Ph(2-F,3-Me) |
| Ph(2-Cl,3-t-Bu) | Ph(2-F,3-OCH$_2$C≡CH) | Ph(2-F,3-Et) |
| Ph(2-F,3-n-Pr) | Ph(2-F,3-OCH$_2$C≡CCF$_3$) | 2-Thienyl(4-OCF$_2$CF$_2$H) |
| Ph(2-F,3-t-Bu) | Ph(2-F,3-OCH$_2$C≡CCF$_2$H) | 2-Thienyl(5-Me) |
| Ph(2-F,3-i-Pr) | Ph(2-F,3-OCH$_2$C≡CCH$_3$) | 2-Thienyl(5-Et) |
| Ph(2-F,3-cyclohexyl) | Ph(2-F,3-OCH$_2$C≡C-c-Pr) | 2-Thienyl(5-i-Pr) |
| Ph(2-F,3-CH═CH$_2$) | Ph(2-F,3-OCH$_2$C≡C-c-Pr) | 2-Thienyl(5-c-Pr) |

-continued

| Q¹ | Q¹ | Q¹ |
|---|---|---|
| Ph(2-F,3-CF₃) | Ph(2-F,3-C≡CCF₂H) | 2-Thienyl(5-CF₂H) |
| Ph(2-F,3-CH₂CF₃) | Ph(2-F,3-C≡CCH₃) | 2-Thienyl(5-OCF₂H) |
| Ph(2-F,3-CF₂H) | Ph(2-F,3-C≡C-c-Pr) | 2-Thienyl(5-OCF₂CF₂H) |
| Ph(2-F,3-CH₂F) | Ph(2-F,3-OPh) | 2-Thienyl(5-OC₂F₅) |
| Ph(2-F,3-OCH₂F) | Ph(2-F,3-C≡CCF₃) | 2-Furanyl(4-F) |
| Ph(2-F,3-OCF₂H) | Ph(2-F,3-CH═CF₂) | 2-Furanyl(4-Cl) |
| Ph(2-F,3-SCF₃) | Ph(2-F,3-CH═CCl₂) | 2-Furanyl(4-CF₃) |
| Ph(2-F,3-SMe) | Ph(2-F,3-CH═CBr₂) | 2-Furanyl(5-F) |
| Ph(2-F,3-SOMe) | Ph(2-F,3-OCH═CH₂) | 2-Furanyl(5-Cl) |
| Ph(2-F,3-SO₂Me) | Ph(2-F,3-OCH═CF₂) | 2-Furanyl(5-CF₃) |
| Ph(2-F,3-OSO₂Me) | Ph(2-F,3-OCH═CCl₂) | 2-Furanyl(4-Me) |
| Ph(2-F,3-C≡CH) | Ph(2-F,3-OCH═CBr₂) | 2-Furanyl(4-Et) |
| Ph(2-F,3-OMe) | Ph(2-F,3-CH₂CH═CH₂) | 2-Furanyl(4-i-Pr) |
| Ph(2-F,3-OEt) | Ph(2-F,3-CH₂CH═CF₂) | 2-Furanyl(4-c-Pr) |
| Ph(2-F,3-NHCO₂-t-Bu) | Ph(2-F,3-CH₂CH═CCl₂) | 2-Furanyl(4-CF₂H) |
| Ph(2-F,3-NHCOMe) | Ph(2-F,3-CH₂CH═CBr₂) | 2-Furanyl(4-OCF₂H) |
| Ph(2-F,3-NHCOCF₃) | Ph(2-F,3-OCH₂CH═CH₂) | 2-Furanyl(4-OCF₂CF₂H) |
| Ph(2-F,3-NO₂) | Ph(2-F,3-OCH₂CH═CF₂) | 2-Furanyl(5-Me) |
| Ph(2-F,3-Ph) | Ph(2-F,3-OCH₂CH═CCl₂) | 2-Furanyl(5-Et) |
| Ph(2-F,3-COMe) | Ph(2-F,3-OCH₂CH═CBr₂) | 2-Furanyl(5-i-Pr) |
| Ph(2-F,3-OCOMe) | Ph(2-F,3-SCF₂H) | 2-Furanyl(5-c-Pr) |
| Ph(2-F,3-CO₂Me) | Ph(2-F,3-SCF₂CF₂H) | 2-Furanyl(5-CF₂H) |
| Ph(2-F,3-OCO₂Me) | Ph(2-F,3-SF₅) | 2-Furanyl(5-OCF₂H) |
| Ph[3-(2-F,1H-imidazol-1-yl)] | 4-Pyridinyl(5-OCF₂H) | 2-Furanyl(5-OCF₂CF₂H) |
| Ph[3-(2-F,3-pyridinyl)] | 4-Pyridinyl(5-CF₂H) | 2-Furanyl(5-OC₂F₅) |
| Ph[3-(2-F,4-pyridinyl)] | 4-Pyridinyl(5-OCF₂CF₂H) | Ph(4-I) |
| Ph[3-(2-F,2-pyridinyl)] | 2-Thienyl(4-Me) | Ph(4-n-Pr) |
| Ph(2-F,3-C₂F₅) | 2-Thienyl(4-Et) | Ph(4-OCHF₂) |
| Ph(2-F,3-CF₂CF₂H) | 2-Thienyl(4-i-Pr) | Ph(4-C₂F₅) |
| Ph(2-F,3-OCF₂CF₂H) | 2-Thienyl(4-c-Pr) | Ph(4-CF₂CF₂H) |
| Ph(2-F,3-OC₂F₅) | 2-Thienyl(4-CF₂H) | Ph(4-OCF₂CF₂H) |
| Ph(2-F,3-OCH₂CF₃) | 2-Thienyl(4-OCF₂H) | Ph(4-OC₂F₅) |
| Ph(4-OCH₂CF₃) | Ph(2-Cl,4-c-Pr) | Ph(2-Cl,4-OCH₂C≡CCH₃) |
| Ph(4-OCH₂C≡CH) | Ph(2-Cl,4-cyclohexyl) | Ph(2-Cl,4-OCH₂C≡C-c-Pr) |
| Ph(4-OCH₂C≡CCF₃) | Ph(2-Cl,4-CH═CH₂) | Ph(2-Cl,4-C≡CCF₂H) |
| Ph(4-OCH₂C≡CCF₂H) | Ph(2-Cl,4-CF₃) | Ph(2-Cl,4-C≡CCH₃) |
| Ph(4-OCH₂C≡CCH₃) | Ph(2-Cl,4-CH₂CF₃) | Ph(2-Cl,4-C≡C-c-Pr) |
| Ph(4-OCH₂C≡C-c-Pr) | Ph(2-Cl,4-CHF₂) | Ph(2-Cl,4-OPh) |
| Ph(4-C≡CCF₂H) | Ph(2-Cl,4-CH₂F) | Ph(2-Cl,4-C≡CCF₃) |
| Ph(4-C≡CCH₃) | Ph(2-Cl,4-OCF₃) | Ph(2-Cl,4-CH═CF₂) |
| Ph(4-C≡C-c-Pr) | Ph(2-Cl,4-OCH₂F) | Ph(2-Cl,4-CH═CCl₂) |
| Ph(4-OPh) | Ph(2-Cl,4-OCHF₂) | Ph(2-Cl,4-CH═CBr₂) |
| Ph(4-C≡CCF₃) | Ph(2-Cl,4-SCF₃) | Ph(2-Cl,4-OCH═CH₂) |
| Ph(4-CH═CF₂) | Ph(2-Cl,4-SMe) | Ph(2-Cl,4-OCH═CF₂) |
| Ph(4-CH═CCl₂) | Ph(2-Cl,4-SOMe) | Ph(2-Cl,4-OCH═CCl₂) |
| Ph(4-CH═CBr₂) | Ph(2-Cl,4-SO₂Me) | Ph(2-Cl,4-OCH═CBr₂) |
| Ph(4-OCH═CH₂) | Ph(2-Cl,4-OSO₂Me) | Ph(2-Cl,4-CH₂CH═CH₂) |
| Ph(4-OCH═CF₂) | Ph(2-Cl,4-C≡CH) | Ph(2-Cl,4-CH₂CH═CF₂) |
| Ph(4-OCH═CCl₂) | Ph(2-Cl,4-OMe) | Ph(2-Cl,4-CH₂CH═CCl₂) |
| Ph(4-OCH═CBr₂) | Ph(2-Cl,4-OEt) | Ph(2-Cl,4-CH₂CH═CBr₂) |
| Ph(4-CH₂CH═CH₂) | Ph(2-Cl,4-NHCO₂-t-Bu) | Ph(2-Cl,4-OCH₂CH═CH₂) |
| Ph(4-CH₂CH═CF₂) | Ph(2-Cl,4-NHCOMe) | Ph(2-Cl,4-OCH₂CH═CF₂) |
| Ph(4-CH₂CH═CCl₂) | Ph(2-Cl,4-NHCOCF₃) | Ph(2-Cl,4-OCH₂CH═CCl₂) |
| Ph(4-CH₂CH═CBr₂) | Ph(2-Cl,4-CN) | Ph(2-Cl,4-OCH₂CH═CBr₂) |
| Ph(4-OCH₂CH═CH₂) | Ph(2-Cl,4-NO₂) | Ph(2-Cl,4-SCF₂H) |
| Ph(4-OCH₂CH═CF₂) | Ph(2-Cl,4-Ph) | Ph(2-Cl,4-SCF₂CF₂H) |
| Ph(4-OCH₂CH═CCl₂) | Ph(2-Cl,4-COMe) | Ph(2-F,4-Cl) |
| Ph(4-OCH₂CH═CBr₂) | Ph(2-Cl,4-OCOMe) | Ph(2,4-di-F) |
| Ph(4-SCF₂H) | Ph(2-Cl,4-CO₂Me) | Ph(2-F,4-Br) |
| Ph(4-SCF₂CF₂H) | Ph(2-Cl,4-OCO₂Me) | Ph(2-F,4-I) |
| Ph(2,4-di-Cl) | Ph(2-Cl,4-TMS) | Ph(2-F,4-Me) |
| Ph(2-Cl,4-F) | Ph(2-Cl,4-C₂F₅) | Ph(2-F,4-Et) |
| Ph(2-Cl,4-Br) | Ph(2-Cl,4-CF₂CF₂H) | Ph(2-F,4-n-Pr) |
| Ph(2-Cl,4-I) | Ph(2-Cl,4-OCF₂CF₂H) | Ph(2-F,4-t-Bu) |
| Ph(2-Cl,4-Me) | Ph(2-Cl,4-OC₂F₅) | Ph(2-F,4-i-Pr) |
| Ph(2-Cl,4-Et) | Ph(2-Cl,4-OCH₂CF₃) | Ph(2-F,4-cyclohexyl) |
| Ph(2-Cl,4-n-Pr) | Ph(2-Cl,4-OCH₂C≡CH) | Ph(2-F,4-CH═CH₂) |
| Ph(2-Cl,4-t-Bu) | Ph(2-Cl,4-OCH₂C≡CCF₃) | Ph(2-F,4-CF₃) |
| Ph(2-Cl,4-i-Pr) | Ph(2-Cl,4-OCH₂C≡CCF₂H) | Ph(2-F,4-CH₂CF₃) |
| Ph(2-F,4-CHF₂) | Ph(2-F,4-C≡CCF₃) | 3-Furanyl(4-CF₂H) |
| Ph(2-F,4-CH₂F) | Ph(2-F,4-CH═CF₂) | 3-Furanyl(4-OCF₂H) |
| Ph(2-F,4-OCF₃) | Ph(2-F,4-CH═CCl₂) | 3-Furanyl(4-OCF₂CF₂H) |
| Ph(2-F,4-OCH₂F) | Ph(2-F,4-CH═CBr₂) | 3-Furanyl(4-OC₂F₅) |
| Ph(2-F,4-OCHF₂) | Ph(2-F,4-OCH═CH₂) | Ph(3-Cl,4-I) |
| Ph(2-F,4-SCF₃) | Ph(2-F,4-OCH═CF₂) | Ph(3-Cl,4-Et) |
| Ph(2-F,4-SMe) | Ph(2-F,4-OCH═CCl₂) | Ph(3-Cl,4-n-Pr) |
| Ph(2-F,4-SOMe) | Ph(2-F,4-OCH═CBr₂) | Ph(3-Cl,4-i-Pr) |

| $Q^1$ | $Q^1$ | $Q^1$ |
|---|---|---|
| Ph(2-F,4-SO$_2$Me) | Ph(2-F,4-CH$_2$CH=CH$_2$) | Ph(3-Cl,4-C$_2$F$_5$) |
| Ph(2-F,4-OSO$_2$Me) | Ph(2-F,4-CH$_2$CH=CF$_2$) | Ph(3-Cl,4-CF$_2$CF$_2$H) |
| Ph(2-F,4-C≡CH) | Ph(2-F,4-CH$_2$CH=CCl$_2$) | Ph(3-Cl,4-CF$_2$H) |
| Ph(2-F,4-OMe) | Ph(2-F,4-CH$_2$CH=CBr$_2$) | Ph(3-Cl,4-OMe) |
| Ph(2-F,4-OEt) | Ph(2-F,4-OCH$_2$CH=CH$_2$) | Ph(3-Cl,4-OCF$_2$CF$_2$H) |
| Ph(2-F,4-NHCO$_2$-t-Bu) | Ph(2-F,4-OCH$_2$CH=CF$_2$) | Ph(3-Cl,4-OC$_2$F$_5$) |
| Ph(2-F,4-NHCOMe) | Ph(2-F,4-OCH$_2$CH=CCl$_2$) | Ph(3,4-di-F) |
| Ph(2-F,4-NHCOCF$_3$) | Ph(2-F,4-OCH$_2$CH=CBr$_2$) | Ph(3-F,4-I) |
| Ph(2-F,4-CN) | Ph(2-F,4-SCF$_2$H) | Ph(3-F,4-Et) |
| Ph(2-F,4-NO$_2$) | Ph(2-F,4-SCF$_2$CF$_2$H) | Ph(3-F,4-n-Pr) |
| Ph(2-F,4-Ph) | Ph(2-F,4-SF$_5$) | Ph(3-F,4-i-Pr) |
| Ph(2-F,4-COMe) | 3-Pyridinyl(5-OCF$_2$H) | Ph(3-F,4-C$_2$F$_5$) |
| Ph(2-F,4-OCOMe) | 3-Pyridinyl(5-CF$_2$H) | Ph(3-F,4-CF$_2$CF$_2$H) |
| Ph(2-F,4-CO$_2$Me) | 3-Pyridinyl(5-OCF$_2$CF$_2$H) | Ph(3-F,4-CF$_2$H) |
| Ph(2-F,4-OCO$_2$Me) | 3-Thienyl(4-Me) | Ph(3-F,4-OMe) |
| Ph(2-F,4-C$_2$F$_5$) | 3-Thienyl(4-Et) | Ph(3-F,4-OCF$_2$CF$_2$H) |
| Ph(2-F,4-CF$_2$CF$_2$H) | 3-Thienyl(4-i-Pr) | Ph(3-F,4-OC$_2$F$_5$) |
| Ph(2-F,4-OCF$_2$CF$_2$H) | 3-Thienyl(4-c-Pr) | Ph(3-Br,4-I) |
| Ph(2-F,4-OC$_2$F$_5$) | 3-Thienyl(4-CF$_2$H) | Ph(3-Br,4-Et) |
| Ph(2-F,4-OCH$_2$CF$_3$) | 3-Thienyl(4-OCF$_2$H) | Ph(3-Br,4-n-Pr) |
| Ph(2-F,4-OCH$_2$C=CH) | 3-Thienyl(4-OCF$_2$CF$_2$H) | Ph(3-Br,4-t-Bu) |
| Ph(2-F,4-OCH$_2$C≡CCF$_3$) | 3-Thienyl(4-OC$_2$F$_5$) | Ph(3-Br,4-i-Pr) |
| Ph(2-F,4-OCH$_2$C≡CCF$_2$H) | 3-Furanyl(5-F) | Ph(3-Br,4-C$_2$F$_5$) |
| Ph(2-F,4-OCH$_2$C≡CCH$_3$) | 3-Furanyl(5-Cl) | Ph(3-Br,4-CF$_2$CF$_2$H) |
| Ph(2-F,4-OCH$_2$C≡C-c-Pr) | 3-Furanyl(5-CF$_3$) | Ph(3-Br,4-CF$_2$H) |
| Ph(2-F,4-C≡CCF$_2$H) | 3-Furanyl(4-Me) | Ph(3-Br,4-OMe) |
| Ph(2-F,4-C≡CCH$_3$) | 3-Furanyl(4-Et) | Ph(3-Br,4-OCF$_2$CF$_2$H) |
| Ph(2-F,4-C≡C-c-Pr) | 3-Furanyl(4-i-Pr) | Ph(3-Br,4-OC$_2$F$_5$) |
| Ph(2-F,4-OPh) | 3-Furanyl(4-c-Pr) | Ph(3-I,4-Cl) |
| Ph(3-I,4-F) | Ph(3-Et,4-n-Pr) | Ph(3-n-Pr,4-CN) |
| Ph(3-I,4-Br) | Ph(3-Et,4-t-Bu) | Ph(3-t-Bu,4-I) |
| Ph(3,4-di-I) | Ph(3-Et,4-i-Pr) | Ph(3-t-Bu,4-Et) |
| Ph(3-I,4-Me) | Ph(3-Et,4-c-Pr) | Ph(3-t-Bu,4-n-Pr) |
| Ph(3-I,4-Et) | Ph(3-Et,4-CF$_3$) | Ph(3-t-Bu,4-i-Pr) |
| Ph(3-I,4-n-Pr) | Ph(3-Et,4-C$_2$F$_5$) | Ph(3-t-Bu,4-C$_2$F$_5$) |
| Ph(3-I,4-t-Bu) | Ph(3-Et,4-CF$_2$CF$_2$H) | Ph(3-t-Bu,4-CF$_2$CF$_2$H) |
| Ph(3-I,4-i-Pr) | Ph(3-Et,4-CF$_2$H) | Ph(3-t-Bu,4-CF$_2$H) |
| Ph(3-I,4-c-Pr) | Ph(3-Et,4-OMe) | Ph(3-t-Bu,4-OMe) |
| Ph(3-I,4-CF$_3$) | Ph(3-Et,4-OCF$_3$) | Ph(3-t-Bu,4-OCF$_2$CF$_2$H) |
| Ph(3-I,4-C$_2$F$_5$) | Ph(3-Et,4-OCHF$_2$) | Ph(3-t-Bu,4-OC$_2$F$_5$) |
| Ph(3-I,4-CF$_2$CF$_2$H) | Ph(3-Et,4-OCF$_2$CF$_2$H) | Ph(3-i-Pr,4-Cl) |
| Ph(3-I,4-CF$_2$H) | Ph(3-Et,4-OC$_2$F$_5$) | Ph(3-i-Pr,4-F) |
| Ph(3-I,4-OMe) | Ph(3-Et,4-SO$_2$Me) | Ph(3-i-Pr,4-Br) |
| Ph(3-I,4-OCF$_3$) | Ph(3-Et,4-TMS) | Ph(3-i-Pr,4-I) |
| Ph(3-I,4-OCHF$_2$) | Ph(3-Et,4-CN) | Ph(3-i-Pr,4-Me) |
| Ph(3-I,4-OCF$_2$CF$_2$H) | Ph(3-n-Pr,4-Cl) | Ph(3-i-Pr,4-Et) |
| Ph(3-I,4-OC$_2$F$_5$) | Ph(3-n-Pr,4-F) | Ph(3-i-Pr,4-n-Pr) |
| Ph(3-I,4-SO$_2$Me) | Ph(3-n-Pr,4-Br) | Ph(3-i-Pr,4-t-Bu) |
| Ph(3-I,4-TMS) | Ph(3-n-Pr,4-I) | Ph(3,4-di-i-Pr) |
| Ph(3-I,4-CN) | Ph(3-n-Pr,4-Me) | Ph(3-i-Pr,4-c-Pr) |
| Ph(3-Me,4-I) | Ph(3-n-Pr,4-Et) | Ph(3-i-Pr,4-CF$_3$) |
| Ph(3-Me,4-Et) | Ph(3,4-di-n-Pr) | Ph(3-i-Pr,4-C$_2$F$_5$) |
| Ph(3-Me,4-n-Pr) | Ph(3-n-Pr,4-t-Bu) | Ph(3-i-Pr,4-CF$_2$CF$_2$H) |
| Ph(3-Me,4-i-Pr) | Ph(3-n-Pr,4-i-Pr) | Ph(3-i-Pr,4-CF$_2$H) |
| Ph(3-Me,4-C$_2$F$_5$) | Ph(3-n-Pr,4-c-Pr) | Ph(3-i-Pr,4-OMe) |
| Ph(3-Me,4-CF$_2$CF$_2$H) | Ph(3-n-Pr,4-CF$_3$) | Ph(3-i-Pr,4-OCF$_3$) |
| Ph(3-Me,4-CF$_2$H) | Ph(3-n-Pr,4-C$_2$F$_5$) | Ph(3-i-Pr,4-OCHF$_2$) |
| Ph(3-Me,4-OMe) | Ph(3-n-Pr,4-CF$_2$CF$_2$H) | Ph(3-i-Pr,4-OCF$_2$CF$_2$H) |
| Ph(3-Me,4-OCF$_2$CF$_2$H) | Ph(3-n-Pr,4-CF$_2$H) | Ph(3-i-Pr,4-OC$_2$F$_5$) |
| Ph(3-Me,4-OC$_2$F$_5$) | Ph(3-n-Pr,4-OMe) | Ph(3-i-Pr,4-SO$_2$Me) |
| Ph(3-Et,4-Cl) | Ph(3-n-Pr,4-OCF$_3$) | Ph(3-i-Pr,4-TMS) |
| Ph(3-Et,4-F) | Ph(3-n-Pr,4-OCHF$_2$) | Ph(3-i-Pr,4-CN) |
| Ph(3-Et,4-Br) | Ph(3-n-Pr,4-OCF$_2$CF$_2$H) | Ph(3-c-Pr,4-I) |
| Ph(3-Et,4-I) | Ph(3-n-Pr,4-OC$_2$F$_5$) | Ph(3-c-Pr,4-Et) |
| Ph(3-Et,4-Me) | Ph(3-n-Pr,4-SO$_2$Me) | Ph(3-c-Pr,4-n-Pr) |
| Ph(3,4-di-Et) | Ph(3-n-Pr,4-TMS) | Ph(3-c-Pr,4-i-Pr) |
| Ph(3-c-Pr,4-C$_2$F$_5$) | Ph(3-C$_2$F$_5$,4-TMS) | Ph(3,4-di-CF$_2$H) |
| Ph(3-c-Pr,4-CF$_2$CF$_2$H) | Ph(3-C$_2$F$_5$,4-CN) | Ph(3-CF$_2$H,4-OMe) |
| Ph(3-c-Pr,4-CF$_2$H) | Ph(3-CF$_2$CF$_2$H,4-Cl) | Ph(3-CF$_2$H,4-OCF$_3$) |
| Ph(3-c-Pr,4-OMe) | Ph(3-CF$_2$CF$_2$H,4-F) | Ph(3-CF$_2$H,4-OCHF$_2$) |
| Ph(3-c-Pr,4-OCF$_2$CF$_2$H) | Ph(3-CF$_2$CF$_2$H,4-Br) | Ph(3-CF$_2$H,4-OCF$_2$CF$_2$H) |
| Ph(3-c-Pr,4-OC$_2$F$_5$) | Ph(3-CF$_2$CF$_2$H,4-I) | Ph(3-CF$_2$H,4-OC$_2$F$_5$) |
| Ph(3-CF$_3$,4-I) | Ph(3-CF$_2$CF$_2$H,4-Me) | Ph(3-CF$_2$H,4-SO$_2$Me) |
| Ph(3-CF$_3$,4-Et) | Ph(3-CF$_2$CF$_2$H,4-Et) | Ph(3-CF$_2$H,4-TMS) |
| Ph(3-CF$_3$,4-n-Pr) | Ph(3-CF$_2$CF$_2$H,4-n-Pr) | Ph(3-CF$_2$H,4-CN) |
| Ph(3-CF$_3$,4-i-Pr) | Ph(3-CF$_2$CF$_2$H,4-t-Bu) | Ph(3-OMe,4-Cl) |
| Ph(3-CF$_3$,4-C$_2$F$_5$) | Ph(3-CF$_2$CF$_2$H,4-i-Pr) | Ph(3-OMe,4-F) |

-continued

| Q¹ | Q¹ | Q¹ |
|---|---|---|
| Ph(3-CF$_3$,4-CF$_2$CF$_2$H) | Ph(3-CF$_2$CF$_2$H,4-c-Pr) | Ph(3-OMe,4-Br) |
| Ph(3-CF$_3$,4-CF$_2$H) | Ph(3-CF$_2$CF$_2$H,4-CF$_3$) | Ph(3-OMe,4-I) |
| Ph(3-CF$_3$,4-OMe) | Ph(3-CF$_2$CF$_2$H,4-C$_2$F$_5$) | Ph(3-OMe,4-Me) |
| Ph(3-CF$_3$,4-OCF$_2$CF$_2$H) | Ph(3,4-di-CF$_2$CF$_2$H) | Ph(3-OMe,4-Et) |
| Ph(3-CF$_3$,4-OC$_2$F$_5$) | Ph(3-CF$_2$CF$_2$H,4-CF$_2$H) | Ph(3-OMe,4-n-Pr) |
| Ph(3-CF$_3$,4-TMS) | Ph(3-CF$_2$CF$_2$H,4-OMe) | Ph(3-OMe,4-t-Bu) |
| Ph(3-C$_2$F$_5$,4-Cl) | Ph(3-CF$_2$CF$_2$H,4-OCF$_3$) | Ph(3-OMe,4-i-Pr) |
| Ph(3-C$_2$F$_5$,4-F) | Ph(3-CF$_2$CF$_2$H,4-OCHF$_2$) | Ph(3-OMe,4-c-Pr) |
| Ph(3-C$_2$F$_5$,4-Br) | Ph(3-CF$_2$CF$_2$H,4-OCF$_2$CF$_2$H) | Ph(3-OMe,4-CF$_3$) |
| Ph(3-C$_2$F$_5$,4-I) | Ph(3-CF$_2$CF$_2$H,4-OC$_2$F$_5$) | Ph(3-OMe,4-C$_2$F$_5$) |
| Ph(3-C$_2$F$_5$,4-Me) | Ph(3-CF$_2$CF$_2$H,4-SO$_2$Me) | Ph(3-OMe,4-CF$_2$CF$_2$H) |
| Ph(3-C$_2$F$_5$,4-Et) | Ph(3-CF$_2$CF$_2$H,4-TMS) | Ph(3-OMe,4-CF$_2$H) |
| Ph(3-C$_2$F$_5$,4-n-Pr) | Ph(3-CF$_2$CF$_2$H,4-CN) | Ph(3,4-di-OMe) |
| Ph(3-C$_2$F$_5$,4-t-Bu) | Ph(3-CF$_2$H,4-Cl) | Ph(3-OMe,4-OCF$_3$) |
| Ph(3-C$_2$F$_5$,4-i-Pr) | Ph(3-CF$_2$H,4-F) | Ph(3-OMe,4-OCHF$_2$) |
| Ph(3-C$_2$F$_5$,4-c-Pr) | Ph(3-CF$_2$H,4-Br) | Ph(3-OMe,4-OCF$_2$CF$_2$H) |
| Ph(3-C$_2$F$_5$CF$_3$,4-CF$_3$) | Ph(3-CF$_2$H,4-I) | Ph(3-OMe,4-OC$_2$F$_5$) |
| Ph(3,4-di-C$_2$F$_5$) | Ph(3-CF$_2$H,4-Me) | Ph(3-OMe,4-SO$_2$Me) |
| Ph(3-C$_2$F$_5$,4-CF$_2$CF$_2$H) | Ph(3-CF$_2$H,4-Et) | Ph(3-OMe,4-TMS) |
| Ph(3-C$_2$F$_5$,4-CF$_2$H) | Ph(3-CF$_2$H,4-n-Pr) | Ph(3-OMe,4-CN) |
| Ph(3-C$_2$F$_5$,4-OMe) | Ph(3-CF$_2$H,4-t-Bu) | Ph(3-OCF$_3$,4-I) |
| Ph(3-C$_2$F$_5$,4-OCF$_3$) | Ph(3-CF$_2$H,4-i-Pr) | Ph(3-OCF$_3$,4-Et) |
| Ph(3-C$_2$F$_5$,4-OCHF$_2$) | Ph(3-CF$_2$H,4-c-Pr) | Ph(3-OCF$_3$,4-n-Pr) |
| Ph(3-C$_2$F$_5$,4-OCF$_2$CF$_2$H) | Ph(3-CF$_2$H,4-CF$_3$) | Ph(3-OCF$_3$,4-i-Pr) |
| Ph(3-C$_2$F$_5$,4-OC$_2$F$_5$) | Ph(3-CF$_2$H,4-C$_2$F$_5$) | Ph(3-OCF$_3$,4-CF$_3$) |
| Ph(3-C$_2$F$_5$,4-SO$_2$Me) | Ph(3-CF$_2$H,4-CF$_2$CF$_2$H) | Ph(3-OCF$_3$,4-C$_2$F$_5$) |
| Ph(3-OCF$_3$,4-CF$_2$CF$_2$H) | Ph(3-OCF$_2$CF$_2$H,4-CF$_3$) | Ph(3-SO$_2$MeCF$_3$,4-CF$_3$) |
| Ph(3-OCF$_3$,4-CF$_2$H) | Ph(3-OCF$_2$CF$_2$H,4-C$_2$F$_5$) | Ph(3-SO$_2$Me,4-C$_2$F$_5$) |
| Ph(3-OCF$_3$,4-OMe) | Ph(3-OCF$_2$CF$_2$H,4-CF$_2$CF$_2$H) | Ph(3-SO$_2$Me,4-CF$_2$CF$_2$H) |
| Ph(3-OCF$_3$,4-OCF$_2$CF$_2$H) | Ph(3-OCF$_2$CF$_2$H,4-CF$_2$H) | Ph(3-SO$_2$Me,4-CF$_2$H) |
| Ph(3-OCF$_3$,4-OC$_2$F$_5$) | Ph(3-OCF$_2$CF$_2$H,4-OMe) | Ph(3-SO$_2$Me,4-OMe) |
| Ph(3-OCHF$_2$,4-Cl) | Ph(3-OCF$_2$CF$_2$H,4-OCF$_3$) | Ph(3-SO$_2$Me,4-OCF$_2$CF$_2$H) |
| Ph(3-OCHF$_2$,4-F) | Ph(3-OCF$_2$CF$_2$H,4-OCHF$_2$) | Ph(3-SO$_2$Me,4-OC$_2$F$_5$) |
| Ph(3-OCHF$_2$,4-Br) | Ph(3,4-di-OCF$_2$CF$_2$H) | Ph(3-TMS,4-Cl) |
| Ph(3-OCHF$_2$,4-I) | Ph(3-OCF$_2$CF$_2$H,4-OC$_2$F$_5$) | Ph(3-TMS,4-F) |
| Ph(3-OCHF$_2$,4-Me) | Ph(3-OCF$_2$CF$_2$H,4-SO$_2$Me) | Ph(3-TMS,4-Br) |
| Ph(3-OCHF$_2$,4-Et) | Ph(3-OCF$_2$CF$_2$H,4-TMS) | Ph(3-TMS,4-I) |
| Ph(3-OCHF$_2$,4-n-Pr) | Ph(3-OCF$_2$CF$_2$H,4-CN) | Ph(3-TMS,4-Me) |
| Ph(3-OCHF$_2$,4-t-Bu) | Ph(3-OC$_2$F$_5$,4-Cl) | Ph(3-TMS,4-Et) |
| Ph(3-OCHF$_2$,4-i-Pr) | Ph(3-OC$_2$F$_5$,4-F) | Ph(3-TMS,4-n-Pr) |
| Ph(3-OCHF$_2$,4-c-Pr) | Ph(3-OC$_2$F$_5$,4-Br) | Ph(3-TMS,4-t-Bu) |
| Ph(3-OCHF$_2$CF$_3$,4-CF$_3$) | Ph(3-OC$_2$F$_5$,4-I) | Ph(3-TMS,4-i-Pr) |
| Ph(3-OC$_2$F$_5$,4-C$_2$F$_5$) | Ph(3-OC$_2$F$_5$,4-Me) | Ph(3-TMS,4-c-Pr) |
| Ph(3-OCHF$_2$,4-CF$_2$CF$_2$H) | Ph(3-OC$_2$F$_5$,4-Et) | Ph(3-TMS,4-CF$_3$) |
| Ph(3-OCHF$_2$,4-CF$_2$H) | Ph(3-OC$_2$F$_5$,4-n-Pr) | Ph(3-TMS,4-C$_2$F$_5$) |
| Ph(3-OCHF$_2$,4-OMe) | Ph(3-OC$_2$F$_5$,4-t-Bu) | Ph(3-TMS,4-CF$_2$CF$_2$H) |
| Ph(3-OCHF$_2$,4-OCF$_3$) | Ph(3-OC$_2$F$_5$,4-i-Pr) | Ph(3-TMS,4-CF$_2$H) |
| Ph(3,4-di-OCHF$_2$) | Ph(3-OC$_2$F$_5$,4-c-Pr) | Ph(3-TMS,4-OMe) |
| Ph(3-OCHF$_2$,4-OCF$_2$CF$_2$H) | Ph(3-OC$_2$F$_5$CF$_3$,4-CF$_3$) | Ph(3-TMS,4-OCF$_3$) |
| Ph(3-OCHF$_2$,4-OC$_2$F$_5$) | Ph(3-OC$_2$F$_5$,4-CF$_2$CF$_2$H) | Ph(3-TMS,4-OCHF$_2$) |
| Ph(3-OCHF$_2$,4-SO$_2$Me) | Ph(3-OC$_2$F$_5$,4-CF$_2$H) | Ph(3-TMS,4-OCF$_2$CF$_2$H) |
| Ph(3-OCHF$_2$,4-TMS) | Ph(3-OC$_2$F$_5$,4-OMe) | Ph(3-TMS,4-OC$_2$F$_5$) |
| Ph(3-OCHF$_2$,4-CN) | Ph(3-OC$_2$F$_5$,4-OCF$_3$) | Ph(3-TMS,4-SO$_2$Me) |
| Ph(3-OCF$_2$CF$_2$H,4-Cl) | Ph(3-OC$_2$F$_5$,4-OCHF$_2$) | Ph(3,4-di-TMS) |
| Ph(3-OCF$_2$CF$_2$H,4-F) | Ph(3-OC$_2$F$_5$,4-OCF$_2$CF$_2$H) | Ph(3-TMS,4-CN) |
| Ph(3-OCF$_2$CF$_2$H,4-Br) | Ph(3,4-di-OC$_2$F$_5$) | Ph(3-CN,4-I) |
| Ph(3-OCF$_2$CF$_2$H,4-I) | Ph(3-OC$_2$F$_5$,4-SO$_2$Me) | Ph(3-CN,4-Et) |
| Ph(3-OCF$_2$CF$_2$H,4-Me) | Ph(3-OC$_2$F$_5$,4-TMS) | Ph(3-CN,4-n-Pr) |
| Ph(3-OCF$_2$CF$_2$H,4-Et) | Ph(3-OC$_2$F$_5$,4-CN) | Ph(3-CN,4-i-Pr) |
| Ph(3-OCF$_2$CF$_2$H,4-n-Pr) | Ph(3-SO$_2$Me,4-I) | Ph(3-CN,4-C$_2$F$_5$) |
| Ph(3-OCF$_2$CF$_2$H,4-t-Bu) | Ph(3-SO$_2$Me,4-Et) | Ph(3-CN,4-CF$_2$CF$_2$H) |
| Ph(3-OCF$_2$CF$_2$H,4-i-Pr) | Ph(3-SO$_2$Me,4-n-Pr) | Ph(3-CN,4-CF$_2$H) |
| Ph(3-OCF$_2$CF$_2$H,4-c-Pr) | Ph(3-SO$_2$Me,4-i-Pr) | Ph(3-CN,4-OMe) |
| Ph(3-CN,4-OCF$_2$CF$_2$H) | Ph(3-F,5-CF$_2$H) | Ph(3-I,5-n-Pr) |
| Ph(3-CN,4-OC$_2$F$_5$) | Ph(3-F,5-OMe) | Ph(3-I,5-t-Bu) |
| Ph(3,5-di-Cl) | Ph(3-F,5-OCF$_3$) | Ph(3-I,5-i-Pr) |
| Ph(3-Cl,5-F) | Ph(3-F,5-OCHF$_2$) | Ph(3-I,5-c-Pr) |
| Ph(3-Cl,5-Br) | Ph(3-F,5-OCF$_2$CF$_2$H) | Ph(3-I,5-CF$_3$) |
| Ph(3-Cl,5-I) | Ph(3-F,5-OC$_2$F$_5$) | Ph(3-I,5-C$_2$F$_5$) |
| Ph(3-Cl,5-Me) | Ph(3-F,5-SO$_2$Me) | Ph(3-I,5-CF$_2$CF$_2$H) |
| Ph(3-Cl,5-Et) | Ph(3-F,5-TMS) | Ph(3-I,5-CF$_2$H) |
| Ph(3-Cl,5-n-Pr) | Ph(3-F,5-CN) | Ph(3-I,5-OMe) |
| Ph(3-Cl,5-t-Bu) | Ph(3-Br,5-Cl) | Ph(3-I,5-OCF$_3$) |
| Ph(3-Cl,5-i-Pr) | Ph(3-Br,5-F) | Ph(3-I,5-OCHF$_2$) |
| Ph(3-Cl,5-c-Pr) | Ph(3,5-di-Br) | Ph(3-I,5-OCF$_2$CF$_2$H) |
| Ph(3-Cl,5-CF$_3$) | Ph(3-Br,5-I) | Ph(3-I,5-OC$_2$F$_5$) |
| Ph(3-Cl,5-C$_2$F$_5$) | Ph(3-Br,5-Me) | Ph(3-I,5-SO$_2$Me) |

-continued

| Q¹ | Q¹ | Q¹ |
|---|---|---|
| Ph(3-Cl,5-CF$_2$CF$_2$H) | Ph(3-Br,5-Et) | Ph(3-I,5-TMS) |
| Ph(3-Cl,5-CF$_2$H) | Ph(3-Br,5-n-Pr) | Ph(3-I,5-CN) |
| Ph(3-Cl,5-OMe) | Ph(3-Br,5-t-Bu) | Ph(3-Me,5-Cl) |
| Ph(3-Cl,5-OCF$_3$) | Ph(3-Br,5-i-Pr) | Ph(3-Me,5-F) |
| Ph(3-Cl,5-OCHF$_2$) | Ph(3-Br,5-c-Pr) | Ph(3-Me,5-Br) |
| Ph(3-Cl,5-OCF$_2$CF$_2$H) | Ph(3-Br,5-CF$_3$) | Ph(3-Me,5-I) |
| Ph(3-Cl,5-OC$_2$F$_5$) | Ph(3-Br,5-C$_2$F$_5$) | Ph(3,5-di-Me) |
| Ph(3-Cl,5-SO$_2$Me) | Ph(3-Br,5-CF$_2$CF$_2$H) | Ph(3-Me,5-Et) |
| Ph(3-Cl,5-TMS) | Ph(3-Br,5-CF$_2$H) | Ph(3-Me,5-n-Pr) |
| Ph(3-Cl,5-CN) | Ph(3-Br,5-OMe) | Ph(3-Me,5-t-Bu) |
| Ph(3-F,5-Cl) | Ph(3-Br,5-OCF$_3$) | Ph(3-Me,5-i-Pr) |
| Ph(3,5-di-F) | Ph(3-Br,5-OCHF$_2$) | Ph(3-Me,5-c-Pr) |
| Ph(3-F,5-Br) | Ph(3-Br,5-OCF$_2$CF$_2$H) | Ph(3-Me,5-CF$_3$) |
| Ph(3-F,5-I) | Ph(3-Br,5-OC$_2$F$_5$) | Ph(3-Me,5-C$_2$F$_5$) |
| Ph(3-F,5-Me) | Ph(3-Br,5-SO$_2$Me) | Ph(3-Me,5-CF$_2$CF$_2$H) |
| Ph(3-F,5-Et) | Ph(3-Br,5-TMS) | Ph(3-Me,5-CF$_2$H) |
| Ph(3-F,5-n-Pr) | Ph(3-Br,5-CN) | Ph(3-Me,5-OMe) |
| Ph(3-F,5-t-Bu) | Ph(3-I,5-Cl) | Ph(3-Me,5-OCF$_3$) |
| Ph(3-F,5-i-Pr) | Ph(3-I,5-F) | Ph(3-Me,5-OCHF$_2$) |
| Ph(3-F,5-c-Pr) | Ph(3-I,5-Br) | Ph(3-Me,5-OCF$_2$CF$_2$H) |
| Ph(3-F,5-CF$_3$) | Ph(3,5-di-I) | Ph(3-Me,5-OC$_2$F$_5$) |
| Ph(3-F,5-C$_2$F$_5$) | Ph(3-I,5-Me) | Ph(3-Me,5-SO$_2$Me) |
| Ph(3-F,5-CF$_2$CF$_2$H) | Ph(3-I,5-Et) | Ph(3-Me,5-TMS) |
| Ph(3-Me,5-CN) | Ph(3-n-Pr,5-OMe) | Ph(3-i-Pr,5-t-Bu) |
| Ph(3-Et,5-Cl) | Ph(3-n-Pr,5-OCF$_3$) | Ph(3,5-di-i-Pr) |
| Ph(3-Et,5-F) | Ph(3-n-Pr,5-OCHF$_2$) | Ph(3-i-Pr,5-c-Pr) |
| Ph(3-Et,5-Br) | Ph(3-n-Pr,5-OCF$_2$CF$_2$H) | Ph(3-i-Pr,5-CF$_3$) |
| Ph(3-Et,5-I) | Ph(3-n-Pr,5-OC$_2$F$_5$) | Ph(3-i-Pr,5-C$_2$F$_5$) |
| Ph(3-Et,5-Me) | Ph(3-n-Pr,5-SO$_2$Me) | Ph(3-i-Pr,5-CF$_2$CF$_2$H) |
| Ph(3,5-di-Et) | Ph(3-n-Pr,5-TMS) | Ph(3-i-Pr,5-CF$_2$H) |
| Ph(3-Et,5-n-Pr) | Ph(3-n-Pr,5-CN) | Ph(3-i-Pr,5-OMe) |
| Ph(3-Et,5-t-Bu) | Ph(3-t-Bu,5-Cl) | Ph(3-i-Pr,5-OCF$_3$) |
| Ph(3-Et,5-i-Pr) | Ph(3-t-Bu,5-F) | Ph(3-i-Pr,5-OCHF$_2$) |
| Ph(3-Et,5-c-Pr) | Ph(3-t-Bu,5-Br) | Ph(3-i-Pr,5-OCF$_2$CF$_2$H) |
| Ph(3-Et,5-CF$_3$) | Ph(3-t-Bu,5-I) | Ph(3-i-Pr,5-OC$_2$F$_5$) |
| Ph(3-Et,5-C$_2$F$_5$) | Ph(3-t-Bu,5-Me) | Ph(3-i-Pr,5-SO$_2$Me) |
| Ph(3-Et,5-CF$_2$CF$_2$H) | Ph(3-t-Bu,5-Et) | Ph(3-i-Pr,5-TMS) |
| Ph(3-Et,5-CF$_2$H) | Ph(3-t-Bu,5-n-Pr) | Ph(3-i-Pr,5-CN) |
| Ph(3-Et,5-OMe) | Ph(3,5-di-t-Bu) | Ph(3-c-Pr,5-Cl) |
| Ph(3-Et,5-OCF$_3$) | Ph(3-t-Bu,5-i-Pr) | Ph(3-c-Pr,5-F) |
| Ph(3-Et,5-OCHF$_2$) | Ph(3-t-Bu,5-c-Pr) | Ph(3-c-Pr,5-Br) |
| Ph(3-Et,5-OCF$_2$CF$_2$H) | Ph(3-t-Bu,5-CF$_3$) | Ph(3-c-Pr,5-I) |
| Ph(3-Et,5-OC$_2$F$_5$) | Ph(3-t-Bu,5-C$_2$F$_5$) | Ph(3-c-Pr,5-Me) |
| Ph(3-Et,5-SO$_2$Me) | Ph(3-t-Bu,5-CF$_2$CF$_2$H) | Ph(3-c-Pr,5-Et) |
| Ph(3-Et,5-TMS) | Ph(3-t-Bu,5-CF$_2$H) | Ph(3-c-Pr,5-n-Pr) |
| Ph(3-Et,5-CN) | Ph(3-t-Bu,5-OMe) | Ph(3-c-Pr,5-t-Bu) |
| Ph(3-n-Pr,5-Cl) | Ph(3-t-Bu,5-OCF$_3$) | Ph(3-c-Pr,5-i-Pr) |
| Ph(3-n-Pr,5-F) | Ph(3-t-Bu,5-OCHF$_2$) | Ph(3,5-di-c-Pr) |
| Ph(3-n-Pr,5-Br) | Ph(3-t-Bu,5-OCF$_2$CF$_2$H) | Ph(3-c-Pr,5-CF$_3$) |
| Ph(3-n-Pr,5-I) | Ph(3-t-Bu,5-OC$_2$F$_5$) | Ph(3-c-Pr,5-C$_2$F$_5$) |
| Ph(3-n-Pr,5-Me) | Ph(3-t-Bu,5-SO$_2$Me) | Ph(3-c-Pr,5-CF$_2$CF$_2$H) |
| Ph(3-n-Pr,5-Et) | Ph(3-t-Bu,5-TMS) | Ph(3-c-Pr,5-CF$_2$H) |
| Ph(3,5-di-n-Pr) | Ph(3-t-Bu,5-CN) | Ph(3-c-Pr,5-OMe) |
| Ph(3-n-Pr,5-t-Bu) | Ph(3-i-Pr,5-Cl) | Ph(3-c-Pr,5-OCF$_3$) |
| Ph(3-n-Pr,5-i-Pr) | Ph(3-i-Pr,5-F) | Ph(3-c-Pr,5-OCHF$_2$) |
| Ph(3-n-Pr,5-c-Pr) | Ph(3-i-Pr,5-Br) | Ph(3-c-Pr,5-OCF$_2$CF$_2$H) |
| Ph(3-n-Pr,5-CF$_3$) | Ph(3-i-Pr,5-I) | Ph(3-c-Pr,5-OC$_2$F$_5$) |
| Ph(3-n-Pr,5-C$_2$F$_5$) | Ph(3-i-Pr,5-Me) | Ph(3-c-Pr,5-SO$_2$Me) |
| Ph(3-n-Pr,5-CF$_2$CF$_2$H) | Ph(3-i-Pr,5-Et) | Ph(3-c-Pr,5-TMS) |
| Ph(3-n-Pr,5-CF$_2$H) | Ph(3-i-Pr,5-n-Pr) | Ph(3-c-Pr,5-CN) |
| Ph(3-CF$_3$,5-Cl) | Ph(3-C$_2$F$_5$,5-OCF$_3$) | Ph(3-CF$_2$H,5-i-Pr) |
| Ph(3-CF$_3$,5-F) | Ph(3-C$_2$F$_5$,5-OCHF$_2$) | Ph(3-CF$_2$H,5-c-Pr) |
| Ph(3-CF$_3$,5-Br) | Ph(3-C$_2$F$_5$,5-OCF$_2$CF$_2$H) | Ph(3-CF$_2$H,5-CF$_3$) |
| Ph(3-CF$_3$,5-I) | Ph(3-C$_2$F$_5$,5-OC$_2$F$_5$) | Ph(3-CF$_2$H,5-C$_2$F$_5$) |
| Ph(3-CF$_3$,5-Me) | Ph(3-C$_2$F$_5$,5-SO$_2$Me) | Ph(3-CF$_2$H,5-CF$_2$CF$_2$H) |
| Ph(3-CF$_3$,5-Et) | Ph(3-C$_2$F$_5$,5-TMS) | Ph(3,5-di-CF$_2$H) |
| Ph(3-CF$_3$,5-n-Pr) | Ph(3-C$_2$F$_5$,5-CN) | Ph(3-CF$_2$H,5-OMe) |
| Ph(3-CF$_3$,5-t-Bu) | Ph(3-CF$_2$CF$_2$H,5-Cl) | Ph(3-CF$_2$H,5-OCF$_3$) |
| Ph(3-CF$_3$,5-i-Pr) | Ph(3-CF$_2$CF$_2$H,5-F) | Ph(3-CF$_2$H,5-OCHF$_2$) |
| Ph(3-CF$_3$,5-c-Pr) | Ph(3-CF$_2$CF$_2$H,5-Br) | Ph(3-CF$_2$H,5-OCF$_2$CF$_2$H) |
| Ph(3,5-di-CF$_3$) | Ph(3-CF$_2$CF$_2$H,5-I) | Ph(3-CF$_2$H,5-OC$_2$F$_5$) |
| Ph(3-CF$_3$,5-C$_2$F$_5$) | Ph(3-CF$_2$CF$_2$H,5-Me) | Ph(3-CF$_2$H,5-SO$_2$Me) |
| Ph(3-CF$_3$,5-CF$_2$CF$_2$H) | Ph(3-CF$_2$CF$_2$H,5-Et) | Ph(3-CF$_2$H,5-TMS) |
| Ph(3-CF$_3$,5-CF$_2$H) | Ph(3-CF$_2$CF$_2$H,5-n-Pr) | Ph(3-CF$_2$H,5-CN) |
| Ph(3-CF$_3$,5-OMe) | Ph(3-CF$_2$CF$_2$H,5-t-Bu) | Ph(3-OMe,5-Cl) |
| Ph(3-CF$_3$,5-OCF$_3$) | Ph(3-CF$_2$CF$_2$H,5-i-Pr) | Ph(3-OMe,5-F) |
| Ph(3-CF$_3$,5-OCHF$_2$) | Ph(3-CF$_2$CF$_2$H,5-c-Pr) | Ph(3-OMe,5-Br) |

-continued

| Q¹ | Q¹ | Q¹ |
|---|---|---|
| Ph(3-CF₃,5-OCF₂CF₂H) | Ph(3-CF₂CF₂H,5-CF₃) | Ph(3-OMe,5-I) |
| Ph(3-CF₃,5-OC₂F₅) | Ph(3-CF₂CF₂H,5-C₂F₅) | Ph(3-OMe,5-Me) |
| Ph(3-CF₃,5-SO₂Me) | Ph(3,5-di-CF₂CF₂H) | Ph(3-OMe,5-Et) |
| Ph(3-CF₃,5-TMS) | Ph(3-CF₂CF₂H,5-CF₂H) | Ph(3-OMe,5-n-Pr) |
| Ph(3-CF₃,5-CN) | Ph(3-CF₂CF₂H,5-OMe) | Ph(3-OMe,5-t-Bu) |
| Ph(3-C₂F₅,5-Cl) | Ph(3-CF₂CF₂H,5-OCF₃) | Ph(3-OMe,5-i-Pr) |
| Ph(3-C₂F₅,5-F) | Ph(3-CF₂CF₂H,5-OCHF₂) | Ph(3-OMe,5-c-Pr) |
| Ph(3-C₂F₅,5-Br) | Ph(3-CF₂CF₂H,5-OCF₂CF₂H) | Ph(3-OMeCF₃,5-CF₃) |
| Ph(3-C₂F₅,5-I) | Ph(3-CF₂CF₂H,5-OC₂F₅) | Ph(3-OMe,5-C₂F₅) |
| Ph(3-C₂F₅,5-Me) | Ph(3-CF₂CF₂H,5-SO₂Me) | Ph(3-OMe,5-CF₂CF₂H) |
| Ph(3-C₂F₅,5-Et) | Ph(3-CF₂CF₂H,5-TMS) | Ph(3-OMe,5-CF₂H) |
| Ph(3-C₂F₅,5-n-Pr) | Ph(3-CF₂CF₂H,5-CN) | Ph(3,5-di-OMe) |
| Ph(3-C₂F₅,5-t-Bu) | Ph(3-CF₂H,5-Cl) | Ph(3-OMe,5-OCF₃) |
| Ph(3-C₂F₅,5-i-Pr) | Ph(3-CF₂H,5-F) | Ph(3-OMe,5-OCHF₂) |
| Ph(3-C₂F₅,5-c-Pr) | Ph(3-CF₂H,5-Br) | Ph(3-OMe,5-OCF₂CF₂H) |
| Ph(3-C₂F₅CF₃,5-CF₃) | Ph(3-CF₂H,5-I) | Ph(3-OMe,5-OC₂F₅) |
| Ph(3,5-di-C₂F₅) | Ph(3-CF₂H,5-Me) | Ph(3-OMe,5-SO₂Me) |
| Ph(3-C₂F₅,5-CF₂CF₂H) | Ph(3-CF₂H,5-Et) | Ph(3-OMe,5-TMS) |
| Ph(3-C₂F₅,5-CF₂H) | Ph(3-CF₂H,5-n-Pr) | Ph(3-OMe,5-CN) |
| Ph(3-C₂F₅,5-OMe) | Ph(3-CF₂H,5-t-Bu) | Ph(3-OCF₃,5-Cl) |
| Ph(3-OCF₃,5-F) | Ph(3,5-di-OCHF₂) | Ph(3-OC₂F₅,5-c-Pr) |
| Ph(3-OCF₃,5-Br) | Ph(3-OCHF₂,5-OCF₂CF₂H) | Ph(3-OC₂F₅CF₃,5-CF₃) |
| Ph(3-OCF₃,5-I) | Ph(3-OCHF₂,5-OC₂F₅) | Ph(3-OC₂F₅,5-CF₂CF₂H) |
| Ph(3-OCF₃,5-Me) | Ph(3-OCHF₂,5-SO₂Me) | Ph(3-OC₂F₅,5-CF₂H) |
| Ph(3-OCF₃,5-Et) | Ph(3-OCHF₂,5-TMS) | Ph(3-OC₂F₅,5-OMe) |
| Ph(3-OCF₃,5-n-Pr) | Ph(3-OCHF₂,5-CN) | Ph(3-OC₂F₅,5-OCF₃) |
| Ph(3-OCF₃,5-t-Bu) | Ph(3-OCF₂CF₂H,5-Cl) | Ph(3-OC₂F₅,5-OCHF₂) |
| Ph(3-OCF₃,5-i-Pr) | Ph(3-OCF₂CF₂H,5-F) | Ph(3,5-di-OC₂F₅) |
| Ph(3-OCF₃,5-c-Pr) | Ph(3-OCF₂CF₂H,5-Br) | Ph(3,5-di-OC₂F₅) |
| Ph(3-OCF₃,5-CF₃) | Ph(3-OCF₂CF₂H,5-I) | Ph(3-OC₂F₅,5-SO₂Me) |
| Ph(3-OCF₃,5-C₂F₅) | Ph(3-OCF₂CF₂H,5-Me) | Ph(3-OC₂F₅,5-TMS) |
| Ph(3-OCF₃,5-CF₂CF₂H) | Ph(3-OCF₂CF₂H,5-Et) | Ph(3-OC₂F₅,5-CN) |
| Ph(3-OCF₃,5-CF₂H) | Ph(3-OCF₂CF₂H,5-n-Pr) | Ph(3-SO₂Me,5-Cl) |
| Ph(3-OCF₃,5-OMe) | Ph(3-OCF₂CF₂H,5-t-Bu) | Ph(3-SO₂Me,5-F) |
| Ph(3,5-di-OCF₃) | Ph(3-OCF₂CF₂H,5-i-Pr) | Ph(3-SO₂Me,5-Br) |
| Ph(3-OCF₃,5-OCHF₂) | Ph(3-OCF₂CF₂H,5-c-Pr) | Ph(3-SO₂Me,5-I) |
| Ph(3-OCF₃,5-OCF₂CF₂H) | Ph(3-OCF₂CF₂H,5-CF₃) | Ph(3-SO₂Me,5-Me) |
| Ph(3-OCF₃,5-OC₂F₅) | Ph(3-OCF₂CF₂H,5-C₂F₅) | Ph(3-SO₂Me,5-Et) |
| Ph(3-OCF₃,5-SO₂Me) | Ph(3-OCF₂CF₂H,5-CF₂CF₂H) | Ph(3-SO₂Me,5-n-Pr) |
| Ph(3-OCF₃,5-TMS) | Ph(3-OCF₂CF₂H,5-CF₂H) | Ph(3-SO₂Me,5-t-Bu) |
| Ph(3-OCF₃,5-CN) | Ph(3-OCF₂CF₂H,5-OMe) | Ph(3-SO₂Me,5-i-Pr) |
| Ph(3-OCHF₂,5-Cl) | Ph(3-OCF₂CF₂H,5-OCF₃) | Ph(3-SO₂Me,5-c-Pr) |
| Ph(3-OCHF₂,5-F) | Ph(3-OCF₂CF₂H,5-OCHF₂) | Ph(3-SO₂MeCF₃,5-CF₃) |
| Ph(3-OCHF₂,5-Br) | Ph(3,5-di-OCF₂CF₂H) | Ph(3-SO₂Me,5-C₂F₅) |
| Ph(3-OCHF₂,5-I) | Ph(3-OCF₂CF₂H,5-OC₂F₅) | Ph(3-SO₂Me,5-CF₂CF₂H) |
| Ph(3-OCHF₂,5-Me) | Ph(3-OCF₂CF₂H,5-SO₂Me) | Ph(3-SO₂Me,5-CF₂H) |
| Ph(3-OCHF₂,5-Et) | Ph(3-OCF₂CF₂H,5-TMS) | Ph(3-SO₂Me,5-OMe) |
| Ph(3-OCHF₂,5-n-Pr) | Ph(3-OCF₂CF₂H,5-CN) | Ph(3-SO₂Me,5-OCF₃) |
| Ph(3-OCHF₂,5-t-Bu) | Ph(3-OC₂F₅,5-Cl) | Ph(3-SO₂Me,5-OCHF₂) |
| Ph(3-OCHF₂,5-i-Pr) | Ph(3-OC₂F₅,5-F) | Ph(3-SO₂Me,5-OCF₂CF₂H) |
| Ph(3-OCHF₂,5-c-Pr) | Ph(3-OC₂F₅,5-Br) | Ph(3-SO₂Me,5-OC₂F₅) |
| Ph(3-OCHF₂CF₃,5-CF₃) | Ph(3-OC₂F₅,5-I) | Ph(3,5-di-SO₂Me) |
| Ph(3-OC₂F₅,5-C₂F₅) | Ph(3-OC₂F₅,5-Me) | Ph(3-SO₂Me,5-TMS) |
| Ph(3-OCHF₂,5-CF₂CF₂H) | Ph(3-OC₂F₅,5-Et) | Ph(3-SO₂Me,5-CN) |
| Ph(3-OCHF₂,5-CF₂H) | Ph(3-OC₂F₅,5-n-Pr) | Ph(3-TMS,5-Cl) |
| Ph(3-OCHF₂,5-OMe) | Ph(3-OC₂F₅,5-t-Bu) | Ph(3-TMS,5-F) |
| Ph(3-OCHF₂,5-OCF₃) | Ph(3-OC₂F₅,5-i-Pr) | Ph(3-TMS,5-Br) |
| Ph(3-TMS,5-I) | Ph(3-CN,5-OC₂F₅) | Ph(2-Cl,3-F,4-C₂F₅) |
| Ph(3-TMS,5-Me) | Ph(3-CN,5-SO₂Me) | Ph(2-Cl,3-F,4-CF₂CF₂H) |
| Ph(3-TMS,5-Et) | Ph(3-CN,5-TMS) | Ph(2-Cl,3-F,4-CF₂H) |
| Ph(3-TMS,5-n-Pr) | Ph(3,5-di-CN) | Ph(2-Cl,3-F,4-OMe) |
| Ph(3-TMS,5-t-Bu) | Ph(2,3,4-tri-Cl) | Ph(2-Cl,3-F,4-OCF₃) |
| Ph(3-TMS,5-i-Pr) | Ph(2-Cl,3-Cl,4-F) | Ph(2-Cl,3-F,4-OCHF₂) |
| Ph(3-TMS,5-c-Pr) | Ph(2-Cl,3-Cl,4-Br) | Ph(2-Cl,3-F,4-OCF₂CF₂H) |
| Ph(3-TMS,5-CF₃) | Ph(2-Cl,3-Cl,4-I) | Ph(2-Cl,3-F,4-OC₂F₅) |
| Ph(3-TMS,5-C₂F₅) | Ph(2-Cl,3-Cl,4-Me) | Ph(2-Cl,3-F,4-SO₂Me) |
| Ph(3-TMS,5-CF₂CF₂H) | Ph(2-Cl,3-Cl,4-Et) | Ph(2-Cl,3-F,4-TMS) |
| Ph(3-TMS,5-CF₂H) | Ph(2-Cl,3-Cl,4-n-Pr) | Ph(2-Cl,3-F,4-CN) |
| Ph(3-TMS,5-OMe) | Ph(2-Cl,3-Cl,4-t-Bu) | Ph(2-Cl,3-Br,4-Cl) |
| Ph(3-TMS,5-OCF₃) | Ph(2-Cl,3-Cl,4-i-Pr) | Ph(2-Cl,3-Br,4-F) |
| Ph(3-TMS,5-OCHF₂) | Ph(2-Cl,3-Cl,4-c-Pr) | Ph(2-Cl,3,4-di-Br) |
| Ph(3-TMS,5-OCF₂CF₂H) | Ph(2-Cl,3-Cl,4-CF₃) | Ph(2-Cl,3-Br,4-I) |
| Ph(3-TMS,5-OC₂F₅) | Ph(2-Cl,3-Cl,4-C₂F₅) | Ph(2-Cl,3-Br,4-Me) |
| Ph(3-TMS,5-SO₂Me) | Ph(2-Cl,3-Cl,4-CF₂CF₂H) | Ph(2-Cl,3-Br,4-Et) |
| Ph(3,5-di-TMS) | Ph(2-Cl,3-Cl,4-CF₂H) | Ph(2-Cl,3-Br,4-n-Pr) |
| Ph(3-TMS,5-CN) | Ph(2-Cl,3-Cl,4-OMe) | Ph(2-Cl,3-Br,4-t-Bu) |
| Ph(3-CN,5-Cl) | Ph(2-Cl,3-Cl,4-OCF₃) | Ph(2-Cl,3-Br,4-i-Pr) |

-continued

| Q¹ | Q¹ | Q¹ |
|---|---|---|
| Ph(3-CN,5-F) | Ph(2-Cl,3-Cl,4-OCHF₂) | Ph(2-Cl,3-Br,4-c-Pr) |
| Ph(3-CN,5-Br) | Ph(2-Cl,3-Cl,4-OCF₂CF₂H) | Ph(2-Cl,3-Br,4-CF₃) |
| Ph(3-CN,5-I) | Ph(2-Cl,3-Cl,4-OC₂F₅) | Ph(2-Cl,3-Br,4-C₂F₅) |
| Ph(3-CN,5-Me) | Ph(2-Cl,3-Cl,4-SO₂Me) | Ph(2-Cl,3-Br,4-CF₂CF₂H) |
| Ph(3-CN,5-Et) | Ph(2-Cl,3-Cl,4-TMS) | Ph(2-Cl,3-Br,4-CF₂H) |
| Ph(3-CN,5-n-Pr) | Ph(2-Cl,3-Cl,4-CN) | Ph(2-Cl,3-Br,4-OMe) |
| Ph(3-CN,5-t-Bu) | Ph(2-Cl,3-F,4-Cl) | Ph(2-Cl,3-Br,4-OCF₃) |
| Ph(3-CN,5-i-Pr) | Ph(2-Cl,3,4-di-F) | Ph(2-Cl,3-Br,4-OCHF₂) |
| Ph(3-CN,5-c-Pr) | Ph(2-Cl,3-F,4-Br) | Ph(2-Cl,3-Br,4-OCF₂CF₂H) |
| Ph(3-CN,5-CF₃) | Ph(2-Cl,3-F,4-I) | Ph(2-Cl,3-Br,4-OC₂F₅) |
| Ph(3-CN,5-C₂F₅) | Ph(2-Cl,3-F,4-Me) | Ph(2-Cl,3-Br,4-SO₂Me) |
| Ph(3-CN,5-CF₂CF₂H) | Ph(2-Cl,3-F,4-Et) | Ph(2-Cl,3-Br,4-TMS) |
| Ph(3-CN,5-CF₂H) | Ph(2-Cl,3-F,4-n-Pr) | Ph(2-Cl,3-Br,4-CN) |
| Ph(3-CN,5-OMe) | Ph(2-Cl,3-F,4-t-Bu) | Ph(2-Cl,3-I,4-Cl) |
| Ph(3-CN,5-OCF₃) | Ph(2-Cl,3-F,4-i-Pr) | Ph(2-Cl,3-I,4-F) |
| Ph(3-CN,5-OCHF₂) | Ph(2-Cl,3-F,4-c-Pr) | Ph(2-Cl,3-I,4-Br) |
| Ph(3-CN,5-OCF₂CF₂H) | Ph(2-Cl,3-F,4-CF₃) | Ph(2-Cl,3,4-di-I) |
| Ph(2-Cl,3-I,4-Me) | Ph(2-Cl,3-Me,4-SO₂Me) | Ph(2-Cl,3-n-Pr,4-CF₂CF₂H) |
| Ph(2-Cl,3-I,4-Et) | Ph(2-Cl,3-Me,4-TMS) | Ph(2-Cl,3-n-Pr,4-CF₂H) |
| Ph(2-Cl,3-I,4-n-Pr) | Ph(2-Cl,3-Me,4-CN) | Ph(2-Cl,3-n-Pr,4-OMe) |
| Ph(2-Cl,3-I,4-t-Bu) | Ph(2-Cl,3-Et,4-Cl) | Ph(2-Cl,3-n-Pr,4-OCF₃) |
| Ph(2-Cl,3-I,4-i-Pr) | Ph(2-Cl,3-Et,4-F) | Ph(2-Cl,3-n-Pr,4-OCHF₂) |
| Ph(2-Cl,3-I,4-c-Pr) | Ph(2-Cl,3-Et,4-Br) | Ph(2-Cl,3-n-Pr,4-OCF₂CF₂H) |
| Ph(2-Cl,3-I,4-CF₃) | Ph(2-Cl,3-Et,4-I) | Ph(2-Cl,3-n-Pr,4-OC₂F₅) |
| Ph(2-Cl,3-I,4-C₂F₅) | Ph(2-Cl,3-Et,4-Me) | Ph(2-Cl,3-n-Pr,4-SO₂Me) |
| Ph(2-Cl,3-I,4-CF₂CF₂H) | Ph(2-Cl,3,4-di-Et) | Ph(2-Cl,3-n-Pr,4-TMS) |
| Ph(2-Cl,3-I,4-CF₂H) | Ph(2-Cl,3-Et,4-n-Pr) | Ph(2-Cl,3-n-Pr,4-CN) |
| Ph(2-Cl,3-I,4-OMe) | Ph(2-Cl,3-Et,4-t-Bu) | Ph(2-Cl,3-t-Bu,4-Cl) |
| Ph(2-Cl,3-I,4-OCF₃) | Ph(2-Cl,3-Et,4-i-Pr) | Ph(2-Cl,3-t-Bu,4-F) |
| Ph(2-Cl,3-I,4-OCHF₂) | Ph(2-Cl,3-Et,4-c-Pr) | Ph(2-Cl,3-t-Bu,4-Br) |
| Ph(2-Cl,3-I,4-OCF₂CF₂H) | Ph(2-Cl,3-Et,4-CF₃) | Ph(2-Cl,3-t-Bu,4-I) |
| Ph(2-Cl,3-I,4-OC₂F₅) | Ph(2-Cl,3-Et,4-C₂F₅) | Ph(2-Cl,3-t-Bu,4-Me) |
| Ph(2-Cl,3-I,4-SO₂Me) | Ph(2-Cl,3-Et,4-CF₂CF₂H) | Ph(2-Cl,3-t-Bu,4-Et) |
| Ph(2-Cl,3-I,4-TMS) | Ph(2-Cl,3-Et,4-CF₂H) | Ph(2-Cl,3-t-Bu,4-n-Pr) |
| Ph(2-Cl,3-I,4-CN) | Ph(2-Cl,3-Et,4-OMe) | Ph(2-Cl,3,4-di-t-Bu) |
| Ph(2-Cl,3-Me,4-Cl) | Ph(2-Cl,3-Et,4-OCF₃) | Ph(2-Cl,3-t-Bu,4-i-Pr) |
| Ph(2-Cl,3-Me,4-F) | Ph(2-Cl,3-Et,4-OCHF₂) | Ph(2-Cl,3-t-Bu,4-c-Pr) |
| Ph(2-Cl,3-Me,4-Br) | Ph(2-Cl,3-Et,4-OCF₂CF₂H) | Ph(2-Cl,3-t-Bu,4-CF₃) |
| Ph(2-Cl,3-Me,4-I) | Ph(2-Cl,3-Et,4-OC₂F₅) | Ph(2-Cl,3-t-Bu,4-C₂F₅) |
| Ph(2-Cl,3,4-di-Me) | Ph(2-Cl,3-Et,4-SO₂Me) | Ph(2-Cl,3-t-Bu,4-CF₂CF₂H) |
| Ph(2-Cl,3-Me,4-Et) | Ph(2-Cl,3-Et,4-TMS) | Ph(2-Cl,3-t-Bu,4-CF₂H) |
| Ph(2-Cl,3-Me,4-n-Pr) | Ph(2-Cl,3-Et,4-CN) | Ph(2-Cl,3-t-Bu,4-OMe) |
| Ph(2-Cl,3-Me,4-t-Bu) | Ph(2-Cl,3-n-Pr,4-Cl) | Ph(2-Cl,3-t-Bu,4-OCF₃) |
| Ph(2-Cl,3-Me,4-i-Pr) | Ph(2-Cl,3-n-Pr,4-F) | Ph(2-Cl,3-t-Bu,4-OCHF₂) |
| Ph(2-Cl,3-Me,4-c-Pr) | Ph(2-Cl,3-n-Pr,4-Br) | Ph(2-Cl,3-t-Bu,4-OCF₂CF₂H) |
| Ph(2-Cl,3-Me,4-CF₃) | Ph(2-Cl,3-n-Pr,4-I) | Ph(2-Cl,3-t-Bu,4-OC₂F₅) |
| Ph(2-Cl,3-Me,4-C₂F₅) | Ph(2-Cl,3-n-Pr,4-Me) | Ph(2-Cl,3-t-Bu,4-SO₂Me) |
| Ph(2-Cl,3-Me,4-CF₂CF₂H) | Ph(2-Cl,3-n-Pr,4-Et) | Ph(2-Cl,3-t-Bu,4-TMS) |
| Ph(2-Cl,3-Me,4-CF₂H) | Ph(2-Cl,3,4-di-n-Pr) | Ph(2-Cl,3-t-Bu,4-CN) |
| Ph(2-Cl,3-Me,4-OMe) | Ph(2-Cl,3-n-Pr,4-t-Bu) | Ph(2-Cl,3-i-Pr,4-Cl) |
| Ph(2-Cl,3-Me,4-OCF₃) | Ph(2-Cl,3-n-Pr,4-i-Pr) | Ph(2-Cl,3-i-Pr,4-F) |
| Ph(2-Cl,3-Me,4-OCHF₂) | Ph(2-Cl,3-n-Pr,4-c-Pr) | Ph(2-Cl,3-i-Pr,4-Br) |
| Ph(2-Cl,3-Me,4-OCF₂CF₂H) | Ph(2-Cl,3-n-Pr,4-CF₃) | Ph(2-Cl,3-i-Pr,4-I) |
| Ph(2-Cl,3-Me,4-OC₂F₅) | Ph(2-Cl,3-n-Pr,4-C₂F₅) | Ph(2-Cl,3-i-Pr,4-Me) |
| Ph(2-Cl,3-i-Pr,4-Et) | Ph(2-Cl,3-c-Pr,4-TMS) | Ph(2-Cl,3-C₂F₅,4-CF₂H) |
| Ph(2-Cl,3-i-Pr,4-n-Pr) | Ph(2-Cl,3-c-Pr,4-CN) | Ph(2-Cl,3-C₂F₅,4-OMe) |
| Ph(2-Cl,3-i-Pr,4-t-Bu) | Ph(2-Cl,3-CF₃,4-Cl) | Ph(2-Cl,3-C₂F₅,4-OCF₃) |
| Ph(2-Cl,3,4-di-i-Pr) | Ph(2-Cl,3-CF₃,4-F) | Ph(2-Cl,3-C₂F₅,4-OCHF₂) |
| Ph(2-Cl,3-i-Pr,4-c-Pr) | Ph(2-Cl,3-CF₃,4-Br) | Ph(2-Cl,3-C₂F₅,4-OCF₂CF₂H) |
| Ph(2-Cl,3-i-Pr,4-CF₃) | Ph(2-Cl,3-CF₃,4-I) | Ph(2-Cl,3-C₂F₅,4-OC₂F₅) |
| Ph(2-Cl,3-i-Pr,4-C₂F₅) | Ph(2-Cl,3-CF₃,4-Me) | Ph(2-Cl,3-C₂F₅,4-SO₂Me) |
| Ph(2-Cl,3-i-Pr,4-CF₂CF₂H) | Ph(2-Cl,3-CF₃,4-Et) | Ph(2-Cl,3-C₂F₅,4-TMS) |
| Ph(2-Cl,3-i-Pr,4-CF₂H) | Ph(2-Cl,3-CF₃,4-n-Pr) | Ph(2-Cl,3-C₂F₅,4-CN) |
| Ph(2-Cl,3-i-Pr,4-OMe) | Ph(2-Cl,3-CF₃,4-t-Bu) | Ph(2-Cl,3-CF₂CF₂H,4-Cl) |
| Ph(2-Cl,3-i-Pr,4-OCF₃) | Ph(2-Cl,3-CF₃,4-i-Pr) | Ph(2-Cl,3-CF₂CF₂H,4-F) |
| Ph(2-Cl,3-i-Pr,4-OCHF₂) | Ph(2-Cl,3-CF₃,4-c-Pr) | Ph(2-Cl,3-CF₂CF₂H,4-Br) |
| Ph(2-Cl,3-i-Pr,4-OCF₂CF₂H) | Ph(2-Cl,3,4-di-CF₃) | Ph(2-Cl,3-CF₂CF₂H,4-I) |
| Ph(2-Cl,3-i-Pr,4-OC₂F₅) | Ph(2-Cl,3-CF₃,4-C₂F₅) | Ph(2-Cl,3-CF₂CF₂H,4-Me) |
| Ph(2-Cl,3-i-Pr,4-SO₂Me) | Ph(2-Cl,3-CF₃,4-CF₂CF₂H) | Ph(2-Cl,3-CF₂CF₂H,4-Et) |
| Ph(2-Cl,3-i-Pr,4-TMS) | Ph(2-Cl,3-CF₃,4-CF₂H) | Ph(2-Cl,3-CF₂CF₂H,4-n-Pr) |
| Ph(2-Cl,3-i-Pr,4-CN) | Ph(2-Cl,3-CF₃,4-OMe) | Ph(2-Cl,3-CF₂CF₂H,4-t-Bu) |
| Ph(2-Cl,3-c-Pr,4-Cl) | Ph(2-Cl,3-CF₃,4-OCF₃) | Ph(2-Cl,3-CF₂CF₂H,4-i-Pr) |
| Ph(2-Cl,3-c-Pr,4-F) | Ph(2-Cl,3-CF₃,4-OCHF₂) | Ph(2-Cl,3-CF₂CF₂H,4-c-Pr) |
| Ph(2-Cl,3-c-Pr,4-Br) | Ph(2-Cl,3-CF₃,4-OCF₂CF₂H) | Ph(2-Cl,3-CF₂CF₂H,4-CF₃) |
| Ph(2-Cl,3-c-Pr,4-I) | Ph(2-Cl,3-CF₃,4-OC₂F₅) | Ph(2-Cl,3-CF₂CF₂H,4-C₂F₅) |
| Ph(2-Cl,3-c-Pr,4-Me) | Ph(2-Cl,3-CF₃,4-SO₂Me) | Ph(2-Cl,3,4-di-CF₂CF₂H) |
| Ph(2-Cl,3-c-Pr,4-Et) | Ph(2-Cl,3-CF₃,4-TMS) | Ph(2-Cl,3-CF₂CF₂H,4-CF₂H) |

| Q¹ | Q¹ | Q¹ |
|---|---|---|
| Ph(2-Cl,3-c-Pr,4-n-Pr) | Ph(2-Cl,3-CF$_3$,4-CN) | Ph(2-Cl,3-CF$_2$CF$_2$H,4-OMe) |
| Ph(2-Cl,3-c-Pr,4-t-Bu) | Ph(2-Cl,3-C$_2$F$_5$,4-Cl) | Ph(2-Cl,3-CF$_2$CF$_2$H,4-OCF$_3$) |
| Ph(2-Cl,3-c-Pr,4-i-Pr) | Ph(2-Cl,3-C$_2$F$_5$,4-F) | Ph(2-Cl,3-CF$_2$CF$_2$H,4-OCHF$_2$) |
| Ph(2-Cl,3,4-di-c-Pr) | Ph(2-Cl,3-C$_2$F$_5$,4-Br) | Ph(2-Cl,3-CF$_2$CF$_2$H,4-OCF$_2$CF$_2$H) |
| Ph(2-Cl,3-c-Pr,4-CF$_3$) | Ph(2-Cl,3-C$_2$F$_5$,4-I) | Ph(2-Cl,3-CF$_2$CF$_2$H,4-OC$_2$F$_5$) |
| Ph(2-Cl,3-c-Pr,4-C$_2$F$_5$) | Ph(2-Cl,3-C$_2$F$_5$,4-Me) | Ph(2-Cl,3-CF$_2$CF$_2$H,4-SO$_2$Me) |
| Ph(2-Cl,3-c-Pr,4-CF$_2$CF$_2$H) | Ph(2-Cl,3-C$_2$F$_5$,4-Et) | Ph(2-Cl,3-CF$_2$CF$_2$H,4-TMS) |
| Ph(2-Cl,3-c-Pr,4-CF$_2$H) | Ph(2-Cl,3-C$_2$F$_5$,4-n-Pr) | Ph(2-Cl,3-CF$_2$CF$_2$H,4-CN) |
| Ph(2-Cl,3-c-Pr,4-OMe) | Ph(2-Cl,3-C$_2$F$_5$,4-t-Bu) | Ph(2-Cl,3-CF$_2$H,4-Cl) |
| Ph(2-Cl,3-c-Pr,4-OCF$_3$) | Ph(2-Cl,3-C$_2$F$_5$,4-i-Pr) | Ph(2-Cl,3-CF$_2$H,4-F) |
| Ph(2-Cl,3-c-Pr,4-OCHF$_2$) | Ph(2-Cl,3-C$_2$F$_5$,4-c-Pr) | Ph(2-Cl,3-CF$_2$H,4-Br) |
| Ph(2-Cl,3-c-Pr,4-OCF$_2$CF$_2$H) | Ph(2-Cl,3-C$_2$F$_5$CF$_3$,4-CF$_3$) | Ph(2-Cl,3-OCHF$_2$,4-c-Pr) |
| Ph(2-Cl,3-c-Pr,4-OC$_2$F$_5$) | Ph(2-Cl,3,4-di-C$_2$F$_5$) | Ph(2-Cl,3-OCHF$_2$CF$_3$,4-CF$_3$) |
| Ph(2-Cl,3-c-Pr,4-SO$_2$Me) | Ph(2-Cl,3-C$_2$F$_5$,4-CF$_2$CF$_2$H) | Ph(2-Cl,3-OC$_2$F$_5$,4-C$_2$F$_5$) |
| Ph(2-Cl,3-CF$_2$H,4-I) | Ph(2-Cl,3-OMe,4-OCF$_2$CF$_2$H) | Ph(2-Cl,3-OCHF$_2$,4-CF$_2$CF$_2$H) |
| Ph(2-Cl,3-CF$_2$H,4-Me) | Ph(2-Cl,3-OMe,4-OC$_2$F$_5$) | Ph(2-Cl,3-OCHF$_2$,4-CF$_2$H) |
| Ph(2-Cl,3-CF$_2$H,4-Et) | Ph(2-Cl,3-OMe,4-SO$_2$Me) | Ph(2-Cl,3-OCHF$_2$,4-OMe) |
| Ph(2-Cl,3-CF$_2$H,4-n-Pr) | Ph(2-Cl,3-OMe,4-TMS) | Ph(2-Cl,3-OCHF$_2$,4-OCF$_3$) |
| Ph(2-Cl,3-CF$_2$H,4-t-Bu) | Ph(2-Cl,3-OMe,4-CN) | Ph(2-Cl,3,4-di-OCHF$_2$) |
| Ph(2-Cl,3-CF$_2$H,4-i-Pr) | Ph(2-Cl,3-OCF$_3$,4-Cl) | Ph(2-Cl,3-OCHF$_2$,4-OCF$_2$CF$_2$H) |
| Ph(2-Cl,3-CF$_2$H,4-c-Pr) | Ph(2-Cl,3-OCF$_3$,4-F) | Ph(2-Cl,3-OCHF$_2$,4-OC$_2$F$_5$) |
| Ph(2-Cl,3-CF$_2$H,4-CF$_3$) | Ph(2-Cl,3-OCF$_3$,4-Br) | Ph(2-Cl,3-OCHF$_2$,4-SO$_2$Me) |
| Ph(2-Cl,3-CF$_2$H,4-C$_2$F$_5$) | Ph(2-Cl,3-OCF$_3$,4-I) | Ph(2-Cl,3-OCHF$_2$,4-TMS) |
| Ph(2-Cl,3-CF$_2$H,4-CF$_2$CF$_2$H) | Ph(2-Cl,3-OCF$_3$,4-Me) | Ph(2-Cl,3-OCHF$_2$,4-CN) |
| Ph(2-Cl,3,4-di-CF$_2$H) | Ph(2-Cl,3-OCF$_3$,4-Et) | Ph(2-Cl,3-OCF$_2$CF$_2$H,4-Cl) |
| Ph(2-Cl,3-CF$_2$H,4-OMe) | Ph(2-Cl,3-OCF$_3$,4-n-Pr) | Ph(2-Cl,3-OCF$_2$CF$_2$H,4-F) |
| Ph(2-Cl,3-CF$_2$H,4-OCF$_3$) | Ph(2-Cl,3-OCF$_3$,4-t-Bu) | Ph(2-Cl,3-OCF$_2$CF$_2$H,4-Br) |
| Ph(2-Cl,3-CF$_2$H,4-OCHF$_2$) | Ph(2-Cl,3-OCF$_3$,4-i-Pr) | Ph(2-Cl,3-OCF$_2$CF$_2$H,4-I) |
| Ph(2-Cl,3-CF$_2$H,4-OCF$_2$CF$_2$H) | Ph(2-Cl,3-OCF$_3$,4-c-Pr) | Ph(2-Cl,3-OCF$_2$CF$_2$H,4-Me) |
| Ph(2-Cl,3-CF$_2$H,4-OC$_2$F$_5$) | Ph(2-Cl,3-OCF$_3$,4-CF$_3$) | Ph(2-Cl,3-OCF$_2$CF$_2$H,4-Et) |
| Ph(2-Cl,3-CF$_2$H,4-SO$_2$Me) | Ph(2-Cl,3-OCF$_3$,4-C$_2$F$_5$) | Ph(2-Cl,3-OCF$_2$CF$_2$H,4-n-Pr) |
| Ph(2-Cl,3-CF$_2$H,4-TMS) | Ph(2-Cl,3-OCF$_3$,4-CF$_2$CF$_2$H) | Ph(2-Cl,3-OCF$_2$CF$_2$H,4-t-Bu) |
| Ph(2-Cl,3-CF$_2$H,4-CN) | Ph(2-Cl,3-OCF$_3$,4-CF$_2$H) | Ph(2-Cl,3-OCF$_2$CF$_2$H,4-i-Pr) |
| Ph(2-Cl,3-OMe,4-Cl) | Ph(2-Cl,3-OCF$_3$,4-OMe) | Ph(2-Cl,3-OCF$_2$CF$_2$H,4-c-Pr) |
| Ph(2-Cl,3-OMe,4-F) | Ph(2-Cl,3,4-di-OCF$_3$) | Ph(2-Cl,3-OCF$_2$CF$_2$H,4-CF$_3$) |
| Ph(2-Cl,3-OMe,4-Br) | Ph(2-Cl,3-OCF$_3$,4-OCHF$_2$) | Ph(2-Cl,3-OCF$_2$CF$_2$H,4-C$_2$F$_5$) |
| Ph(2-Cl,3-OMe,4-I) | Ph(2-Cl,3-OCF$_3$,4-OCF$_2$CF$_2$H) | Ph(2-Cl,3-OCF$_2$CF$_2$H,4-CF$_2$CF$_2$H) |
| Ph(2-Cl,3-OMe,4-Me) | Ph(2-Cl,3-OCF$_3$,4-OC$_2$F$_5$) | Ph(2-Cl,3-OCF$_2$CF$_2$H,4-CF$_2$H) |
| Ph(2-Cl,3-OMe,4-Et) | Ph(2-Cl,3-OCF$_3$,4-SO$_2$Me) | Ph(2-Cl,3-OCF$_2$CF$_2$H,4-OMe) |
| Ph(2-Cl,3-OMe,4-n-Pr) | Ph(2-Cl,3-OCF$_3$,4-TMS) | Ph(2-Cl,3-OCF$_2$CF$_2$H,4-OCF$_3$) |
| Ph(2-Cl,3-OMe,4-t-Bu) | Ph(2-Cl,3-OCF$_3$,4-CN) | Ph(2-Cl,3-OCF$_2$CF$_2$H,4-OCHF$_2$) |
| Ph(2-Cl,3-OMe,4-i-Pr) | Ph(2-Cl,3-OCHF$_2$,4-Cl) | Ph(2-Cl,3,4-di-OCF$_2$CF$_2$H) |
| Ph(2-Cl,3-OMe,4-c-Pr) | Ph(2-Cl,3-OCHF$_2$,4-F) | Ph(2-Cl,3-CN,4-Cl) |
| Ph(2-Cl,3-OMe,4-CF$_3$) | Ph(2-Cl,3-OCHF$_2$,4-Br) | Ph(2-Cl,3-CN,4-F) |
| Ph(2-Cl,3-OMe,4-C$_2$F$_5$) | Ph(2-Cl,3-OCHF$_2$,4-I) | Ph(2-Cl,3-CN,4-Br) |
| Ph(2-Cl,3-OMe,4-CF$_2$CF$_2$H) | Ph(2-Cl,3-OCHF$_2$,4-Me) | Ph(2-Cl,3-CN,4-I) |
| Ph(2-Cl,3-OMe,4-CF$_2$H) | Ph(2-Cl,3-OCHF$_2$,4-Et) | Ph(2-Cl,3-CN,4-Me) |
| Ph(2-Cl,3,4-di-OMe) | Ph(2-Cl,3-OCHF$_2$,4-n-Pr) | Ph(2-Cl,3-CN,4-Et) |
| Ph(2-Cl,3-OMe,4-OCF$_3$) | Ph(2-Cl,3-OCHF$_2$,4-t-Bu) | Ph(2-Cl,3-CN,4-n-Pr) |
| Ph(2-Cl,3-OMe,4-OCHF$_2$) | Ph(2-Cl,3-OCHF$_2$,4-i-Pr) | Ph(2-Cl,3-CN,4-t-Bu) |
| Ph(2-Cl,3-OCF$_2$CF$_2$H,4-OC$_2$F$_5$) | Ph(2-Cl,3-SO$_2$Me,4-c-Pr) | Ph(2-Cl,3-CN,4-i-Pr) |
| Ph(2-Cl,3-OCF$_2$CF$_2$H,4-SO$_2$Me) | Ph(2-Cl,3-SO$_2$MeCF$_3$,4-CF$_3$) | Ph(2-Cl,3-CN,4-c-Pr) |
| Ph(2-Cl,3-OCF$_2$CF$_2$H,4-TMS) | Ph(2-Cl,3-SO$_2$Me,4-C$_2$F$_5$) | Ph(2-Cl,3-CN,4-CF$_3$) |
| Ph(2-Cl,3-OCF$_2$CF$_2$H,4-CN) | Ph(2-Cl,3-SO$_2$Me,4-CF$_2$CF$_2$H) | Ph(2-Cl,3-CN,4-C$_2$F$_5$) |
| Ph(2-Cl,3-OC$_2$F$_5$,4-Cl) | Ph(2-Cl,3-SO$_2$Me,4-CF$_2$H) | Ph(2-Cl,3-CN,4-CF$_2$CF$_2$H) |
| Ph(2-Cl,3-OC$_2$F$_5$,4-F) | Ph(2-Cl,3-SO$_2$Me,4-OMe) | Ph(2-Cl,3-CN,4-CF$_2$H) |
| Ph(2-Cl,3-OC$_2$F$_5$,4-Br) | Ph(2-Cl,3-SO$_2$Me,4-OCF$_3$) | Ph(2-Cl,3-CN,4-OMe) |
| Ph(2-Cl,3-OC$_2$F$_5$,4-I) | Ph(2-Cl,3-SO$_2$Me,4-OCHF$_2$) | Ph(2-Cl,3-CN,4-OCF$_3$) |
| Ph(2-Cl,3-OC$_2$F$_5$,4-Me) | Ph(2-Cl,3-SO$_2$Me,4-OCF$_2$CF$_2$H) | Ph(2-Cl,3-CN,4-OCHF$_2$) |
| Ph(2-Cl,3-OC$_2$F$_5$,4-Et) | Ph(2-Cl,3-SO$_2$Me,4-OC$_2$F$_5$) | Ph(2-Cl,3-CN,4-OCF$_2$CF$_2$H) |
| Ph(2-Cl,3-OC$_2$F$_5$,4-n-Pr) | Ph(2-Cl,3,4-di-SO$_2$Me) | Ph(2-Cl,3-CN,4-OC$_2$F$_5$) |
| Ph(2-Cl,3-OC$_2$F$_5$,4-t-Bu) | Ph(2-Cl,3-SO$_2$Me,4-TMS) | Ph(2-Cl,3-CN,4-SO$_2$Me) |
| Ph(2-Cl,3-OC$_2$F$_5$,4-i-Pr) | Ph(2-Cl,3-SO$_2$Me,4-CN) | Ph(2-Cl,3-CN,4-TMS) |
| Ph(2-Cl,3-OC$_2$F$_5$,4-c-Pr) | Ph(2-Cl,3-TMS,4-Cl) | Ph(2-Cl,3,4-di-CN) |
| Ph(2-Cl,3-OC$_2$F$_5$CF$_3$,4-CF$_3$) | Ph(2-Cl,3-TMS,4-F) | Ph(2,3,5-tri-Cl) |
| Ph(2-Cl,3-OC$_2$F$_5$,4-CF$_2$CF$_2$H) | Ph(2-Cl,3-TMS,4-Br) | Ph(2-Cl,3-Cl,5-F) |
| Ph(2-Cl,3-OC$_2$F$_5$,4-CF$_2$H) | Ph(2-Cl,3-TMS,4-I) | Ph(2-Cl,3-Cl,5-Br) |
| Ph(2-Cl,3-OC$_2$F$_5$,4-OMe) | Ph(2-Cl,3-TMS,4-Me) | |
| Ph(2-Cl,3-OC$_2$F$_5$,4-OCF$_3$) | Ph(2-Cl,3-TMS,4-Et) | |
| Ph(2-Cl,3-OC$_2$F$_5$,4-OCHF$_2$) | Ph(2-Cl,3-TMS,4-n-Pr) | |
| Ph(2-Cl,3-OC$_2$F$_5$,4-OCF$_2$CF$_2$H) | Ph(2-Cl,3-TMS,4-t-Bu) | |
| Ph(2-Cl,3,4-di-OC$_2$F$_5$) | Ph(2-Cl,3-TMS,4-i-Pr) | |
| Ph(2-Cl,3-OC$_2$F$_5$,4-SO$_2$Me) | Ph(2-Cl,3-TMS,4-c-Pr) | |
| | Ph(2-Cl,3-TMS,4-CF$_3$) | Ph(2-Cl,3-Cl,5-I) |

-continued

| Q¹ | Q¹ | Q¹ |
|---|---|---|
| Ph(2-Cl,3-OC₂F₅,4-TMS) | Ph(2-Cl,3-TMS,4-C₂F₅) | Ph(2-Cl,3-Cl,5-Me) |
| Ph(2-Cl,3-OC₂F₅,4-CN) | Ph(2-Cl,3-TMS,4-CF₂CF₂H) | Ph(2-Cl,3-Cl,5-Et) |
| Ph(2-Cl,3-SO₂Me,4-Cl) | Ph(2-Cl,3-TMS,4-CF₂H) | Ph(2-Cl,3-Cl,5-n-Pr) |
| Ph(2-Cl,3-SO₂Me,4-F) | Ph(2-Cl,3-TMS,4-OMe) | Ph(2-Cl,3-Cl,5-t-Bu) |
| Ph(2-Cl,3-SO₂Me,4-Br) | Ph(2-Cl,3-TMS,4-OCF₃) | Ph(2-Cl,3-Cl,5-i-Pr) |
| Ph(2-Cl,3-SO₂Me,4-I) | Ph(2-Cl,3-TMS,4-OCHF₂) | Ph(2-Cl,3-Cl,5-c-Pr) |
| Ph(2-Cl,3-SO₂Me,4-Me) | Ph(2-Cl,3-TMS,4-OCF₂CF₂H) | Ph(2-Cl,3-Cl,5-CF₃) |
| Ph(2-Cl,3-SO₂Me,4-Et) | Ph(2-Cl,3-TMS,4-OC₂F₅) | Ph(2-Cl,3-Cl,5-C₂F₅) |
| Ph(2-Cl,3-SO₂Me,4-n-Pr) | Ph(2-Cl,3-TMS,4-SO₂Me) | Ph(2-Cl,3-Cl,5-CF₂CF₂H) |
| Ph(2-Cl,3-SO₂Me,4-t-Bu) | Ph(2-Cl,3,4-di-TMS) | Ph(2-Cl,3-Cl,5-CF₂H) |
| Ph(2-Cl,3-SO₂Me,4-i-Pr) | Ph(2-Cl,3-TMS,4-CN) | Ph(2-Cl,3-Cl,5-OMe) |
| Ph(2-Cl,3-Cl,5-OCF₃) | Ph(2-Cl,3-Br,5-i-Pr) | Ph(2-Cl,3-Me,5-F) |
| Ph(2-Cl,3-Cl,5-OCHF₂) | Ph(2-Cl,3-Br,5-c-Pr) | Ph(2-Cl,3-Me,5-Br) |
| Ph(2-Cl,3-Cl,5-OCF₂CF₂H) | Ph(2-Cl,3-Br,5-CF₃) | Ph(2-Cl,3-Me,5-I) |
| Ph(2-Cl,3-Cl,5-OC₂F₅) | Ph(2-Cl,3-Br,5-C₂F₅) | Ph(2-Cl,3,5-di-Me) |
| Ph(2-Cl,3-Cl,5-SO₂Me) | Ph(2-Cl,3-Br,5-CF₂CF₂H) | Ph(2-Cl,3-Me,5-Et) |
| Ph(2-Cl,3-Cl,5-TMS) | Ph(2-Cl,3-Br,5-CF₂H) | Ph(2-Cl,3-Me,5-n-Pr) |
| Ph(2-Cl,3-Cl,5-CN) | Ph(2-Cl,3-Br,5-OMe) | Ph(2-Cl,3-Me,5-t-Bu) |
| Ph(2-Cl,3-F,5-Cl) | Ph(2-Cl,3-Br,5-OCF₃) | Ph(2-Cl,3-Me,5-i-Pr) |
| Ph(2-Cl,3,5-di-F) | Ph(2-Cl,3-Br,5-OCHF₂) | Ph(2-Cl,3-Me,5-c-Pr) |
| Ph(2-Cl,3-F,5-Br) | Ph(2-Cl,3-Br,5-OCF₂CF₂H) | Ph(2-Cl,3-Me,5-CF₃) |
| Ph(2-Cl,3-F,5-I) | Ph(2-Cl,3-Br,5-OC₂F₅) | Ph(2-Cl,3-Me,5-C₂F₅) |
| Ph(2-Cl,3-F,5-Me) | Ph(2-Cl,3-Br,5-SO₂Me) | Ph(2-Cl,3-Me,5-CF₂CF₂H) |
| Ph(2-Cl,3-F,5-Et) | Ph(2-Cl,3-Br,5-TMS) | Ph(2-Cl,3-Me,5-CF₂H) |
| Ph(2-Cl,3-F,5-n-Pr) | Ph(2-Cl,3-Br,5-CN) | Ph(2-Cl,3-Me,5-OMe) |
| Ph(2-Cl,3-F,5-t-Bu) | Ph(2-Cl,3-I,5-Cl) | Ph(2-Cl,3-Me,5-OCF₃) |
| Ph(2-Cl,3-F,5-i-Pr) | Ph(2-Cl,3-I,5-F) | Ph(2-Cl,3-Me,5-OCHF₂) |
| Ph(2-Cl,3-F,5-c-Pr) | Ph(2-Cl,3-I,5-Br) | Ph(2-Cl,3-Me,5-OCF₂CF₂H) |
| Ph(2-Cl,3-F,5-CF₃) | Ph(2-Cl,3,5-di-I) | Ph(2-Cl,3-Me,5-OC₂F₅) |
| Ph(2-Cl,3-F,5-C₂F₅) | Ph(2-Cl,3-I,5-Me) | Ph(2-Cl,3-Me,5-SO₂Me) |
| Ph(2-Cl,3-F,5-CF₂CF₂H) | Ph(2-Cl,3-I,5-Et) | Ph(2-Cl,3-Me,5-TMS) |
| Ph(2-Cl,3-F,5-CF₂H) | Ph(2-Cl,3-I,5-n-Pr) | Ph(2-Cl,3-Me,5-CN) |
| Ph(2-Cl,3-F,5-OMe) | Ph(2-Cl,3-I,5-t-Bu) | Ph(2-Cl,3-Et,5-Cl) |
| Ph(2-Cl,3-F,5-OCF₃) | Ph(2-Cl,3-I,5-i-Pr) | Ph(2-Cl,3-Et,5-F) |
| Ph(2-Cl,3-F,5-OCHF₂) | Ph(2-Cl,3-I,5-c-Pr) | Ph(2-Cl,3-Et,5-Br) |
| Ph(2-Cl,3-F,5-OCF₂CF₂H) | Ph(2-Cl,3-I,5-CF₃) | Ph(2-Cl,3-Et,5-I) |
| Ph(2-Cl,3-F,5-OC₂F₅) | Ph(2-Cl,3-I,5-C₂F₅) | Ph(2-Cl,3-Et,5-Me) |
| Ph(2-Cl,3-F,5-SO₂Me) | Ph(2-Cl,3-I,5-CF₂CF₂H) | Ph(2-Cl,3,5-di-Et) |
| Ph(2-Cl,3-F,5-TMS) | Ph(2-Cl,3-I,5-CF₂H) | Ph(2-Cl,3-Et,5-n-Pr) |
| Ph(2-Cl,3-F,5-CN) | Ph(2-Cl,3-I,5-OMe) | Ph(2-Cl,3-Et,5-t-Bu) |
| Ph(2-Cl,3-Br,5-Cl) | Ph(2-Cl,3-I,5-OCF₃) | Ph(2-Cl,3-Et,5-i-Pr) |
| Ph(2-Cl,3-Br,5-F) | Ph(2-Cl,3-I,5-OCHF₂) | Ph(2-Cl,3-Et,5-c-Pr) |
| Ph(2-Cl,3,5-di-Br) | Ph(2-Cl,3-I,5-OCF₂CF₂H) | Ph(2-Cl,3-Et,5-CF₃) |
| Ph(2-Cl,3-Br,5-I) | Ph(2-Cl,3-I,5-OC₂F₅) | Ph(2-Cl,3-Et,5-C₂F₅) |
| Ph(2-Cl,3-Br,5-Me) | Ph(2-Cl,3-I,5-SO₂Me) | Ph(2-Cl,3-Et,5-CF₂CF₂H) |
| Ph(2-Cl,3-Br,5-Et) | Ph(2-Cl,3-I,5-TMS) | Ph(2-Cl,3-Et,5-CF₂H) |
| Ph(2-Cl,3-Br,5-n-Pr) | Ph(2-Cl,3-I,5-CN) | Ph(2-Cl,3-Et,5-OMe) |
| Ph(2-Cl,3-Br,5-t-Bu) | Ph(2-Cl,3-Me,5-Cl) | Ph(2-Cl,3-Et,5-OCF₃) |
| Ph(2-Cl,3-Et,5-OCHF₂) | Ph(2-Cl,3-t-Bu,5-c-Pr) | Ph(2-Cl,3-c-Pr,5-Br) |
| Ph(2-Cl,3-Et,5-OCF₂CF₂H) | Ph(2-Cl,3-t-Bu,5-CF₃) | Ph(2-Cl,3-c-Pr,5-I) |
| Ph(2-Cl,3-Et,5-OC₂F₅) | Ph(2-Cl,3-t-Bu,5-C₂F₅) | Ph(2-Cl,3-c-Pr,5-Me) |
| Ph(2-Cl,3-Et,5-SO₂Me) | Ph(2-Cl,3-t-Bu,5-CF₂CF₂H) | Ph(2-Cl,3-c-Pr,5-Et) |
| Ph(2-Cl,3-Et,5-TMS) | Ph(2-Cl,3-t-Bu,5-CF₂H) | Ph(2-Cl,3-c-Pr,5-n-Pr) |
| Ph(2-Cl,3-Et,5-CN) | Ph(2-Cl,3-t-Bu,5-OMe) | Ph(2-Cl,3-c-Pr,5-t-Bu) |
| Ph(2-Cl,3-n-Pr,5-Cl) | Ph(2-Cl,3-t-Bu,5-OCF₃) | Ph(2-Cl,3-c-Pr,5-i-Pr) |
| Ph(2-Cl,3-n-Pr,5-F) | Ph(2-Cl,3-t-Bu,5-OCHF₂) | Ph(2-Cl,3,5-di-c-Pr) |
| Ph(2-Cl,3-n-Pr,5-Br) | Ph(2-Cl,3-t-Bu,5-OCF₂CF₂H) | Ph(2-Cl,3-c-Pr,5-CF₃) |
| Ph(2-Cl,3-n-Pr,5-I) | Ph(2-Cl,3-t-Bu,5-OC₂F₅) | Ph(2-Cl,3-c-Pr,5-C₂F₅) |
| Ph(2-Cl,3-n-Pr,5-Me) | Ph(2-Cl,3-t-Bu,5-SO₂Me) | Ph(2-Cl,3-c-Pr,5-CF₂CF₂H) |
| Ph(2-Cl,3-n-Pr,5-Et) | Ph(2-Cl,3-t-Bu,5-TMS) | Ph(2-Cl,3-c-Pr,5-CF₂H) |
| Ph(2-Cl,3,5-di-n-Pr) | Ph(2-Cl,3-t-Bu,5-CN) | Ph(2-Cl,3-c-Pr,5-OMe) |
| Ph(2-Cl,3-n-Pr,5-t-Bu) | Ph(2-Cl,3-i-Pr,5-Cl) | Ph(2-Cl,3-c-Pr,5-OCF₃) |
| Ph(2-Cl,3-n-Pr,5-i-Pr) | Ph(2-Cl,3-i-Pr,5-F) | Ph(2-Cl,3-c-Pr,5-OCHF₂) |
| Ph(2-Cl,3-n-Pr,5-c-Pr) | Ph(2-Cl,3-i-Pr,5-Br) | Ph(2-Cl,3-c-Pr,5-OCF₂CF₂H) |
| Ph(2-Cl,3-n-Pr,5-CF₃) | Ph(2-Cl,3-i-Pr,5-I) | Ph(2-Cl,3-c-Pr,5-OC₂F₅) |
| Ph(2-Cl,3-n-Pr,5-C₂F₅) | Ph(2-Cl,3-i-Pr,5-Me) | Ph(2-Cl,3-c-Pr,5-SO₂Me) |
| Ph(2-Cl,3-n-Pr,5-CF₂CF₂H) | Ph(2-Cl,3-i-Pr,5-Et) | Ph(2-Cl,3-c-Pr,5-TMS) |
| Ph(2-Cl,3-n-Pr,5-CF₂H) | Ph(2-Cl,3-i-Pr,5-n-Pr) | Ph(2-Cl,3-c-Pr,5-CN) |
| Ph(2-Cl,3-n-Pr,5-OMe) | Ph(2-Cl,3-i-Pr,5-t-Bu) | Ph(2-Cl,3-CF₃,5-Cl) |
| Ph(2-Cl,3-n-Pr,5-OCF₃) | Ph(2-Cl,3,5-di-i-Pr) | Ph(2-Cl,3-CF₃,5-F) |
| Ph(2-Cl,3-n-Pr,5-OCHF₂) | Ph(2-Cl,3-i-Pr,5-c-Pr) | Ph(2-Cl,3-CF₃,5-Br) |
| Ph(2-Cl,3-n-Pr,5-OCF₂CF₂H) | Ph(2-Cl,3-i-Pr,5-CF₃) | Ph(2-Cl,3-CF₃,5-I) |
| Ph(2-Cl,3-n-Pr,5-OC₂F₅) | Ph(2-Cl,3-i-Pr,5-C₂F₅) | Ph(2-Cl,3-CF₃,5-Me) |
| Ph(2-Cl,3-n-Pr,5-SO₂Me) | Ph(2-Cl,3-i-Pr,5-CF₂CF₂H) | Ph(2-Cl,3-CF₃,5-Et) |
| Ph(2-Cl,3-n-Pr,5-TMS) | Ph(2-Cl,3-i-Pr,5-CF₂H) | Ph(2-Cl,3-CF₃,5-n-Pr) |
| Ph(2-Cl,3-n-Pr,5-CN) | Ph(2-Cl,3-i-Pr,5-OMe) | Ph(2-Cl,3-CF₃,5-t-Bu) |
| Ph(2-Cl,3-t-Bu,5-Cl) | Ph(2-Cl,3-i-Pr,5-OCF₃) | Ph(2-Cl,3-CF₃,5-i-Pr) |

-continued

| Q¹ | Q¹ | Q¹ |
|---|---|---|
| Ph(2-Cl,3-t-Bu,5-F) | Ph(2-Cl,3-i-Pr,5-OCHF₂) | Ph(2-Cl,3-CF₃,5-c-Pr) |
| Ph(2-Cl,3-t-Bu,5-Br) | Ph(2-Cl,3-i-Pr,5-OCF₂CF₂H) | Ph(2-Cl,3,5-di-CF₃) |
| Ph(2-Cl,3-t-Bu,5-I) | Ph(2-Cl,3-i-Pr,5-OC₂F₅) | Ph(2-Cl,3-CF₃,5-C₂F₅) |
| Ph(2-Cl,3-t-Bu,5-Me) | Ph(2-Cl,3-i-Pr,5-SO₂Me) | Ph(2-Cl,3-CF₃,5-CF₂CF₂H) |
| Ph(2-Cl,3-t-Bu,5-Et) | Ph(2-Cl,3-i-Pr,5-TMS) | Ph(2-Cl,3-CF₃,5-CF₂H) |
| Ph(2-Cl,3-t-Bu,5-n-Pr) | Ph(2-Cl,3-i-Pr,5-CN) | Ph(2-Cl,3-CF₃,5-OMe) |
| Ph(2-Cl,3,5-di-t-Bu) | Ph(2-Cl,3-c-Pr,5-Cl) | Ph(2-Cl,3-CF₃,5-OCF₃) |
| Ph(2-Cl,3-t-Bu,5-i-Pr) | Ph(2-Cl,3-c-Pr,5-F) | Ph(2-Cl,3-CF₃,5-OCHF₂) |
| Ph(2-Cl,3-CF₃,5-OCF₂CF₂H) | Ph(2-Cl,3-CF₂CF₂H,5-CF₃) | Ph(2-Cl,3-CF₂H,5-CN) |
| Ph(2-Cl,3-CF₃,5-OC₂F₅) | Ph(2-Cl,3-CF₂CF₂H,5-C₂F₅) | Ph(2-Cl,3-OMe,5-Cl) |
| Ph(2-Cl,3-CF₃,5-SO₂Me) | Ph(2-Cl,3,5-di-CF₂CF₂H) | Ph(2-Cl,3-OMe,5-F) |
| Ph(2-Cl,3-CF₃,5-TMS) | Ph(2-Cl,3-CF₂CF₂H,5-CF₂H) | Ph(2-Cl,3-OMe,5-Br) |
| Ph(2-Cl,3-CF₃,5-CN) | Ph(2-Cl,3-CF₂CF₂H,5-OMe) | Ph(2-Cl,3-OMe,5-I) |
| Ph(2-Cl,3-C₂F₅,5-Cl) | Ph(2-Cl,3-CF₂CF₂H,5-OCF₃) | Ph(2-Cl,3-OMe,5-Me) |
| Ph(2-Cl,3-C₂F₅,5-F) | Ph(2-Cl,3-CF₂CF₂H,5-OCHF₂) | Ph(2-Cl,3-OMe,5-Et) |
| Ph(2-Cl,3-C₂F₅,5-Br) | Ph(2-Cl,3-CF₂CF₂H,5-OCF₂CF₂H) | Ph(2-Cl,3-OMe,5-n-Pr) |
| Ph(2-Cl,3-C₂F₅,5-I) | | Ph(2-Cl,3-OMe,5-t-Bu) |
| Ph(2-Cl,3-C₂F₅,5-Me) | Ph(2-Cl,3-CF₂CF₂H,5-OC₂F₅) | Ph(2-Cl,3-OMe,5-i-Pr) |
| Ph(2-Cl,3-C₂F₅,5-Et) | Ph(2-Cl,3-CF₂CF₂H,5-SO₂Me) | Ph(2-Cl,3-OMe,5-c-Pr) |
| Ph(2-Cl,3-C₂F₅,5-n-Pr) | | Ph(2-Cl,3-OMe,5-CF₃) |
| Ph(2-Cl,3-C₂F₅,5-t-Bu) | Ph(2-Cl,3-CF₂CF₂H,5-TMS) | Ph(2-Cl,3-OMe,5-C₂F₅) |
| Ph(2-Cl,3-C₂F₅,5-i-Pr) | Ph(2-Cl,3-CF₂CF₂H,5-CN) | Ph(2-Cl,3-OMe,5-CF₂CF₂H) |
| Ph(2-Cl,3-C₂F₅,5-c-Pr) | Ph(2-Cl,3-CF₂H,5-Cl) | Ph(2-Cl,3-OMe,5-CF₂H) |
| Ph(2-Cl,3-C₂F₅CF₃,5-CF₃) | Ph(2-Cl,3-CF₂H,5-F) | Ph(2-Cl,3,5-di-OMe) |
| Ph(2-Cl,3,5-di-C₂F₅) | Ph(2-Cl,3-CF₂H,5-Br) | Ph(2-Cl,3-OMe,5-OCF₃) |
| Ph(2-Cl,3-C₂F₅,5-CF₂CF₂H) | Ph(2-Cl,3-CF₂H,5-I) | Ph(2-Cl,3-OMe,5-OCHF₂) |
| Ph(2-Cl,3-C₂F₅,5-CF₂H) | Ph(2-Cl,3-CF₂H,5-Me) | Ph(2-Cl,3-OMe,5-OCF₂CF₂H) |
| Ph(2-Cl,3-C₂F₅,5-OMe) | Ph(2-Cl,3-CF₂H,5-Et) | Ph(2-Cl,3-OMe,5-OC₂F₅) |
| Ph(2-Cl,3-C₂F₅,5-OCF₃) | Ph(2-Cl,3-CF₂H,5-n-Pr) | Ph(2-Cl,3-OMe,5-SO₂Me) |
| Ph(2-Cl,3-C₂F₅,5-OCHF₂) | Ph(2-Cl,3-CF₂H,5-t-Bu) | Ph(2-Cl,3-OMe,5-TMS) |
| Ph(2-Cl,3-C₂F₅,5-OCF₂CF₂H) | Ph(2-Cl,3-CF₂H,5-i-Pr) | Ph(2-Cl,3-OMe,5-CN) |
| Ph(2-Cl,3-C₂F₅,5-OC₂F₅) | Ph(2-Cl,3-CF₂H,5-c-Pr) | Ph(2-Cl,3-OCF₃,5-Cl) |
| Ph(2-Cl,3-C₂F₅,5-SO₂Me) | Ph(2-Cl,3-CF₂H,5-CF₃) | Ph(2-Cl,3-OCF₃,5-F) |
| Ph(2-Cl,3-C₂F₅,5-TMS) | Ph(2-Cl,3-CF₂H,5-C₂F₅) | Ph(2-Cl,3-OCF₃,5-Br) |
| Ph(2-Cl,3-C₂F₅,5-CN) | Ph(2-Cl,3-CF₂H,5-CF₂CF₂H) | Ph(2-Cl,3-OCF₃,5-I) |
| Ph(2-Cl,3-CF₂CF₂H,5-Cl) | Ph(2-Cl,3,5-di-CF₂H) | Ph(2-Cl,3-OCF₃,5-Me) |
| Ph(2-Cl,3-CF₂CF₂H,5-F) | Ph(2-Cl,3-CF₂H,5-OMe) | Ph(2-Cl,3-OCF₃,5-Et) |
| Ph(2-Cl,3-CF₂CF₂H,5-Br) | Ph(2-Cl,3-CF₂H,5-OCF₃) | Ph(2-Cl,3-OCF₃,5-n-Pr) |
| Ph(2-Cl,3-CF₂CF₂H,5-I) | Ph(2-Cl,3-CF₂H,5-OCHF₂) | Ph(2-Cl,3-OCF₃,5-t-Bu) |
| Ph(2-Cl,3-CF₂CF₂H,5-Me) | Ph(2-Cl,3-CF₂H,5-OCF₂CF₂H) | Ph(2-Cl,3-OCF₃,5-i-Pr) |
| Ph(2-Cl,3-CF₂CF₂H,5-Et) | | Ph(2-Cl,3-OCF₃,5-c-Pr) |
| Ph(2-Cl,3-CF₂CF₂H,5-n-Pr) | Ph(2-Cl,3-CF₂H,5-OC₂F₅) | Ph(2-Cl,3-OCF₃,5-CF₃) |
| Ph(2-Cl,3-CF₂CF₂H,5-t-Bu) | Ph(2-Cl,3-CF₂H,5-SO₂Me) | Ph(2-Cl,3-OCF₃,5-C₂F₅) |
| Ph(2-Cl,3-CF₂CF₂H,5-i-Pr) | Ph(2-Cl,3-CF₂H,5-TMS) | Ph(2-Cl,3-OCF₃,5-CF₂CF₂H) |
| Ph(2-Cl,3-CF₂CF₂H,5-c-Pr) | Ph(2-Cl,3-CF₂H,5-CN) | Ph(2-Cl,3-OCF₃,5-CF₂H) |
| Ph(2-Cl,3-OCF₃,5-OMe) | Ph(2-Cl,3-OCF₂CF₂H,5-Me) | Ph(2-Cl,3-OC₂F₅,5-OMe) |
| Ph(2-Cl,3,5-di-OCF₃) | Ph(2-Cl,3-OCF₂CF₂H,5-Et) | Ph(2-Cl,3-OC₂F₅,5-OCF₃) |
| Ph(2-Cl,3-OCF₃,5-OCHF₂) | Ph(2-Cl,3-OCF₂CF₂H,5-n-Pr) | Ph(2-Cl,3-OC₂F₅,5-OCHF₂) |
| Ph(2-Cl,3-OCF₃,5-OCF₂CF₂H) | Ph(2-Cl,3-OCF₂CF₂H,5-t-Bu) | Ph(2-Cl,3-OC₂F₅,5-OCF₂CF₂H) |
| Ph(2-Cl,3-OCF₃,5-OC₂F₅) | Ph(2-Cl,3-OCF₂CF₂H,5-i-Pr) | Ph(2-Cl,3,5-di-OC₂F₅) |
| Ph(2-Cl,3-OCF₃,5-SO₂Me) | Ph(2-Cl,3-OCF₂CF₂H,5-c-Pr) | Ph(2-Cl,3-OC₂F₅,5-SO₂Me) |
| Ph(2-Cl,3-OCF₃,5-TMS) | Ph(2-Cl,3-OCF₂CF₂H,5-CF₃) | Ph(2-Cl,3-OC₂F₅,5-TMS) |
| Ph(2-Cl,3-OCF₃,5-CN) | Ph(2-Cl,3-OCF₂CF₂H,5-C₂F₅) | Ph(2-Cl,3-OC₂F₅,5-CN) |
| Ph(2-Cl,3-OCHF₂,5-Cl) | Ph(2-Cl,3-OCF₂CF₂H,5-CF₂CF₂H) | Ph(2-Cl,3-SO₂Me,5-Cl) |
| Ph(2-Cl,3-OCHF₂,5-F) | | Ph(2-Cl,3-SO₂Me,5-F) |
| Ph(2-Cl,3-OCHF₂,5-Br) | Ph(2-Cl,3-OCF₂CF₂H,5-CF₂H) | Ph(2-Cl,3-SO₂Me,5-Br) |
| Ph(2-Cl,3-OCHF₂,5-I) | Ph(2-Cl,3-OCF₂CF₂H,5-OMe) | Ph(2-Cl,3-SO₂Me,5-I) |
| Ph(2-Cl,3-OCHF₂,5-Me) | Ph(2-Cl,3-OCF₂CF₂H,5-OCF₃) | Ph(2-Cl,3-SO₂Me,5-Me) |
| Ph(2-Cl,3-OCHF₂,5-Et) | | Ph(2-Cl,3-SO₂Me,5-Et) |
| Ph(2-Cl,3-OCHF₂,5-n-Pr) | Ph(2-Cl,3-OCF₂CF₂H,5-OCHF₂) | Ph(2-Cl,3-SO₂Me,5-n-Pr) |
| Ph(2-Cl,3-OCHF₂,5-t-Bu) | Ph(2-Cl,3,5-di-OCF₂CF₂H) | Ph(2-Cl,3-SO₂Me,5-t-Bu) |
| Ph(2-Cl,3-OCHF₂,5-i-Pr) | Ph(2-Cl,3-OCF₂CF₂H,5-OC₂F₅) | Ph(2-Cl,3-SO₂Me,5-i-Pr) |
| Ph(2-Cl,3-OCHF₂,5-c-Pr) | | Ph(2-Cl,3-SO₂Me,5-c-Pr) |
| Ph(2-Cl,3-OCHF₂CF₃,5-CF₃) | Ph(2-Cl,3-OCF₂CF₂H,5-SO₂Me) | Ph(2-Cl,3-SO₂MeCF₃,5-CF₃) |
| Ph(2-Cl,3-OC₂F₅,5-C₂F₅) | Ph(2-Cl,3-OCF₂CF₂H,5-TMS) | Ph(2-Cl,3-SO₂Me,5-C₂F₅) |
| Ph(2-Cl,3-OCHF₂,5-CF₂CF₂H) | Ph(2-Cl,3-OCF₂CF₂H,5-CN) | Ph(2-Cl,3-SO₂Me,5-CF₂CF₂H) |
| Ph(2-Cl,3-OCHF₂,5-CF₂H) | Ph(2-Cl,3-OC₂F₅,5-Cl) | Ph(2-Cl,3-SO₂Me,5-CF₂H) |
| Ph(2-Cl,3-OCHF₂,5-OMe) | Ph(2-Cl,3-OC₂F₅,5-F) | Ph(2-Cl,3-SO₂Me,5-OMe) |
| Ph(2-Cl,3-OCHF₂,5-OCF₃) | Ph(2-Cl,3-OC₂F₅,5-Br) | Ph(2-Cl,3-SO₂Me,5-OCF₃) |
| Ph(2-Cl,3,5-di-OCHF₂) | Ph(2-Cl,3-OC₂F₅,5-I) | Ph(2-Cl,3-SO₂Me,5-OCHF₂) |
| Ph(2-Cl,3-OCHF₂,5-OCF₂CF₂H) | Ph(2-Cl,3-OC₂F₅,5-Me) | Ph(2-Cl,3-SO₂Me,5-OCF₂CF₂H) |
| Ph(2-Cl,3-OCHF₂,5-OC₂F₅) | Ph(2-Cl,3-OC₂F₅,5-Et) | Ph(2-Cl,3-SO₂Me,5-OC₂F₅) |
| Ph(2-Cl,3-OCHF₂,5-SO₂Me) | Ph(2-Cl,3-OC₂F₅,5-n-Pr) | Ph(2-Cl,3,5-di-SO₂Me) |
| Ph(2-Cl,3-OCHF₂,5-TMS) | Ph(2-Cl,3-OC₂F₅,5-t-Bu) | Ph(2-Cl,3-SO₂Me,5-TMS) |

-continued

| Q¹ | Q¹ | Q¹ |
|---|---|---|
| Ph(2-Cl,3-OCHF₂,5-CN) | Ph(2-Cl,3-OC₂F₅,5-i-Pr) | Ph(2-Cl,3-SO₂Me,5-CN) |
| Ph(2-Cl,3-OCF₂CF₂H,5-Cl) | Ph(2-Cl,3-OC₂F₅,5-c-Pr) | Ph(2-Cl,3-TMS,5-Cl) |
| Ph(2-Cl,3-OCF₂CF₂H,5-F) | Ph(2-Cl,3-OC₂F₅CF₃,5-CF₃) | Ph(2-Cl,3-TMS,5-F) |
| Ph(2-Cl,3-OCF₂CF₂H,5-Br) | Ph(2-Cl,3-OC₂F₅,5-CF₂CF₂H) | Ph(2-Cl,3-TMS,5-Br) |
| Ph(2-Cl,3-OCF₂CF₂H,5-I) | Ph(2-Cl,3-OC₂F₅,5-CF₂H) | Ph(2-Cl,3-TMS,5-I) |
| Ph(2-Cl,3-TMS,5-Me) | Ph(2-Cl,3-CN,5-SO₂Me) | Ph(2-Cl,4-F,5-CF₂CF₂H) |
| Ph(2-Cl,3-TMS,5-Et) | Ph(2-Cl,3-CN,5-TMS) | Ph(2-Cl,4-F,5-CF₂H) |
| Ph(2-Cl,3-TMS,5-n-Pr) | Ph(2-Cl,3,5-di-CN) | Ph(2-Cl,4-F,5-OMe) |
| Ph(2-Cl,3-TMS,5-t-Bu) | Ph(2,4,5-tri-Cl) | Ph(2-Cl,4-F,5-OCF₃) |
| Ph(2-Cl,3-TMS,5-i-Pr) | Ph(2-Cl,4-Cl,5-F) | Ph(2-Cl,4-F,5-OCHF₂) |
| Ph(2-Cl,3-TMS,5-c-Pr) | Ph(2-Cl,4-Cl,5-Br) | Ph(2-Cl,4-F,5-OCF₂CF₂H) |
| Ph(2-Cl,3-TMS,5-CF₃) | Ph(2-Cl,4-Cl,5-I) | Ph(2-Cl,4-F,5-OC₂F₅) |
| Ph(2-Cl,3-TMS,5-C₂F₅) | Ph(2-Cl,4-Cl,5-Me) | Ph(2-Cl,4-F,5-SO₂Me) |
| Ph(2-Cl,3-TMS,5-CF₂CF₂H) | Ph(2-Cl,4-Cl,5-Et) | Ph(2-Cl,4-F,5-TMS) |
| Ph(2-Cl,3-TMS,5-CF₂H) | Ph(2-Cl,4-Cl,5-n-Pr) | Ph(2-Cl,4-F,5-CN) |
| Ph(2-Cl,3-TMS,5-OMe) | Ph(2-Cl,4-Cl,5-t-Bu) | Ph(2-Cl,4-Br,5-Cl) |
| Ph(2-Cl,3-TMS,5-OCF₃) | Ph(2-Cl,4-Cl,5-i-Pr) | Ph(2-Cl,4-Br,5-F) |
| Ph(2-Cl,3-TMS,5-OCHF₂) | Ph(2-Cl,4-Cl,5-c-Pr) | Ph(2-Cl,4,5-di-Br) |
| Ph(2-Cl,3-TMS,5-OCF₂CF₂H) | Ph(2-Cl,4-Cl,5-CF₃) | Ph(2-Cl,4-Br,5-I) |
| Ph(2-Cl,3-TMS,5-OC₂F₅) | Ph(2-Cl,4-Cl,5-C₂F₅) | Ph(2-Cl,4-Br,5-Me) |
| Ph(2-Cl,3-TMS,5-SO₂Me) | Ph(2-Cl,4-Cl,5-CF₂CF₂H) | Ph(2-Cl,4-Br,5-Et) |
| Ph(2-Cl,3,5-di-TMS) | Ph(2-Cl,4-Cl,5-CF₂H) | Ph(2-Cl,4-Br,5-n-Pr) |
| Ph(2-Cl,3-TMS,5-CN) | Ph(2-Cl,4-Cl,5-OMe) | Ph(2-Cl,4-Br,5-t-Bu) |
| Ph(2-Cl,3-CN,5-Cl) | Ph(2-Cl,4-Cl,5-OCF₃) | Ph(2-Cl,4-Br,5-i-Pr) |
| Ph(2-Cl,3-CN,5-F) | Ph(2-Cl,4-Cl,5-OCHF₂) | Ph(2-Cl,4-Br,5-c-Pr) |
| Ph(2-Cl,3-CN,5-Br) | Ph(2-Cl,4-Cl,5-OCF₂CF₂H) | Ph(2-Cl,4-Br,5-CF₃) |
| Ph(2-Cl,3-CN,5-I) | Ph(2-Cl,4-Cl,5-OC₂F₅) | Ph(2-Cl,4-Br,5-C₂F₅) |
| Ph(2-Cl,3-CN,5-Me) | Ph(2-Cl,4-Cl,5-SO₂Me) | Ph(2-Cl,4-Br,5-CF₂CF₂H) |
| Ph(2-Cl,3-CN,5-Et) | Ph(2-Cl,4-Cl,5-TMS) | Ph(2-Cl,4-Br,5-CF₂H) |
| Ph(2-Cl,3-CN,5-n-Pr) | Ph(2-Cl,4-Cl,5-CN) | Ph(2-Cl,4-Br,5-OMe) |
| Ph(2-Cl,3-CN,5-t-Bu) | Ph(2-Cl,4-F,5-Cl) | Ph(2-Cl,4-Br,5-OCF₃) |
| Ph(2-Cl,3-CN,5-i-Pr) | Ph(2-Cl,4,5-di-F) | Ph(2-Cl,4-Br,5-OCHF₂) |
| Ph(2-Cl,3-CN,5-c-Pr) | Ph(2-Cl,4-F,5-Br) | Ph(2-Cl,4-Br,5-OCF₂CF₂H) |
| Ph(2-Cl,3-CN,5-CF₃) | Ph(2-Cl,4-F,5-I) | Ph(2-Cl,4-Br,5-OC₂F₅) |
| Ph(2-Cl,3-CN,5-C₂F₅) | Ph(2-Cl,4-F,5-Me) | Ph(2-Cl,4-Br,5-SO₂Me) |
| Ph(2-Cl,3-CN,5-CF₂CF₂H) | Ph(2-Cl,4-F,5-Et) | Ph(2-Cl,4-Br,5-TMS) |
| Ph(2-Cl,3-CN,5-CF₂H) | Ph(2-Cl,4-F,5-n-Pr) | Ph(2-Cl,4-Br,5-CN) |
| Ph(2-Cl,3-CN,5-OMe) | Ph(2-Cl,4-F,5-t-Bu) | Ph(2-Cl,4-I,5-Cl) |
| Ph(2-Cl,3-CN,5-OCF₃) | Ph(2-Cl,4-F,5-i-Pr) | Ph(2-Cl,4-I,5-F) |
| Ph(2-Cl,3-CN,5-OCHF₂) | Ph(2-Cl,4-F,5-c-Pr) | Ph(2-Cl,4-I,5-Br) |
| Ph(2-Cl,3-CN,5-OCF₂CF₂H) | Ph(2-Cl,4-F,5-CF₃) | Ph(2-Cl,4,5-di-I) |
| Ph(2-Cl,3-CN,5-OC₂F₅) | Ph(2-Cl,4-F,5-C₂F₅) | Ph(2-Cl,4-I,5-Me) |
| Ph(2-Cl,4-I,5-Et) | Ph(2-Cl,4-Me,5-TMS) | Ph(2-Cl,4-n-Pr,5-CF₂H) |
| Ph(2-Cl,4-I,5-n-Pr) | Ph(2-Cl,4-Me,5-CN) | Ph(2-Cl,4-n-Pr,5-OMe) |
| Ph(2-Cl,4-I,5-t-Bu) | Ph(2-Cl,4-Et,5-Cl) | Ph(2-Cl,4-n-Pr,5-OCF₃) |
| Ph(2-Cl,4-I,5-i-Pr) | Ph(2-Cl,4-Et,5-F) | Ph(2-Cl,4-n-Pr,5-OCHF₂) |
| Ph(2-Cl,4-I,5-c-Pr) | Ph(2-Cl,4-Et,5-Br) | Ph(2-Cl,4-n-Pr,5-OCF₂CF₂H) |
| Ph(2-Cl,4-I,5-CF₃) | Ph(2-Cl,4-Et,5-I) | Ph(2-Cl,4-n-Pr,5-OC₂F₅) |
| Ph(2-Cl,4-I,5-C₂F₅) | Ph(2-Cl,4-Et,5-Me) | Ph(2-Cl,4-n-Pr,5-SO₂Me) |
| Ph(2-Cl,4-I,5-CF₂CF₂H) | Ph(2-Cl,4,5-di-Et) | Ph(2-Cl,4-n-Pr,5-TMS) |
| Ph(2-Cl,4-I,5-CF₂H) | Ph(2-Cl,4-Et,5-n-Pr) | Ph(2-Cl,4-n-Pr,5-CN) |
| Ph(2-Cl,4-I,5-OMe) | Ph(2-Cl,4-Et,5-t-Bu) | Ph(2-Cl,4-t-Bu,5-Cl) |
| Ph(2-Cl,4-I,5-OCF₃) | Ph(2-Cl,4-Et,5-i-Pr) | Ph(2-Cl,4-t-Bu,5-F) |
| Ph(2-Cl,4-I,5-OCHF₂) | Ph(2-Cl,4-Et,5-c-Pr) | Ph(2-Cl,4-t-Bu,5-Br) |
| Ph(2-Cl,4-I,5-OCF₂CF₂H) | Ph(2-Cl,4-Et,5-CF₃) | Ph(2-Cl,4-t-Bu,5-I) |
| Ph(2-Cl,4-I,5-OC₂F₅) | Ph(2-Cl,4-Et,5-C₂F₅) | Ph(2-Cl,4-t-Bu,5-Me) |
| Ph(2-Cl,4-I,5-SO₂Me) | Ph(2-Cl,4-Et,5-CF₂CF₂H) | Ph(2-Cl,4-t-Bu,5-Et) |
| Ph(2-Cl,4-I,5-TMS) | Ph(2-Cl,4-Et,5-CF₂H) | Ph(2-Cl,4-t-Bu,5-n-Pr) |
| Ph(2-Cl,4-I,5-CN) | Ph(2-Cl,4-Et,5-OMe) | Ph(2-Cl,4,5-di-t-Bu) |
| Ph(2-Cl,4-Me,5-Cl) | Ph(2-Cl,4-Et,5-OCF₃) | Ph(2-Cl,4-t-Bu,5-i-Pr) |
| Ph(2-Cl,4-Me,5-F) | Ph(2-Cl,4-Et,5-OCHF₂) | Ph(2-Cl,4-t-Bu,5-c-Pr) |
| Ph(2-Cl,4-Me,5-Br) | Ph(2-Cl,4-Et,5-OCF₂CF₂H) | Ph(2-Cl,4-t-Bu,5-CF₃) |
| Ph(2-Cl,4-Me,5-I) | Ph(2-Cl,4-Et,5-OC₂F₅) | Ph(2-Cl,4-t-Bu,5-C₂F₅) |
| Ph(2-Cl,4,5-di-Me) | Ph(2-Cl,4-Et,5-SO₂Me) | Ph(2-Cl,4-t-Bu,5-CF₂CF₂H) |
| Ph(2-Cl,4-Me,5-Et) | Ph(2-Cl,4-Et,5-TMS) | Ph(2-Cl,4-t-Bu,5-CF₂H) |
| Ph(2-Cl,4-Me,5-n-Pr) | Ph(2-Cl,4-Et,5-CN) | Ph(2-Cl,4-t-Bu,5-OMe) |
| Ph(2-Cl,4-Me,5-t-Bu) | Ph(2-Cl,4-n-Pr,5-Cl) | Ph(2-Cl,4-t-Bu,5-OCF₃) |
| Ph(2-Cl,4-Me,5-i-Pr) | Ph(2-Cl,4-n-Pr,5-F) | Ph(2-Cl,4-t-Bu,5-OCHF₂) |
| Ph(2-Cl,4-Me,5-c-Pr) | Ph(2-Cl,4-n-Pr,5-Br) | Ph(2-Cl,4-t-Bu,5-OCF₂CF₂H) |
| Ph(2-Cl,4-Me,5-CF₃) | Ph(2-Cl,4-n-Pr,5-I) | Ph(2-Cl,4-t-Bu,5-OC₂F₅) |
| Ph(2-Cl,4-Me,5-C₂F₅) | Ph(2-Cl,4-n-Pr,5-Me) | Ph(2-Cl,4-t-Bu,5-SO₂Me) |
| Ph(2-Cl,4-Me,5-CF₂CF₂H) | Ph(2-Cl,4-n-Pr,5-Et) | Ph(2-Cl,4-t-Bu,5-TMS) |
| Ph(2-Cl,4-Me,5-CF₂H) | Ph(2-Cl,4,5-di-n-Pr) | Ph(2-Cl,4-t-Bu,5-CN) |
| Ph(2-Cl,4-Me,5-OMe) | Ph(2-Cl,4-n-Pr,5-t-Bu) | Ph(2-Cl,4-i-Pr,5-Cl) |
| Ph(2-Cl,4-Me,5-OCF₃) | Ph(2-Cl,4-n-Pr,5-i-Pr) | Ph(2-Cl,4-i-Pr,5-F) |
| Ph(2-Cl,4-Me,5-OCHF₂) | Ph(2-Cl,4-n-Pr,5-c-Pr) | Ph(2-Cl,4-i-Pr,5-Br) |
| Ph(2-Cl,4-Me,5-OCF₂CF₂H) | Ph(2-Cl,4-n-Pr,5-CF₃) | Ph(2-Cl,4-i-Pr,5-I) |

| Q¹ | Q¹ | Q¹ |
| --- | --- | --- |
| Ph(2-Cl,4-Me,5-OC$_2$F$_5$) | Ph(2-Cl,4-n-Pr,5-C$_2$F$_5$) | Ph(2-Cl,4-i-Pr,5-Me) |
| Ph(2-Cl,4-Me,5-SO$_2$Me) | Ph(2-Cl,4-n-Pr,5-CF$_2$CF$_2$H) | Ph(2-Cl,4-i-Pr,5-Et) |
| Ph(2-Cl,4-i-Pr,5-n-Pr) | Ph(2-Cl,4-c-Pr,5-CN) | Ph(2-Cl,4-CF$_2$CF$_3$,5-CF$_2$H) |
| Ph(2-Cl,4-i-Pr,5-t-Bu) | Ph(2-Cl,4-CF$_3$,5-Cl) | Ph(2-Cl,4-CF$_2$CF$_3$,5-OMe) |
| Ph(2-Cl,4,5-di-i-Pr) | Ph(2-Cl,4-CF$_3$,5-F) | Ph(2-Cl,4-CF$_2$CF$_3$,5-OCF$_3$) |
| Ph(2-Cl,4-i-Pr,5-c-Pr) | Ph(2-Cl,4-CF$_3$,5-Br) | Ph(2-Cl,4-CF$_2$CF$_3$,5-OCHF$_2$) |
| Ph(2-Cl,4-i-Pr,5-CF$_3$) | Ph(2-Cl,4-CF$_3$,5-I) | Ph(2-Cl,4-CF$_2$CF$_3$,5-OCF$_2$CF$_2$H) |
| Ph(2-Cl,4-i-Pr,5-C$_2$F$_5$) | Ph(2-Cl,4-CF$_3$,5-Me) | Ph(2-Cl,4-CF$_2$CF$_3$,5-OC$_2$F$_5$) |
| Ph(2-Cl,4-i-Pr,5-CF$_2$CF$_2$H) | Ph(2-Cl,4-CF$_3$,5-Et) | Ph(2-Cl,4-CF$_2$CF$_3$,5-SO$_2$Me) |
| Ph(2-Cl,4-i-Pr,5-CF$_2$H) | Ph(2-Cl,4-CF$_3$,5-n-Pr) | Ph(2-Cl,4-CF$_2$CF$_3$,5-TMS) |
| Ph(2-Cl,4-i-Pr,5-OMe) | Ph(2-Cl,4-CF$_3$,5-t-Bu) | Ph(2-Cl,4-CF$_2$CF$_3$,5-CN) |
| Ph(2-Cl,4-i-Pr,5-OCF$_3$) | Ph(2-Cl,4-CF$_3$,5-i-Pr) | Ph(2-Cl,4-CF$_2$CF$_2$H,5-Cl) |
| Ph(2-Cl,4-i-Pr,5-OCHF$_2$) | Ph(2-Cl,4-CF$_3$,5-c-Pr) | Ph(2-Cl,4-CF$_2$CF$_2$H,5-F) |
| Ph(2-Cl,4-i-Pr,5-OCF$_2$CF$_2$H) | Ph(2-Cl,4,5-di-CF$_3$) | Ph(2-Cl,4-CF$_2$CF$_2$H,5-Br) |
| Ph(2-Cl,4-i-Pr,5-OC$_2$F$_5$) | Ph(2-Cl,4-CF$_3$,5-C$_2$F$_5$) | Ph(2-Cl,4-CF$_2$CF$_2$H,5-I) |
| Ph(2-Cl,4-i-Pr,5-SO$_2$Me) | Ph(2-Cl,4-CF$_3$,5-CF$_2$CF$_2$H) | Ph(2-Cl,4-CF$_2$CF$_2$H,5-Me) |
| Ph(2-Cl,4-i-Pr,5-TMS) | Ph(2-Cl,4-CF$_3$,5-CF$_2$H) | Ph(2-Cl,4-CF$_2$CF$_2$H,5-Et) |
| Ph(2-Cl,4-i-Pr,5-CN) | Ph(2-Cl,4-CF$_3$,5-OMe) | Ph(2-Cl,4-CF$_2$CF$_2$H,5-n-Pr) |
| Ph(2-Cl,4-c-Pr,5-Cl) | Ph(2-Cl,4-CF$_3$,5-OCF$_3$) | Ph(2-Cl,4-CF$_2$CF$_2$H,5-t-Bu) |
| Ph(2-Cl,4-c-Pr,5-F) | Ph(2-Cl,4-CF$_3$,5-OCHF$_2$) | Ph(2-Cl,4-CF$_2$CF$_2$H,5-i-Pr) |
| Ph(2-Cl,4-c-Pr,5-Br) | Ph(2-Cl,4-CF$_3$,5-OCF$_2$CF$_2$H) | Ph(2-Cl,4-CF$_2$CF$_2$H,5-c-Pr) |
| Ph(2-Cl,4-c-Pr,5-I) | Ph(2-Cl,4-CF$_3$,5-OC$_2$F$_5$) | Ph(2-Cl,4-CF$_2$CF$_2$CF$_3$H,5-CF$_3$) |
| Ph(2-Cl,4-c-Pr,5-Me) | Ph(2-Cl,4-CF$_3$,5-SO$_2$Me) | Ph(2-Cl,4-CF$_2$CF$_2$H,5-C$_2$F$_5$) |
| Ph(2-Cl,4-c-Pr,5-Et) | Ph(2-Cl,4-CF$_3$,5-TMS) | Ph(2-Cl,4,5-di-CF$_2$CF$_2$H) |
| Ph(2-Cl,4-c-Pr,5-n-Pr) | Ph(2-Cl,4-CF$_3$,5-CN) | Ph(2-Cl,4-CF$_2$CF$_2$H,5-CF$_2$H) |
| Ph(2-Cl,4-c-Pr,5-t-Bu) | Ph(2-Cl,4-CF$_2$CF$_3$,5-Cl) | Ph(2-Cl,4-CF$_2$CF$_2$H,5-OMe) |
| Ph(2-Cl,4-c-Pr,5-i-Pr) | Ph(2-Cl,4-CF$_2$CF$_3$,5-F) | Ph(2-Cl,4-CF$_2$CF$_2$H,5-OCF$_3$) |
| Ph(2-Cl,4,5-di-c-Pr) | Ph(2-Cl,4-CF$_2$CF$_3$,5-Br) | Ph(2-Cl,4-CF$_2$CF$_2$H,5-OCHF$_2$) |
| Ph(2-Cl,4-c-Pr,5-CF$_3$) | Ph(2-Cl,4-CF$_2$CF$_3$,5-I) | Ph(2-Cl,4-CF$_2$CF$_2$H,5-OCF$_2$CF$_2$H) |
| Ph(2-Cl,4-c-Pr,5-C$_2$F$_5$) | Ph(2-Cl,4-CF$_2$CF$_3$,5-Me) | Ph(2-Cl,4-CF$_2$CF$_2$H,5-OC$_2$F$_5$) |
| Ph(2-Cl,4-c-Pr,5-CF$_2$CF$_2$H) | Ph(2-Cl,4-CF$_2$CF$_3$,5-Et) | Ph(2-Cl,4-CF$_2$CF$_2$H,5-SO$_2$Me) |
| Ph(2-Cl,4-c-Pr,5-CF$_2$H) | Ph(2-Cl,4-CF$_2$CF$_3$,5-n-Pr) | Ph(2-Cl,4-CF$_2$CF$_2$H,5-TMS) |
| Ph(2-Cl,4-c-Pr,5-OMe) | Ph(2-Cl,4-CF$_2$CF$_3$,5-t-Bu) | Ph(2-Cl,4-CF$_2$CF$_2$H,5-CN) |
| Ph(2-Cl,4-c-Pr,5-OCF$_3$) | Ph(2-Cl,4-CF$_2$CF$_3$,5-i-Pr) | Ph(2-Cl,4-CF$_2$H,5-Cl) |
| Ph(2-Cl,4-c-Pr,5-OCHF$_2$) | Ph(2-Cl,4-CF$_2$CF$_3$,5-c-Pr) | Ph(2-Cl,4-OCHF$_2$,5-t-Bu) |
| Ph(2-Cl,4-c-Pr,5-OCF$_2$CF$_2$H) | Ph(2-Cl,4-C$_2$F$_5$CF$_3$,5-CF$_3$) | Ph(2-Cl,4-OCHF$_2$,5-i-Pr) |
| Ph(2-Cl,4-c-Pr,5-OC$_2$F$_5$) | Ph(2-Cl,4,5-di-C$_2$F$_5$) | Ph(2-Cl,4-OCHF$_2$,5-c-Pr) |
| Ph(2-Cl,4-c-Pr,5-SO$_2$Me) | Ph(2-Cl,4-CF$_2$CF$_3$,5-CF$_2$CF$_2$H) | Ph(2-Cl,4-OCHF$_2$CF$_3$,5-CF$_3$) |
| Ph(2-Cl,4-c-Pr,5-TMS) | Ph(2-Cl,4-OMe,5-OCF$_3$) | Ph(2-Cl,4-OCF$_2$CF$_3$,5-C$_2$F$_5$) |
| Ph(2-Cl,4-CF$_2$H,5-F) | Ph(2-Cl,4-OMe,5-OCHF$_2$) | Ph(2-Cl,4-OCHF$_2$,5-CF$_2$CF$_2$H) |
| Ph(2-Cl,4-CF$_2$H,5-Br) | Ph(2-Cl,4-OMe,5-OCF$_2$CF$_2$H) | |
| Ph(2-Cl,4-CF$_2$H,5-I) | Ph(2-Cl,4-OMe,5-OC$_2$F$_5$) | Ph(2-Cl,4-OCHF$_2$,5-CF$_2$H) |
| Ph(2-Cl,4-CF$_2$H,5-Me) | Ph(2-Cl,4-OMe,5-SO$_2$Me) | Ph(2-Cl,4-OCHF$_2$,5-OMe) |
| Ph(2-Cl,4-CF$_2$H,5-Et) | Ph(2-Cl,4-OMe,5-TMS) | Ph(2-Cl,4-OCHF$_2$,5-OCF$_3$) |
| Ph(2-Cl,4-CF$_2$H,5-n-Pr) | Ph(2-Cl,4-OMe,5-CN) | Ph(2-Cl,4,5-di-OCHF$_2$) |
| Ph(2-Cl,4-CF$_2$H,5-t-Bu) | Ph(2-Cl,4-OCF$_3$,5-Cl) | Ph(2-Cl,4-OCHF$_2$,5-OCF$_2$CF$_2$H) |
| Ph(2-Cl,4-CF$_2$H,5-i-Pr) | Ph(2-Cl,4-OCF$_3$,5-F) | |
| Ph(2-Cl,4-CF$_2$H,5-c-Pr) | Ph(2-Cl,4-OCF$_3$,5-Br) | Ph(2-Cl,4-OCHF$_2$,5-OC$_2$F$_5$) |
| Ph(2-Cl,4-CF$_2$H,5-CF$_3$) | Ph(2-Cl,4-OCF$_3$,5-I) | Ph(2-Cl,4-OCHF$_2$,5-SO$_2$Me) |
| Ph(2-Cl,4-CF$_2$H,5-C$_2$F$_5$) | Ph(2-Cl,4-OCF$_3$,5-Me) | Ph(2-Cl,4-OCHF$_2$,5-TMS) |
| Ph(2-Cl,4-CF$_2$H,5-CF$_2$CF$_2$H) | Ph(2-Cl,4-OCF$_3$,5-Et) | Ph(2-Cl,4-OCHF$_2$,5-CN) |
| Ph(2-Cl,4,5-di-CF$_2$H) | Ph(2-Cl,4-OCF$_3$,5-n-Pr) | Ph(2-Cl,4-OCF$_2$CF$_2$H,5-Cl) |
| Ph(2-Cl,4-CF$_2$H,5-OMe) | Ph(2-Cl,4-OCF$_3$,5-t-Bu) | Ph(2-Cl,4-OCF$_2$CF$_2$H,5-F) |
| Ph(2-Cl,4-CF$_2$H,5-OCF$_3$) | Ph(2-Cl,4-OCF$_3$,5-i-Pr) | Ph(2-Cl,4-OCF$_2$CF$_2$H,5-Br) |
| Ph(2-Cl,4-CF$_2$H,5-OCHF$_2$) | Ph(2-Cl,4-OCF$_3$,5-c-Pr) | Ph(2-Cl,4-OCF$_2$CF$_2$H,5-I) |
| Ph(2-Cl,4-CF$_2$H,5-OCF$_2$CF$_2$H) | Ph(2-Cl,4-OCF$_3$,5-CF$_3$) | Ph(2-Cl,4-OCF$_2$CF$_2$H,5-Me) |
| | Ph(2-Cl,4-OCF$_3$,5-C$_2$F$_5$) | Ph(2-Cl,4-OCF$_2$CF$_2$H,5-Et) |
| Ph(2-Cl,4-CF$_2$H,5-OC$_2$F$_5$) | Ph(2-Cl,4-OCF$_3$,5-CF$_2$CF$_2$H) | Ph(2-Cl,4-OCF$_2$CF$_2$H,5-n-Pr) |
| Ph(2-Cl,4-CF$_2$H,5-SO$_2$Me) | Ph(2-Cl,4-OCF$_3$,5-CF$_2$H) | Ph(2-Cl,4-OCF$_2$CF$_2$H,5-t-Bu) |
| Ph(2-Cl,4-CF$_2$H,5-TMS) | Ph(2-Cl,4-OCF$_3$,5-OMe) | Ph(2-Cl,4-OCF$_2$CF$_2$H,5-i-Pr) |
| Ph(2-Cl,4-CF$_2$H,5-CN) | Ph(2-Cl,4,5-di-OCF$_3$) | Ph(2-Cl,4-OCF$_2$CF$_2$H,5-c-Pr) |
| Ph(2-Cl,4-OMe,5-Cl) | Ph(2-Cl,4-OCF$_3$,5-OCHF$_2$) | Ph(2-Cl,4-OCF$_2$CF$_2$CF$_3$H,5-CF$_3$) |
| Ph(2-Cl,4-OMe,5-F) | Ph(2-Cl,4-OCF$_3$,5-OCF$_2$CF$_2$H) | |
| Ph(2-Cl,4-OMe,5-Br) | | Ph(2-Cl,4-OCF$_2$CF$_2$H,5-C$_2$F$_5$) |
| Ph(2-Cl,4-OMe,5-I) | Ph(2-Cl,4-OCF$_3$,5-OC$_2$F$_5$) | Ph(2-Cl,4-OCF$_2$CF$_2$H,5-CF$_2$CF$_2$H) |
| Ph(2-Cl,4-OMe,5-Me) | Ph(2-Cl,4-OCF$_3$,5-SO$_2$Me) | |
| Ph(2-Cl,4-OMe,5-Et) | Ph(2-Cl,4-OCF$_3$,5-TMS) | Ph(2-Cl,4-OCF$_2$CF$_2$H,5-CF$_2$H) |
| Ph(2-Cl,4-OMe,5-n-Pr) | Ph(2-Cl,4-OCF$_3$,5-CN) | Ph(2-Cl,4-OCF$_2$CF$_2$H,5-OMe) |
| Ph(2-Cl,4-OMe,5-t-Bu) | Ph(2-Cl,4-OCHF$_2$,5-Cl) | Ph(2-Cl,4-OCF$_2$CF$_2$H,5-OCF$_3$) |
| Ph(2-Cl,4-OMe,5-i-Pr) | Ph(2-Cl,4-OCHF$_2$,5-F) | |
| Ph(2-Cl,4-OMe,5-c-Pr) | Ph(2-Cl,4-OCHF$_2$,5-Br) | Ph(2-Cl,4-OCF$_2$CF$_2$H,5-OCF$_2$CF$_2$H) |
| Ph(2-Cl,4-OMeCF$_3$,5-CF$_3$) | Ph(2-Cl,4-OCHF$_2$,5-I) | |
| Ph(2-Cl,4-OMe,5-C$_2$F$_5$) | Ph(2-Cl,4-OCHF$_2$,5-Me) | Ph(2-Cl,4-OCF$_2$CF$_2$H,5-OMe) |
| Ph(2-Cl,4-OMe,5-CF$_2$CF$_2$H) | Ph(2-Cl,4-OCHF$_2$,5-Et) | Ph(2-Cl,4-OCF$_2$CF$_2$H,5-OCF$_3$) |
| Ph(2-Cl,4-OMe,5-CF$_2$H) | Ph(2-Cl,4-OCHF$_2$,5-n-Pr) | |
| Ph(2-Cl,4,5-di-OMe) | Ph(2-Cl,4-SO$_2$Me,5-I) | Ph(2-Cl,4-TMS,5-OCHF$_2$) |
| Ph(2-Cl,4-OCF$_2$CF$_2$H,5- | | |

-continued

| Q¹ | Q¹ | Q¹ |
|---|---|---|
| OCHF₂) | Ph(2-Cl,4-SO₂Me,5-Me) | Ph(2-Cl,4-TMS,5-OCF₂CF₂H) |
| Ph(2-Cl,4,5-di-OCF₂CF₂H) | Ph(2-Cl,4-SO₂Me,5-Et) | Ph(2-Cl,4-TMS,5-OC₂F₅) |
| Ph(2-Cl,4-OCF₂CF₂H,5-OC₂F₅) | Ph(2-Cl,4-SO₂Me,5-n-Pr) | Ph(2-Cl,4-TMS,5-SO₂Me) |
| Ph(2-Cl,4-OCF₂CF₂H,5-SO₂Me) | Ph(2-Cl,4-SO₂Me,5-t-Bu) | Ph(2-Cl,4,5-di-TMS) |
| Ph(2-Cl,4-OCF₂CF₂H,5-TMS) | Ph(2-Cl,4-SO₂Me,5-i-Pr) | Ph(2-Cl,4-TMS,5-CN) |
| Ph(2-Cl,4-OCF₂CF₂H,5-CN) | Ph(2-Cl,4-SO₂Me,5-c-Pr) | Ph(2-Cl,4-CN,5-Cl) |
| Ph(2-Cl,4-OCF₂CF₃,5-Cl) | Ph(2-Cl,4-SO₂MeCF₃,5-CF₃) | Ph(2-Cl,4-CN,5-F) |
| Ph(2-Cl,4-OCF₂CF₃,5-F) | Ph(2-Cl,4-SO₂Me,5-C₂F₅) | Ph(2-Cl,4-CN,5-Br) |
| Ph(2-Cl,4-OCF₂CF₃,5-Br) | Ph(2-Cl,4-SO₂Me,5-CF₂CF₂H) | Ph(2-Cl,4-CN,5-I) |
| Ph(2-Cl,4-OCF₂CF₃,5-I) | Ph(2-Cl,4-SO₂Me,5-CF₂H) | Ph(2-Cl,4-CN,5-Me) |
| Ph(2-Cl,4-OCF₂CF₃,5-Me) | Ph(2-Cl,4-SO₂Me,5-OMe) | Ph(2-Cl,4-CN,5-Et) |
| Ph(2-Cl,4-OCF₂CF₃,5-Et) | Ph(2-Cl,4-SO₂Me,5-OCF₃) | Ph(2-Cl,4-CN,5-n-Pr) |
| Ph(2-Cl,4-OCF₂CF₃,5-n-Pr) | Ph(2-Cl,4-SO₂Me,5-OCHF₂) | Ph(2-Cl,4-CN,5-t-Bu) |
| Ph(2-Cl,4-OCF₂CF₃,5-t-Bu) | Ph(2-Cl,4-SO₂Me,5-OCF₂CF₂H) | Ph(2-Cl,4-CN,5-i-Pr) |
| Ph(2-Cl,4-OCF₂CF₃,5-i-Pr) | Ph(2-Cl,4-SO₂Me,5-OC₂F₅) | Ph(2-Cl,4-CN,5-c-Pr) |
| Ph(2-Cl,4-OCF₂CF₃,5-c-Pr) | Ph(2-Cl,4,5-di-SO₂Me) | Ph(2-Cl,4-CN,5-CF₃) |
| Ph(2-Cl,4-OC₂F₅CF₃,5-CF₃) | Ph(2-Cl,4-SO₂Me,5-TMS) | Ph(2-Cl,4-CN,5-C₂F₅) |
| Ph(2-Cl,4-OCF₂CF₃,5-CF₂CF₂H) | Ph(2-Cl,4-SO₂Me,5-CN) | Ph(2-Cl,4-CN,5-CF₂CF₂H) |
| Ph(2-Cl,4-OCF₂CF₃,5-CF₂H) | Ph(2-Cl,4-TMS,5-Cl) | Ph(2-Cl,4-CN,5-CF₂H) |
| Ph(2-Cl,4-OCF₂CF₃,5-OMe) | Ph(2-Cl,4-TMS,5-F) | Ph(2-Cl,4-CN,5-OMe) |
| Ph(2-Cl,4-OCF₂CF₃,5-OCF₃) | Ph(2-Cl,4-TMS,5-Br) | Ph(2-Cl,4-CN,5-OCF₃) |
| Ph(2-Cl,4-OCF₂CF₃,5-OCHF₂) | Ph(2-Cl,4-TMS,5-I) | Ph(2-Cl,4-CN,5-OCHF₂) |
| Ph(2-Cl,4-OCF₂CF₃,5-OCF₂CF₂H) | Ph(2-Cl,4-TMS,5-Me) | Ph(2-Cl,4-CN,5-OCF₂CF₂H) |
| Ph(2-Cl,4,5-di-OC₂F₅) | Ph(2-Cl,4-TMS,5-Et) | Ph(2-Cl,4-CN,5-OC₂F₅) |
| Ph(2-Cl,4-OCF₂CF₃,5-SO₂Me) | Ph(2-Cl,4-TMS,5-n-Pr) | Ph(2-Cl,4-CN,5-SO₂Me) |
| Ph(2-Cl,4-OCF₂CF₃,5-TMS) | Ph(2-Cl,4-TMS,5-t-Bu) | Ph(2-Cl,4-CN,5-TMS) |
| Ph(2-Cl,4-OCF₂CF₃,5-CN) | Ph(2-Cl,4-TMS,5-i-Pr) | Ph(2-Cl,4,5-di-CN) |
| Ph(2-Cl,4-SO₂Me,5-Cl) | Ph(2-Cl,4-TMS,5-c-Pr) | Ph(2-F,3,4-di-Cl) |
| Ph(2-Cl,4-SO₂Me,5-F) | Ph(2-Cl,4-TMS,5-CF₃) | Ph(2-F,3-Cl,4-I) |
| Ph(2-Cl,4-SO₂Me,5-Br) | Ph(2-Cl,4-TMS,5-C₂F₅) | Ph(2-F,3-Cl,4-Me) |
| Ph(2-F,3-Cl,4-CF₂H) | Ph(2-Cl,4-TMS,5-CF₂CF₂H) | Ph(2-F,3-Cl,4-Et) |
| Ph(2-F,3-Cl,4-OMe) | Ph(2-Cl,4-TMS,5-CF₂H) | Ph(2-F,3-Cl,4-n-Pr) |
| Ph(2-F,3-Cl,4-OCHF₂) | Ph(2-Cl,4-TMS,5-OMe) | Ph(2-F,3-Cl,4-i-Pr) |
| Ph(2-F,3-Cl,4-OCF₂CF₂H) | Ph(2-Cl,4-TMS,5-OCF₃) | Ph(2-F,3-Cl,4-CF₃) |
| Ph(2-F,3-Cl,4-OC₂F₅) | Ph(2-F,3-I,4-Br) | Ph(2-F,3-Cl,4-C₂F₅) |
| Ph(2,3,4-tri-F) | Ph(2-F,3,4-di-I) | Ph(2-F,3-Cl,4-CF₂CF₂H) |
| Ph(2-F,3-F,4-Br) | Ph(2-F,3-I,4-Me) | Ph(2-F,3,4-di-Et) |
| Ph(2-F,3-F,4-I) | Ph(2-F,3-I,4-Et) | Ph(2-F,3-Et,4-n-Pr) |
| Ph(2-F,3-F,4-Et) | Ph(2-F,3-I,4-t-Bu) | Ph(2-F,3-Et,4-t-Bu) |
| Ph(2-F,3-F,4-n-Pr) | Ph(2-F,3-I,4-i-Pr) | Ph(2-F,3-Et,4-i-Pr) |
| Ph(2-F,3-F,4-t-Bu) | Ph(2-F,3-I,4-c-Pr) | Ph(2-F,3-Et,4-c-Pr) |
| Ph(2-F,3-F,4-i-Pr) | Ph(2-F,3-I,4-CF₃) | Ph(2-F,3-Et,4-CF₃) |
| Ph(2-F,3-F,4-CF₃) | Ph(2-F,3-I,4-C₂F₅) | Ph(2-F,3-Et,4-C₂F₅) |
| Ph(2-F,3-F,4-C₂F₅) | Ph(2-F,3-I,4-CF₂CF₂H) | Ph(2-F,3-Et,4-CF₂CF₂H) |
| Ph(2-F,3-F,4-CF₂CF₂H) | Ph(2-F,3-I,4-CF₂H) | Ph(2-F,3-Et,4-CF₂H) |
| Ph(2-F,3-F,4-CF₂H) | Ph(2-F,3-I,4-OMe) | Ph(2-F,3-Et,4-OMe) |
| Ph(2-F,3-F,4-OMe) | Ph(2-F,3-I,4-OCF₃) | Ph(2-F,3-Et,4-OCF₃) |
| Ph(2-F,3-F,4-OCHF₂) | Ph(2-F,3-I,4-OCHF₂) | Ph(2-F,3-Et,4-OCHF₂) |
| Ph(2-F,3-F,4-OCF₂CF₂H) | Ph(2-F,3-I,4-OCF₂CF₂H) | Ph(2-F,3-Et,4-OCF₂CF₂H) |
| Ph(2-F,3-F,4-OC₂F₅) | Ph(2-F,3-I,4-OC₂F₅) | Ph(2-F,3-Et,4-OC₂F₅) |
| Ph(2-F,3-Br,4-Cl) | Ph(2-F,3-I,4-SO₂Me) | Ph(2-F,3-Et,4-SO₂Me) |
| Ph(2-F,3,4-di-Br) | Ph(2-F,3-I,4-TMS) | Ph(2-F,3-Et,4-TMS) |
| Ph(2-F,3-Br,4-I) | Ph(2-F,3-I,4-CN) | Ph(2-F,3-Et,4-CN) |
| Ph(2-F,3-Br,4-Me) | Ph(2-F,3-Me,4-I) | Ph(2-F,3-n-Pr,4-Cl) |
| Ph(2-F,3-Br,4-Et) | Ph(2-F,3,4-di-Me) | Ph(2-F,3-n-Pr,4-F) |
| Ph(2-F,3-Br,4-n-Pr) | Ph(2-F,3-Me,4-Et) | Ph(2-F,3-n-Pr,4-Br) |
| Ph(2-F,3-Br,4-t-Bu) | Ph(2-F,3-Me,4-n-Pr) | Ph(2-F,3-n-Pr,4-I) |
| Ph(2-F,3-Br,4-i-Pr) | Ph(2-F,3-Me,4-i-Pr) | Ph(2-F,3-n-Pr,4-Me) |
| Ph(2-F,3-Br,4-CF₃) | Ph(2-F,3-Me,4-c-Pr) | Ph(2-F,3-n-Pr,4-Et) |
| Ph(2-F,3-Br,4-C₂F₅) | Ph(2-F,3-Me,4-C₂F₅) | Ph(2-F,3,4-di-n-Pr) |
| Ph(2-F,3-Br,4-CF₂CF₂H) | Ph(2-F,3-Me,4-CF₂CF₂H) | Ph(2-F,3-n-Pr,4-t-Bu) |
| Ph(2-F,3-Br,4-CF₂H) | Ph(2-F,3-Me,4-CF₂H) | Ph(2-F,3-n-Pr,4-i-Pr) |
| Ph(2-F,3-Br,4-OMe) | Ph(2-F,3-Me,4-OMe) | Ph(2-F,3-n-Pr,4-c-Pr) |
| Ph(2-F,3-Br,4-OCF₂CF₂H) | Ph(2-F,3-Me,4-OCF₂CF₂H) | Ph(2-F,3-n-Pr,4-CF₃) |
| Ph(2-F,3-Br,4-OC₂F₅) | Ph(2-F,3-Me,4-OC₂F₅) | Ph(2-F,3-n-Pr,4-C₂F₅) |
| Ph(2-F,3-I,4-Cl) | Ph(2-F,3-Et,4-Cl) | Ph(2-F,3-n-Pr,4-CF₂CF₂H) |
| Ph(2-F,3-I,4-F) | Ph(2-F,3-Et,4-F) | Ph(2-F,3-n-Pr,4-CF₂H) |
| Ph(2-F,3-n-Pr,4-TMS) | Ph(2-F,3-Et,4-Br) | Ph(2-F,3-n-Pr,4-OMe) |
| Ph(2-F,3-n-Pr,4-CN) | Ph(2-F,3-Et,4-I) | Ph(2-F,3-n-Pr,4-OCF₃) |
| Ph(2-F,3-t-Bu,4-I) | Ph(2-F,3-Et,4-Me) | Ph(2-F,3-n-Pr,4-OCHF₂) |
| Ph(2-F,3-t-Bu,4-Et) | Ph(2-F,3-c-Pr,4-n-Pr) | Ph(2-F,3-n-Pr,4-OCF₂CF₂H) |
|  | Ph(2-F,3-c-Pr,4-i-Pr) | Ph(2-F,3-n-Pr,4-OC₂F₅) |
|  | Ph(2-F,3-c-Pr,4-C₂F₅) | Ph(2-F,3-n-Pr,4-SO₂Me) |
|  | Ph(2-F,3-c-Pr,4-CF₂CF₂H) | Ph(2-F,3-C₂F₅,4-OMe) |
|  |  | Ph(2-F,3-C₂F₅,4-OCF₃) |
|  |  | Ph(2-F,3-C₂F₅,4-OCHF₂) |
|  |  | Ph(2-F,3-C₂F₅,4-OCF₂CF₂H) |

| $Q^1$ | $Q^1$ | $Q^1$ |
|---|---|---|
| Ph(2-F,3-t-Bu,4-n-Pr) | Ph(2-F,3-c-Pr,4-$CF_2H$) | Ph(2-F,3-$C_2F_5$,4-$OC_2F_5$) |
| Ph(2-F,3,4-di-t-Bu) | Ph(2-F,3-c-Pr,4-OMe) | Ph(2-F,3-$C_2F_5$,4-$SO_2Me$) |
| Ph(2-F,3-t-Bu,4-i-Pr) | Ph(2-F,3-c-Pr,4-$OCF_2CF_2H$) | Ph(2-F,3-$C_2F_5$,4-TMS) |
| Ph(2-F,3-t-Bu,4-$C_2F_5$) | Ph(2-F,3-c-Pr,4-$OC_2F_5$) | Ph(2-F,3-$C_2F_5$,4-CN) |
| Ph(2-F,3-t-Bu,4-$CF_2CF_2H$) | Ph(2-F,3-$CF_3$,4-I) | Ph(2-F,3-$CF_2CF_2H$,4-Cl) |
| Ph(2-F,3-t-Bu,4-$CF_2H$) | Ph(2-F,3-$CF_3$,4-Et) | Ph(2-F,3-$CF_2CF_2H$,4-F) |
| Ph(2-F,3-t-Bu,4-OMe) | Ph(2-F,3-$CF_3$,4-n-Pr) | Ph(2-F,3-$CF_2CF_2H$,4-Br) |
| Ph(2-F,3-t-Bu,4-$OCF_2CF_2H$) | Ph(2-F,3-$CF_3$,4-i-Pr) | Ph(2-F,3-$CF_2CF_2H$,4-I) |
| Ph(2-F,3-t-Bu,4-$OC_2F_5$) | Ph(2-F,3,4-di-$CF_3$) | Ph(2-F,3-$CF_2CF_2H$,4-Me) |
| Ph(2-F,3-i-Pr,4-Cl) | Ph(2-F,3-$CF_3$,4-$C_2F_5$) | Ph(2-F,3-$CF_2CF_2H$,4-Et) |
| Ph(2-F,3-i-Pr,4-F) | Ph(2-F,3-$CF_3$,4-$CF_2CF_2H$) | Ph(2-F,3-$CF_2CF_2H$,4-n-Pr) |
| Ph(2-F,3-i-Pr,4-Br) | Ph(2-F,3-$CF_3$,4-$CF_2H$) | Ph(2-F,3-$CF_2CF_2H$,4-t-Bu) |
| Ph(2-F,3-i-Pr,4-I) | Ph(2-F,3-$CF_3$,4-OMe) | Ph(2-F,3-$CF_2CF_2H$,4-i-Pr) |
| Ph(2-F,3-i-Pr,4-Me) | Ph(2-F,3-$CF_3$,4-$OCF_3$) | Ph(2-F,3-$CF_2CF_2H$,4-c-Pr) |
| Ph(2-F,3-i-Pr,4-Et) | Ph(2-F,3-$CF_3$,4-$OCHF_2$) | Ph(2-F,3-$CF_2CF_2H$,4-$CF_3$) |
| Ph(2-F,3-i-Pr,4-n-Pr) | Ph(2-F,3-$CF_3$,4-$OCF_2CF_2H$) | Ph(2-F,3-$CF_2CF_2H$,4-$C_2F_5$) |
| Ph(2-F,3-i-Pr,4-t-Bu) | Ph(2-F,3-$CF_3$,4-$OC_2F_5$) | Ph(2-F,3,4-di-$CF_2CF_2H$) |
| Ph(2-F,3,4-di-i-Pr) | Ph(2-F,3-$CF_3$,4-TMS) | Ph(2-F,3-$CF_2CF_2H$,4-$CF_2H$) |
| Ph(2-F,3-i-Pr,4-c-Pr) | Ph(2-F,3-$CF_3$,4-CN) | Ph(2-F,3-$CF_2CF_2H$,4-OMe) |
| Ph(2-F,3-i-Pr,4-$CF_3$) | Ph(2-F,3-$C_2F_5$,4-Cl) | Ph(2-F,3-$CF_2CF_2H$,4-$OCF_3$) |
| Ph(2-F,3-i-Pr,4-$C_2F_5$) | Ph(2-F,3-$C_2F_5$,4-F) | Ph(2-F,3-$CF_2CF_2H$,4-$OCHF_2$) |
| Ph(2-F,3-i-Pr,4-$CF_2CF_2H$) | Ph(2-F,3-$C_2F_5$,4-Br) | Ph(2-F,3-$CF_2CF_2H$,4-$OCF_2CF_2H$) |
| Ph(2-F,3-i-Pr,4-$CF_2H$) | Ph(2-F,3-$C_2F_5$,4-I) | Ph(2-F,3-$CF_2CF_2H$,4-$OC_2F_5$) |
| Ph(2-F,3-i-Pr,4-OMe) | Ph(2-F,3-$C_2F_5$,4-Me) | Ph(2-F,3-$CF_2CF_2H$,4-$SO_2Me$) |
| Ph(2-F,3-i-Pr,4-$OCF_3$) | Ph(2-F,3-$C_2F_5$,4-Et) | Ph(2-F,3-$CF_2CF_2H$,4-TMS) |
| Ph(2-F,3-i-Pr,4-$OCHF_2$) | Ph(2-F,3-$C_2F_5$,4-n-Pr) | Ph(2-F,3-$CF_2CF_2H$,4-CN) |
| Ph(2-F,3-i-Pr,4-$OCF_2CF_2H$) | Ph(2-F,3-$C_2F_5$,4-t-Bu) | Ph(2-F,3-$CF_2H$,4-Cl) |
| Ph(2-F,3-i-Pr,4-$OC_2F_5$) | Ph(2-F,3-$C_2F_5$,4-i-Pr) | Ph(2-F,3-$CF_2H$,4-F) |
| Ph(2-F,3-i-Pr,4-$SO_2Me$) | Ph(2-F,3-$C_2F_5$,4-c-Pr) | Ph(2-F,3-$CF_2H$,4-Br) |
| Ph(2-F,3-i-Pr,4-TMS) | Ph(2-F,3-$C_2F_5CF_3$,4-$CF_3$) | Ph(2-F,3-$CF_2H$,4-I) |
| Ph(2-F,3-i-Pr,4-CN) | Ph(2-F,3,4-di-$C_2F_5$) | Ph(2-F,3-$CF_2H$,4-Me) |
| Ph(2-F,3-c-Pr,4-I) | Ph(2-F,3-$C_2F_5$,4-$CF_2CF_2H$) | Ph(2-F,3-$CF_2H$,4-Et) |
| Ph(2-F,3-c-Pr,4-Et) | Ph(2-F,3-$C_2F_5$,4-$CF_2H$) | Ph(2-F,3-$OCHF_2$,4-$OC_2F_5$) |
| Ph(2-F,3-$CF_2H$,4-n-Pr) | Ph(2-F,3-OMe,4-CN) | Ph(2-F,3-$OCHF_2$,4-$SO_2Me$) |
| Ph(2-F,3-$CF_2H$,4-t-Bu) | Ph(2-F,3-$OCF_3$,4-Cl) | Ph(2-F,3-$OCHF_2$,4-TMS) |
| Ph(2-F,3-$CF_2H$,4-i-Pr) | Ph(2-F,3-$OCF_3$,4-F) | Ph(2-F,3-$OCHF_2$,4-CN) |
| Ph(2-F,3-$CF_2H$,4-c-Pr) | Ph(2-F,3-$OCF_3$,4-Br) | Ph(2-F,3-$OCF_2CF_2H$,4-Cl) |
| Ph(2-F,3-$CF_2H$,4-$CF_3$) | Ph(2-F,3-$OCF_3$,4-I) | Ph(2-F,3-$OCF_2CF_2H$,4-F) |
| Ph(2-F,3-$CF_2H$,4-$C_2F_5$) | Ph(2-F,3-$OCF_3$,4-Me) | Ph(2-F,3-$OCF_2CF_2H$,4-Br) |
| Ph(2-F,3-$CF_2H$,4-$CF_2CF_2H$) | Ph(2-F,3-$OCF_3$,4-Et) | Ph(2-F,3-$OCF_2CF_2H$,4-I) |
| Ph(2-F,3,4-di-$CF_2H$) | Ph(2-F,3-$OCF_3$,4-n-Pr) | Ph(2-F,3-$OCF_2CF_2H$,4-Me) |
| Ph(2-F,3-$CF_2H$,4-OMe) | Ph(2-F,3-$OCF_3$,4-t-Bu) | Ph(2-F,3-$OCF_2CF_2H$,4-Et) |
| Ph(2-F,3-$CF_2H$,4-$OCF_3$) | Ph(2-F,3-$OCF_3$,4-i-Pr) | Ph(2-F,3-$OCF_2CF_2H$,4-n-Pr) |
| Ph(2-F,3-$CF_2H$,4-$OCHF_2$) | Ph(2-F,3-$OCF_3$,4-$CF_3$) | Ph(2-F,3-$OCF_2CF_2H$,4-t-Bu) |
| Ph(2-F,3-$CF_2H$,4-$OCF_2CF_2H$) | Ph(2-F,3-$OCF_3$,4-$C_2F_5$) | Ph(2-F,3-$OCF_2CF_2H$,4-i-Pr) |
| Ph(2-F,3-$CF_2H$,4-$OC_2F_5$) | Ph(2-F,3-$OCF_3$,4-$CF_2CF_2H$) | Ph(2-F,3-$OCF_2CF_2H$,4-c-Pr) |
| Ph(2-F,3-$CF_2H$,4-$SO_2Me$) | Ph(2-F,3-$OCF_3$,4-$CF_2H$) | Ph(2-F,3-$OCF_2CF_2H$,4-$CF_3$) |
| Ph(2-F,3-$CF_2H$,4-TMS) | Ph(2-F,3-$OCF_3$,4-OMe) | Ph(2-F,3-$OCF_2CF_2H$,4-$C_2F_5$) |
| Ph(2-F,3-$CF_2H$,4-CN) | Ph(2-F,3,4-di-$OCF_3$) | Ph(2-F,3-$OCF_2CF_2H$,4-$CF_2CF_2H$) |
| Ph(2-F,3-OMe,4-Cl) | Ph(2-F,3-$OCF_3$,4-$OCF_2CF_2H$) | Ph(2-F,3-$OCF_2CF_2H$,4-$CF_2H$) |
| Ph(2-F,3-OMe,4-F) | Ph(2-F,3-$OCF_3$,4-$OC_2F_5$) | Ph(2-F,3-$OCF_2CF_2H$,4-OMe) |
| Ph(2-F,3-OMe,4-Br) | Ph(2-F,3-$OCHF_2$,4-Cl) | Ph(2-F,3-$OCF_2CF_2H$,4-$OCF_3$) |
| Ph(2-F,3-OMe,4-I) | Ph(2-F,3-$OCHF_2$,4-F) | Ph(2-F,3-$OCF_2CF_2H$,4-$OCHF_2$) |
| Ph(2-F,3-OMe,4-Me) | Ph(2-F,3-$OCHF_2$,4-Br) | Ph(2-F,3,4-di-$OCF_2CF_2H$) |
| Ph(2-F,3-OMe,4-Et) | Ph(2-F,3-$OCHF_2$,4-I) | Ph(2-F,3-$OCF_2CF_2H$,4-$OC_2F_5$) |
| Ph(2-F,3-OMe,4-n-Pr) | Ph(2-F,3-$OCHF_2$,4-Me) | Ph(2-F,3-$OCF_2CF_2H$,4-$SO_2Me$) |
| Ph(2-F,3-OMe,4-t-Bu) | Ph(2-F,3-$OCHF_2$,4-Et) | |
| Ph(2-F,3-OMe,4-i-Pr) | Ph(2-F,3-$OCHF_2$,4-n-Pr) | Ph(2-F,3-$OCF_2CF_2H$,4-TMS) |
| Ph(2-F,3-OMe,4-c-Pr) | Ph(2-F,3-$OCHF_2$,4-t-Bu) | Ph(2-F,3-$OCF_2CF_2H$,4-CN) |
| Ph(2-F,3-OMe,4-$CF_3$) | Ph(2-F,3-$OCHF_2$,4-i-Pr) | Ph(2-F,3-$OC_2F_5$,4-Cl) |
| Ph(2-F,3-OMe,4-$C_2F_5$) | Ph(2-F,3-$OCHF_2$,4-c-Pr) | Ph(2-F,3-$OC_2F_5$,4-F) |
| Ph(2-F,3-OMe,4-$CF_2CF_2H$) | Ph(2-F,3-$OCHF_2CF_3$,4-$CF_3$) | Ph(2-F,3-$OC_2F_5$,4-Br) |
| Ph(2-F,3-OMe,4-$CF_2H$) | Ph(2-F,3-$OC_2F_5$,4-$C_2F_5$) | Ph(2-F,3-$OC_2F_5$,4-I) |
| Ph(2-F,3,4-di-OMe) | Ph(2-F,3-$OCHF_2$,4-$CF_2CF_2H$) | Ph(2-F,3-$OC_2F_5$,4-Me) |
| Ph(2-F,3-OMe,4-$OCF_3$) | Ph(2-F,3-$OCHF_2$,4-$CF_2H$) | Ph(2-F,3-$OC_2F_5$,4-Et) |
| Ph(2-F,3-OMe,4-$OCHF_2$) | Ph(2-F,3-$OCHF_2$,4-OMe) | Ph(2-F,3-$OC_2F_5$,4-Br) |
| Ph(2-F,3-OMe,4-$OCF_2CF_2H$) | Ph(2-F,3-$OCHF_2$,4-$OCF_3$) | Ph(2-F,3-$OC_2F_5$,4-n-Pr) |
| Ph(2-F,3-OMe,4-$OC_2F_5$) | Ph(2-F,3,4-di-$OCHF_2$) | |
| Ph(2-F,3-OMe,4-$SO_2Me$) | Ph(2-F,3-$OCHF_2$,4-$OCF_2CF_2H$) | |
| Ph(2-F,3-OMe,4-TMS) | | Ph(2-F,3,5-di-Cl) |
| Ph(2-F,3-$OC_2F_5$,4-t-Bu) | Ph(2-F,3-TMS,4-Et) | Ph(2-F,3-Cl,5-F) |
| Ph(2-F,3-$OC_2F_5$,4-i-Pr) | Ph(2-F,3-TMS,4-n-Pr) | Ph(2-F,3-Cl,5-Br) |
| Ph(2-F,3-$OC_2F_5$,4-c-Pr) | Ph(2-F,3-TMS,4-t-Bu) | Ph(2-F,3-Cl,5-I) |
| Ph(2-F,3-$OC_2F_5CF_3$,4-$CF_3$) | Ph(2-F,3-TMS,4-i-Pr) | Ph(2-F,3-Cl,5-Me) |
| Ph(2-F,3-$OC_2F_5$,4-$CF_2CF_2H$) | Ph(2-F,3-TMS,4-c-Pr) | Ph(2-F,3-Cl,5-Et) |
| Ph(2-F,3-$OC_2F_5$,4-$CF_2H$) | Ph(2-F,3-TMS,4-$CF_3$) | Ph(2-F,3-Cl,5-n-Pr) |
| Ph(2-F,3-$OC_2F_5$,4-OMe) | Ph(2-F,3-TMS,4-$C_2F_5$) | |

-continued

| Q¹ | Q¹ | Q¹ |
|---|---|---|
| Ph(2-F,3-OC$_2$F$_5$,4-OCF$_3$) | Ph(2-F,3-TMS,4-CF$_2$CF$_2$H) | Ph(2-F,3-Cl,5-t-Bu) |
| Ph(2-F,3-OC$_2$F$_5$,4-OCHF$_2$) | Ph(2-F,3-TMS,4-CF$_2$H) | Ph(2-F,3-Cl,5-i-Pr) |
| Ph(2-F,3-OC$_2$F$_5$,4-OCF$_2$CF$_2$H) | Ph(2-F,3-TMS,4-OMe) | Ph(2-F,3-Cl,5-c-Pr) |
| Ph(2-F,3,4-di-OC$_2$F$_5$) | Ph(2-F,3-TMS,4-OCF$_3$) | Ph(2-F,3-Cl,5-CF$_3$) |
| Ph(2-F,3-OC$_2$F$_5$,4-SO$_2$Me) | Ph(2-F,3-TMS,4-OCHF$_2$) | Ph(2-F,3-Cl,5-C$_2$F$_5$) |
| Ph(2-F,3-OC$_2$F$_5$,4-TMS) | Ph(2-F,3-TMS,4-OCF$_2$CF$_2$H) | Ph(2-F,3-Cl,5-CF$_2$CF$_2$H) |
| Ph(2-F,3-OC$_2$F$_5$,4-CN) | Ph(2-F,3-TMS,4-OC$_2$F$_5$) | Ph(2-F,3-Cl,5-CF$_2$H) |
| Ph(2-F,3-SO$_2$Me,4-Cl) | Ph(2-F,3-TMS,4-SO$_2$Me) | Ph(2-F,3-Cl,5-OMe) |
| Ph(2-F,3-SO$_2$Me,4-Br) | Ph(2-F,3,4-di-TMS) | Ph(2-F,3-Cl,5-OCF$_3$) |
| Ph(2-F,3-SO$_2$Me,4-I) | Ph(2-F,3-TMS,4-CN) | Ph(2-F,3-Cl,5-OCHF$_2$) |
| Ph(2-F,3-SO$_2$Me,4-Me) | Ph(2-F,3-CN,4-F) | Ph(2-F,3-Cl,5-OCF$_2$CF$_2$H) |
| Ph(2-F,3-SO$_2$Me,4-Et) | Ph(2-F,3-CN,4-Br) | Ph(2-F,3-Cl,5-OC$_2$F$_5$) |
| Ph(2-F,3-SO$_2$Me,4-n-Pr) | Ph(2-F,3-CN,4-I) | Ph(2-F,3-Cl,5-SO$_2$Me) |
| Ph(2-F,3-SO$_2$Me,4-t-Bu) | Ph(2-F,3-CN,4-Me) | Ph(2-F,3-Cl,5-TMS) |
| Ph(2-F,3-SO$_2$Me,4-i-Pr) | Ph(2-F,3-CN,4-Et) | Ph(2-F,3-Cl,5-CN) |
| Ph(2-F,3-SO$_2$MeCF$_3$,4-CF$_3$) | Ph(2-F,3-CN,4-n-Pr) | Ph(2-F,3-F,5-Cl) |
| Ph(2-F,3-SO$_2$Me,4-C$_2$F$_5$) | Ph(2-F,3-CN,4-t-Bu) | Ph(2,3,5-tri-F) |
| Ph(2-F,3-SO$_2$Me,4-CF$_2$CF$_2$H) | Ph(2-F,3-CN,4-i-Pr) | Ph(2-F,3-F,5-Br) |
| Ph(2-F,3-SO$_2$Me,4-CF$_2$H) | Ph(2-F,3-CN,4-c-Pr) | Ph(2-F,3-F,5-I) |
| Ph(2-F,3-SO$_2$Me,4-OMe) | Ph(2-F,3-CN,4-CF$_3$) | Ph(2-F,3-F,5-Me) |
| Ph(2-F,3-SO$_2$Me,4-OCHF$_2$) | Ph(2-F,3-CN,4-C$_2$F$_5$) | Ph(2-F,3-F,5-Et) |
| Ph(2-F,3-SO$_2$Me,4-OCF$_2$CF$_2$H) | Ph(2-F,3-CN,4-CF$_2$CF$_2$H) | Ph(2-F,3-F,5-n-Pr) |
| Ph(2-F,3-SO$_2$Me,4-OC$_2$F$_5$) | Ph(2-F,3-CN,4-CF$_2$H) | Ph(2-F,3-F,5-t-Bu) |
| Ph(2-F,3-TMS,4-Cl) | Ph(2-F,3-CN,4-OMe) | Ph(2-F,3-F,5-i-Pr) |
| Ph(2-F,3-TMS,4-F) | Ph(2-F,3-CN,4-OCF$_3$) | Ph(2-F,3-F,5-c-Pr) |
| Ph(2-F,3-TMS,4-Br) | Ph(2-F,3-CN,4-OCHF$_2$) | Ph(2-F,3-F,5-CF$_3$) |
| Ph(2-F,3-TMS,4-I) | Ph(2-F,3-CN,4-OCF$_2$CF$_2$H) | Ph(2-F,3-F,5-C$_2$F$_5$) |
| Ph(2-F,3-TMS,4-Me) | Ph(2-F,3-CN,4-OC$_2$F$_5$) | Ph(2-F,3-F,5-CF$_2$CF$_2$H) |
| Ph(2-F,3-F,5-OCF$_3$) | Ph(2-F,3-CN,4-TMS) | Ph(2-F,3-F,5-CF$_2$H) |
| Ph(2-F,3-F,5-OCHF$_2$) | Ph(2-F,3,4-di-CN) | Ph(2-F,3-F,5-OMe) |
| Ph(2-F,3-F,5-OCF$_2$CF$_2$H) | Ph(2-F,3-I,5-i-Pr) | Ph(2-F,3-Et,5-F) |
| Ph(2-F,3-F,5-OC$_2$F$_5$) | Ph(2-F,3-I,5-c-Pr) | Ph(2-F,3-Et,5-Br) |
| Ph(2-F,3-F,5-SO$_2$Me) | Ph(2-F,3-I,5-CF$_3$) | Ph(2-F,3-Et,5-I) |
| Ph(2-F,3-F,5-TMS) | Ph(2-F,3-I,5-C$_2$F$_5$) | Ph(2-F,3-Et,5-Me) |
| Ph(2-F,3-F,5-CN) | Ph(2-F,3-I,5-CF$_2$CF$_2$H) | Ph(2-F,3,5-di-Et) |
| Ph(2-F,3-Br,5-Cl) | Ph(2-F,3-I,5-CF$_2$H) | Ph(2-F,3-Et,5-n-Pr) |
| Ph(2-F,3-Br,5-F) | Ph(2-F,3-I,5-OMe) | Ph(2-F,3-Et,5-t-Bu) |
| Ph(2-F,3,5-di-Br) | Ph(2-F,3-I,5-OCF$_3$) | Ph(2-F,3-Et,5-i-Pr) |
| Ph(2-F,3-Br,5-I) | Ph(2-F,3-I,5-OCHF$_2$) | Ph(2-F,3-Et,5-c-Pr) |
| Ph(2-F,3-Br,5-Me) | Ph(2-F,3-I,5-OCF$_2$CF$_2$H) | Ph(2-F,3-Et,5-CF$_3$) |
| Ph(2-F,3-Br,5-Et) | Ph(2-F,3-I,5-OC$_2$F$_5$) | Ph(2-F,3-Et,5-C$_2$F$_5$) |
| Ph(2-F,3-Br,5-n-Pr) | Ph(2-F,3-I,5-SO$_2$Me) | Ph(2-F,3-Et,5-CF$_2$CF$_2$H) |
| Ph(2-F,3-Br,5-t-Bu) | Ph(2-F,3-I,5-TMS) | Ph(2-F,3-Et,5-CF$_2$H) |
| Ph(2-F,3-Br,5-i-Pr) | Ph(2-F,3-I,5-CN) | Ph(2-F,3-Et,5-OMe) |
| Ph(2-F,3-Br,5-c-Pr) | Ph(2-F,3-Me,5-Cl) | Ph(2-F,3-Et,5-OCF$_3$) |
| Ph(2-F,3-Br,5-CF$_3$) | Ph(2-F,3-Me,5-F) | Ph(2-F,3-Et,5-OCHF$_2$) |
| Ph(2-F,3-Br,5-C$_2$F$_5$) | Ph(2-F,3-Me,5-Br) | Ph(2-F,3-Et,5-OCF$_2$CF$_2$H) |
| Ph(2-F,3-Br,5-CF$_2$CF$_2$H) | Ph(2-F,3-Me,5-I) | Ph(2-F,3-Et,5-OC$_2$F$_5$) |
| Ph(2-F,3-Br,5-CF$_2$H) | Ph(2-F,3,5-di-Me) | Ph(2-F,3-Et,5-SO$_2$Me) |
| Ph(2-F,3-Br,5-OMe) | Ph(2-F,3-Me,5-Et) | Ph(2-F,3-Et,5-TMS) |
| Ph(2-F,3-Br,5-OCF$_3$) | Ph(2-F,3-Me,5-n-Pr) | Ph(2-F,3-Et,5-CN) |
| Ph(2-F,3-Br,5-OCHF$_2$) | Ph(2-F,3-Me,5-t-Bu) | Ph(2-F,3-n-Pr,5-Cl) |
| Ph(2-F,3-Br,5-OCF$_2$CF$_2$H) | Ph(2-F,3-Me,5-i-Pr) | Ph(2-F,3-n-Pr,5-F) |
| Ph(2-F,3-Br,5-OC$_2$F$_5$) | Ph(2-F,3-Me,5-c-Pr) | Ph(2-F,3-n-Pr,5-Br) |
| Ph(2-F,3-Br,5-SO$_2$Me) | Ph(2-F,3-Me,5-CF$_3$) | Ph(2-F,3-n-Pr,5-I) |
| Ph(2-F,3-Br,5-TMS) | Ph(2-F,3-Me,5-C$_2$F$_5$) | Ph(2-F,3-n-Pr,5-Me) |
| Ph(2-F,3-Br,5-CN) | Ph(2-F,3-Me,5-CF$_2$CF$_2$H) | Ph(2-F,3-n-Pr,5-Et) |
| Ph(2-F,3-I,5-Cl) | Ph(2-F,3-Me,5-CF$_2$H) | Ph(2-F,3,5-di-n-Pr) |
| Ph(2-F,3-I,5-F) | Ph(2-F,3-Me,5-OMe) | Ph(2-F,3-n-Pr,5-t-Bu) |
| Ph(2-F,3-I,5-Br) | Ph(2-F,3-Me,5-OCF$_3$) | Ph(2-F,3-n-Pr,5-i-Pr) |
| Ph(2-F,3,5-di-I) | Ph(2-F,3-Me,5-OCHF$_2$) | Ph(2-F,3-n-Pr,5-c-Pr) |
| Ph(2-F,3-I,5-Me) | Ph(2-F,3-Me,5-OCF$_2$CF$_2$H) | Ph(2-F,3-n-Pr,5-CF$_3$) |
| Ph(2-F,3-I,5-Et) | Ph(2-F,3-Me,5-OC$_2$F$_5$) | Ph(2-F,3-n-Pr,5-C$_2$F$_5$) |
| Ph(2-F,3-I,5-n-Pr) | Ph(2-F,3-Me,5-SO$_2$Me) | Ph(2-F,3-n-Pr,5-CF$_2$CF$_2$H) |
| Ph(2-F,3-I,5-t-Bu) | Ph(2-F,3-Me,5-TMS) | Ph(2-F,3-n-Pr,5-CF$_2$H) |
| Ph(2-F,3-n-Pr,5-OCHF$_2$) | Ph(2-F,3-Me,5-CN) | Ph(2-F,3-n-Pr,5-OMe) |
| Ph(2-F,3-n-Pr,5-OCF$_2$CF$_2$H) | Ph(2-F,3-Et,5-Cl) | Ph(2-F,3-n-Pr,5-OCF$_3$) |
| Ph(2-F,3-n-Pr,5-OC$_2$F$_5$) | Ph(2-F,3-i-Pr,5-c-Pr) | Ph(2-F,3-CF$_3$,5-Br) |
| Ph(2-F,3-n-Pr,5-SO$_2$Me) | Ph(2-F,3-i-Pr,5-CF$_3$) | Ph(2-F,3-CF$_3$,5-I) |
| Ph(2-F,3-n-Pr,5-TMS) | Ph(2-F,3-i-Pr,5-C$_2$F$_5$) | Ph(2-F,3-CF$_3$,5-Me) |
| Ph(2-F,3-n-Pr,5-CN) | Ph(2-F,3-i-Pr,5-CF$_2$CF$_2$H) | Ph(2-F,3-CF$_3$,5-Et) |
| Ph(2-F,3-t-Bu,5-Cl) | Ph(2-F,3-i-Pr,5-CF$_2$H) | Ph(2-F,3-CF$_3$,5-n-Pr) |
| Ph(2-F,3-t-Bu,5-F) | Ph(2-F,3-i-Pr,5-OMe) | Ph(2-F,3-CF$_3$,5-t-Bu) |
| Ph(2-F,3-t-Bu,5-Br) | Ph(2-F,3-i-Pr,5-OCF$_3$) | Ph(2-F,3-CF$_3$,5-i-Pr) |
| Ph(2-F,3-t-Bu,5-I) | Ph(2-F,3-i-Pr,5-OCHF$_2$) | Ph(2-F,3-CF$_3$,5-c-Pr) |
|  | Ph(2-F,3-i-Pr,5-OCF$_2$CF$_2$H) | Ph(2-F,3,5-di-CF$_3$) |
|  | Ph(2-F,3-i-Pr,5-OC$_2$F$_5$) | Ph(2-F,3-CF$_3$,5-C$_2$F$_5$) |

-continued

| Q¹ | Q¹ | Q¹ |
|---|---|---|
| Ph(2-F,3-t-Bu,5-Me) | Ph(2-F,3-i-Pr,5-SO₂Me) | Ph(2-F,3-CF₃,5-CF₂CF₂H) |
| Ph(2-F,3-t-Bu,5-Et) | Ph(2-F,3-i-Pr,5-TMS) | Ph(2-F,3-CF₃,5-CF₂H) |
| Ph(2-F,3-t-Bu,5-n-Pr) | Ph(2-F,3-i-Pr,5-CN) | Ph(2-F,3-CF₃,5-OMe) |
| Ph(2-F,3,5-di-t-Bu) | Ph(2-F,3-c-Pr,5-Cl) | Ph(2-F,3-CF₃,5-OCF₃) |
| Ph(2-F,3-t-Bu,5-i-Pr) | Ph(2-F,3-c-Pr,5-F) | Ph(2-F,3-CF₃,5-OCHF₂) |
| Ph(2-F,3-t-Bu,5-c-Pr) | Ph(2-F,3-c-Pr,5-Br) | Ph(2-F,3-CF₃,5-OCF₂CF₂H) |
| Ph(2-F,3-t-Bu,5-CF₃) | Ph(2-F,3-c-Pr,5-I) | Ph(2-F,3-CF₃,5-OC₂F₅) |
| Ph(2-F,3-t-Bu,5-C₂F₅) | Ph(2-F,3-c-Pr,5-Me) | Ph(2-F,3-CF₃,5-SO₂Me) |
| Ph(2-F,3-t-Bu,5-CF₂CF₂H) | Ph(2-F,3-c-Pr,5-Et) | Ph(2-F,3-CF₃,5-TMS) |
| Ph(2-F,3-t-Bu,5-CF₂H) | Ph(2-F,3-c-Pr,5-n-Pr) | Ph(2-F,3-CF₃,5-CN) |
| Ph(2-F,3-t-Bu,5-OMe) | Ph(2-F,3-c-Pr,5-t-Bu) | Ph(2-F,3-C₂F₅,5-Cl) |
| Ph(2-F,3-t-Bu,5-OCF₃) | Ph(2-F,3-c-Pr,5-i-Pr) | Ph(2-F,3-C₂F₅,5-F) |
| Ph(2-F,3-t-Bu,5-OCHF₂) | Ph(2-F,3,5-di-c-Pr) | Ph(2-F,3-C₂F₅,5-Br) |
| Ph(2-F,3-t-Bu,5-OCF₂CF₂H) | Ph(2-F,3-c-Pr,5-CF₃) | Ph(2-F,3-C₂F₅,5-I) |
| Ph(2-F,3-t-Bu,5-OC₂F₅) | Ph(2-F,3-c-Pr,5-C₂F₅) | Ph(2-F,3-C₂F₅,5-Me) |
| Ph(2-F,3-t-Bu,5-SO₂Me) | Ph(2-F,3-c-Pr,5-CF₂CF₂H) | Ph(2-F,3-C₂F₅,5-Et) |
| Ph(2-F,3-t-Bu,5-TMS) | Ph(2-F,3-c-Pr,5-CF₂H) | Ph(2-F,3-C₂F₅,5-n-Pr) |
| Ph(2-F,3-t-Bu,5-CN) | Ph(2-F,3-c-Pr,5-OMe) | Ph(2-F,3-C₂F₅,5-t-Bu) |
| Ph(2-F,3-i-Pr,5-Cl) | Ph(2-F,3-c-Pr,5-OCF₃) | Ph(2-F,3-C₂F₅,5-i-Pr) |
| Ph(2-F,3-i-Pr,5-F) | Ph(2-F,3-c-Pr,5-OCHF₂) | Ph(2-F,3-C₂F₅,5-c-Pr) |
| Ph(2-F,3-i-Pr,5-Br) | Ph(2-F,3-c-Pr,5-OCF₂CF₂H) | Ph(2-F,3-C₂F₅CF₃,5-CF₃) |
| Ph(2-F,3-i-Pr,5-I) | Ph(2-F,3-c-Pr,5-OC₂F₅) | Ph(2-F,3,5-di-C₂F₅) |
| Ph(2-F,3-i-Pr,5-Me) | Ph(2-F,3-c-Pr,5-SO₂Me) | Ph(2-F,3-C₂F₅,5-CF₂CF₂H) |
| Ph(2-F,3-i-Pr,5-Et) | Ph(2-F,3-c-Pr,5-TMS) | Ph(2-F,3-C₂F₅,5-CF₂H) |
| Ph(2-F,3-i-Pr,5-n-Pr) | Ph(2-F,3-c-Pr,5-CN) | Ph(2-F,3-C₂F₅,5-OMe) |
| Ph(2-F,3-i-Pr,5-t-Bu) | Ph(2-F,3-CF₃,5-Cl) | Ph(2-F,3-C₂F₅,5-OCF₃) |
| Ph(2-F,3,5-di-i-Pr) | Ph(2-F,3-CF₃,5-F) | Ph(2-F,3-C₂F₅,5-OCHF₂) |
| Ph(2-F,3-C₂F₅,5-OCF₂CF₂H) | Ph(2-F,3-CF₂H,5-c-Pr) | Ph(2-F,3-OCF₃,5-Br) |
| Ph(2-F,3-C₂F₅,5-OC₂F₅) | Ph(2-F,3-CF₂H,5-CF₃) | Ph(2-F,3-OCF₃,5-I) |
| Ph(2-F,3-C₂F₅,5-SO₂Me) | Ph(2-F,3-CF₂H,5-C₂F₅) | Ph(2-F,3-OCF₃,5-Me) |
| Ph(2-F,3-C₂F₅,5-TMS) | Ph(2-F,3-CF₂H,5-CF₂CF₂H) | Ph(2-F,3-OCF₃,5-Et) |
| Ph(2-F,3-C₂F₅,5-CN) | Ph(2-F,3,5-di-CF₂H) | Ph(2-F,3-OCF₃,5-n-Pr) |
| Ph(2-F,3-CF₂CF₂H,5-Cl) | Ph(2-F,3-CF₂H,5-OMe) | Ph(2-F,3-OCF₃,5-t-Bu) |
| Ph(2-F,3-CF₂CF₂H,5-F) | Ph(2-F,3-CF₂H,5-OCF₃) | Ph(2-F,3-OCF₃,5-i-Pr) |
| Ph(2-F,3-CF₂CF₂H,5-Br) | Ph(2-F,3-CF₂H,5-OCHF₂) | Ph(2-F,3-OCF₃,5-c-Pr) |
| Ph(2-F,3-CF₂CF₂H,5-I) | Ph(2-F,3-CF₂H,5-OCF₂CF₂H) | Ph(2-F,3-OCF₃,5-CF₃) |
| Ph(2-F,3-CF₂CF₂H,5-Me) | Ph(2-F,3-CF₂H,5-OC₂F₅) | Ph(2-F,3-OCF₃,5-C₂F₅) |
| Ph(2-F,3-CF₂CF₂H,5-Et) | Ph(2-F,3-CF₂H,5-SO₂Me) | Ph(2-F,3-OCF₃,5-CF₂CF₂H) |
| Ph(2-F,3-CF₂CF₂H,5-n-Pr) | Ph(2-F,3-CF₂H,5-TMS) | Ph(2-F,3-OCF₃,5-CF₂H) |
| Ph(2-F,3-CF₂CF₂H,5-t-Bu) | Ph(2-F,3-CF₂H,5-CN) | Ph(2-F,3-OCF₃,5-OMe) |
| Ph(2-F,3-CF₂CF₂H,5-i-Pr) | Ph(2-F,3-OMe,5-Cl) | Ph(2-F,3,5-di-OCF₃) |
| Ph(2-F,3-CF₂CF₂H,5-c-Pr) | Ph(2-F,3-OMe,5-F) | Ph(2-F,3-OCF₃,5-OCHF₂) |
| Ph(2-F,3-CF₂CF₂H,5-CF₃) | Ph(2-F,3-OMe,5-Br) | Ph(2-F,3-OCF₃,5-OCF₂CF₂H) |
| Ph(2-F,3-CF₂CF₂H,5-C₂F₅) | Ph(2-F,3-OMe,5-I) | Ph(2-F,3-OCF₃,5-OC₂F₅) |
| Ph(2-F,3,5-di-CF₂CF₂H) | Ph(2-F,3-OMe,5-Me) | Ph(2-F,3-OCF₃,5-SO₂Me) |
| Ph(2-F,3-CF₂CF₂H,5-CF₂H) | Ph(2-F,3-OMe,5-Et) | Ph(2-F,3-OCF₃,5-TMS) |
| Ph(2-F,3-CF₂CF₂H,5-OMe) | Ph(2-F,3-OMe,5-n-Pr) | Ph(2-F,3-OCF₃,5-CN) |
| Ph(2-F,3-CF₂CF₂H,5-OCF₃) | Ph(2-F,3-OMe,5-t-Bu) | Ph(2-F,3-OCHF₂,5-Cl) |
| Ph(2-F,3-CF₂CF₂H,5-OCHF₂) | Ph(2-F,3-OMe,5-i-Pr) | Ph(2-F,3-OCHF₂,5-F) |
| Ph(2-F,3-CF₂CF₂H,5-OCF₂CF₂H) | Ph(2-F,3-OMe,5-c-Pr) | Ph(2-F,3-OCHF₂,5-Br) |
| Ph(2-F,3-CF₂CF₂H,5-OC₂F₅) | Ph(2-F,3-OMe,5-CF₃) | Ph(2-F,3-OCHF₂,5-I) |
| Ph(2-F,3-CF₂CF₂H,5-SO₂Me) | Ph(2-F,3-OMe,5-C₂F₅) | Ph(2-F,3-OCHF₂,5-Me) |
| Ph(2-F,3-CF₂CF₂H,5-TMS) | Ph(2-F,3-OMe,5-CF₂CF₂H) | Ph(2-F,3-OCHF₂,5-Et) |
| Ph(2-F,3-CF₂CF₂H,5-CN) | Ph(2-F,3-OMe,5-CF₂H) | Ph(2-F,3-OCHF₂,5-n-Pr) |
| Ph(2-F,3-CF₂H,5-Cl) | Ph(2-F,3,5-di-OMe) | Ph(2-F,3-OCHF₂,5-t-Bu) |
| Ph(2-F,3-CF₂H,5-F) | Ph(2-F,3-OMe,5-OCF₃) | Ph(2-F,3-OCHF₂,5-i-Pr) |
| Ph(2-F,3-CF₂H,5-Br) | Ph(2-F,3-OMe,5-OCHF₂) | Ph(2-F,3-OCHF₂,5-c-Pr) |
| Ph(2-F,3-CF₂H,5-I) | Ph(2-F,3-OMe,5-OCF₂CF₂H) | Ph(2-F,3-OCHF₂CF₃,5-CF₃) |
| Ph(2-F,3-CF₂H,5-Me) | Ph(2-F,3-OMe,5-OC₂F₅) | Ph(2-F,3-OC₂F₅,5-C₂F₅) |
| Ph(2-F,3-CF₂H,5-Et) | Ph(2-F,3-OMe,5-SO₂Me) | Ph(2-F,3-OCHF₂,5-CF₂CF₂H) |
| Ph(2-F,3-CF₂H,5-n-Pr) | Ph(2-F,3-OMe,5-TMS) | Ph(2-F,3-OCHF₂,5-CF₂H) |
| Ph(2-F,3-CF₂H,5-t-Bu) | Ph(2-F,3-OMe,5-CN) | Ph(2-F,3-OCHF₂,5-OMe) |
| Ph(2-F,3-CF₂H,5-i-Pr) | Ph(2-F,3-OCF₃,5-Cl) | Ph(2-F,3-OCHF₂,5-OCF₃) |
| Ph(2-F,3-OCHF₂,5-OCF₂CF₂H) | Ph(2-F,3-OCF₃,5-F) | Ph(2-F,3,5-di-OCHF₂) |
| Ph(2-F,3-OCHF₂,5-OC₂F₅) | Ph(2-F,3-OC₂F₅,5-Et) | Ph(2-F,3,5-di-SO₂Me) |
| Ph(2-F,3-OCHF₂,5-SO₂Me) | Ph(2-F,3-OC₂F₅,5-n-Pr) | Ph(2-F,3-SO₂Me,5-TMS) |
| Ph(2-F,3-OCHF₂,5-TMS) | Ph(2-F,3-OC₂F₅,5-t-Bu) | Ph(2-F,3-SO₂Me,5-CN) |
| Ph(2-F,3-OCHF₂,5-CN) | Ph(2-F,3-OC₂F₅,5-i-Pr) | Ph(2-F,3-TMS,5-Cl) |
| Ph(2-F,3-OCF₂CF₂H,5-Cl) | Ph(2-F,3-OC₂F₅,5-c-Pr) | Ph(2-F,3-TMS,5-F) |
| Ph(2-F,3-OCF₂CF₂H,5-F) | Ph(2-F,3-OC₂F₅CF₃,5-CF₃) | Ph(2-F,3-TMS,5-Br) |
| Ph(2-F,3-OCF₂CF₂H,5-Br) | Ph(2-F,3-OC₂F₅,5-CF₂CF₂H) | Ph(2-F,3-TMS,5-I) |
| Ph(2-F,3-OCF₂CF₂H,5-I) | Ph(2-F,3-OC₂F₅,5-CF₂H) | Ph(2-F,3-TMS,5-Me) |
| Ph(2-F,3-OCF₂CF₂H,5-Me) | Ph(2-F,3-OC₂F₅,5-OMe) | Ph(2-F,3-TMS,5-Et) |
| Ph(2-F,3-OCF₂CF₂H,5-Et) | Ph(2-F,3-OC₂F₅,5-OCF₃) | Ph(2-F,3-TMS,5-n-Pr) |
| Ph(2-F,3-OCF₂CF₂H,5-n-Pr) | Ph(2-F,3-OC₂F₅,5-OCHF₂) | Ph(2-F,3-TMS,5-t-Bu) |
| | Ph(2-F,3-OC₂F₅,5-OCF₂CF₂H) | Ph(2-F,3-TMS,5-i-Pr) |
| | | Ph(2-F,3-TMS,5-c-Pr) |

| Q¹ | Q¹ | Q¹ |
|---|---|---|
| Ph(2-F,3-OCF₂CF₂H,5-t-Bu) | Ph(2-F,3,5-di-OC₂F₅) | Ph(2-F,3-TMS,5-CF₃) |
| Ph(2-F,3-OCF₂CF₂H,5-i-Pr) | Ph(2-F,3-OC₂F₅,5-SO₂Me) | Ph(2-F,3-TMS,5-C₂F₅) |
| Ph(2-F,3-OCF₂CF₂H,5-c-Pr) | Ph(2-F,3-OC₂F₅,5-TMS) | Ph(2-F,3-TMS,5-CF₂CF₂H) |
| Ph(2-F,3-OCF₂CF₂H,5-CF₃) | Ph(2-F,3-OC₂F₅,5-CN) | Ph(2-F,3-TMS,5-CF₂H) |
| Ph(2-F,3-OCF₂CF₂H,5-C₂F₅) | Ph(2-F,3-SO₂Me,5-Cl) | Ph(2-F,3-TMS,5-OMe) |
| Ph(2-F,3-OCF₂CF₂H,5-CF₂CF₂H) | Ph(2-F,3-SO₂Me,5-F) | Ph(2-F,3-TMS,5-OCF₃) |
| Ph(2-F,3-OCF₂CF₂H,5-CF₂H) | Ph(2-F,3-SO₂Me,5-Br) | Ph(2-F,3-TMS,5-OCHF₂) |
| Ph(2-F,3-OCF₂CF₂H,5-OMe) | Ph(2-F,3-SO₂Me,5-I) | Ph(2-F,3-TMS,5-OCF₂CF₂H) |
| Ph(2-F,3-OCF₂CF₂H,5-OCF₃) | Ph(2-F,3-SO₂Me,5-Me) | Ph(2-F,3-TMS,5-OC₂F₅) |
| Ph(2-F,3-OCF₂CF₂H,5-OCHF₂) | Ph(2-F,3-SO₂Me,5-Et) | Ph(2-F,3-TMS,5-SO₂Me) |
| Ph(2-F,3,5-di-OCF₂CF₂H) | Ph(2-F,3-SO₂Me,5-n-Pr) | Ph(2-F,3,5-di-TMS) |
| Ph(2-F,3-OCF₂CF₂H,5-OC₂F₅) | Ph(2-F,3-SO₂Me,5-t-Bu) | Ph(2-F,3-TMS,5-CN) |
| Ph(2-F,3-OCF₂CF₂H,5-SO₂Me) | Ph(2-F,3-SO₂Me,5-i-Pr) | Ph(2-F,3-CN,5-Cl) |
| Ph(2-F,3-OCF₂CF₂H,5-TMS) | Ph(2-F,3-SO₂Me,5-c-Pr) | Ph(2-F,3-CN,5-F) |
| Ph(2-F,3-OCF₂CF₂H,5-CN) | Ph(2-F,3-SO₂MeCF₃,5-CF₃) | Ph(2-F,3-CN,5-Br) |
| Ph(2-F,3-OC₂F₅,5-Cl) | Ph(2-F,3-SO₂Me,5-C₂F₅) | Ph(2-F,3-CN,5-I) |
| Ph(2-F,3-OC₂F₅,5-F) | Ph(2-F,3-SO₂Me,5-CF₂CF₂H) | Ph(2-F,3-CN,5-Me) |
| Ph(2-F,3-OC₂F₅,5-Br) | Ph(2-F,3-SO₂Me,5-CF₂H) | Ph(2-F,3-CN,5-Et) |
| Ph(2-F,3-OC₂F₅,5-I) | Ph(2-F,3-SO₂Me,5-OMe) | Ph(2-F,3-CN,5-n-Pr) |
| Ph(2-F,3-OC₂F₅,5-Me) | Ph(2-F,3-SO₂Me,5-OCF₃) | Ph(2-F,3-CN,5-t-Bu) |
| Ph(2-F,3-CN,5-CF₂CF₂H) | Ph(2-F,3-SO₂Me,5-OCHF₂) | Ph(2-F,3-CN,5-i-Pr) |
| Ph(2-F,3-CN,5-CF₂H) | Ph(2-F,3-SO₂Me,5-OCF₂CF₂H) | Ph(2-F,3-CN,5-c-Pr) |
| Ph(2-F,3-CN,5-OMe) | Ph(2-F,3-SO₂Me,5-OC₂F₅) | Ph(2-F,3-CN,5-CF₃) |
| Ph(2-F,3-CN,5-OCF₃) | Ph(2-F,4-F,5-Et) | Ph(2-F,3-CN,5-C₂F₅) |
| Ph(2-F,3-CN,5-OCHF₂) | Ph(2-F,4-F,5-n-Pr) | Ph(2-F,4-Br,5-TMS) |
| Ph(2-F,3-CN,5-OCF₂CF₂H) | Ph(2-F,4-F,5-t-Bu) | Ph(2-F,4-Br,5-CN) |
| Ph(2-F,3-CN,5-OC₂F₅) | Ph(2-F,4-F,5-i-Pr) | Ph(2-F,4-I,5-Cl) |
| Ph(2-F,3-CN,5-SO₂Me) | Ph(2-F,4-F,5-c-Pr) | Ph(2-F,4-I,5-F) |
| Ph(2-F,3-CN,5-TMS) | Ph(2-F,4-F,5-CF₃) | Ph(2-F,4-I,5-Br) |
| Ph(2-F,3,5-di-CN) | Ph(2-F,4-F,5-C₂F₅) | Ph(2-F,4,5-di-I) |
| Ph(2-F,4,5-di-Cl) | Ph(2-F,4-F,5-CF₂CF₂H) | Ph(2-F,4-I,5-Me) |
| Ph(2-F,4-Cl,5-F) | Ph(2-F,4-F,5-CF₂H) | Ph(2-F,4-I,5-Et) |
| Ph(2-F,4-Cl,5-Br) | Ph(2-F,4-F,5-OMe) | Ph(2-F,4-I,5-n-Pr) |
| Ph(2-F,4-Cl,5-I) | Ph(2-F,4-F,5-OCF₃) | Ph(2-F,4-I,5-t-Bu) |
| Ph(2-F,4-Cl,5-Me) | Ph(2-F,4-F,5-OCHF₂) | Ph(2-F,4-I,5-i-Pr) |
| Ph(2-F,4-Cl,5-Et) | Ph(2-F,4-F,5-OCF₂CF₂H) | Ph(2-F,4-I,5-c-Pr) |
| Ph(2-F,4-Cl,5-n-Pr) | Ph(2-F,4-F,5-OC₂F₅) | Ph(2-F,4-I,5-CF₃) |
| Ph(2-F,4-Cl,5-t-Bu) | Ph(2-F,4-F,5-SO₂Me) | Ph(2-F,4-I,5-C₂F₅) |
| Ph(2-F,4-Cl,5-i-Pr) | Ph(2-F,4-F,5-TMS) | Ph(2-F,4-I,5-CF₂CF₂H) |
| Ph(2-F,4-Cl,5-c-Pr) | Ph(2-F,4-F,5-CN) | Ph(2-F,4-I,5-CF₂H) |
| Ph(2-F,4-Cl,5-CF₃) | Ph(2-F,4-Br,5-Cl) | Ph(2-F,4-I,5-OMe) |
| Ph(2-F,4-Cl,5-C₂F₅) | Ph(2-F,4-Br,5-F) | Ph(2-F,4-I,5-OCF₃) |
| Ph(2-F,4-Cl,5-CF₂CF₂H) | Ph(2-F,4,5-di-Br) | Ph(2-F,4-I,5-OCHF₂) |
| Ph(2-F,4-Cl,5-CF₂H) | Ph(2-F,4-Br,5-I) | Ph(2-F,4-I,5-OCF₂CF₂H) |
| Ph(2-F,4-Cl,5-OMe) | Ph(2-F,4-Br,5-Me) | Ph(2-F,4-I,5-OC₂F₅) |
| Ph(2-F,4-Cl,5-OCF₃) | Ph(2-F,4-Br,5-Et) | Ph(2-F,4-I,5-SO₂Me) |
| Ph(2-F,4-Cl,5-OCHF₂) | Ph(2-F,4-Br,5-n-Pr) | Ph(2-F,4-I,5-TMS) |
| Ph(2-F,4-Cl,5-OCF₂CF₂H) | Ph(2-F,4-Br,5-t-Bu) | Ph(2-F,4-I,5-CN) |
| Ph(2-F,4-Cl,5-OC₂F₅) | Ph(2-F,4-Br,5-i-Pr) | Ph(2-F,4-Me,5-Cl) |
| Ph(2-F,4-Cl,5-SO₂Me) | Ph(2-F,4-Br,5-c-Pr) | Ph(2-F,4-Me,5-F) |
| Ph(2-F,4-Cl,5-TMS) | Ph(2-F,4-Br,5-CF₃) | Ph(2-F,4-Me,5-Br) |
| Ph(2-F,4-Cl,5-CN) | Ph(2-F,4-Br,5-C₂F₅) | Ph(2-F,4-Me,5-I) |
| Ph(2-F,4-F,5-Cl) | Ph(2-F,4-Br,5-CF₂CF₂H) | Ph(2-F,4,5-di-Me) |
| Ph(2,4,5-tri-F) | Ph(2-F,4-Br,5-CF₂H) | Ph(2-F,4-Me,5-Et) |
| Ph(2-F,4-F,5-Br) | Ph(2-F,4-Br,5-OMe) | Ph(2-F,4-Me,5-n-Pr) |
| Ph(2-F,4-F,5-I) | Ph(2-F,4-Br,5-OCF₃) | Ph(2-F,4-Me,5-t-Bu) |
| Ph(2-F,4-F,5-Me) | Ph(2-F,4-Br,5-OCHF₂) | Ph(2-F,4-Me,5-i-Pr) |
| Ph(2-F,4-Me,5-CF₂H) | Ph(2-F,4-Br,5-OCF₂CF₂H) | Ph(2-F,4-Me,5-c-Pr) |
| Ph(2-F,4-Me,5-OMe) | Ph(2-F,4-Br,5-OC₂F₅) | Ph(2-F,4-Me,5-CF₃) |
| Ph(2-F,4-Me,5-OCF₃) | Ph(2-F,4-Br,5-SO₂Me) | Ph(2-F,4-Me,5-C₂F₅) |
| Ph(2-F,4-Me,5-OCHF₂) | Ph(2-F,4,5-di-n-Pr) | Ph(2-F,4-Me,5-CF₂CF₂H) |
| Ph(2-F,4-Me,5-OCF₂CF₂H) | Ph(2-F,4-n-Pr,5-t-Bu) | Ph(2-F,4-t-Bu,5-CN) |
| Ph(2-F,4-Me,5-OC₂F₅) | Ph(2-F,4-n-Pr,5-i-Pr) | Ph(2-F,4-i-Pr,5-Cl) |
| Ph(2-F,4-Me,5-SO₂Me) | Ph(2-F,4-n-Pr,5-c-Pr) | Ph(2-F,4-i-Pr,5-F) |
| Ph(2-F,4-Me,5-TMS) | Ph(2-F,4-n-Pr,5-CF₃) | Ph(2-F,4-i-Pr,5-Br) |
| Ph(2-F,4-Me,5-CN) | Ph(2-F,4-n-Pr,5-I) | Ph(2-F,4-i-Pr,5-I) |
| Ph(2-F,4-Et,5-Cl) | Ph(2-F,4-n-Pr,5-C₂F₅) | Ph(2-F,4-i-Pr,5-Me) |
| Ph(2-F,4-Et,5-F) | Ph(2-F,4-n-Pr,5-CF₂CF₂H) | Ph(2-F,4-i-Pr,5-Et) |
| Ph(2-F,4-Et,5-Br) | Ph(2-F,4-n-Pr,5-CF₂H) | Ph(2-F,4-i-Pr,5-n-Pr) |
| Ph(2-F,4-Et,5-I) | Ph(2-F,4-n-Pr,5-OMe) | Ph(2-F,4-i-Pr,5-t-Bu) |
| Ph(2-F,4-Et,5-Me) | Ph(2-F,4-n-Pr,5-OCF₃) | Ph(2-F,4,5-di-i-Pr) |
| Ph(2-F,4,5-di-Et) | Ph(2-F,4-n-Pr,5-OCHF₂) | Ph(2-F,4-i-Pr,5-c-Pr) |
| Ph(2-F,4-Et,5-n-Pr) | Ph(2-F,4-n-Pr,5-OCF₂CF₂H) | Ph(2-F,4-i-Pr,5-CF₃) |
| | Ph(2-F,4-n-Pr,5-OC₂F₅) | Ph(2-F,4-i-Pr,5-C₂F₅) |
| | Ph(2-F,4-n-Pr,5-SO₂Me) | Ph(2-F,4-i-Pr,5-CF₂CF₂H) |
| | Ph(2-F,4-n-Pr,5-TMS) | Ph(2-F,4-i-Pr,5-CF₂H) |
| | Ph(2-F,4-n-Pr,5-CN) | Ph(2-F,4-i-Pr,5-OMe) |

-continued

| Q¹ | Q¹ | Q¹ |
| --- | --- | --- |
| Ph(2-F,4-Et,5-t-Bu) | Ph(2-F,4-t-Bu,5-Cl) | Ph(2-F,4-i-Pr,5-OCF₃) |
| Ph(2-F,4-Et,5-i-Pr) | Ph(2-F,4-t-Bu,5-F) | Ph(2-F,4-i-Pr,5-OCHF₂) |
| Ph(2-F,4-Et,5-c-Pr) | Ph(2-F,4-t-Bu,5-Br) | Ph(2-F,4-i-Pr,5-OCF₂CF₂H) |
| Ph(2-F,4-Et,5-CF₃) | Ph(2-F,4-t-Bu,5-I) | Ph(2-F,4-i-Pr,5-OC₂F₅) |
| Ph(2-F,4-Et,5-C₂F₅) | Ph(2-F,4-t-Bu,5-Me) | Ph(2-F,4-i-Pr,5-SO₂Me) |
| Ph(2-F,4-Et,5-CF₂CF₂H) | Ph(2-F,4-t-Bu,5-Et) | Ph(2-F,4-i-Pr,5-TMS) |
| Ph(2-F,4-Et,5-CF₂H) | Ph(2-F,4-t-Bu,5-n-Pr) | Ph(2-F,4-i-Pr,5-CN) |
| Ph(2-F,4-Et,5-OMe) | Ph(2-F,4,5-di-t-Bu) | Ph(2-F,4-c-Pr,5-Cl) |
| Ph(2-F,4-Et,5-OCF₃) | Ph(2-F,4-t-Bu,5-i-Pr) | Ph(2-F,4-c-Pr,5-F) |
| Ph(2-F,4-Et,5-OCHF₂) | Ph(2-F,4-t-Bu,5-c-Pr) | Ph(2-F,4-c-Pr,5-Br) |
| Ph(2-F,4-Et,5-OCF₂CF₂H) | Ph(2-F,4-t-Bu,5-CF₃) | Ph(2-F,4-c-Pr,5-I) |
| Ph(2-F,4-Et,5-OC₂F₅) | Ph(2-F,4-t-Bu,5-C₂F₅) | Ph(2-F,4-c-Pr,5-Me) |
| Ph(2-F,4-Et,5-SO₂Me) | Ph(2-F,4-t-Bu,5-CF₂CF₂H) | Ph(2-F,4-c-Pr,5-Et) |
| Ph(2-F,4-Et,5-TMS) | Ph(2-F,4-t-Bu,5-CF₂H) | Ph(2-F,4-c-Pr,5-n-Pr) |
| Ph(2-F,4-Et,5-CN) | Ph(2-F,4-t-Bu,5-OMe) | Ph(2-F,4-c-Pr,5-t-Bu) |
| Ph(2-F,4-n-Pr,5-Cl) | Ph(2-F,4-t-Bu,5-OCF₃) | Ph(2-F,4-c-Pr,5-i-Pr) |
| Ph(2-F,4-n-Pr,5-F) | Ph(2-F,4-t-Bu,5-OCHF₂) | Ph(2-F,4,5-di-c-Pr) |
| Ph(2-F,4-n-Pr,5-Br) | Ph(2-F,4-t-Bu,5-OCF₂CF₂H) | Ph(2-F,4-c-Pr,5-CF₃) |
| Ph(2-F,4-n-Pr,5-I) | Ph(2-F,4-t-Bu,5-OC₂F₅) | Ph(2-F,4-c-Pr,5-C₂F₅) |
| Ph(2-F,4-n-Pr,5-Me) | Ph(2-F,4-t-Bu,5-SO₂Me) | Ph(2-F,4-c-Pr,5-CF₂CF₂H) |
| Ph(2-F,4-n-Pr,5-Et) | Ph(2-F,4-t-Bu,5-TMS) | Ph(2-F,4-c-Pr,5-CF₂H) |
| Ph(2-F,4-c-Pr,5-OMe) | Ph(2-F,4-CF₂CF₃,5-t-Bu) | Ph(2-F,4-CF₂CF₂H,5-TMS) |
| Ph(2-F,4-c-Pr,5-OCF₃) | Ph(2-F,4-CF₂CF₃,5-i-Pr) | Ph(2-F,4-CF₂CF₂H,5-CN) |
| Ph(2-F,4-c-Pr,5-OCHF₂) | Ph(2-F,4-CF₂CF₃,5-c-Pr) | Ph(2-F,4-CF₂H,5-Cl) |
| Ph(2-F,4-c-Pr,5-OCF₂CF₂H) | Ph(2-F,4-C₂F₅CF₃,5-CF₃) | Ph(2-F,4-CF₂H,5-F) |
| Ph(2-F,4-c-Pr,5-OC₂F₅) | Ph(2-F,4,5-di-C₂F₅) | Ph(2-F,4-CF₂H,5-Br) |
| Ph(2-F,4-c-Pr,5-SO₂Me) | Ph(2-F,4-CF₂CF₃,5-CF₂CF₂H) | Ph(2-F,4-CF₂H,5-I) |
| Ph(2-F,4-c-Pr,5-TMS) | Ph(2-F,4-CF₂CF₃,5-CF₂H) | Ph(2-F,4-CF₂H,5-Me) |
| Ph(2-F,4-c-Pr,5-CN) | Ph(2-F,4-CF₂CF₃,5-OMe) | Ph(2-F,4-CF₂H,5-Et) |
| Ph(2-F,4-CF₃,5-Cl) | Ph(2-F,4-CF₂CF₃,5-OCF₃) | Ph(2-F,4-CF₂H,5-n-Pr) |
| Ph(2-F,4-CF₃,5-F) | Ph(2-F,4-CF₂CF₃,5-OCHF₂) | Ph(2-F,4-CF₂H,5-t-Bu) |
| Ph(2-F,4-CF₃,5-Br) | Ph(2-F,4-CF₂CF₃,5-OCF₂CF₂H) | Ph(2-F,4-CF₂H,5-i-Pr) |
| Ph(2-F,4-CF₃,5-I) | Ph(2-F,4-CF₂CF₃,5-OC₂F₅) | Ph(2-F,4-CF₂H,5-c-Pr) |
| Ph(2-F,4-CF₃,5-Me) | Ph(2-F,4-CF₂CF₃,5-SO₂Me) | Ph(2-F,4-CF₂H,5-CF₃) |
| Ph(2-F,4-CF₃,5-Et) | Ph(2-F,4-CF₂CF₃,5-TMS) | Ph(2-F,4-CF₂H,5-C₂F₅) |
| Ph(2-F,4-CF₃,5-n-Pr) | Ph(2-F,4-CF₂CF₃,5-CN) | Ph(2-F,4-CF₂H,5-CF₂CF₂H) |
| Ph(2-F,4-CF₃,5-t-Bu) | Ph(2-F,4-CF₂CF₂H,5-Cl) | Ph(2-F,4,5-di-CF₂H) |
| Ph(2-F,4-CF₃,5-i-Pr) | Ph(2-F,4-CF₂CF₂H,5-F) | Ph(2-F,4-CF₂H,5-OMe) |
| Ph(2-F,4-CF₃,5-c-Pr) | Ph(2-F,4-CF₂CF₂H,5-Br) | Ph(2-F,4-CF₂H,5-OCF₃) |
| Ph(2-F,4,5-di-CF₃) | Ph(2-F,4-CF₂CF₂H,5-I) | Ph(2-F,4-CF₂H,5-OCHF₂) |
| Ph(2-F,4-CF₃,5-C₂F₅) | Ph(2-F,4-CF₂CF₂H,5-Me) | Ph(2-F,4-CF₂H,5-OCF₂CF₂H) |
| Ph(2-F,4-CF₃,5-CF₂CF₂H) | Ph(2-F,4-CF₂CF₂H,5-Et) | Ph(2-F,4-CF₂H,5-OC₂F₅) |
| Ph(2-F,4-CF₃,5-CF₂H) | Ph(2-F,4-CF₂CF₂H,5-n-Pr) | Ph(2-F,4-CF₂H,5-SO₂Me) |
| Ph(2-F,4-CF₃,5-OMe) | Ph(2-F,4-CF₂CF₂H,5-t-Bu) | Ph(2-F,4-CF₂H,5-TMS) |
| Ph(2-F,4-CF₃,5-OCF₃) | Ph(2-F,4-CF₂CF₂H,5-i-Pr) | Ph(2-F,4-CF₂H,5-CN) |
| Ph(2-F,4-CF₃,5-OCHF₂) | Ph(2-F,4-CF₂CF₂H,5-c-Pr) | Ph(2-F,4-OMe,5-Cl) |
| Ph(2-F,4-CF₃,5-OCF₂CF₂H) | Ph(2-F,4-CF₂CF₂CF₃H,5-CF₃) | Ph(2-F,4-OMe,5-F) |
| Ph(2-F,4-CF₃,5-OC₂F₅) | Ph(2-F,4-CF₂CF₂H,5-C₂F₅) | Ph(2-F,4-OMe,5-Br) |
| Ph(2-F,4-CF₃,5-SO₂Me) | Ph(2-F,4,5-di-CF₂CF₂H) | Ph(2-F,4-OMe,5-I) |
| Ph(2-F,4-CF₃,5-TMS) | Ph(2-F,4-CF₂CF₂H,5-CF₂H) | Ph(2-F,4-OMe,5-Me) |
| Ph(2-F,4-CF₃,5-CN) | Ph(2-F,4-CF₂CF₂H,5-OMe) | Ph(2-F,4-OMe,5-Et) |
| Ph(2-F,4-CF₂CF₃,5-Cl) | Ph(2-F,4-CF₂CF₂H,5-OCF₃) | Ph(2-F,4-OMe,5-n-Pr) |
| Ph(2-F,4-CF₂CF₃,5-F) | Ph(2-F,4-CF₂CF₂H,5-OCHF₂) | Ph(2-F,4-OMe,5-t-Bu) |
| Ph(2-F,4-CF₂CF₃,5-Br) | Ph(2-F,4-CF₂CF₂H,5-OCF₂CF₂H) | Ph(2-F,4-OMe,5-i-Pr) |
| Ph(2-F,4-CF₂CF₃,5-I) | Ph(2-F,4-CF₂CF₂H,5-OC₂F₅) | Ph(2-F,4-OMe,5-c-Pr) |
| Ph(2-F,4-CF₂CF₃,5-Me) | Ph(2-F,4-CF₂CF₂H,5-SO₂Me) | Ph(2-F,4-OMe,5-CF₃) |
| Ph(2-F,4-CF₂CF₃,5-Et) | Ph(2-F,4-OCHF₂,5-n-Pr) | Ph(2-F,4-OMe,5-C₂F₅) |
| Ph(2-F,4-CF₂CF₃,5-n-Pr) | Ph(2-F,4-OCHF₂,5-t-Bu) | Ph(2-F,4-OMe,5-CF₂CF₂H) |
| Ph(2-F,4-OMe,5-CF₂H) | Ph(2-F,4-OCHF₂,5-i-Pr) | Ph(2-F,4,5-di-OCF₂CF₂H) |
| Ph(2-F,4,5-di-OMe) | Ph(2-F,4-OCHF₂,5-c-Pr) | Ph(2-F,4-OCF₂CF₂H,5-OC₂F₅) |
| Ph(2-F,4-OMe,5-OCF₃) | Ph(2-F,4-OCHF₂CF₃,5-CF₃) | |
| Ph(2-F,4-OMe,5-OCHF₂) | Ph(2-F,4-OCHF₂CF₃,5-C₂F₅) | Ph(2-F,4-OCF₂CF₂H,5-SO₂Me) |
| Ph(2-F,4-OMe,5-OCF₂CF₂H) | Ph(2-F,4-OCHF₂,5-CF₂CF₂H) | |
| Ph(2-F,4-OMe,5-OC₂F₅) | Ph(2-F,4-OCHF₂,5-CF₂H) | Ph(2-F,4-OCF₂CF₂H,5-TMS) |
| Ph(2-F,4-OMe,5-SO₂Me) | Ph(2-F,4-OCHF₂,5-OMe) | Ph(2-F,4-OCF₂CF₂H,5-CN) |
| Ph(2-F,4-OMe,5-TMS) | Ph(2-F,4-OCHF₂,5-OCF₃) | Ph(2-F,4-OC₂F₅CF₃,5-Cl) |
| Ph(2-F,4-OMe,5-CN) | Ph(2-F,4,5-di-OCHF₂) | Ph(2-F,4-OC₂F₅CF₃,5-F) |
| Ph(2-F,4-OCF₃,5-Cl) | Ph(2-F,4-OCHF₂,5-OCF₂CF₂H) | Ph(2-F,4-OC₂F₅CF₃,5-Br) |
| Ph(2-F,4-OCF₃,5-F) | | Ph(2-F,4-OC₂F₅CF₃,5-I) |
| Ph(2-F,4-OCF₃,5-Br) | Ph(2-F,4-OCHF₂,5-OC₂F₅) | Ph(2-F,4-OC₂F₅CF₃,5-Me) |
| Ph(2-F,4-OCF₃,5-I) | Ph(2-F,4-OCHF₂,5-SO₂Me) | Ph(2-F,4-OC₂F₅CF₃,5-Et) |
| Ph(2-F,4-OCF₃,5-Me) | Ph(2-F,4-OCHF₂,5-TMS) | Ph(2-F,4-OC₂F₅CF₃,5-n-Pr) |
| Ph(2-F,4-OCF₃,5-Et) | Ph(2-F,4-OCHF₂,5-CN) | Ph(2-F,4-OC₂F₅CF₃,5-t-Bu) |
| Ph(2-F,4-OCF₃,5-n-Pr) | Ph(2-F,4-OCF₂CF₂H,5-Cl) | Ph(2-F,4-OC₂F₅CF₃,5-i-Pr) |
| Ph(2-F,4-OCF₃,5-t-Bu) | Ph(2-F,4-OCF₂CF₂H,5-F) | Ph(2-F,4-OC₂F₅CF₃,5-c-Pr) |
| Ph(2-F,4-OCF₃,5-i-Pr) | | Ph(2-F,4-OC₂F₅CF₃,5-CF₃) |
| Ph(2-F,4-OCF₃,5-c-Pr) | | Ph(2-F,4-OC₂F₅CF₃,5- |

-continued

| Q¹ | Q¹ | Q¹ |
| --- | --- | --- |
| Ph(2-F,4-OCF₃,5-CF₃) | Ph(2-F,4-OCF₂CF₂H,5-Br) | CF₂CF₂H) |
| Ph(2-F,4-OCF₃,5-C₂F₅) | Ph(2-F,4-OCF₂CF₂H,5-I) | Ph(2-F,4-OCF₂CF₃,5-CF₂H) |
| Ph(2-F,4-OCF₃,5-CF₂CF₂H) | Ph(2-F,4-OCF₂CF₂H,5-Me) | Ph(2-F,4-OCF₂CF₃,5-OMe) |
| Ph(2-F,4-OCF₃,5-CF₂H) | Ph(2-F,4-OCF₂CF₂H,5-Et) | Ph(2-F,4-OCF₂CF₃,5-OCF₃) |
| Ph(2-F,4-OCF₃,5-OMe) | Ph(2-F,4-OCF₂CF₂H,5-n-Pr) | Ph(2-F,4-OCF₂CF₃,5-OCHF₂) |
| Ph(2-F,4,5-di-OCF₃) | Ph(2-F,4-OCF₂CF₂H,5-t-Bu) | Ph(2-F,4-OCF₂CF₃,5- |
| Ph(2-F,4-OCF₃,5-OCHF₂) | Ph(2-F,4-OCF₂CF₂H,5-i-Pr) | OCF₂CF₂H) |
| Ph(2-F,4-OCF₃,5-OCF₂CF₂H) | Ph(2-F,4-OCF₂CF₂H,5-c-Pr) | Ph(2-F,4,5-di-OC₂F₅) |
| Ph(2-F,4-OCF₃,5-OC₂F₅) | Ph(2-F,4-OCF₂CF₃H,5- | Ph(2-F,4-OCF₂CF₃,5-SO₂Me) |
| Ph(2-F,4-OCF₃,5-SO₂Me) | CF₃) | Ph(2-F,4-OCF₂CF₃,5-TMS) |
| Ph(2-F,4-OCF₃,5-TMS) | Ph(2-F,4-OCF₂CF₂H,5-C₂F₅) | Ph(2-F,4-OCF₂CF₃,5-CN) |
| Ph(2-F,4-OCF₃,5-CN) | Ph(2-F,4-OCF₂CF₂H,5- | Ph(2-F,4-SO₂Me,5-Cl) |
| Ph(2-F,4-OCHF₂,5-Cl) | CF₂CF₂H) | Ph(2-F,4-SO₂Me,5-F) |
| Ph(2-F,4-OCHF₂,5-F) | Ph(2-F,4-OCF₂CF₂H,5-CF₂H) | Ph(2-F,4-SO₂Me,5-Br) |
| Ph(2-F,4-OCHF₂,5-Br) | Ph(2-F,4-OCF₂CF₂H,5-OMe) | Ph(2-F,4-SO₂Me,5-I) |
| Ph(2-F,4-OCHF₂,5-I) | Ph(2-F,4-OCF₂CF₂H,5-OCF₃) | Ph(2-F,4-SO₂Me,5-Me) |
| Ph(2-F,4-OCHF₂,5-Me) | Ph(2-F,4-OCF₂CF₂H,5- | Ph(2-F,4-SO₂Me,5-Et) |
| Ph(2-F,4-OCHF₂,5-Et) | OCHF₂) | Ph(2-F,4-SO₂Me,5-n-Pr) |
| Ph(2-F,4-SO₂Me,5-t-Bu) | Ph(2-F,4-TMS,5-CN) | Ph(3-Cl,4-OMe,5-Cl) |
| Ph(2-F,4-SO₂Me,5-i-Pr) | Ph(2-F,4-CN,5-Cl) | Ph(3-Cl,4-OCF₃,5-Cl) |
| Ph(2-F,4-SO₂Me,5-c-Pr) | Ph(2-F,4-CN,5-F) | Ph(3-Cl,4-OCHF₂,5-Cl) |
| Ph(2-F,4-SO₂MeCF₃,5-CF₃) | Ph(2-F,4-CN,5-Br) | Ph(3-Cl,4-OCF₂CF₂H,5-Cl) |
| Ph(2-F,4-SO₂Me,5-C₂F₅) | Ph(2-F,4-CN,5-I) | Ph(3-Cl,4-OC₂F₅,5-Cl) |
| Ph(2-F,4-SO₂Me,5-CF₂CF₂H) | Ph(2-F,4-CN,5-Me) | Ph(3-Cl,4-SO₂Me,5-Cl) |
| Ph(2-F,4-SO₂Me,5-CF₂H) | Ph(2-F,4-CN,5-Et) | Ph(3-Cl,4-TMS,5-Cl) |
| Ph(2-F,4-SO₂Me,5-OMe) | Ph(2-F,4-CN,5-n-Pr) | Ph(3-Cl,4-CN,5-Cl) |
| Ph(2-F,4-SO₂Me,5-OCF₃) | Ph(2-F,4-CN,5-t-Bu) | Ph(3-F,4-Cl,5-F) |
| Ph(2-F,4-SO₂Me,5-OCHF₂) | Ph(2-F,4-CN,5-i-Pr) | Ph(3,4,5-tri-F) |
| Ph(2-F,4-SO₂Me,5- | Ph(2-F,4-CN,5-c-Pr) | Ph(3-F,4-Br,5-F) |
| OCF₂CF₂H) | Ph(2-F,4-CN,5-CF₃) | Ph(3-F,4-I,5-F) |
| Ph(2-F,4-SO₂Me,5-OC₂F₅) | Ph(2-F,4-CN,5-C₂F₅) | Ph(3-F,4-Me,5-F) |
| Ph(2-F,4,5-di-SO₂Me) | Ph(2-F,4-CN,5-CF₂CF₂H) | Ph(3-F,4-Et,5-F) |
| Ph(2-F,4-SO₂Me,5-TMS) | Ph(2-F,4-CN,5-CF₂H) | Ph(3-F,4-n-Pr,5-F) |
| Ph(2-F,4-SO₂Me,5-CN) | Ph(2-F,4-CN,5-OMe) | Ph(3-F,4-t-Bu,5-F) |
| Ph(2-F,4-TMS,5-Cl) | Ph(2-F,4-CN,5-OCF₃) | Ph(3-F,4-i-Pr,5-F) |
| Ph(2-F,4-TMS,5-F) | Ph(2-F,4-CN,5-OCHF₂) | Ph(3-F,4-c-Pr,5-F) |
| Ph(2-F,4-TMS,5-Br) | Ph(2-F,4-CN,5-OCF₂CF₂H) | Ph(3-F,4-CF₃,5-F) |
| Ph(2-F,4-TMS,5-I) | Ph(2-F,4-CN,5-OC₂F₅) | Ph(3-F,4-C₂F₅,5-F) |
| Ph(2-F,4-TMS,5-Me) | Ph(2-F,4-CN,5-SO₂Me) | Ph(3-F,4-CF₂CF₂H,5-F) |
| Ph(2-F,4-TMS,5-Et) | Ph(2-F,4-CN,5-TMS) | Ph(3-F,4-CF₂H,5-F) |
| Ph(2-F,4-TMS,5-n-Pr) | Ph(2-F,4,5-di-CN) | Ph(3-F,4-OMe,5-F) |
| Ph(2-F,4-TMS,5-t-Bu) | Ph(3,4,5-tri-Cl) | Ph(3-F,4-OCF₃,5-F) |
| Ph(2-F,4-TMS,5-i-Pr) | Ph(3-Cl,4-F,5-Cl) | Ph(3-F,4-OCHF₂,5-F) |
| Ph(2-F,4-TMS,5-c-Pr) | Ph(3-Cl,4-Br,5-Cl) | Ph(3-F,4-OCF₂CF₂H,5-F) |
| Ph(2-F,4-TMS,5-CF₃) | Ph(3-Cl,4-I,5-Cl) | Ph(3-F,4-OC₂F₅,5-F) |
| Ph(2-F,4-TMS,5-C₂F₅) | Ph(3-Cl,4-Me,5-Cl) | Ph(3-F,4-SO₂Me,5-F) |
| Ph(2-F,4-TMS,5-CF₂CF₂H) | Ph(3-Cl,4-Et,5-Cl) | Ph(3-F,4-TMS,5-F) |
| Ph(2-F,4-TMS,5-CF₂H) | Ph(3-Cl,4-n-Pr,5-Cl) | Ph(3-F,4-CN,5-F) |
| Ph(2-F,4-TMS,5-OMe) | Ph(3-Cl,4-t-Bu,5-Cl) | Ph(3-Br,4-Cl,5-Br) |
| Ph(2-F,4-TMS,5-OCF₃) | Ph(3-Cl,4-i-Pr,5-Cl) | Ph(3-Br,4-F,5-Br) |
| Ph(2-F,4-TMS,5-OCHF₂) | Ph(3-Cl,4-c-Pr,5-Cl) | Ph(3,4,5-tri-Br) |
| Ph(2-F,4-TMS,5-OCF₂CF₂H) | Ph(3-Cl,4-CF₃,5-Cl) | Ph(3-Br,4-I,5-Br) |
| Ph(2-F,4-TMS,5-OC₂F₅) | Ph(3-Cl,4-C₂F₅,5-Cl) | Ph(3-Br,4-Me,5-Br) |
| Ph(2-F,4-TMS,5-SO₂Me) | Ph(3-Cl,4-CF₂CF₂H,5-Cl) | Ph(3-Br,4-Et,5-Br) |
| Ph(2-F,4,5-di-TMS) | Ph(3-Cl,4-CF₂H,5-Cl) | Ph(3-Br,4-n-Pr,5-Br) |
| Ph(2-Br,4-t-Bu,5-Br) | Ph(3-CF₃,4-Cl,5-CF₃) | Ph(3-OCHF₂,4-CF₂H,5- |
| Ph(3-Br,4-i-Pr,5-Br) | Ph(3-CF₃,4-F,5-CF₃) | OCHF₂) |
| Ph(3-Br,4-c-Pr,5-Br) | Ph(3-CF₃,4-Br,5-CF₃) | Ph(3-OCHF₂,4-OMe,5- |
| Ph(3-Br,4-CF₃,5-Br) | Ph(3-CF₃,4-I,5-CF₃) | OCHF₂) |
| Ph(3-Br,4-C₂F₅,5-Br) | Ph(3-CF₃,4-Me,5-CF₃) | Ph(3-OCHF₂,4-OCF₃,5- |
| Ph(3-Br,4-CF₂CF₂H,5-Br) | Ph(3-CF₃,4-Et,5-CF₃) | OCHF₂) |
| Ph(3-Br,4-CF₂H,5-Br) | Ph(3-CF₃,4-n-Pr,5-CF₃) | Ph(3,4,5-tri-OCHF₂) |
| Ph(3-Br,4-OMe,5-Br) | Ph(3-CF₃,4-t-Bu,5-CF₃) | Ph(3,5-di-OCHF₂,4- |
| Ph(3-Br,4-OCF₃,5-Br) | Ph(3-CF₃,4-i-Pr,5-CF₃) | OCF₂CF₂H) |
| Ph(3-Br,4-OCHF₂,5-Br) | Ph(3-CF₃,4-c-Pr,5-CF₃) | Ph(3,5-di-OCHF₂,4-OC₂F₅) |
| Ph(3-Br,4-OCF₂CF₂H,5-Br) | Ph(3,4,5-tri-CF₃) | Ph(3,5-di-OCHF₂,4-SO₂Me) |
| Ph(3-Br,4-OC₂F₅,5-Br) | Ph(3-CF₃,4-C₂F₅,5-CF₃) | Ph(3-OCHF₂,4-TMS,5- |
| Ph(3-Br,4-SO₂Me,5-Br) | Ph(3-CF₃,4-CF₂CF₂H,5-CF₃) | OCHF₂) |
| Ph(3-Br,4-TMS,5-Br) | Ph(3-CF₃,4-CF₂H,5-CF₃) | Ph(3-OCHF₂,4-CN,5-OCHF₂) |
| Ph(3-Br,4-CN,5-Br) | Ph(3-CF₃,4-OMe,5-CF₃) | Ph(2,3,4,5-tetra-Cl) |
| Ph(3-Me,4-Cl,5-Me) | Ph(3-CF₃,4-OCF₃,5-CF₃) | Ph(2-Cl,3-Cl,4-F,5-Cl) |
| Ph(3-Me,4-F,5-Me) | Ph(3-CF₃,4-OCHF₂,5-CF₃) | Ph(2-Cl,3-Cl,4-Br,5-Cl) |
| Ph(3-Me,4-Br,5-Me) | Ph(3-CF₃,4-OCF₂CF₂H,5- | Ph(2-Cl,3-Cl,4-I,5-Cl) |
| Ph(3-Me,4-I,5-Me) | CF₃) | Ph(2-Cl,3-Cl,4-Me,5-Cl) |
| Ph(3,4-tri-Me) | Ph(3,5-di-CF₃,4-OC₂F₅) | Ph(2-Cl,3-Cl,4-Et,5-Cl) |
| Ph(3-Me,4-Et,5-Me) | Ph(3-CF₃,4-SO₂Me,5-CF₃) | Ph(2-Cl,3-Cl,4-n-Pr,5-Cl) |
| Ph(3-Me,4-n-Pr,5-Me) | Ph(3-CF₃,4-TMS,5-CF₃) | Ph(2-Cl,3-Cl,4-t-Bu,5-Cl) |

-continued

| Q¹ | Q¹ | Q¹ |
|---|---|---|
| Ph(3-Me,4-t-Bu,5-Me) | Ph(3-CF$_3$,4-CN,5-CF$_3$) | Ph(2-Cl,3-Cl,4-i-Pr,5-Cl) |
| Ph(3-Me,4-i-Pr,5-Me) | Ph(3-OCHF$_2$,4-Cl,5-OCHF$_2$) | Ph(2-Cl,3-Cl,4-c-Pr,5-Cl) |
| Ph(3-Me,4-c-Pr,5-Me) | Ph(3-OCHF$_2$,4-F,5-OCHF$_2$) | Ph(2-Cl,3-Cl,4-CF$_3$,5-Cl) |
| Ph(3-Me,4-CF$_3$,5-Me) | Ph(3-OCHF$_2$,4-Br,5-OCHF$_2$) | Ph(2-Cl,3,5-di-Cl,4-C$_2$F$_5$) |
| Ph(3-Me,4-C$_2$F$_5$,5-Me) | Ph(3-OCHF$_2$,4-I,5-OCHF$_2$) | Ph(2-Cl,3-Cl,4-CF$_2$CF$_2$H,5-Cl) |
| Ph(3-Me,4-CF$_2$CF$_2$H,5-Me) | Ph(3-OCHF$_2$,4-Me,5-OCHF$_2$) | Ph(2-Cl,3-Cl,4-CF$_2$H,5-Cl) |
| Ph(3-Me,4-CF$_2$H,5-Me) | Ph(3-OCHF$_2$,4-Et,5-OCHF$_2$) | Ph(2-Cl,3-Cl,4-OMe,5-Cl) |
| Ph(3-Me,4-OMe,5-Me) | Ph(3-OCHF$_2$,4-n-Pr,5-OCHF$_2$) | Ph(2-Cl,3-Cl,4-OCF$_3$,5-Cl) |
| Ph(3-Me,4-OCF$_3$,5-Me) | Ph(3-OCHF$_2$,4-t-Bu,5-OCHF$_2$) | Ph(2-Cl,3-Cl,4-OCHF$_2$,5-Cl) |
| Ph(3-Me,4-OCHF$_2$,5-Me) | Ph(3-OCHF$_2$,4-i-Pr,5-OCHF$_2$) | Ph(2-Cl,3-Cl,4-OCF$_2$CF$_2$H,5-Cl) |
| Ph(3-Me,4-OCF$_2$CF$_2$H,5-Me) | Ph(3-OCHF$_2$,4-c-Pr,5-OCHF$_2$) | Ph(2-Cl,3,5-di-Cl,4-OC$_2$F$_5$) |
| Ph(3-Me,4-OC$_2$F$_5$,5-Me) | Ph(3,5-di-OCHF$_2$CF$_3$,4-CF$_3$,) | Ph(2-Cl,3-Cl,4-SO$_2$Me,5-Cl) |
| Ph(3-Me,4-SO$_2$Me,5-Me) | Ph(3-OC$_2$F$_5$,4-C$_2$F$_5$,5-OCHF$_2$) | Ph(2-Cl,3-Cl,4-TMS,5-Cl) |
| Ph(3-Me,4-TMS,5-Me) | Ph(3,5-di-OCHF$_2$,4-CF$_2$CF$_2$H) | Ph(2-Cl,3-Cl,4-CN,5-Cl) |
| Ph(3-Me,4-CN,5-Me) | Ph(2-Cl,3-Br,4-OMe,5-Br) | Ph(2-Cl,3-CF$_3$,4-Me,5-CF$_3$) |
| Ph(2-Cl,3-F,4-Cl,5-F) | Ph(2-Cl,3-Br,4-OCF$_3$,5-Br) | Ph(2-Cl,3-CF$_3$,4-Et,5-CF$_3$) |
| Ph(2-Cl,3,4,5-tri-F) | Ph(2-Cl,3-Br,4-OCHF$_2$,5-Br) | Ph(2-Cl,3-CF$_3$,4-n-Pr,5-CF$_3$) |
| Ph(2-Cl,3-F,4-Br,5-F) | Ph(2-Cl,3-Br,4-OCF$_2$CF$_2$H,5-Br) | Ph(2-Cl,3-CF$_3$,4-t-Bu,5-CF$_3$) |
| Ph(2-Cl,3-F,4-I,5-F) | Ph(2-Cl,3,5-di-Br,4-OC$_2$F$_5$) | Ph(2-Cl,3-CF$_3$,4-i-Pr,5-CF$_3$) |
| Ph(2-Cl,3-F,4-Me,5-F) | Ph(2-Cl,3-Br,4-SO$_2$Me,5-Br) | Ph(2-Cl,3-CF$_3$,4-c-Pr,5-CF$_3$) |
| Ph(2-Cl,3-F,4-Et,5-F) | Ph(2-Cl,3-Br,4-TMS,5-Br) | Ph(2-Cl,3,4,5-tri-CF$_3$) |
| Ph(2-Cl,3-F,4-n-Pr,5-F) | Ph(2-Cl,3-Br,4-CN,5-Br) | Ph(2-Cl,3,5-di-CF$_3$,4-C$_2$F$_5$) |
| Ph(2-Cl,3-F,4-t-Bu,5-F) | Ph(2-Cl,3-Me,4-Cl,5-Me) | Ph(2-Cl,3,5-di-CF$_3$,4-CF$_2$CF$_2$H) |
| Ph(2-Cl,3-F,4-i-Pr,5-F) | Ph(2-Cl,3-Me,4-F,5-Me) | Ph(2-Cl,3-CF$_3$,4-CF$_2$H,5-CF$_3$) |
| Ph(2-Cl,3-F,4-c-Pr,5-F) | Ph(2-Cl,3-Me,4-Br,5-Me) | Ph(2-Cl,3-CF$_3$,4-OMe,5-CF$_3$) |
| Ph(2-Cl,3-F,4-CF$_3$,5-F) | Ph(2-Cl,3-Me,4-I,5-Me) | Ph(2-Cl,3-CF$_3$,4-OCF$_3$,5-CF$_3$) |
| Ph(2-Cl,3-F,4-C$_2$F$_5$,5-F) | Ph(2-Cl,3,4-tri-Me) | Ph(2-Cl,3-CF$_3$,4-OCHF$_2$,5-CF$_3$) |
| Ph(2-Cl,3-F,4-CF$_2$CF$_2$H,5-F) | Ph(2-Cl,3-Me,4-Et,5-Me) | Ph(2-Cl,3,5-di-CF$_3$,4-OCF$_2$CF$_2$H—) |
| Ph(2-Cl,3-F,4-CF$_2$H,5-F) | Ph(2-Cl,3-Me,4-n-Pr,5-Me) | Ph(2-Cl,3,5-di-CF$_3$,4-OC$_2$F$_5$) |
| Ph(2-Cl,3-F,4-OMe,5-F) | Ph(2-Cl,3-Me,4-t-Bu,5-Me) | Ph(2-Cl,3,5-di-CF$_3$,4-SO$_2$Me) |
| Ph(2-Cl,3-F,4-OCF$_3$,5-F) | Ph(2-Cl,3-Me,4-i-Pr,5-Me) | Ph(2-Cl,3,5-di-CF$_3$,4-TMS) |
| Ph(2-Cl,3-F,4-OCHF$_2$,5-F) | Ph(2-Cl,3-Me,4-c-Pr,5-Me) | Ph(2-Cl,3-CF$_3$,4-CN,5-CF$_3$) |
| Ph(2-Cl,3-F,4-OCF$_2$CF$_2$H,5-F) | Ph(2-Cl,3-Me,4-CF$_3$,5-Me) | Ph(2-Cl,3,5-di-OCHF$_2$,4-Cl) |
| Ph(2-Cl,3,5-di-F,4-OC$_2$F$_5$,) | Ph(2-Cl,3,5-di-Me,4-C$_2$F$_5$) | Ph(2-Cl,3-OCHF$_2$,4-F,5-OCHF$_2$) |
| Ph(2-Cl,3-F,4-SO$_2$Me,5-F) | Ph(2-Cl,3-Me,4-CF$_2$CF$_2$H,5-Me) | Ph(2-Cl,3,5-di-OCHF$_2$,4-Br) |
| Ph(2-Cl,3-F,4-TMS,5-F) | Ph(2-Cl,3-Me,4-CF$_2$H,5-Me) | Ph(2-Cl,3-OCHF$_2$,4-I,5-OCHF$_2$) |
| Ph(2-Cl,3-F,4-CN,5-F) | Ph(2-Cl,3-Me,4-OMe,5-Me) | Ph(2-Cl,3,5-di-OCHF$_2$,4-Me) |
| Ph(2-Cl,3-Br,4-Cl,5-Br) | Ph(2-Cl,3-Me,4-OCF$_3$,5-Me) | Ph(2-Cl,3,5-di-OCHF$_2$,4-Et) |
| Ph(2-Cl,3-Br,4-F,5-Br) | Ph(2-Cl,3-Me,4-OCHF$_2$,5-Me) | Ph(2-Cl,3,5-di-OCHF$_2$,4-n-Pr) |
| Ph(2-Cl,3,4,5-tri-Br) | Ph(2-Cl,3,5-di-Me,4-OCF$_2$CF$_2$H) | Ph(2-Cl,3,5-di-OCHF$_2$,4-t-Bu) |
| Ph(2-Cl,3-Br,4-I,5-Br) | Ph(2-Cl,3-Me,4-OC$_2$F$_5$,5-Me) | Ph(2-Cl,3,5-di-OCHF$_2$,4-i-Pr) |
| Ph(2-Cl,3-Br,4-Me,5-Br) | Ph(2-Cl,3,5-di-Me,4-SO$_2$Me) | Ph(2-Cl,3,5-di-OCHF$_2$,4-c-Pr) |
| Ph(2-Cl,3-Br,4-Et,5-Br) | Ph(2-Cl,3-Me,4-TMS,5-Me) | Ph(2-Cl,3,5-di-OCHF$_2$CF$_3$,4-CF$_3$) |
| Ph(2-Cl,3-Br,4-n-Pr,5-Br) | Ph(2-Cl,3-Me,4-CN,5-Me) | Ph(2-Cl,3-OC$_2$F$_5$,4-C$_2$F$_5$,5-OCHF$_2$) |
| Ph(2-Cl,3-Br,4-t-Bu,5-Br) | Ph(2-Cl,3-CF$_3$,4-Cl,5-CF$_3$) | Ph(2-F,3-Br,4-CF$_2$H,5-Br) |
| Ph(2-Cl,3-Br,4-i-Pr,5-Br) | Ph(2-Cl,3-CF$_3$,4-F,5-CF$_3$) | Ph(2-F,3-Br,4-OMe,5-Br) |
| Ph(2-Cl,3-Br,4-c-Pr,5-Br) | Ph(2-Cl,3-CF$_3$,4-Br,5-CF$_3$) | Ph(2-F,3-Br,4-OCF$_3$,5-Br) |
| Ph(2-Cl,3-Br,4-CF$_3$,5-Br) | Ph(2-Cl,3-CF$_3$,4-I,5-CF$_3$) | Ph(2-F,3-Br,4-OCHF$_2$,5-Br) |
| Ph(2-Cl,3,5-di-Br,4-C$_2$F$_5$) | Ph(2-F,3-Cl,4-TMS,5-Cl) | Ph(2-F,3-Br,4-OCF$_2$CF$_2$H,5-Br) |
| Ph(2-Cl,3-Br,4-CF$_2$CF$_2$H,5-Br) | Ph(2-F,3-Cl,4-CN,5-Cl) | Ph(2-F,3-Br,4-OC$_2$F$_5$,5-Br) |
| Ph(2-Cl,3-Br,4-CF$_2$H,5-Br) | Ph(2-F,3-F,4-Cl,5-F) | Ph(2-F,3-Br,4-SO$_2$Me,5-Br) |
| Ph(2-Cl,3,5-di-OCHF$_2$,4-CF$_2$CF$_2$H) | Ph(2,3,4,5-tetra-F) | Ph(2-F,3-Br,4-TMS,5-Br) |
| Ph(2-Cl,3-OCHF$_2$,4-CF$_2$H,5-OCHF$_2$) | Ph(2-F,3-F,4-Br,5-F) | Ph(2-F,3-Br,4-CN,5-Br) |
| Ph(2-Cl,3,5-di OCHF$_2$,4-OMe) | Ph(2-F,3-F,4-I,5-F) | Ph(2-F,3-Me,4-Cl,5-Me) |
| Ph(2-Cl,3,5-di-OCHF$_2$,4-OCF$_3$) | Ph(2-F,3-F,4-Me,5-F) | Ph(2-F,3-Me,4-F,5-Me) |
| Ph(2-Cl,3,4,5-tri-OCHF$_2$) | Ph(2-F,3-F,4-Et,5-F) | Ph(2-F,3-Me,4-Br,5-Me) |
| Ph(2-Cl,3-OCHF$_2$,4-OCF$_2$CF$_2$H,5-OCHF$_2$) | Ph(2-F,3-F,4-n-Pr,5-F) | Ph(2-F,3-Me,4-I,5-Me) |
| Ph(2-Cl,3-OCHF$_2$,4-OC$_2$F$_5$,5-OCHF$_2$) | Ph(2-F,3-F,4-t-Bu,5-F) | Ph(2-F,3,4-tri-Me) |
| Ph(2-Cl,3,5-di-OCHF$_2$,4-SO$_2$Me) | Ph(2-F,3-F,4-i-Pr,5-F) | Ph(2-F,3-Me,4-Et,5-Me) |
| Ph(2-Cl,3,5-di-OCHF$_2$,4-TMS) | Ph(2-F,3-F,4-c-Pr,5-F) | Ph(2-F,3-Me,4-n-Pr,5-Me) |
| Ph(2-Cl,3,5-di-OCHF$_2$,4-CN) | Ph(2-F,3-F,4-CF$_3$,5-F) | Ph(2-F,3-Me,4-t-Bu,5-Me) |
| Ph(2-F,3,4,5-tri-Cl) | Ph(2-F,3-F,4-C$_2$F$_5$,5-F) | Ph(2-F,3-Me,4-i-Pr,5-Me) |
| Ph(2-F,3-Cl,4-F,5-Cl) | Ph(2-F,3-F,4-CF$_2$CF$_2$H,5-F) | Ph(2-F,3-Me,4-c-Pr,5-Me) |
| Ph(2-F,3-Cl,4-Br,5-Cl) | Ph(2-F,3-F,4-CF$_2$H,5-F) | Ph(2-F,3-Me,4-CF$_3$,5-Me) |
| Ph(2-F,3-Cl,4-I,5-Cl) | Ph(2-F,3-F,4-OMe,5-F) | Ph(2-F,3-Me,4-C$_2$F$_5$,5-Me) |
| Ph(2-F,3-Cl,4-Me,5-Cl) | Ph(2-F,3-F,4-OCF$_3$,5-F) | Ph(2-F,3-Me,4-CF$_2$CF$_2$H,5-Me) |
| Ph(2-F,3-Cl,4-Et,5-Cl) | Ph(2-F,3-F,4-OCHF$_2$,5-F) | |
| Ph(2-F,3-Cl,4-n-Pr,5-Cl) | Ph(2-F,3-F,4-OCF$_2$CF$_2$H,5-F) | |
| Ph(2-F,3-Cl,4-t-Bu,5-Cl) | Ph(2-F,3-F,4-OC$_2$F$_5$,5-F) | |
| Ph(2-F,3-Cl,4-i-Pr,5-Cl) | Ph(2-F,3-F,4-SO$_2$Me,5-F) | |
| | Ph(2-F,3-F,4-TMS,5-F) | |
| | Ph(2-F,3-F,4-CN,5-F) | |
| | Ph(2-F,3-Br,4-Cl,5-Br) | Ph(2-F,3-Me,4-CF$_2$H,5-Me) |

| Q¹ | Q¹ | Q¹ |
|---|---|---|
| Ph(2-F,3-Cl,4-c-Pr,5-Cl) | Ph(2-F,3-Br,4-F,5-Br) | Ph(2-F,3-Me,4-OMe,5-Me) |
| Ph(2-F,3-Cl,4-CF₃,5-Cl) | Ph(2-F,3,4,5-tri-Br) | Ph(2-F,3-Me,4-OCF₃,5-Me) |
| Ph(2-F,3-Cl,4-C₂F₅,5-Cl) | Ph(2-F,3-Br,4-I,5-Br) | Ph(2-F,3-Me,4-OCHF₂,5-Me) |
| Ph(2-F,3-Cl,4-CF₂CF₂H,5-Cl) | Ph(2-F,3-Br,4-Me,5-Br) | Ph(2-F,3-Me,4-OCF₂CF₂H,5-Me) |
| Ph(2-F,3-Cl,4-CF₂H,5-Cl) | Ph(2-F,3-Br,4-Et,5-Br) | |
| Ph(2-F,3-Cl,4-OMe,5-Cl) | Ph(2-F,3-Br,4-n-Pr,5-Br) | Ph(2-F,3-Me,4-OC₂F₅,5-Me) |
| Ph(2-F,3-Cl,4-OCF₃,5-Cl) | Ph(2-F,3-Br,4-t-Bu,5-Br) | Ph(2-F,3-Me,4-SO₂Me,5-Me) |
| Ph(2-F,3-Cl,4-OCHF₂,5-Cl) | Ph(2-F,3-Br,4-i-Pr,5-Br) | Ph(2-F,3-Me,4-TMS,5-Me) |
| Ph(2-F,3-Cl,4-OCF₂CF₂H,5-Cl) | Ph(2-F,3-Br,4-c-Pr,5-Br) | Ph(2-F,3-Me,4-CN,5-Me) |
| Ph(2-F,3,5-di-Cl,4-OC₂F₅) | Ph(2-F,3-Br,4-CF₃,5-Br) | Ph(2-F,3-CF₃,4-Cl,5-CF₃) |
| Ph(2-F,3-Cl,4-SO₂Me,5-Cl) | Ph(2-F,3,5-di-Br,4-C₂F₅) | Ph(2-F,3-CF₃,4-F,5-CF₃) |
| Ph(2-F,3-CF₃,4-I,5-CF₃) | Ph(2-F,3-Br,4-CF₂CF₂H,5-Br) | Ph(2-F,3-CF₃,4-Br,5-CF₃) |
| Ph(2-F,3-CF₃,4-Me,5-CF₃) | Ph(2-F,3-OCHF₂,4-Et,5-OCHF₂) | 1H-Imidazol-2-yl(1-CF₂CF₂H,5-F) |
| Ph(2-F,3-CF₃,4-Et,5-CF₃) | Ph(2-F,3-OCHF₂,4-n-Pr,5-OCHF₂) | 1H-Imidazol-2-yl(1-CH₂CF₃,5-Cl) |
| Ph(2-F,3-CF₃,4-n-Pr,5-CF₃) | Ph(2-F,3-OCHF₂,4-t-Bu,5-OCHF₂) | 1H-Imidazol-2-yl(1-CH₂CF₃,5-F) |
| Ph(2-F,3-CF₃,4-t-Bu,5-CF₃) | Ph(2-F,3-OCHF₂,4-i-Pr,5-OCHF₂) | 1H-Imidazol-2-yl(1-Me,5-CF₂H) |
| Ph(2-F,3-CF₃,4-i-Pr,5-CF₃) | Ph(2-F,3,5-di-OCHF₂,4-c-Pr) | 1H-Imidazol-2-yl(1-CF₂CF₂H,5-CF₂H) |
| Ph(2-F,3,4,5-tri-CF₃) | Ph(2-F,3-OCHF₂CF₃,4-CF₃,5-OCHF₂) | 1H-Imidazol-2-yl(1-CH₂CF₃,5-CF₂H) |
| Ph(2-F,3-CF₃,4-C₂F₅,5-CF₃) | Ph(2-F,3-OC₂F₅,4-C₂F₅,5-OCHF₂) | 1H-Imidazol-2-yl(1-Me,5-CF₃) |
| Ph(2-F,3-CF₃,4-CF₂CF₂H,5-CF₃) | Ph(2-F,3,5-di-OCHF₂,4-CF₂CF₂H) | 1H-Imidazol-2-yl(1-CF₂CF₂H,5-CF₃) |
| Ph(2-F,3-CF₃,4-CF₂H,5-CF₃) | Ph(2-F,3-OCHF₂,4-CF₂H,5-OCHF₂) | 1H-Imidazol-2-yl(1-CH₂CF₃,5-CF₃) |
| Ph(2-F,3-CF₃,4-OMe,5-CF₃) | Ph(2-F,3-OCHF₂,4-OMe,5-OCHF₂) | 1,3-Benzodioxol-4-yl |
| Ph(2-F,3-CF₃,4-OCF₃,5-CF₃) | Ph(2-F,3-OCHF₂,4-OCF₃,5-OCHF₂) | 1,3-Benzodioxol-4-yl(2,2-di-Me) |
| Ph(2-F,3-CF₃,4-OCHF₂,5-CF₃) | | 1,4-Benzodioxol-4-yl(2,3-dihydro) |
| Ph(2-F,3-CF₃,4-OCF₂CF₂H,5-CF₃) | Ph(2-F,3,4,5-tri-OCHF₂) | 1,4-Benzodioxol-4-yl(2,2,3,3-tetrafluoro) |
| Ph(2-F,3-CF₃,4-OC₂F₅,5-CF₃) | Ph(2-F,3-OCHF₂,4-OCF₂CF₂H,5-OCHF₂) | |
| Ph(2-F,3-CF₃,4-SO₂Me,5-CF₃) | Ph(2-F,3-OCHF₂,4-OC₂F₅,5-OCHF₂) | 1H-Pyrazol-3-yl(1-CH₂CF₃,4-F) |
| Ph(2-F,3-CF₃,4-TMS,5-CF₃) | Ph(2-F,3-OCHF₂,4-SO₂Me,5-OCHF₂) | 1H-Pyrazol-3-yl(1-CH₂CF₃,4-Cl) |
| Ph(2-F,3-CF₃,4-CN,5-CF₃) | Ph(2-F,3-OCHF₂,4-TMS,5-OCHF₂) | 1H-Pyrazol-3-yl(1-CF₂CF₂H,4-F) |
| Ph(2-F,3-OCHF₂,4-Cl,5-OCHF₂) | Ph(2-F,3-OCHF₂,4-CN,5-OCHF₂) | 1H-Pyrazol-3-yl(1-CF₂CF₂H,4-Cl) |
| Ph(2-F,3-OCHF₂,4-F,5-OCHF₂) | 1H-Imidazol-2-yl(1-CF₂CF₂H,5-Cl) | 1,3-Benzodioxol-4-yl(2,2-di-F) |
| Ph(2-F,3-OCHF₂,4-Br,5-OCHF₂) | | |
| Ph(2-F,3-OCHF₂,4-I,5-OCHF₂) | | |
| Ph(2-F,3-OCHF₂,4-Me,5-OCHF₂) | | |

Table 2 is constructed in the same manner except that the Row Heading "Y is O; J² is —CH₂—; Q² is Ph(2-F); and Q¹ is" is replaced with the Row Heading listed for Table 2 below (i.e. "Y is O; J² is —CH₂—; Q² is Ph(2,3-F); and Q¹ is"). Therefore, the first entry in Table 2 is a compound of Formula 1 wherein Y is O; J² is —CH₂—; Q² is Ph(2,3-di-F); and Q¹ is Ph(3-Cl) (i.e. 3-chlorophenyl). Tables 3 through 64 are constructed similarly.

| Table | Row Heading |
|---|---|
| 2 | Y is O; J² is —CH₂—; Q² is Ph(2,3-di-F); and Q¹ is |
| 3 | Y is O; J² is —CH₂—; Q² is Ph(2,4-di-F); and Q¹ is |
| 4 | Y is O; J² is —CH₂—; Q² is Ph(2,5-di-F); and Q¹ is |
| 5 | Y is O; J² is —CH₂—; Q² is Ph(2,3,4-tri-F); and Q¹ is |
| 6 | Y is O; J² is —CH₂—; Q² is Ph(2-F,3-Me); and Q¹ is |
| 7 | Y is O; J² is —CH₂—; Q² is Ph(2-Me,3-F); and Q¹ is |
| 8 | Y is O; J² is —CH₂—; Q² is Ph(2-CF₃); and Q¹ is |
| 9 | Y is O; J² is —CH₂—; Q² is Ph(2-Me); and Q¹ is |
| 10 | Y is O; J² is —CH₂—; Q² is Ph(2-NO₂); and Q¹ is |
| 11 | Y is O; J² is —CH₂—; Q² is Ph(2-Cl); and Q¹ is |
| 12 | Y is O; J² is —CH₂—; Q² is Ph(2-SO₂Me); and Q¹ is |
| 13 | Y is O; J² is —CH₂—; Q² is Ph(2-F,3-Cl); and Q¹ is |
| 14 | Y is O; J² is —CH₂—; Q² is 2-Pyridinyl(6-F); and Q¹ is |
| 15 | Y is O; J² is —CH₂—; Q² is 2-Pyridinyl(6-Cl); and Q¹ is |
| 16 | Y is O; J² is —CH₂—; Q² is 2-Pyridinyl(6-Me); and Q¹ is |
| 17 | Y is S; J² is —CH₂—; Q² is Ph(2-F); and Q¹ is |
| 18 | Y is S; J² is —CH₂—; Q² is Ph(2,3-di-F); and Q¹ is |
| 19 | Y is S; J² is —CH₂—; Q² is Ph(2,4-di-F); and Q¹ is |
| 20 | Y is S; J² is —CH₂—; Q² is Ph(2,5-di-F); and Q¹ is |
| 21 | Y is S; J² is —CH₂—; Q² is Ph(2,3,4-tri-F); and Q¹ is |
| 22 | Y is S; J² is —CH₂—; Q² is Ph(2-F,3-Me); and Q¹ is |
| 23 | Y is S; J² is —CH₂—; Q² is Ph(2-Me,3-F); and Q¹ is |
| 24 | Y is S; J² is —CH₂—; Q² is Ph(2-CF₃); and Q¹ is |
| 25 | Y is S; J² is —CH₂—; Q² is Ph(2-Me); and Q¹ is |
| 26 | Y is S; J² is —CH₂—; Q² is Ph(2-NO₂); and Q¹ is |
| 27 | Y is S; J² is —CH₂—; Q² is Ph(2-Cl); and Q¹ is |
| 28 | Y is S; J² is —CH₂—; Q² is Ph(2-SO₂Me); and Q¹ is |
| 29 | Y is S; J² is —CH₂—; Q² is Ph(2-F,3-Cl); and Q¹ is |
| 30 | Y is S; J² is —CH₂—; Q² is 2-Pyridinyl(6-F); and Q¹ is |
| 31 | Y is S; J² is —CH₂—; Q² is 2-Pyridinyl(6-Cl); and Q¹ is |
| 32 | Y is S; J² is —CH₂—; Q² is 2-Pyridinyl(6-Me); and Q¹ is |
| 33 | Y is O; J² is —CH₂CH₂—; Q² is Ph(2-F); and Q¹ is |
| 34 | Y is O; J² is —CH₂CH₂—; Q² is Ph(2,3-di-F); and Q¹ is |
| 35 | Y is O; J² is —CH₂CH₂—; Q² is Ph(2,4-di-F); and Q¹ is |
| 36 | Y is O; J² is —CH₂CH₂—; Q² is Ph(2,5-di-F); and Q¹ is |
| 37 | Y is O; J² is —CH₂CH₂—; Q² is Ph(2,3,4-tri-F); and Q¹ is |
| 38 | Y is O; J² is —CH₂CH₂—; Q² is Ph(2-F,3-Me); and Q¹ is |
| 39 | Y is O; J² is —CH₂CH₂—; Q² is Ph(2-Me,3-F); and Q¹ is |

-continued

| Table | Row Heading |
|---|---|
| 40 | Y is O; $J^2$ is —CH$_2$CH$_2$—; $Q^2$ is Ph(2-CF$_3$); and $Q^1$ is |
| 41 | Y is O; $J^2$ is —CH$_2$CH$_2$—; $Q^2$ is Ph(2-Me); and $Q^1$ is |
| 42 | Y is O; $J^2$ is —CH$_2$CH$_2$—; $Q^2$ is Ph(2-NO$_2$); and $Q^1$ is |
| 43 | Y is O; $J^2$ is —CH$_2$CH$_2$—; $Q^2$ is Ph(2-Cl); and $Q^1$ is |
| 44 | Y is O; $J^2$ is —CH$_2$CH$_2$—; $Q^2$ is Ph(2-SO$_2$Me); and $Q^1$ is |
| 45 | Y is O; $J^2$ is —CH$_2$CH$_2$—; $Q^2$ is Ph(2-F,3-Cl); and $Q^1$ is |
| 46 | Y is O; $J^2$ is —CH$_2$CH$_2$—; $Q^2$ is 2-Pyridinyl(6-F); and $Q^1$ is |
| 47 | Y is O; $J^2$ is —CH$_2$CH$_2$—; $Q^2$ is 2-Pyridinyl(6-Cl); and $Q^1$ is |
| 48 | Y is O; $J^2$ is —CH$_2$CH$_2$—; $Q^2$ is 2-Pyridinyl(6-Me); and $Q^1$ is |
| 49 | Y is S; $J^2$ is —CH$_2$CH$_2$—; $Q^2$ is Ph(2-F); and $Q^1$ is |
| 50 | Y is S; $J^2$ is —CH$_2$CH$_2$—; $Q^2$ is Ph(2,3-di-F); and $Q^1$ is |
| 51 | Y is S; $J^2$ is —CH$_2$CH$_2$—; $Q^2$ is Ph(2,4-di-F); and $Q^1$ is |
| 52 | Y is S; $J^2$ is —CH$_2$CH$_2$—; $Q^2$ is Ph(2,5-di-F); and $Q^1$ is |
| 53 | Y is S; $J^2$ is —CH$_2$CH$_2$—; $Q^2$ is Ph(2,3,4-tri-F); and $Q^1$ is |
| 54 | Y is S; $J^2$ is —CH$_2$CH$_2$—; $Q^2$ is Ph(2-F,3-Me); and $Q^1$ is |
| 55 | Y is S; $J^2$ is —CH$_2$CH$_2$—; $Q^2$ is Ph(2-Me,3-F); and $Q^1$ is |
| 56 | Y is S; $J^2$ is —CH$_2$CH$_2$—; $Q^2$ is Ph(2-CF$_3$); and $Q^1$ is |
| 57 | Y is S; $J^2$ is —CH$_2$CH$_2$—; $Q^2$ is Ph(2-Me); and $Q^1$ is |
| 58 | Y is S; $J^2$ is —CH$_2$CH$_2$—; $Q^2$ is Ph(2-NO$_2$); and $Q^1$ is |
| 59 | Y is S; $J^2$ is —CH$_2$CH$_2$—; $Q^2$ is Ph(2-Cl); and $Q^1$ is |
| 60 | Y is S; $J^2$ is —CH$_2$CH$_2$—; $Q^2$ is Ph(2-SO$_2$Me); and $Q^1$ is |
| 61 | Y is S; $J^2$ is —CH$_2$CH$_2$—; $Q^2$ is Ph(2-F,3-Cl); and $Q^1$ is |
| 62 | Y is S; $J^2$ is —CH$_2$CH$_2$—; $Q^2$ is 2-Pyridinyl(6-F); and $Q^1$ is |
| 63 | Y is S; $J^2$ is —CH$_2$CH$_2$—; $Q^2$ is 2-Pyridinyl(6-Cl); and $Q^1$ is |
| 64 | Y is S; $J^2$ is —CH$_2$CH$_2$—; $Q^2$ is 2-Pyridinyl(6-Me); and $Q^1$ is |

Table 65

Table 65 is constructed the same way as Table 1 above, except the structure is replaced with the following:

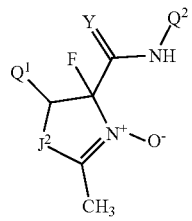

Tables 66 Through 128

This disclosure also includes Tables 66 through 128, each Table is constructed in the same fashion as Tables 2 through 64 above, except that the structure is replaced with the structure in Table 65 above.

Table 129

Table 129 is constructed the same way as Table 1 above, except the structure is replaced with the following:

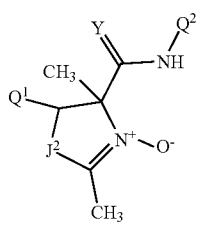

Tables 130 Through 192

This disclosure also includes Tables 130 through 192, each Table is constructed in the same fashion as Tables 2 through 64 above, except that the structure is replaced with the structure in Table 129 above.

TABLE 193

$J^2$ is —CH$_2$—; A is —CH$_2$—; $Q^2$ is Ph(2-F); and $J^1$ is

| $J^1$ |
|---|
| Ph(3-Cl) |
| Ph(3-F) |
| Ph(3-Br) |
| Ph(3-Me) |
| Ph(3-CF$_3$) |
| Ph(3-OCF$_3$) |
| Ph(3-OCF$_2$H) |
| Ph(3-OMe) |
| Ph(3-OCF$_2$CF$_2$H) |
| Ph(2-Cl) |
| Ph(2-F) |
| Ph(2-Br) |
| Ph(2-Me) |
| Ph(2-CF$_3$) |
| Ph(2-OCF$_3$) |
| Ph(2-OCF$_2$H) |
| Ph(2-OMe) |
| Ph(2-OCF$_2$CF$_2$H) |
| Ph(4-Cl) |
| Ph(4-F) |
| Ph(4-Br) |
| Ph(4-Me) |
| Ph(4-CF$_3$) |
| Ph(4-OCF$_3$) |
| Ph(4-OCF$_2$H) |
| Ph(4-OMe) |
| 2-Thienyl |
| 2-Thienyl(4-CF$_3$) |
| 2-Thienyl(5-CF$_3$) |
| 3-Thienyl |
| 3-Thienyl(4-CF$_3$) |
| 3-Thienyl(5-CF$_3$) |
| 2-Furanyl |
| 2-Furanyl(4-CF$_3$) |
| 2-Furanyl(5-CF$_3$) |
| 3-Furanyl |
| 3-Furanyl(4-CF$_3$) |
| 3-Furanyl(5-CF$_3$) |
| Pyrazol-1-yl |
| Pyrazol-1-yl(4-CF$_3$) |
| Imidazol-1-yl |
| Imidazol-1-yl(4-CF$_3$) |
| Imidazol-1-yl(2-CF$_3$) |
| Imidazol-2-yl(1-Me) |
| Imidazol-4-yl(1-Me) |
| Imidazol-4-yl(2-Me) |
| Pyrazol-4-yl(1-Me) |
| Triazol-4-yl(1-Me) |
| Triazol-4-yl(2-Me) |
| Triazol-2-yl(4-Me) |
| Triazol-1-yl(4-Me) |
| Pyrazin-2-yl |
| Pyrazin-2-yl(5-CF$_3$) |
| Pyrimidin-2-yl |
| Pyrimidin-2-yl(5-CF$_3$) |
| Pyrimidin-5-yl |

TABLE 193-continued

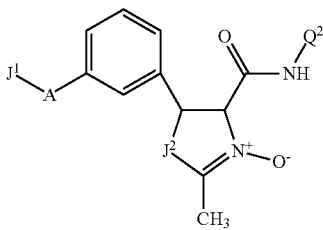

$J^2$ is —CH$_2$—; A is —CH$_2$—; Q$^2$ is Ph(2-F); and J$^1$ is

| J$^1$ |
|---|
| Pyrimidin-5-yl(2-CF$_3$) |
| 1,3,5-Triazin-2-yl |
| Thiazol-2-yl |
| Thiazol-2-yl(5-CF$_3$) |
| Thiazol-5-yl |
| Thiazol-5-yl(2-CF$_3$) |
| Oxazol-2-yl |
| 5-(1,1,2,2-tetrafluoroethoxy)pentyl |
| 2-(1,1,2,2-tetrafluoroethoxy)ethyl |
| 5-(trifloromethoxy)pentyl |
| 2-(trifluoromethoxy)ethyl |
| 4-(1,1,2,2,-tetrafluoroethoxy)butoxy |
| 2-(1,1,2,2,-tetrafluoroethoxy)ethoxy |
| 4-(trifluoromethoxy)butoxy |
| 2(trifluoromethoxy)ethoxy |
| Trifluoromethyl |
| 3,3,3-trifluoropropyl |
| 2-fluorocyclopropyl |
| 4,4-difluorocyclohexyl |
| Acetoxy |
| 2,2-dimethylpropanoyloxy |
| 3-methylbutanoyloxy |
| 2,2,2-trifluoroacetyloxy |
| 4,4,4-trifluorobutanoyloxy |
| Ph(4-OCF$_2$CF$_2$H) |
| Ph(2,3-di-F) |
| Ph(2,4-di-F) |
| Ph(2,5-di-F) |
| Ph(2,6-di-F) |
| Ph(3,4-di-F) |
| Ph(3,5-di-F) |
| Ph(3-Me,4-F) |
| Ph(3-F,4-Me) |
| Ph(3-CF$_3$,4-F) |
| Ph(3-F,4-CF$_3$) |
| Ph(2,3,4-tri-F) |
| Ph(3,4,5-tri-F) |
| 2-Pyridinyl |
| 2-Pyridinyl(6-F) |
| 2-Pyridinyl(6-CF$_3$) |
| 2-Pyridinyl(6-Me) |
| 2-Pyridinyl(5-F) |
| 2-Pyridinyl(5-CF$_3$) |
| 2-Pyridinyl(5-Me) |
| 2-Pyridinyl(4-F) |
| 2-Pyridinyl(4-CF$_3$) |
| 2-Pyridinyl(4-Me) |
| 2-Pyridinyl(3-F) |
| 2-Pyridinyl(3-CF$_3$) |
| 2-Pyridinyl(3-Me) |
| Oxazol-2-yl(5-CF$_3$) |
| Oxazol-5-yl |
| Oxazol-5-yl(2-CF$_3$) |
| Isothiazol-5-yl |
| Isothiazol-5-yl(3-CF$_3$) |
| Isothiazol-3-yl |
| Isothiazol-3-yl(5-CF$_3$) |
| Isoxazol-5-yl |
| Isoxazol-5-yl(3-CF$_3$) |
| Isoxazol-3-yl |
| Isoxazol-3-yl(5-CF$_3$) |
| Tetrazol-1-yl |
| Tetrazol-1-yl(5-Me) |
| Tetrazol-5-yl(1-Me) |

TABLE 193-continued

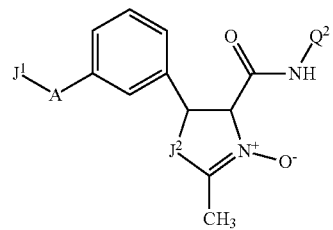

$J^2$ is —CH$_2$—; A is —CH$_2$—; Q$^2$ is Ph(2-F); and J$^1$ is

| J$^1$ |
|---|
| 1,2,4-Triazol-1-yl |
| 1,3,4-Oxadiazol-2-yl |
| 1,3,4-Thiadiazol-2-yl |
| 1,2,4-Oxadiazol-3-yl |
| 1,2,4-Thiadiazol-3-yl |
| Tetrahydropyran-2-yl |
| Tetrahydropyran-3-yl |
| Tetrahydrofuran-2-yl |
| Tetrahydrofuran-3-yl |
| Oxetan-2-yl |
| Oxetan-3-yl |
| Oxiran-2-yl |
| 1,3-Dioxolan-4-yl |
| 2,2-difluoro-1,3-Dioxolan-4-yl |
| 1,3-Dithiolan-4-yl |
| 1,4-Dioxolan-2-yl |
| 1,4-Dithiolan-2-yl |
| 1-naphthyl |
| 2-naphthyl |
| Benzofuran-2-yl |
| Benzothiophen-2-yl |
| 1,3-Benzoxazol-2-yl |
| 3-Pyridinyl |
| 3-Pyridinyl(6-F) |
| 3-Pyridinyl(6-CF$_3$) |
| 3-Pyridinyl(6-Me) |
| 3-Pyridinyl(5-F) |
| 3-Pyridinyl(5-CF$_3$) |
| 3-Pyridinyl(5-Me) |
| 3-Pyridinyl(4-F) |
| 3-Pyridinyl(4-CF$_3$) |
| 3-Pyridinyl(4-Me) |
| 3-Pyridinyl(2-F) |
| 3-Pyridinyl(2-CF$_3$) |
| 3-Pyridinyl(2-Me) |
| 4-Pyridinyl |
| 4-Pyridinyl(6-F) |
| 4-Pyridinyl(6-CF$_3$) |
| 4-Pyridinyl(6-Me) |
| 4-Pyridinyl(5-F) |
| 4-Pyridinyl(5-CF$_3$) |
| 4-Pyridinyl(5-Me) |
| 4-Pyridinyl(3-F) |
| 4-Pyridinyl(3-CF$_3$) |
| 4-Pyridinyl(3-Me) |
| 4-Pyridinyl(2-F) |
| 4-Pyridinyl(2-CF$_3$) |
| 4-Pyridinyl(2-Me) |
| 1,3-Benzthiazol-2-yl |
| 7-quinolyl |
| Indazol-1-yl |
| Benzimidazol-1-yl |
| Indol-1-yl |
| Pyrrolo[2,3-c]pyridin-1-yl |
| Cyclopropylmethoxy |
| 2-cyclopropylethoxy |
| 4-cyclohexylbutoxy |
| Cyclopropylmethyl |
| 4-cyclohexylbutyl |
| Oct-7-enoxy |
| [(E)-but-2-enoxy] |
| 2,2-difluorovinyloxy |
| 3,3-dichloroallyloxy |
| 2-methoxyethoxy |

TABLE 193-continued

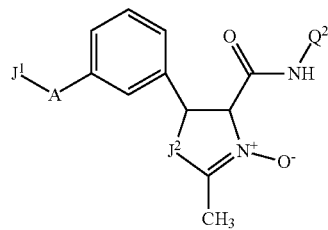

$J^2$ is —CH$_2$—; A is —CH$_2$—; Q$^2$ is Ph(2-F); and J$^1$ is

| J$^1$ |
|---|
| 3-propoxypropoxy |
| 2-methylthioethyl |
| 2-methylsulfinylethyl |
| 2-methylsulfonylethyl |
| 2-CF$_3$SO$_2$CH$_2$CH$_2$O |
| Methylsulfanyl |
| Trifluoromethylthio |
| Cyclopropylthio |
| Methylsulfinyl |
| Trifluoromethylsulfinyl |
| Cyclopropylsulfinyl |
| Methylsulfonyl |
| Trifluoromethylsulfonyl |
| Cyclopropylsulfonyl |
| Prop-2-ynyl |
| But-2-ynyl |
| 3-fluoroprop-2-ynyl |
| 3-chloroprop-2-ynyl |
| 5-propoxypentyl |
| 2-ethoxyethyl |

Table 194-448

Table 194 is constructed in the same manner except that the Row heading "J$^2$ is —CH$_2$—; A is —CH$_2$—; Q$^2$ is Ph(2-F); and J$^1$ is" is replaced with the Row Heading listed for Table 194 below (i.e. "J$^2$ is —CH$_2$—; A is —CH$_2$—; Q$^2$ is Ph(2,3-di-F); and J$^1$ is"). Therefore the first entry in Table 194 is a compound of Formula 1 wherein J$^2$ is —CH$_2$—; A is —CH$_2$—; Q$^2$ is Ph(2,3-di-F); and J$^1$ is Ph(3-Cl) (i.e. 3-chlorophenyl). Tables 195 through 448 are constructed similarly.

| | Table Row Heading |
|---|---|
| 194 | J$^2$ is —CH$_2$—; A is —CH$_2$—; Q$^2$ is Ph(2,3-di-F); and J$^1$ is |
| 195 | J$^2$ is —CH$_2$—; A is —CH$_2$—; Q$^2$ is Ph(2,4-di-F); and J$^1$ is |
| 196 | J$^2$ is —CH$_2$—; A is —CH$_2$—; Q$^2$ is Ph(2,5-di-F); and J$^1$ is |
| 197 | J$^2$ is —CH$_2$—; A is —CH$_2$—; Q$^2$ is Ph(2,3,4-tri-F); and J$^1$ is |
| 198 | J$^2$ is —CH$_2$—; A is —CH$_2$—; Q$^2$ is Ph(2-F,3-Me); and J$^1$ is |
| 199 | J$^2$ is —CH$_2$—; A is —CH$_2$—; Q$^2$ is Ph(2-Me,3-F); and J$^1$ is |
| 200 | J$^2$ is —CH$_2$—; A is —CH$_2$—; Q$^2$ is Ph(2-CF$_3$); and J$^1$ is |
| 201 | J$^2$ is —CH$_2$—; A is —CH$_2$—; Q$^2$ is Ph(2-Me); and J$^1$ is |
| 202 | J$^2$ is —CH$_2$—; A is —CH$_2$—; Q$^2$ is Ph(2-NO$_2$); and J$^1$ is |
| 203 | J$^2$ is —CH$_2$—; A is —CH$_2$—; Q$^2$ is Ph(2-Cl); and J$^1$ is |
| 204 | J$^2$ is —CH$_2$—; A is —CH$_2$—; Q$^2$ is Ph(2-SO$_2$Me); and J$^1$ is |
| 205 | J$^2$ is —CH$_2$—; A is —CH$_2$—; Q$^2$ is Ph(2-F,3-Cl); and J$^1$ is |
| 206 | J$^2$ is —CH$_2$—; A is —CH$_2$—; Q$^2$ is 2-Pyridinyl(6-F); and J$^1$ is |
| 207 | J$^2$ is —CH$_2$—; A is —CH$_2$—; Q$^2$ is 2-Pyridinyl(6-Cl); and J$^1$ is |
| 208 | J$^2$ is —CH$_2$—; A is —CH$_2$—; Q$^2$ is 2-Pyridinyl(6-Me); and J$^1$ is |
| 209 | J$^2$ is —CH$_2$CH$_2$—; A is —CH$_2$—; Q$^2$ is Ph(2-F); and J$^1$ is |
| 210 | J$^2$ is —CH$_2$CH$_2$—; A is —CH$_2$—; Q$^2$ is Ph(2,3-di-F); and J$^1$ is |
| 211 | J$^2$ is —CH$_2$CH$_2$—; A is —CH$_2$—; Q$^2$ is Ph(2,4-di-F); and J$^1$ is |
| 212 | J$^2$ is —CH$_2$CH$_2$—; A is —CH$_2$—; Q$^2$ is Ph(2,5-di-F); and J$^1$ is |
| 213 | J$^2$ is —CH$_2$CH$_2$—; A is —CH$_2$—; Q$^2$ is Ph(2,3,4-tri-F); and J$^1$ is |
| 214 | J$^2$ is —CH$_2$CH$_2$—; A is —CH$_2$—; Q$^2$ is Ph(2-F,3-Me); and J$^1$ is |
| 215 | J$^2$ is —CH$_2$CH$_2$—; A is —CH$_2$—; Q$^2$ is Ph(2-Me,3-F); and J$^1$ is |
| 216 | J$^2$ is —CH$_2$CH$_2$—; A is —CH$_2$—; Q$^2$ is Ph(2-CF$_3$); and J$^1$ is |
| 217 | J$^2$ is —CH$_2$CH$_2$—; A is —CH$_2$—; Q$^2$ is Ph(2-Me); and J$^1$ is |
| 218 | J$^2$ is —CH$_2$CH$_2$—; A is —CH$_2$—; Q$^2$ is Ph(2-NO$_2$); and J$^1$ is |
| 219 | J$^2$ is —CH$_2$CH$_2$—; A is —CH$_2$—; Q$^2$ is Ph(2-Cl); and J$^1$ is |
| 220 | J$^2$ is —CH$_2$CH$_2$—; A is —CH$_2$—; Q$^2$ is Ph(2-SO$_2$Me); and J$^1$ is |
| 221 | J$^2$ is —CH$_2$CH$_2$—; A is —CH$_2$—; Q$^2$ is Ph(2-F,3-Cl); and J$^1$ is |
| 222 | J$^2$ is —CH$_2$CH$_2$—; A is —CH$_2$—; Q$^2$ is 2-Pyridinyl(6-F); and J$^1$ is |
| 223 | J$^2$ is —CH$_2$CH$_2$—; A is —CH$_2$—; Q$^2$ is 2-Pyridinyl(6-Cl); and J$^1$ is |
| 224 | J$^2$ is —CH$_2$CH$_2$—; A is —CH$_2$—; Q$^2$ is 2-Pyridinyl(6-Me); and J$^1$ is |
| 225 | J$^2$ is —CH$_2$—; A is —CH$_2$CH$_2$—; Q$^2$ is Ph(2-F); and J$^1$ is |
| 226 | J$^2$ is —CH$_2$—; A is —CH$_2$CH$_2$—; Q$^2$ is Ph(2,3-di-F); and J$^1$ is |
| 227 | J$^2$ is —CH$_2$—; A is —CH$_2$CH$_2$—; Q$^2$ is Ph(2,4-di-F); and J$^1$ is |
| 228 | J$^2$ is —CH$_2$—; A is —CH$_2$CH$_2$—; Q$^2$ is Ph(2,5-di-F); and J$^1$ is |
| 229 | J$^2$ is —CH$_2$—; A is —CH$_2$CH$_2$—; Q$^2$ is Ph(2,3,4-tri-F); and J$^1$ is |
| 230 | J$^2$ is —CH$_2$—; A is —CH$_2$CH$_2$—; Q$^2$ is Ph(2-F,3-Me); and J$^1$ is |
| 231 | J$^2$ is —CH$_2$—; A is —CH$_2$CH$_2$—; Q$^2$ is Ph(2-Me,3-F); and J$^1$ is |
| 232 | J$^2$ is —CH$_2$—; A is —CH$_2$CH$_2$—; Q$^2$ is Ph(2-CF$_3$); and J$^1$ is |
| 233 | J$^2$ is —CH$_2$—; A is —CH$_2$CH$_2$—; Q$^2$ is Ph(2-Me); and J$^1$ is |
| 234 | J$^2$ is —CH$_2$—; A is —CH$_2$CH$_2$—; Q$^2$ is Ph(2-NO$_2$); and J$^1$ is |
| 235 | J$^2$ is —CH$_2$—; A is —CH$_2$CH$_2$—; Q$^2$ is Ph(2-Cl); and J$^1$ is |
| 236 | J$^2$ is —CH$_2$—; A is —CH$_2$CH$_2$—; Q$^2$ is Ph(2-SO$_2$Me); and J$^1$ is |
| 237 | J$^2$ is —CH$_2$—; A is —CH$_2$CH$_2$—; Q$^2$ is Ph(2-F,3-Cl); and J$^1$ is |
| 238 | J$^2$ is —CH$_2$—; A is —CH$_2$CH$_2$—; Q$^2$ is 2-Pyridinyl(6-F); and J$^1$ is |
| 239 | J$^2$ is —CH$_2$—; A is —CH$_2$CH$_2$—; Q$^2$ is 2-Pyridinyl(6-Cl); and J$^1$ is |
| 240 | J$^2$ is —CH$_2$—; A is —CH$_2$CH$_2$—; Q$^2$ is 2-Pyridinyl(6-Me); and J$^1$ is |
| 241 | J$^2$ is —CH$_2$CH$_2$—; A is —CH$_2$CH$_2$—; Q$^2$ is Ph(2-F); and J$^1$ is |
| 242 | J$^2$ is —CH$_2$CH$_2$—; A is —CH$_2$CH$_2$—; Q$^2$ is Ph(2,3-di-F); and J$^1$ is |
| 243 | J$^2$ is —CH$_2$CH$_2$—; A is —CH$_2$CH$_2$—; Q$^2$ is Ph(2,4-di-F); and J$^1$ is |
| 244 | J$^2$ is —CH$_2$CH$_2$—; A is —CH$_2$CH$_2$—; Q$^2$ is Ph(2,5-di-F); and J$^1$ is |
| 245 | J$^2$ is —CH$_2$CH$_2$—; A is —CH$_2$CH$_2$—; Q$^2$ is Ph(2,3,4-tri-F); and J$^1$ is |
| 246 | J$^2$ is —CH$_2$CH$_2$—; A is —CH$_2$CH$_2$—; Q$^2$ is Ph(2-F,3-Me); and J$^1$ is |
| 247 | J$^2$ is —CH$_2$CH$_2$—; A is —CH$_2$CH$_2$—; Q$^2$ is Ph(2-Me,3-F); and J$^1$ is |
| 248 | J$^2$ is —CH$_2$CH$_2$—; A is —CH$_2$CH$_2$—; Q$^2$ is Ph(2-CF$_3$); and J$^1$ is |
| 249 | J$^2$ is —CH$_2$CH$_2$—; A is —CH$_2$CH$_2$—; Q$^2$ is Ph(2-Me); and J$^1$ is |
| 250 | J$^2$ is —CH$_2$CH$_2$—; A is —CH$_2$CH$_2$—; Q$^2$ is Ph(2-NO$_2$); and J$^1$ is |
| 251 | J$^2$ is —CH$_2$CH$_2$—; A is —CH$_2$CH$_2$—; Q$^2$ is Ph(2-Cl); and J$^1$ is |
| 252 | J$^2$ is —CH$_2$CH$_2$—; A is —CH$_2$CH$_2$—; Q$^2$ is Ph(2-SO$_2$Me); and J$^1$ is |
| 253 | J$^2$ is —CH$_2$CH$_2$—; A is —CH$_2$CH$_2$—; Q$^2$ is Ph(2-F,3-Cl); and J$^1$ is |
| 254 | J$^2$ is —CH$_2$CH$_2$—; A is —CH$_2$CH$_2$—; Q$^2$ is 2-Pyridinyl(6-F); and J$^1$ is |
| 255 | J$^2$ is —CH$_2$CH$_2$—; A is —CH$_2$CH$_2$—; Q$^2$ is 2-Pyridinyl(6-Cl); and J$^1$ is |
| 256 | J$^2$ is —CH$_2$CH$_2$—; A is —CH$_2$CH$_2$—; Q$^2$ is 2-Pyridinyl(6-Me); and J$^1$ is |
| 257 | J$^2$ is —CH$_2$—; A is —CH$_2$CH$_2$CH$_2$—; Q$^2$ is Ph(2-F); and J$^1$ is |
| 258 | J$^2$ is —CH$_2$—; A is —CH$_2$CH$_2$CH$_2$—; Q$^2$ is Ph(2,3-di-F); and J$^1$ is |
| 259 | J$^2$ is —CH$_2$—; A is —CH$_2$CH$_2$CH$_2$—; Q$^2$ is Ph(2,4-di-F); and J$^1$ is |
| 260 | J$^2$ is —CH$_2$—; A is —CH$_2$CH$_2$CH$_2$—; Q$^2$ is Ph(2,5-di-F); and J$^1$ is |
| 261 | J$^2$ is —CH$_2$—; A is —CH$_2$CH$_2$CH$_2$—; Q$^2$ is Ph(2,3,4-tri-F); and J$^1$ is |
| 262 | J$^2$ is —CH$_2$—; A is —CH$_2$CH$_2$CH$_2$—; Q$^2$ is Ph(2-F,3-Me); and J$^1$ is |
| 263 | J$^2$ is —CH$_2$—; A is —CH$_2$CH$_2$CH$_2$—; Q$^2$ is Ph(2-Me,3-F); and J$^{11}$ is |
| 264 | J$^2$ is —CH$_2$—; A is —CH$_2$CH$_2$CH$_2$—; Q$^2$ is Ph(2-CF$_3$); and J$^1$ is |
| 265 | J$^2$ is —CH$_2$—; A is —CH$_2$CH$_2$CH$_2$—; Q$^2$ is Ph(2-Me); and J$^{11}$ is |
| 266 | J$^2$ is —CH$_2$—; A is —CH$_2$CH$_2$CH$_2$—; Q$^2$ is Ph(2-NO$_2$); and J$^1$ is |
| 267 | J$^2$ is —CH$_2$—; A is —CH$_2$CH$_2$CH$_2$—; Q$^2$ is Ph(2-Cl); and J$^1$ is |
| 268 | J$^2$ is —CH$_2$—; A is —CH$_2$CH$_2$CH$_2$—; Q$^2$ is Ph(2-SO$_2$Me); and J$^1$ is |
| 269 | J$^2$ is —CH$_2$—; A is —CH$_2$CH$_2$CH$_2$—; Q$^2$ is Ph(2-F,3-Cl); and J$^1$ is |
| 270 | J$^2$ is —CH$_2$—; A is —CH$_2$CH$_2$CH$_2$—; Q$^2$ is 2-Pyridinyl(6-F); and J$^1$ is |
| 271 | J$^2$ is —CH$_2$—; A is —CH$_2$CH$_2$CH$_2$—; Q$^2$ is 2-Pyridinyl(6-Cl); and J$^1$ is |
| 272 | J$^2$ is —CH$_2$—; A is —CH$_2$CH$_2$CH$_2$—; Q$^2$ is 2-Pyridinyl(6-Me); and J$^1$ is |
| 273 | J$^2$ is —CH$_2$CH$_2$—; A is —CH$_2$CH$_2$CH$_2$—; Q$^2$ is Ph(2-F); and J$^1$ is |

| Table Row Heading | |
|---|---|
| 274 | J² is —CH₂CH₂—; A is —CH₂CH₂CH₂—; Q² is Ph(2,3-di-F); and J¹ is |
| 275 | J² is —CH₂CH₂—; A is —CH₂CH₂CH₂—; Q² is Ph(2,4-di-F); and J¹ is |
| 276 | J² is —CH₂CH₂—; A is —CH₂CH₂CH₂—; Q² is Ph(2,5-di-F); and J¹ is |
| 277 | J² is —CH₂CH₂—; A is —CH₂CH₂CH₂—; Q² is Ph(2,3,4-tri-F); and J¹ is |
| 278 | J² is —CH₂CH₂—; A is —CH₂CH₂CH₂—; Q² is Ph(2-F,3-Me); and J¹ is |
| 279 | J² is —CH₂CH₂—; A is —CH₂CH₂CH₂—; Q² is Ph(2-Me,3-F); and J¹ is |
| 280 | J² is —CH₂CH₂—; A is —CH₂CH₂CH₂—; Q² is Ph(2-CF₃); and J¹ is |
| 281 | J² is —CH₂CH₂—; A is —CH₂CH₂CH₂—; Q² is Ph(2-Me); and J¹ is |
| 282 | J² is —CH₂CH₂—; A is —CH₂CH₂CH₂—; Q² is Ph(2-NO₂); and J¹ is |
| 283 | J² is —CH₂CH₂—; A is —CH₂CH₂CH₂—; Q² is Ph(2-Cl); and J¹ is |
| 284 | J² is —CH₂CH₂—; A is —CH₂CH₂CH₂—; Q² is Ph(2-SO₂Me); and J¹¹ is |
| 285 | J² is —CH₂CH₂—; A is —CH₂CH₂CH₂—; Q² is Ph(2-F,3-Cl); and J¹ is |
| 286 | J² is —CH₂CH₂—; A is —CH₂CH₂CH₂—; Q² is 2-Pyridinyl(6-F); and J¹ is |
| 287 | J² is —CH₂CH₂—; A is —CH₂CH₂CH₂—; Q² is 2-Pyridinyl(6-Cl); and J¹ is |
| 288 | J² is —CH₂CH₂—; A is —CH₂CH₂CH₂—; Q² is 2-Pyridinyl(6-Me); and J¹ is |
| 289 | J² is —CH₂—; A is —O—; Q² is Ph(2-F); and J¹ is |
| 290 | J² is —CH₂—; A is —O—; Q² is Ph(2,3-di-F); and J¹ is |
| 291 | J² is —CH₂—; A is —O—; Q² is Ph(2,4-di-F); and J¹ is |
| 292 | J² is —CH₂—; A is —O—; Q² is Ph(2,5-di-F); and J¹ is |
| 293 | J² is —CH₂—; A is —O—; Q² is Ph(2,3,4-tri-F); and J¹ is |
| 294 | J² is —CH₂—; A is —O—; Q² is Ph(2-F,3-Me); and J¹ is |
| 295 | J² is —CH₂—; A is —O—; Q² is Ph(2-Me,3-F); and J¹ is |
| 296 | J² is —CH₂—; A is —O—; Q² is Ph(2-CF₃); and J¹ is |
| 297 | J² is —CH₂—; A is —O—; Q² is Ph(2-Me); and J¹ is |
| 298 | J² is —CH₂—; A is —O—; Q² is Ph(2-NO₂); and J¹ is |
| 299 | J² is —CH₂—; A is —O—; Q² is Ph(2-Cl); and J¹ is |
| 300 | J² is —CH₂—; A is —O—; Q² is Ph(2-SO₂Me); and J¹ is |
| 301 | J² is —CH₂—; A is —O—; Q² is Ph(2-F,3-Cl); and J¹ is |
| 302 | J² is —CH₂—; A is —O—; Q² is 2-Pyridinyl(6-F); and J¹ is |
| 303 | J² is —CH₂—; A is —O—; Q² is 2-Pyridinyl(6-Cl); and J¹ is |
| 304 | J² is —CH₂—; A is —O—; Q² is 2-Pyridinyl(6-Me); and J¹ is |
| 305 | J² is —CH₂CH₂—; A is —O—; Q² is Ph(2-F); and J¹ is |
| 306 | J² is —CH₂CH₂—; A is —O—; Q² is Ph(2,3-di-F); and J¹ is |
| 307 | J² is —CH₂CH₂—; A is —O—; Q² is Ph(2,4-di-F); and J¹ is |
| 308 | J² is —CH₂CH₂—; A is —O—; Q² is Ph(2,5-di-F); and J¹ is |
| 309 | J² is —CH₂CH₂—; A is —O—; Q² is Ph(2,3,4-tri-F); and J¹ is |
| 310 | J² is —CH₂CH₂—; A is —O—; Q² is Ph(2-F,3-Me); and J¹ is |
| 311 | J² is —CH₂CH₂—; A is —O—; Q² is Ph(2-Me,3-F); and J¹ is |
| 312 | J² is —CH₂CH₂—; A is —O—; Q² is Ph(2-CF₃); and J¹ is |
| 313 | J² is —CH₂CH₂—; A is —O—; Q² is Ph(2-Me); and J¹ is |
| 314 | J² is —CH₂CH₂—; A is —O—; Q² is Ph(2-NO₂); and J¹ is |
| 315 | J² is —CH₂CH₂—; A is —O—; Q² is Ph(2-Cl); and J¹ is |
| 316 | J² is —CH₂CH₂—; A is —O—; Q² is Ph(2-SO₂Me); and J¹ is |
| 317 | J² is —CH₂CH₂—; A is —O—; Q² is Ph(2-F,3-Cl); and J¹ is |
| 318 | J² is —CH₂CH₂—; A is —O—; Q² is 2-Pyridinyl(6-F); and J¹ is |
| 319 | J² is —CH₂CH₂—; A is —O—; Q² is 2-Pyridinyl(6-Cl); and J¹ is |
| 320 | J² is —CH₂CH₂—; A is —O—; Q² is 2-Pyridinyl(6-Me); and J¹ is |
| 321 | J² is —CH₂—; A is —OCH₂—; Q² is Ph(2-F); and J¹ is |
| 322 | J² is —CH₂—; A is —OCH₂—; Q² is Ph(2,3-di-F); and J¹ is |
| 323 | J² is —CH₂—; A is —OCH₂—; Q² is Ph(2,4-di-F); and J¹ is |
| 324 | J² is —CH₂—; A is —OCH₂—; Q² is Ph(2,5-di-F); and J¹ is |
| 325 | J² is —CH₂—; A is —OCH₂—; Q² is Ph(2,3,4-tri-F); and J¹ is |
| 326 | J² is —CH₂—; A is —OCH₂—; Q² is Ph(2-F,3-Me); and J¹ is |
| 327 | J² is —CH₂—; A is —OCH₂—; Q² is Ph(2-Me,3-F); and J¹¹ is |
| 328 | J² is —CH₂—; A is —OCH₂—; Q² is Ph(2-CF₃); and J¹ is |
| 329 | J² is —CH₂—; A is —OCH₂—; Q² is Ph(2-Me); and J¹ is |
| 330 | J² is —CH₂—; A is —OCH₂—; Q² is Ph(2-NO₂); and J¹ is |
| 331 | J² is —CH₂—; A is —OCH₂—; Q² is Ph(2-Cl); and J¹ is |
| 332 | J² is —CH₂—; A is —OCH₂—; Q² is Ph(2-SO₂Me); and J¹ is |
| 333 | J² is —CH₂—; A is —OCH₂—; Q² is Ph(2-F,3-Cl); and J¹ is |
| 334 | J² is —CH₂—; A is —OCH₂—; Q² is 2-Pyridinyl(6-F); and J¹ is |
| 335 | J² is —CH₂—; A is —OCH₂—; Q² is 2-Pyridinyl(6-Cl); and J¹ is |
| 336 | J² is —CH₂—; A is —OCH₂—; Q² is 2-Pyridinyl(6-Me); and J¹ is |
| 337 | J² is —CH₂CH₂—; A is —OCH₂—; Q² is Ph(2-F); and J¹ is |
| 338 | J² is —CH₂CH₂—; A is —OCH₂—; Q² is Ph(2,3-di-F); and J¹ is |
| 339 | J² is —CH₂CH₂—; A is —OCH₂—; Q² is Ph(2,4-di-F); and J¹ is |
| 340 | J² is —CH₂CH₂—; A is —OCH₂—; Q² is Ph(2,5-di-F); and J¹ is |
| 341 | J² is —CH₂CH₂—; A is —OCH₂—; Q² is Ph(2,3,4-tri-F); and J¹ is |
| 342 | J² is —CH₂CH₂—; A is —OCH₂—; Q² is Ph(2-F,3-Me); and J¹ is |
| 343 | J² is —CH₂CH₂—; A is —OCH₂—; Q² is Ph(2-Me,3-F); and J¹ is |
| 344 | J² is —CH₂CH₂—; A is —OCH₂—; Q² is Ph(2-CF₃); and J¹ is |
| 345 | J² is —CH₂CH₂—; A is —OCH₂—; Q² is Ph(2-Me); and J¹ is |
| 346 | J² is —CH₂CH₂—; A is —OCH₂—; Q² is Ph(2-NO₂); and J¹ is |
| 347 | J² is —CH₂CH₂—; A is —OCH₂—; Q² is Ph(2-Cl); and J¹ is |
| 348 | J² is —CH₂CH₂—; A is —OCH₂—; Q² is Ph(2-SO₂Me); and J¹ is |
| 349 | J² is —CH₂CH₂—; A is —OCH₂—; Q² is Ph(2-F,3-Cl); and J¹ is |
| 350 | J² is —CH₂CH₂—; A is —OCH₂—; Q² is 2-Pyridinyl(6-F); and J¹ is |
| 351 | J² is —CH₂CH₂—; A is —OCH₂—; Q² is 2-Pyridinyl(6-Cl); and J¹ is |
| 352 | J² is —CH₂CH₂—; A is —OCH₂—; Q² is 2-Pyridinyl(6-Me); and J¹ is |
| 353 | J² is —CH₂—; A is —OCH₂CH₂—; Q² is Ph(2-F); and J¹ is |
| 354 | J² is —CH₂—; A is —OCH₂CH₂—; Q² is Ph(2,3-di-F); and J¹ is |
| 355 | J² is —CH₂—; A is —OCH₂CH₂—; Q² is Ph(2,4-di-F); and J¹ is |
| 356 | J² is —CH₂—; A is —OCH₂CH₂—; Q² is Ph(2,5-di-F); and J¹ is |
| 357 | J² is —CH₂—; A is —OCH₂CH₂—; Q² is Ph(2,3,4-tri-F); and J¹ is |
| 358 | J² is —CH₂—; A is —OCH₂CH₂—; Q² is Ph(2-F,3-Me); and J¹ is |
| 359 | J² is —CH₂—; A is —OCH₂CH₂—; Q² is Ph(2-Me,3-F); and J¹ is |
| 360 | J² is —CH₂—; A is —OCH₂CH₂—; Q² is Ph(2-CF₃); and J¹ is |
| 361 | J² is —CH₂—; A is —OCH₂CH₂—; Q² is Ph(2-Me); and J¹ is |
| 362 | J² is —CH₂—; A is —OCH₂CH₂—; Q² is Ph(2-NO₂); and J¹ is |
| 363 | J² is —CH₂—; A is —OCH₂CH₂—; Q² is Ph(2-Cl); and J¹ is |
| 364 | J² is —CH₂—; A is —OCH₂CH₂—; Q² is Ph(2-SO₂Me); and J¹ is |
| 365 | J² is —CH₂—; A is —OCH₂CH₂—; Q² is Ph(2-F,3-Cl); and J¹ is |
| 366 | J² is —CH₂—; A is —OCH₂CH₂—; Q² is 2-Pyridinyl(6-F); and J¹ is |
| 367 | J² is —CH₂—; A is —OCH₂CH₂—; Q² is 2-Pyridinyl(6-Cl); and J¹ is |
| 368 | J² is —CH₂—; A is —OCH₂CH₂—; Q² is 2-Pyridinyl(6-Me); and J¹ is |
| 369 | J² is —CH₂CH₂—; A is —OCH₂CH₂—; Q² is Ph(2-F); and J¹ is |
| 370 | J² is —CH₂CH₂—; A is —OCH₂CH₂—; Q² is Ph(2,3-di-F); and J¹ is |
| 371 | J² is —CH₂CH₂—; A is —OCH₂CH₂—; Q² is Ph(2,4-di-F); and J¹ is |
| 372 | J² is —CH₂CH₂—; A is —OCH₂CH₂—; Q² is Ph(2,5-di-F); and J¹ is |
| 373 | J² is —CH₂CH₂—; A is —OCH₂CH₂—; Q² is Ph(2,3,4-tri-F); and J¹ is |
| 374 | J² is —CH₂CH₂—; A is —OCH₂CH₂—; Q² is Ph(2-F,3-Me); and J¹ is |
| 375 | J² is —CH₂CH₂—; A is —OCH₂CH₂—; Q² is Ph(2-Me,3-F); and J¹ is |
| 376 | J² is —CH₂CH₂—; A is —OCH₂CH₂—; Q² is Ph(2-CF₃); and J¹ is |
| 377 | J² is —CH₂CH₂—; A is —OCH₂CH₂—; Q² is Ph(2-Me); and J¹ is |
| 378 | J² is —CH₂CH₂—; A is —OCH₂CH₂—; Q² is Ph(2-NO₂); and J¹ is |
| 379 | J² is —CH₂CH₂—; A is —OCH₂CH₂—; Q² is Ph(2-Cl); and J¹ is |
| 380 | J² is —CH₂CH₂—; A is —OCH₂CH₂—; Q² is Ph(2-SO₂Me); and J¹ is |
| 381 | J² is —CH₂CH₂—; A is —OCH₂CH₂—; Q² is Ph(2-F,3-Cl); and J¹ is |
| 382 | J² is —CH₂CH₂—; A is —OCH₂CH₂—; Q² is 2-Pyridinyl(6-F); and J¹ is |
| 383 | J² is —CH₂CH₂—; A is —OCH₂CH₂—; Q² is 2-Pyridinyl(6-Cl); and J¹ is |
| 384 | J² is —CH₂CH₂—; A is —OCH₂CH₂—; Q² is 2-Pyridinyl(6-Me); and J¹ is |
| 385 | J² is —CH₂—; A is —CH₂O—; Q² is Ph(2-F); and J¹ is |
| 386 | J² is —CH₂—; A is —CH₂O—; Q² is Ph(2,3-di-F); and J¹ is |
| 387 | J² is —CH₂—; A is —CH₂O—; Q² is Ph(2,4-di-F); and J¹ is |
| 388 | J² is —CH₂—; A is —CH₂O—; Q² is Ph(2,5-di-F); and J¹ is |
| 389 | J² is —CH₂—; A is —CH₂O—; Q² is Ph(2,3,4-tri-F); and J¹ is |
| 390 | J² is —CH₂—; A is —CH₂O—; Q² is Ph(2-F,3-Me); and J¹ is |
| 391 | J² is —CH₂—; A is —CH₂O—; Q² is Ph(2-Me,3-F); and J¹ is |
| 392 | J² is —CH₂—; A is —CH₂O—; Q² is Ph(2-CF₃); and J¹ is |
| 393 | J² is —CH₂—; A is —CH₂O—; Q² is Ph(2-Me); and J¹ is |
| 394 | J² is —CH₂—; A is —CH₂O—; Q² is Ph(2-NO₂); and J¹ is |
| 395 | J² is —CH₂—; A is —CH₂O—; Q² is Ph(2-Cl); and J¹ is |

| Table Row Heading |
|---|
| 396 $J^2$ is —$CH_2$—; A is —$CH_2O$—; $Q^2$ is Ph(2-$SO_2$Me); and $J^1$ is |
| 397 $J^2$ is —$CH_2$—; A is —$CH_2O$—; $Q^2$ is Ph(2-F,3-Cl); and $J^1$ is |
| 398 $J^2$ is —$CH_2$—; A is —$CH_2O$—; $Q^2$ is 2-Pyridinyl(6-F); and $J^1$ is |
| 399 $J^2$ is —$CH_2$—; A is —$CH_2O$—; $Q^2$ is 2-Pyridinyl(6-Cl); and $J^1$ is |
| 400 $J^2$ is —$CH_2$—; A is —$CH_2O$—; $Q^2$ is 2-Pyridinyl(6-Me); and $J^1$ is |
| 401 $J^2$ is —$CH_2CH_2$—; A is —$CH_2O$—; $Q^2$ is Ph(2-F); and $J^1$ is |
| 402 $J^2$ is —$CH_2CH_2$—; A is —$CH_2O$—; $Q^2$ is Ph(2,3-di-F); and $J^1$ is |
| 403 $J^2$ is —$CH_2CH_2$—; A is —$CH_2O$—; $Q^2$ is Ph(2,4-di-F); and $J^1$ is |
| 404 $J^2$ is —$CH_2CH_2$—; A is —$CH_2O$—; $Q^2$ is Ph(2,5-di-F); and $J^1$ is |
| 405 $J^2$ is —$CH_2CH_2$—; A is —$CH_2O$—; $Q^2$ is Ph(2,3,4-tri-F); and $J^1$ is |
| 406 $J^2$ is —$CH_2CH_2$—; A is —$CH_2O$—; $Q^2$ is Ph(2-F,3-Me); and $J^1$ is |
| 407 $J^2$ is —$CH_2CH_2$—; A is —$CH_2O$—; $Q^2$ is Ph(2-Me,3-F); and $J^1$ is |
| 408 $J^2$ is —$CH_2CH_2$—; A is —$CH_2O$—; $Q^2$ is Ph(2-$CF_3$); and $J^1$ is |
| 409 $J^2$ is —$CH_2CH_2$—; A is —$CH_2O$—; $Q^2$ is Ph(2-Me); and $J^1$ is |
| 410 $J^2$ is —$CH_2CH_2$—; A is —$CH_2O$—; $Q^2$ is Ph(2-$NO_2$); and $J^1$ is |
| 411 $J^2$ is —$CH_2CH_2$—; A is —$CH_2O$—; $Q^2$ is Ph(2-Cl); and $J^1$ is |
| 412 $J^2$ is —$CH_2CH_2$—; A is —$CH_2O$—; $Q^2$ is Ph(2-$SO_2$Me); and $J^1$ is |
| 413 $J^2$ is —$CH_2CH_2$—; A is —$CH_2O$—; $Q^2$ is Ph(2-F,3-Cl); and $J^1$ is |
| 414 $J^2$ is —$CH_2CH_2$—; A is —$CH_2O$—; $Q^2$ is 2-Pyridinyl(6-F); and $J^1$ is |
| 415 $J^2$ is —$CH_2CH_2$—; A is —$CH_2O$—; $Q^2$ is 2-Pyridinyl(6-Cl); and $J^1$ is |
| 416 $J^2$ is —$CH_2CH_2$—; A is —$CH_2O$—; $Q^2$ is 2-Pyridinyl(6-Me); and $J^1$ is |
| 417 $J^2$ is —$CH_2$—; A is —$CH_2CH_2O$—; $Q^2$ is Ph(2-F); and $J^1$ is |
| 418 $J^2$ is —$CH_2$—; A is —$CH_2CH_2O$—; $Q^2$ is Ph(2,3-di-F); and $J^1$ is |
| 419 $J^2$ is —$CH_2$—; A is —$CH_2CH_2O$—; $Q^2$ is Ph(2,4-di-F); and $J^1$ is |
| 420 $J^2$ is —$CH_2$—; A is —$CH_2CH_2O$—; $Q^2$ is Ph(2,5-di-F); and $J^1$ is |
| 421 $J^2$ is —$CH_2$—; A is —$CH_2CH_2O$—; $Q^2$ is Ph(2,3,4-tri-F); and $J^1$ is |
| 422 $J^2$ is —$CH_2$—; A is —$CH_2CH_2O$—; $Q^2$ is Ph(2-F,3-Me); and $J^1$ is |
| 423 $J^2$ is —$CH_2$—; A is —$CH_2CH_2O$—; $Q^2$ is Ph(2-Me,3-F); and $J^1$ is |
| 424 $J^2$ is —$CH_2$—; A is —$CH_2CH_2O$—; $Q^2$ is Ph(2-$CF_3$); and $J^1$ is |
| 425 $J^2$ is —$CH_2$—; A is —$CH_2CH_2O$—; $Q^2$ is Ph(2-Me); and $J^1$ is |
| 426 $J^2$ is —$CH_2$—; A is —$CH_2CH_2O$—; $Q^2$ is Ph(2-$NO_2$); and $J^1$ is |
| 427 $J^2$ is —$CH_2$—; A is —$CH_2CH_2O$—; $Q^2$ is Ph(2-Cl); and $J^1$ is |
| 428 $J^2$ is —$CH_2$—; A is —$CH_2CH_2O$—; $Q^2$ is Ph(2-$SO_2$Me); and $J^1$ is |
| 429 $J^2$ is —$CH_2$—; A is —$CH_2CH_2O$—; $Q^2$ is Ph(2-F,3-Cl); and $J^1$ is |
| 430 $J^2$ is —$CH_2$—; A is —$CH_2CH_2O$—; $Q^2$ is 2-Pyridinyl(6-F); and $J^1$ is |
| 431 $J^2$ is —$CH_2$—; A is —$CH_2CH_2O$—; $Q^2$ is 2-Pyridinyl(6-Cl); and $J^1$ is |
| 432 $J^2$ is —$CH_2$—; A is —$CH_2CH_2O$—; $Q^2$ is 2-Pyridinyl(6-Me); and $J^1$ is |
| 433 $J^2$ is —$CH_2CH_2$—; A is —$CH_2CH_2O$—; $Q^2$ is Ph(2-F); and $J^1$ is |
| 434 $J^2$ is —$CH_2CH_2$—; A is —$CH_2CH_2O$—; $Q^2$ is Ph(2,3-di-F); and $J^1$ is |
| 435 $J^2$ is —$CH_2CH_2$—; A is —$CH_2CH_2O$—; $Q^2$ is Ph(2,4-di-F); and $J^1$ is |
| 436 $J^2$ is —$CH_2CH_2$—; A is —$CH_2CH_2O$—; $Q^2$ is Ph(2,5-di-F); and $J^1$ is |
| 437 $J^2$ is —$CH_2CH_2$—; A is —$CH_2CH_2O$—; $Q^2$ is Ph(2,3,4-tri-F); and $J^1$ is |
| 438 $J^2$ is —$CH_2CH_2$—; A is —$CH_2CH_2O$—; $Q^2$ is Ph(2-F,3-Me); and $J^1$ is |
| 439 $J^2$ is —$CH_2CH_2$—; A is —$CH_2CH_2O$—; $Q^2$ is Ph(2-Me,3-F); and $J^1$ is |
| 440 $J^2$ is —$CH_2CH_2$—; A is —$CH_2CH_2O$—; $Q^2$ is Ph(2-$CF_3$); and $J^1$ is |
| 441 $J^2$ is —$CH_2CH_2$—; A is —$CH_2CH_2O$—; $Q^2$ is Ph(2-Me); and $J^1$ is |
| 442 $J^2$ is —$CH_2CH_2$—; A is —$CH_2CH_2O$—; $Q^2$ is Ph(2-$NO_2$); and $J^1$ is |
| 443 $J^2$ is —$CH_2CH_2$—; A is —$CH_2CH_2O$—; $Q^2$ is Ph(2-Cl); and $J^1$ is |
| 444 $J^2$ is —$CH_2CH_2$—; A is —$CH_2CH_2O$—; $Q^2$ is Ph(2-$SO_2$Me); and $J^1$ is |
| 445 $J^2$ is —$CH_2CH_2$—; A is —$CH_2CH_2O$—; $Q^2$ is Ph(2-F,3-Cl); and $J^1$ is |
| 446 $J^2$ is —$CH_2CH_2$—; A is —$CH_2CH_2O$—; $Q^2$ is 2-Pyridinyl(6-F); and $J^1$ is |
| 447 $J^2$ is —$CH_2CH_2$—; A is —$CH_2CH_2O$—; $Q^2$ is 2-Pyridinyl(6-Cl); and $J^1$ is |
| 448 $J^2$ is —$CH_2CH_2$—; A is —$CH_2CH_2O$—; $Q^2$ is 2-Pyridinyl(6-Me); and $J^1$ is |

Table 449

Table 449 is constructed the same way as Table 193 above, except the structure is replaced with the following:

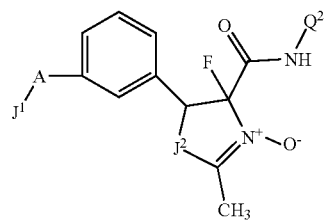

Tables 450 Through 704

This disclosure also includes Tables 450 through 704, each Table is constructed in the same fashion as Tables 194 through 448 above, except that the structure is replaced with the structure in Table 449 above.

Table 705

Table 705 is constructed the same way as Table 193 above, except the structure is replaced with the following:

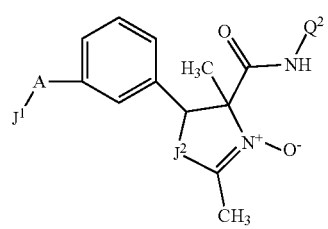

Tables 706 Through 960

This disclosure also includes Tables 706 through 960, each Table is constructed in the same fashion as Tables 194 through 448 above, except that the structure is replaced with the structure in Table 705 above.

A compound of this disclosure will generally be used as a herbicidal active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions, oil-in-water emulsions, flowable concentrates and/or suspoemulsions) and the like, which optionally can be thickened into gels. The general types of aqueous liquid compositions are soluble concentrate, suspension concentrate, capsule suspension, concentrated emulsion, microemulsion, oil-in-water emulsion, flowable concentrate and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethyl phosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters, alkyl and aryl benzoates and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present disclosure often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this disclosure may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in McCutcheon's Volume 2: Functional Materials, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 m range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", Chemical Engineering, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food—Environment Challenge*, T. Brooks and T. R. Roberts, Eds. Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, U K, 2000.

In the following Examples, all percentages are by weight and all formulations are prepared in conventional ways. Compound numbers refer to compounds in Index Table A. Without further elaboration, it is believed that one skilled in the art using the preceding description can utilize the present disclosure to its fullest extent. The following Examples are, therefore, to be construed as merely illustrative, and not limiting of the disclosure in any way whatsoever. Percentages are by weight except where otherwise indicated.

Example A

High Strength Concentrate

| | |
|---|---|
| Compound 2 | 98.5% |
| silica aerogel | 0.5% |
| synthetic amorphous fine silica | 1.0% |

Example B

Wettable Powder

| | |
|---|---|
| Compound 2 | 65.0% |
| dodecylphenol polyethylene glycol ether | 2.0% |
| sodium ligninsulfonate | 4.0% |

Example C

Granule

| | |
|---|---|
| Compound 2 | 10.0% |
| attapulgite granules (low volatile matter, 0.71/0.30 mm; U.S.S. No. 25-50 sieves) | 90.0% |

Example D

Extruded Pellet

| | |
|---|---|
| Compound 2 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

Emulsifiable Concentrate

| | |
|---|---|
| Compound 2 | 10.0% |
| polyoxyethylene sorbitol hexoleate | 20.0% |
| $C_6$-$C_{10}$ fatty acid methyl ester | 70.0% |

Example F

Microemulsion

| | |
|---|---|
| Compound 2 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

Suspension Concentrate

| | |
|---|---|
| Compound 2 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

-continued

| | |
|---|---|
| sodium silicoaluminate | 6.0% |
| montmorillonite (calcined) | 23.0% |

Example H

Emulsion in Water

| | |
|---|---|
| Compound 2 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Example I

Oil Dispersion

| | |
|---|---|
| Compound 2 | 25% |
| polyoxyethylene sorbitol hexaoleate | 15% |
| organically modified bentonite clay | 2.5% |
| fatty acid methyl ester | 57.5% |

The present disclosure also includes Examples A through I above except "Compound 2" is replaced with "Compound 1", "Compound 3", "Compound 4", "Compound 5", "Compound 6", "Compound 7", "Compound 8", "Compound 9", "Compound 10", "Compound 11", "Compound 12", "Compound 13", "Compound 14", "Compound 15", "Compound 16", "Compound 17", "Compound 18", "Compound 19", "Compound 20", "Compound 21", "Compound 22", "Compound 23", "Compound 24", "Compound 25", "Compound 26", "Compound 27", "Compound 28", "Compound 29", "Compound 30", "Compound 31", "Compound 32", "Compound 33", "Compound 34", "Compound 35", "Compound 36", "Compound 37", "Compound 38", "Compound 39", "Compound 40", "Compound 41" "Compound 42", "Compound 43", "Compound 44", "Compound 45", "Compound 46", "Compound 47", "Compound 48", "Compound 49", "Compound 50", "Compound 51", "Compound 52", "Compound 53", "Compound 54", "Compound 55", "Compound 56", "Compound 57", "Compound 58", "Compound 59", "Compound 60", "Compound 61", "Compound 62", "Compound 63", "Compound 64", "Compound 65", "Compound 66", "Compound 67", "Compound 68", "Compound 69", "Compound 70", "Compound 71", "Compound 72", "Compound 73", "Compound 74", "Compound 75", "Compound 76", "Compound 77", "Compound 78", "Compound 79", "Compound 80", "Compound 81", "Compound 82", "Compound 83", "Compound 84", "Compound 85", "Compound 86", "Compound 87", "Compound 88", "Compound 89", "Compound 90", "Compound 91", "Compound 92", "Compound 93", "Compound 94", "Compound 95", "Compound 96", "Compound 97", "Compound 98", "Compound 99", "Compound 100", "Compound 101", "Compound 102", "Compound 103", "Compound 104", "Compound 105", "Compound 106", "Compound 107", "Compound 108", "Compound 109", "Compound 110", "Compound 111", "Compound 112", "Compound 113", "Compound 114", "Compound 115", "Compound 116", "Compound 117", "Compound 118", "Compound 119", "Compound 120", "Compound 121" and "Compound 122".

Test results indicate that the compounds of the present disclosure are highly active preemergent and/or postemergent herbicides and/or plant growth regulators. The compounds of the invention generally show highest activity for postemergence weed control (i.e. applied after weed seedlings emerge from the soil) and preemergence weed control (i.e. applied before weed seedlings emerge from the soil). Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Many of the compounds of this disclosure, by virtue of selective metabolism in crops versus weeds, or by selective activity at the locus of physiological inhibition in crops and weeds, or by selective placement on or within the environment of a mixture of crops and weeds, are useful for the selective control of grass and broadleaf weeds within a crop/weed mixture. One skilled in the art will recognize that the preferred combination of these selectivity factors within a compound or group of compounds can readily be determined by performing routine biological and/or biochemical assays. Compounds of this disclosure may show tolerance to important agronomic crops including, but is not limited to, alfalfa, barley, cotton, wheat, rape, sugar beets, corn (maize), sorghum, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as eucalyptus and conifers (e.g., loblolly pine), and turf species (e.g., Kentucky bluegrass, St. Augustine grass, Kentucky fescue and Bermuda grass). Compounds of this disclosure can be used in crops genetically transformed or bred to incorporate resistance to herbicides, express proteins toxic to invertebrate pests (such as *Bacillus thuringiensis* toxin), and/or express other useful traits. Those skilled in the art will appreciate that not all compounds are equally effective against all weeds. Alternatively, the subject compounds are useful to modify plant growth.

As the compounds of the disclosure have (both preemergent and postemergent herbicidal) activity, to control undesired vegetation by killing or injuring the vegetation or reducing its growth, the compounds can be usefully applied by a variety of methods involving contacting a herbicidally effective amount of a compound of the disclosure, or a composition comprising said compound and at least one of a surfactant, a solid diluent or a liquid diluent, to the foliage or other part of the undesired vegetation or to the environment of the undesired vegetation such as the soil or water in which the undesired vegetation is growing or which surrounds the seed or other propagule of the undesired vegetation.

A herbicidally effective amount of the compounds of this disclosure is determined by a number of factors. These factors include: formulation selected, method of application, amount and type of vegetation present, growing conditions, etc. In general, a herbicidally effective amount of compounds of this disclosure is about 0.001 to 20 kg/ha with a preferred range of about 0.004 to 1 kg/ha. One skilled in the art can easily determine the herbicidally effective amount necessary for the desired level of weed control.

In one common embodiment, a compound of the disclosure is applied, typically in a formulated composition, to a locus comprising desired vegetation (e.g., crops) and undesired vegetation (i.e. weeds), both of which may be seeds, seedlings and/or larger plants, in contact with a growth medium (e.g., soil). In this locus, a composition comprising a compound of the disclosure can be directly applied to a plant or a part thereof, particularly of the undesired vegetation, and/or to the growth medium in contact with the plant.

Plant varieties and cultivars of the desired vegetation in the locus treated with a compound of the disclosure can be obtained by conventional propagation and breeding methods or by genetic engineering methods. Genetically modified plants (transgenic plants) are those in which a heterologous gene (transgene) has been stably integrated into the plant's genome. A transgene that is defined by its particular location in the plant genome is called a transformation or transgenic event.

Genetically modified plant cultivars in the locus which can be treated according to the disclosure include those that are resistant against one or more biotic stresses (pests such as nematodes, insects, mites, fungi, etc.) or abiotic stresses (drought, cold temperature, soil salinity, etc.), or that contain other desirable characteristics. Plants can be genetically modified to exhibit traits of, for example, herbicide tolerance, insect-resistance, modified oil profiles or drought tolerance. Useful genetically modified plants containing single gene transformation events or combinations of transformation events are listed in Exhibit C. Additional information for the genetic modifications listed in Exhibit C can be obtained from publicly available databases maintained, for example, by the U.S. Department of Agriculture.

The following abbreviations, T1 through T37, are used in Exhibit C for traits. A "-" means the entry is not available; "tol." means "tolerance" and "res." means resistance.

| Trait | Description |
| --- | --- |
| T1 | Glyphosate tol. |
| T2 | High lauric acid oil |
| T3 | Glufosinate tol. |
| T4 | Phytate breakdown |
| T5 | Oxynil tol. |
| T6 | Disease res. |
| T7 | Insect res. |
| T9 | Modified flower color |
| T11 | ALS Herbicide tol. |
| T12 | Dicamba tol. |
| T13 | Anti-allergy |
| T14 | Salt tol. |
| T15 | Cold tol. |
| T16 | Imidazolinone herb. tol. |
| T17 | Modified alpha-amylase |
| T18 | Pollination control |
| T19 | 2,4-D tol. |
| T20 | Increased lysine |
| T21 | Drought tol. |
| T22 | Delayed ripening/senescence |
| T23 | Modified product quality |
| T24 | High cellulose |
| T25 | Modified starch/carbohydrate |
| T26 | Insect & disease resist. |
| T27 | High tryptophan |
| T28 | Erect leaves semidwarf |
| T29 | Semidwarf |
| T30 | Low iron tol. |
| T31 | Modified oil/fatty acid |
| T32 | HPPD tol. |
| T33 | High oil |
| T34 | Aryloxyalkanoate tol. |
| T35 | Mesotrione tol. |
| T36 | Reduced nicotine |
| T37 | Modified product |

| Exhibit C | | | | |
|---|---|---|---|---|
| Crop | Event Name | Event Code | Trait(s) | Gene(s) |
| Alfalfa | J101 | MON-00101-8 | T1 | cp4 epsps (aroA:CP4) |
| Alfalfa | J163 | MON-ØØ163-7 | T1 | cp4 epsps (aroA:CP4) |
| Canola* | 23-18-17 (Event 18) | CGN-89465-2 | T2 | te |
| Canola* | 23-198 (Event 23) | CGN-89465-2 | T2 | te |
| Canola* | 61061 | DP-Ø61Ø61-7 | T1 | gat4621 |
| Canola* | 73496 | DP-Ø73496-4 | T1 | gat4621 |
| Canola* | GT200 (RT200) | MON-89249-2 | T1 | cp4 epsps (aroA:CP4); goxv247 |
| Canola* | GT73 (RT73) | MON-ØØØ73-7 | T1 | cp4 epsps (aroA:CP4); goxv247 |
| Canola* | HCN10 (Topas 19/2) | — | T3 | bar |
| Canola* | HCN28 (T45) | ACS-BNØØ8-2 | T3 | pat (syn) |
| Canola* | HCN92 (Topas 19/2) | ACS-BNØØ7-1 | T3 | bar |
| Canola* | MON88302 | MON-883Ø2-9 | T1 | cp4 epsps (aroA:CP4) |
| Canola* | MPS961 | — | T4 | phyA |
| Canola* | MPS962 | — | T4 | phyA |
| Canola* | MPS963 | — | T4 | phyA |
| Canola* | MPS964 | — | T4 | phyA |
| Canola* | MPS965 | — | T4 | phyA |
| Canola* | MS1 (B91-4) | ACS-BNØØ4-7 | T3 | bar |
| Canola* | MS8 | ACS-BNØØ5-8 | T3 | bar |
| Canola* | OXY-235 | ACS-BNØ11-5 | T5 | bxn |
| Canola* | PHY14 | — | T3 | bar |
| Canola* | PHY23 | — | T3 | bar |
| Canola* | PHY35 | — | T3 | bar |
| Canola* | PHY36 | — | T3 | bar |
| Canola* | RF1 (B93-101) | ACS-BNØØ1-4 | T3 | bar |
| Canola* | RF2 (B94-2) | ACS-BNØØ2-5 | T3 | bar |
| Canola* | RF3 | ACS-BNØØ3-6 | T3 | bar |
| Bean | EMBRAPA 5.1 | EMB-PV051-1 | T6 | ac1 (sense and antisense) |
| Brinjal # | EE-1 | — | T7 | cry1Ac |
| Cotton | 19-51a | DD-Ø1951A-7 | T11 | S4-HrA |
| Cotton | 281-24-236 | DAS-24236-5 | T3, T7 | pat (syn); cry1F |
| Cotton | 3006-210-23 | DAS-21Ø23-5 | T3, T7 | pat (syn); cry1Ac |
| Cotton | 31707 | — | T5, T7 | bxn; cry1Ac |
| Cotton | 31803 | — | T5, T7 | bxn; cry1Ac |
| Cotton | 31807 | — | T5, T7 | bxn; cry1Ac |
| Cotton | 31808 | — | T5, T7 | bxn; cry1Ac |
| Cotton | 42317 | — | T5, T7 | bxn; cry1Ac |
| Cotton | BNLA-601 | — | T7 | cry1Ac |
| Cotton | BXN10211 | BXN10211-9 | T5 | bxn; cry1Ac |
| Cotton | BXN10215 | BXN10215-4 | T5 | bxn; cry1Ac |
| Cotton | BXN10222 | BXN10222-2 | T5 | bxn; cry1Ac |
| Cotton | BXN10224 | BXN10224-4 | T5 | bxn; cry1Ac |
| Cotton | COT102 | SYN-IR102-7 | T7 | vip3A(a) |
| Cotton | COT67B | SYN-IR67B-1 | T7 | cry1Ab |
| Cotton | COT202 | — | T7 | vip3A |
| Cotton | Event 1 | — | T7 | cry1Ac |
| Cotton | GMF Cry1A | GTL-GMF311-7 | T7 | cry1Ab-Ac |
| Cotton | GHB119 | BCS-GH005-8 | T7 | cry2Ae |
| Cotton | GHB614 | BCS-GH002-5 | T1 | 2mepsps |
| Cotton | GK12 | — | T7 | cry1Ab-Ac |
| Cotton | LLCotton25 | ACS-GH001-3 | T3 | bar |
| Cotton | MLS 9124 | — | T7 | cry1C |
| Cotton | MON1076 | MON-89924-2 | T7 | cry1Ac |
| Cotton | MON1445 | MON-01445-2 | T1 | cp4 epsps (aroA:CP4) |
| Cotton | MON15985 | MON-15985-7 | T7 | cry1Ac; cry2Ab2 |
| Cotton | MON1698 | MON-89383-1 | T7 | cp4 epsps (aroA:CP4) |
| Cotton | MON531 | MON-00531-6 | T7 | cry1Ac |
| Cotton | MON757 | MON-00757-7 | T7 | cry1Ac |
| Cotton | MON88913 | MON-88913-8 | T1 | cp4 epsps (aroA:CP4) |
| Cotton | Nqwe Chi 6 Bt | — | T7 | — |
| Cotton | SKG321 | — | T7 | cry1A; CpTI |
| Cotton | T303-3 | BCS-GH003-6 | T3, T7 | cry1Ab; bar |
| Cotton | T304-40 | BCS-GH004-7 | T3, T7 | cry1Ab; bar |
| Cotton | CE43-67B | — | T7 | cry1Ab |
| Cotton | CE46-02A | — | T7 | cry1Ab |
| Cotton | CE44-69D | — | T7 | cry1Ab |
| Cotton | 1143-14A | — | T7 | cry1Ab |

Exhibit C

| Crop | Event Name | Event Code | Trait(s) | Gene(s) |
|---|---|---|---|---|
| Cotton | 1143-51B | — | T7 | cry1Ab |
| Cotton | T342-142 | — | T7 | cry1Ab |
| Cotton | PV-GHGT07 (1445) | — | T1 | cp4 epsps (aroA:CP4) |
| Cotton | EE-GH3 | — | T1 | mepsps |
| Cotton | EE-GH5 | — | T7 | cry1Ab |
| Cotton | MON88701 | MON-88701-3 | T3, T12 | Modified dmo; bar |
| Cotton | OsCr11 | — | T13 | Modified Cry j |
| Flax | FP967 | CDC-FL001-2 | T11 | als |
| Lentil | RH44 | — | T16 | als |
| Maize | 3272 | SYN-E3272-5 | T17 | amy797E |
| Maize | 5307 | SYN-05307-1 | T7 | ecry3.1Ab |
| Maize | 59122 | DAS-59122-7 | T3, T7 | cry34Ab1; cry35Ab1; pat |
| Maize | 676 | PH-000676-7 | T3, T18 | pat; dam |
| Maize | 678 | PH-000678-9 | T3, T18 | pat; dam |
| Maize | 680 | PH-000680-2 | T3, T18 | pat; dam |
| Maize | 98140 | DP-098140-6 | T1, T11 | gat4621; zm-hra |
| Maize | Bt10 | — | T3, T7 | cry1Ab; pat |
| Maize | Bt176 (176) | SYN-EV176-9 | T3, T7 | cry1Ab; bar |
| Maize | BVLA430101 | — | T4 | phyA2 |
| Maize | CBH-351 | ACS-ZM004-3 | T3, T7 | cry9C; bar |
| Maize | DAS40278-9 | DAS40278-9 | T19 | aad-1 |
| Maize | DBT418 | DKB-89614-9 | T3, T7 | cry1Ac; pinII; bar |
| Maize | DLL25 (B16) | DKB-89790-5 | T3 | bar |
| Maize | GA21 | MON-00021-9 | T1 | mepsps |
| Maize | GG25 | — | T1 | mepsps |
| Maize | GJ11 | — | T1 | mepsps |
| Maize | Fl117 | — | T1 | mepsps |
| Maize | GAT-ZM1 | — | T3 | pat |
| Maize | LY038 | REN-00038-3 | T20 | cordapA |
| Maize | MIR162 | SYN-IR162-4 | T7 | vip3Aa20 |
| Maize | MIR604 | SYN-IR604-5 | T7 | mcry3A |
| Maize | MON801 (MON80100) | MON801 | T1, T7 | cry1Ab; cp4 epsps (aroA:CP4); goxv247 |
| Maize | MON802 | MON-80200-7 | T1, T7 | cry1Ab; cp4 epsps (aroA:CP4); goxv247 |
| Maize | MON809 | PH-MON-809-2 | T1, T7 | cry1Ab; cp4 epsps (aroA:CP4); goxv247 |
| Maize | MON810 | MON-00810-6 | T1, T7 | cry1Ab; cp4 epsps (aroA:CP4); goxv247 |
| Maize | MON832 | — | T1 | cp4 epsps (aroA:CP4); goxv247 |
| Maize | MON863 | MON-00863-5 | T7 | cry3Bb1 |
| Maize | MON87427 | MON-87427-7 | T1 | cp4 epsps (aroA:CP4) |
| Maize | MON87460 | MON-87460-4 | T21 | cspB |
| Maize | MON88017 | MON-88017-3 | T1, T7 | cry3Bb1; cp4 epsps (aroA:CP4) |
| Maize | MON89034 | MON-89034-3 | T7 | cry2Ab2; cry1A.105 |
| Maize | MS3 | ACS-ZM001-9 | T3, T18 | bar; barnase |
| Maize | MS6 | ACS-ZM005-4 | T3, T18 | bar; barnase |
| Maize | NK603 | MON-00603-6 | T1 | cp4 epsps (aroA:CP4) |
| Maize | T14 | ACS-ZM002-1 | T3 | pat (syn) |
| Maize | T25 | ACS-ZM003-2 | T3 | pat (syn) |
| Maize | TC1507 | DAS-01507-1 | T3, T7 | cry1Fa2; pat |
| Maize | TC6275 | DAS-06275-8 | T3, T7 | mocry1F; bar |
| Maize | VIP1034 | — | T3, T7 | vip3A; pat |
| Maize | 43A47 | DP-043A47-3 | T3, T7 | cry1F; cry34Ab1; cry35Ab1; pat |
| Maize | 40416 | DP-040416-8 | T3, T7 | cry1F; cry34Ab1; cry35Ab1; pat |
| Maize | 32316 | DP-032316-8 | T3, T7 | cry1F; cry34Ab1; cry35Ab1; pat |
| Maize | 4114 | DP-004114-3 | T3, T7 | cry1F; cry34Ab1; cry35Ab1; pat |
| Melon | Melon A | — | T22 | sam-k |
| Melon | Melon B | — | T22 | sam-k |
| Papaya | 55-1 | CUH-CP551-8 | T6 | prsv cp |
| Papaya | 63-1 | CUH-CP631-7 | T6 | prsv cp |
| Papaya | Huanong No. 1 | — | T6 | prsv rep |
| Papaya | X17-2 | UFL-X17CP-6 | T6 | prsv cp |
| Plum | C-5 | ARS-PLMC5-6 | T6 | ppv cp |
| Canola** | ZSR500 | — | T1 | cp4 epsps (aroA:CP4); goxv247 |
| Canola** | ZSR502 | — | T1 | cp4 epsps (aroA:CP4); goxv247 |
| Canola** | ZSR503 | — | T1 | cp4 epsps (aroA:CP4); goxv247 |
| Rice | 7Crp#242-95-7 | — | T13 | 7crp |
| Rice | 7Crp#10 | — | T13 | 7crp |
| Rice | GM Shanyou 63 | — | T7 | cry1Ab; cry1Ac |
| Rice | Huahui-1/TT51-1 | — | T7 | cry1Ab; cry1Ac |
| Rice | LLRICE06 | ACS-OS001-4 | T3 | bar |
| Rice | LLRICE601 | BCS-OS003-7 | T3 | bar |
| Rice | LLRICE62 | ACS-OS002-5 | T3 | bar |
| Rice | Tarom molaii + cry1Ab | — | T7 | cry1Ab (truncated) |

Exhibit C

| Crop | Event Name | Event Code | Trait(s) | Gene(s) |
|---|---|---|---|---|
| Rice | GAT-OS2 | — | T3 | bar |
| Rice | GAT-OS3 | — | T3 | bar |
| Rice | PE-7 | — | T7 | Cry1Ac |
| Rice | 7Crp#10 | — | T13 | 7crp |
| Rice | KPD627-8 | — | T27 | OASA1D |
| Rice | KPD722-4 | — | T27 | OASA1D |
| Rice | KA317 | — | T27 | OASA1D |
| Rice | HW5 | — | T27 | OASA1D |
| Rice | HW1 | — | T27 | OASA1D |
| Rice | B-4-1-18 | — | T28 | Δ OsBRI1 |
| Rice | G-3-3-22 | — | T29 | OSGA2ox1 |
| Rice | AD77 | — | T6 | DEF |
| Rice | AD51 | — | T6 | DEF |
| Rice | AD48 | — | T6 | DEF |
| Rice | AD41 | — | T6 | DEF |
| Rice | 13pNasNa800725atAprt1 | — | T30 | HvNAS1; HvNAAT-A; APRT |
| Rice | 13pAprt1 | — | T30 | APRT |
| Rice | gHvNAS1-gHvNAAT-1 | — | T30 | HvNAS1; HvNAAT-A; HvNAAT-B |
| Rice | gHvIDS3-1 | — | T30 | HvIDS3 |
| Rice | gHvNAAT1 | — | T30 | HvNAAT-A; HvNAAT-B |
| Rice | gHvNAS1-1 | — | T30 | HvNAS1 |
| Rice | NIA-OS006-4 | — | T6 | WRKY45 |
| Rice | NIA-OS005-3 | — | T6 | WRKY45 |
| Rice | NIA-OS004-2 | — | T6 | WRKY45 |
| Rice | NIA-OS003-1 | — | T6 | WRKY45 |
| Rice | NIA-OS002-9 | — | T6 | WRKY45 |
| Rice | NIA-OS001-8 | — | T6 | WRKY45 |
| Rice | OsCr11 | — | T13 | Modified Cry j |
| Rice | 17053 | — | T1 | cp4 epsps (aroA:CP4) |
| Rice | 17314 | — | T1 | cp4 epsps (aroA:CP4) |
| Rose | WKS82/130-4-1 | IFD-52401-4 | T9 | 5AT; bp40 (f3'5'h) |
| Rose | WKS92/130-9-1 | IFD-52901-9 | T9 | 5AT; bp40 (f3'5'h) |
| Soybean | 260-05 (G94-1, G94-19, G168) | — | T9 | gm-fad2-1 (silencing locus) |
| Soybean | A2704-12 | ACS-GM005-3 | T3 | pat |
| Soybean | A2704-21 | ACS-GM004-2 | T3 | pat |
| Soybean | A5547-127 | ACS-GM006-4 | T3 | pat |
| Soybean | A5547-35 | ACS-GM008-6 | T3 | pat |
| Soybean | CV127 | BPS-CV127-9 | T16 | csr1-2 |
| Soybean | DAS68416-4 | DAS68416-4 | T3 | pat |
| Soybean | DP305423 | DP-305423-1 | T11, T31 | gm-fad2-1 (silencing locus); gm-hra |
| Soybean | DP356043 | DP-356043-5 | T1, T31 | gm-fad2-1 (silencing locus); gat4601 |
| Soybean | FG72 | MST-FG072-3 | T32, T1 | 2mepsps; hppdPF W336 |
| Soybean | GTS 40-3-2 (40-3-2) | MON-04032-6 | T1 | cp4 epsps (aroA:CP4) |
| Soybean | GU262 | ACS-GM003-1 | T3 | pat |
| Soybean | MON87701 | MON-87701-2 | T7 | cry1Ac |
| Soybean | MON87705 | MON-87705-6 | T1, T31 | fatb1-A (sense & antisense); fad2-1A (sense & antisense); cp4 epsps (aroA:CP4) |
| Soybean | MON87708 | MON-87708-9 | T1, T12 | dmo; cp4 epsps (aroA:CP4) |
| Soybean | MON87769 | MON-87769-7 | T1, T31 | Pj.D6D; Nc.Fad3; cp4 epsps (aroA:CP4) |
| Soybean | MON89788 | MON-89788-1 | T1 | cp4 epsps (aroA:CP4) |
| Soybean | W62 | ACS-GM002-9 | T3 | bar |
| Soybean | W98 | ACS-GM001-8 | T3 | bar |
| Soybean | MON87754 | MON-87754-1 | T33 | dgat2A |
| Soybean | DAS21606 | DAS-21606 | T34, T3 | Modified aad-12; pat |
| Soybean | DAS44406 | DAS-44406-6 | T1, T3, T34 | Modified aad-12; 2mepsps; pat |
| Soybean | SYHT04R | SYN-0004R-8 | T35 | Modified avhppd |
| Soybean | 9582.814.19.1 | — | T3, T7 | cry1Ac, cry1F, PAT |
| Squash | CZW3 | SEM-ØCZW3-2 | T6 | cmv cp, zymv cp, wmv cp |
| Squash | ZW20 | SEM-0ZW20-7 | T6 | zymv cp, wmv cp |
| Sugar Beet | GTSB77 (T9100152) | SY-GTSB77-8 | T1 | cp4 epsps (aroA:CP4); goxv247 |
| Sugar Beet | H7-1 | KM-000H71-4 | T1 | cp4 epsps (aroA:CP4) |
| Sugar Beet | T120-7 | ACS-BV001-3 | T3 | pat |
| Sugar Beet | T227-1 | — | T1 | cp4 epsps (aroA:CP4) |
| Sugarcane | NXI-1T | — | T21 | EcbetA |
| Sunflower | X81359 | — | T16 | als |
| Pepper | PK-SP01 | — | T6 | cmv cp |
| Tobacco | C/F/93/08-02 | — | T5 | bxn |
| Tobacco | Vector 21-41 | — | T36 | NtQPT1 (antisense) |
| Sunflower | X81359 | — | T16 | als |

-continued

Exhibit C

| Crop | Event Name | Event Code | Trait(s) | Gene(s) |
|---|---|---|---|---|
| Wheat | MON71800 | MON-718ØØ-3 | T1 | cp4 epsps (aroA:CP4) |

*Argentine (*Brassica napus*),
**Polish (*B. rapa*),
Eggplant

Although most typically, compounds of the disclosure are used to control undesired vegetation, contact of desired vegetation in the treated locus with compounds of the disclosure may result in super-additive or synergistic effects with genetic traits in the desired vegetation, including traits incorporated through genetic modification. For example, resistance to phytophagous insect pests or plant diseases, tolerance to biotic/abiotic stresses or storage stability may be greater than expected from the genetic traits in the desired vegetation.

Compounds of this disclosure can also be mixed with one or more other biologically active compounds or agents including herbicides, herbicide safeners, fungicides, insecticides, nematocides, bactericides, acaricides, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Mixtures of the compounds of the disclosure with other herbicides can broaden the spectrum of activity against additional weed species, and suppress the proliferation of any resistant biotypes. Thus the present disclosure also pertains to a composition comprising a compound of Formula 1 (in a herbicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present disclosure, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

A mixture of one or more of the following herbicides with a compound of this disclosure may be particularly useful for weed control: acetochlor, acifluorfen and its sodium salt, aclonifen, acrolein (2-propenal), alachlor, alloxydim, ametryn, amicarbazone, amidosulfuron, aminocyclopyrachlor and its esters (e.g., methyl, ethyl) and salts (e.g., sodium, potassium), aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bicyclopyrone, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clacyfos, clefoxydim, clethodim, clodinafop-propargyl, clomazone, clomeprop, clopyralid, clopyralid-olamine, cloransulam-methyl, cumyluron, cyanazine, cycloate, cyclopyrimorate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethiozin, ethofumesate, ethoxyfen, ethoxysulfuron, etobenzanid, fenoxaprop-ethyl, fenoxaprop-P-ethyl, fenoxasulfone, fenquinotrione, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, fluazolate, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupoxam, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glufosinate-P, glyphosate and its salts such as ammonium, isopropylammonium, potassium, sodium (including sesquisodium) and trimesium (alternatively named sulfosate), halauxifen, halauxifen-methyl, halosulfuron-methyl, haloxyfop-etotyl, haloxyfop-methyl, hexazinone, hydantocidin, imazamethabenz-methyl, imazamox, imazapic, imazapyr, imazaquin, imazaquin-ammonium, imazethapyr, imazethapyr-ammonium, imazosulfuron, indanofan, indaziflam, iofensulfuron, iodosulfuron-methyl, ioxynil, ioxynil octanoate, ioxynil-sodium, ipfencarbazone, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, metazosulfuron, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, metsulfuron-methyl, molinate, monolinuron, naproanilide, napropamide, napropamide-M, naptalam, neburon, nicosulfuron, norflurazon, orbencarb, orthosulfamuron, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxamid, pethoxyamid, phenmedipham, picloram, picloram-potassium, picolinafen, pinoxaden, piperophos, pretilachlor, primisulfuron-methyl, prodiamine, profoxydim, prometon, prometryn, propachlor, propanil, propaquizafop, propazine, propham, propisochlor, propoxycarbazone, propyrisulfuron, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxasulfone, pyroxsulam, quinclorac, quinmerac, quinoclamine, quizalofop-ethyl, quizalofop-P-ethyl, quizalofop-P-tefuryl, rimsulfuron, saflufenacil, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiafenacil, tiocarbazil, tolpyralate, topramezone, tralkoxydim, triallate, triafamone, triasulfuron, triaziflam, tribenuron-methyl, triclopyr, triclopyr-butotyl, triclopyr-triethylammonium, tridiphane, trietazine, trifloxysulfuron, trifludimoxazin, trifluralin, triflusulfuron-methyl, tritosulfuron, vernolate, 3-(2-chloro-3,6-difluorophenyl)-4-hydroxy-1-methyl-1,5-naphthyridin-2(1H)-one, 5-chloro-3-[(2-hydroxy-6-oxo-1-cyclohexen-1-yl)carbonyl]-1-(4-methoxyphenyl)-2(1H)-quinoxalinone, 2-chloro-N-(1-methyl-1H-tetrazol-5-yl)-6-(trifluoromethyl)-3-pyridinecarboxamide, 7-(3,5-dichloro-4-pyridinyl)-5-(2,2-difluoroethyl)-8-hydroxypyrido[2,3-b]pyrazin-6(5H)-one), 4-(2,6-diethyl-4-methylphenyl)-5-hydroxy-2,6-dimethyl-3(2H)-pyridazinone), 5-[[(2,6-difluorophenyl)methoxy]methyl]-4,5-dihydro-5-methyl-3-(3-methyl-2-thienyl)isoxazole (previously methioxolin), 4-(4-fluorophenyl)-6-[(2-hydroxy-6-oxo-1-cyclohexen-1-yl)carbonyl]-2-methyl-1,2,4-triazine-3,5(2H,4H)-dione, methyl 4-amino-3-chloro-6-(4-chloro-2-fluoro-3-methoxyphenyl)-5-fluoro-2-pyridinecarboxylate, 2-methyl-3-(methylsulfonyl)-N-(1-methyl-1H-tetrazol-5-yl)-4-(trifluoromethyl)benzamide and 2-methyl-N-(4-methyl-1,2,5-oxadiazol-3-yl)-3-(methylsulfinyl)-4-(trifluoromethyl)benzamide. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub.

Compounds of this disclosure can also be used in combination with plant growth regulators such as aviglycine, N-(phenylmethyl)-1H-purin-6-amine, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

General references for agricultural protectants (i.e. herbicides, herbicide safeners, insecticides, fungicides, nematocides, acaricides and biological agents) include *The Pesticide Manual*, 13th Edition, C. D. S. Tomlin, Ed., British Crop Protection Council, Farnham, Surrey, U. K., 2003 and *The BioPesticide Manual*, 2nd Edition, L. G. Copping, Ed., British Crop Protection Council, Farnham, Surrey, U. K., 2001.

For embodiments where one or more of these various mixing partners are used, the mixing partners are typically used in the amounts similar to amounts customary when the mixture partners are used alone. More particularly in mixtures, active ingredients are often applied at an application rate between one-half and the full application rate specified on product labels for use of active ingredient alone. These amounts are listed in references such as *The Pesticide Manual* and *The BioPesticide Manual*. The weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of weeds controlled beyond the spectrum controlled by the compound of Formula 1 alone.

In certain instances, combinations of a compound of this disclosure with other biologically active (particularly herbicidal) compounds or agents (i.e. active ingredients) can result in a greater-than-additive (i.e. synergistic) effect on weeds and/or a less-than-additive effect (i.e. safening) on crops or other desirable plants. Reducing the quantity of active ingredients released in the environment while ensuring effective pest control is always desirable. Ability to use greater amounts of active ingredients to provide more effective weed control without excessive crop injury is also desirable. When synergism of herbicidal active ingredients occurs on weeds at application rates giving agronomically satisfactory levels of weed control, such combinations can be advantageous for reducing crop production cost and decreasing environmental load. When safening of herbicidal active ingredients occurs on crops, such combinations can be advantageous for increasing crop protection by reducing weed competition.

Of note is a combination of a compound of the disclosure with at least one other herbicidal active ingredient. Of particular note is such a combination where the other herbicidal active ingredient has different site of action from the compound of the disclosure. In certain instances, a combination with at least one other herbicidal active ingredient having a similar spectrum of control but a different site of action will be particularly advantageous for resistance management. Thus, a composition of the present disclosure can further comprise (in a herbicidally effective amount) at least one additional herbicidal active ingredient having a similar spectrum of control but a different site of action.

Compounds of this disclosure can also be used in combination with herbicide safeners such as allidochlor, benoxacor, cloquintocet-mexyl, cumyluron, cyometrinil, cyprosulfonamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone naphthalic anhydride (1,8-naphthalic anhydride), oxabetrinil, N-(aminocarbonyl)-2-methylbenzenesulfonamide, N-(aminocarbonyl)-2-fluorobenzenesulfonamide, 1-bromo-4-[(chloromethyl)sulfonyl]benzene (BCS), 4-(dichloroacetyl)-1-oxa-4-azospiro[4.5]decane (MON 4660), 2-(dichloromethyl)-2-methyl-1,3-dioxolane (MG 191), ethyl 1,6-dihydro-1-(2-methoxyphenyl)-6-oxo-2-phenyl-5-pyrimidinecarboxylate, 2-hydroxy-N,N-dimethyl-6-(trifluoromethyl)pyridine-3-carboxamide, and 3-oxo-1-cyclohexen-1-yl 1-(3,4-dimethylphenyl)-1,6-dihydro-6-oxo-2-phenyl-5-pyrimidinecarboxylate, 2,2-dichloro-1-(2,2,5-trimethyl-3-oxazolidinyl)-ethanone and 2-methoxy-N-[[4-[[(methylamino)carbonyl]amino]phenyl]sulfonyl]-benzamide to increase safety to certain crops. Antidotally effective amounts of the herbicide safeners can be applied at the same time as the compounds of this disclosure, or applied as seed treatments. Therefore an aspect of the present disclosure relates to a herbicidal mixture comprising a compound of this disclosure and an antidotally effective amount of a herbicide safener. Seed treatment is particularly useful for selective weed control, because it physically restricts antidoting to the crop plants. Therefore a particularly useful embodiment of the present disclosure is a method for selectively controlling the growth of undesired vegetation in a crop comprising contacting the locus of the crop with a herbicidally effective amount of a compound of this disclosure wherein seed from which the crop is grown is treated with an antidotally effective amount of safener. Antidotally effective amounts of safeners can be easily determined by one skilled in the art through simple experimentation.

Compounds of the disclosure cans also be mixed with: (1) polynucleotides including but not limited to DNA, RNA, and/or chemically modified nucleotides influencing the amount of a particular target through down regulation, interference, suppression or silencing of the genetically derived transcript that render a herbicidal effect; or (2) polynucleotides including but not limited to DNA, RNA, and/or chemically modified nucleotides influencing the amount of a particular target through down regulation, interference, suppression or silencing of the genetically derived transcript that render a safening effect.

Of note is a composition comprising a compound of the disclosure (in a herbicidally effective amount), at least one additional active ingredient selected from the group consisting of other herbicides and herbicide safeners (in an effective amount), and at least one component selected from the group consisting of surfactants, solid diluents and liquid diluents.

Preferred for better control of undesired vegetation (e.g., lower use rate such as from synergism, broader spectrum of weeds controlled, or enhanced crop safety) or for preventing the development of resistant weeds are mixtures of a compound of this disclosure with another herbicide. Table A1 lists specific combinations of a Component (a) (i.e. a specific compound of the present disclosure) with another herbicide as Component (b) illustrative of the mixtures, compositions and methods of the present disclosure. Compound 1 in the Component (a) column is identified in Index Table A. The second column of Table A1 lists the specific Component (b) compound (e.g., "2,4-D" in the first line). The third, fourth and fifth columns of Table A1 lists ranges of weight ratios for rates at which the Component (a) compound is typically applied to a field-grown crop relative to Component (b) (i.e. (a):(b)). Thus, for example, the first line of Table A1 specifically discloses the combination of Component (a) (i.e. Compound 1 in Index Table A) with 2,4-D is typically applied in a weight ratio between 1:192-6:1. The remaining lines of Table A1 are to be construed similarly.

TABLE A1

| Component (a) (Compound #) | Component (b) | Typical Weight Ratio | More Typical Weight Ratio | Most Typical Weight Ratio |
| --- | --- | --- | --- | --- |
| 1 | 2,4-D | 1:192-6:1 | 1:64-2:1 | 1:24-1:3 |
| 1 | Acetochlor | 1:768-2:1 | 1:256-1:2 | 1:96-1:11 |
| 1 | Acifluorfen | 1:96-12:1 | 1:32-4:1 | 1:12-1:2 |
| 1 | Aclonifen | 1:857-2:1 | 1:285-1:3 | 1:107-1:12 |
| 1 | Alachlor | 1:768-2:1 | 1:256-1:2 | 1:96-1:11 |
| 1 | Ametryn | 1:384-3:1 | 1:128-1:1 | 1:48-1:6 |
| 1 | Amicarbazone | 1:192-6:1 | 1:64-2:1 | 1:24-1:3 |
| 1 | Amidosulfuron | 1:6-168:1 | 1:2-56:1 | 1:1-11:1 |
| 1 | Aminocyclopyrachlor | 1:48-24:1 | 1:16-8:1 | 1:6-2:1 |
| 1 | Aminopyralid | 1:20-56:1 | 1:6-19:1 | 1:2-4:1 |
| 1 | Amitrole | 1:768-2:1 | 1:256-1:2 | 1:96-1:11 |
| 1 | Anilofos | 1:96-12:1 | 1:32-4:1 | 1:12-1:2 |
| 1 | Asulam | 1:960-2:1 | 1:320-1:3 | 1:120-1:14 |
| 1 | Atrazine | 1:192-6:1 | 1:64-2:1 | 1:24-1:3 |
| 1 | Azimsulfuron | 1:6-168:1 | 1:2-56:1 | 1:1-11:1 |
| 1 | Beflubutamid | 1:342-4:1 | 1:114-2:1 | 1:42-1:5 |
| 1 | Benfuresate | 1:617-2:1 | 1:205-1:2 | 1:77-1:9 |
| 1 | Bensulfuron-methyl | 1:25-45:1 | 1:8-15:1 | 1:3-3:1 |
| 1 | Bentazone | 1:192-6:1 | 1:64-2:1 | 1:24-1:3 |
| 1 | Benzobicyclon | 1:85-14:1 | 1:28-5:1 | 1:10-1:2 |
| 1 | Benzofenap | 1:257-5:1 | 1:85-2:1 | 1:32-1:4 |
| 1 | Bicyclopyrone | 1:42-27:1 | 1:14-9:1 | 1:5-2:1 |
| 1 | Bifenox | 1:257-5:1 | 1:85-2:1 | 1:32-1:4 |
| 1 | Bispyribac-sodium | 1:10-112:1 | 1:3-38:1 | 1:1-7:1 |
| 1 | Bromacil | 1:384-3:1 | 1:128-1:1 | 1:48-1:6 |
| 1 | Bromobutide | 1:384-3:1 | 1:128-1:1 | 1:48-1:6 |
| 1 | Bromoxynil | 1:96-12:1 | 1:32-4:1 | 1:12-1:2 |
| 1 | Butachlor | 1:768-2:1 | 1:256-1:2 | 1:96-1:11 |
| 1 | Butafenacil | 1:42-27:1 | 1:14-9:1 | 1:5-2:1 |
| 1 | Butylate | 1:1542-1:2 | 1:514-1:5 | 1:192-1:22 |
| 1 | Carfenstrole | 1:192-6:1 | 1:64-2:1 | 1:24-1:3 |
| 1 | Carfentrazone-ethyl | 1:128-9:1 | 1:42-3:1 | 1:16-1:2 |
| 1 | Chlorimuron-ethyl | 1:8-135:1 | 1:2-45:1 | 1:1-9:1 |
| 1 | Chlorotoluron | 1:768-2:1 | 1:256-1:2 | 1:96-1:11 |
| 1 | Chlorsulfuron | 1:6-168:1 | 1:2-56:1 | 1:1-11:1 |
| 1 | Cincosulfuron | 1:17-68:1 | 1:5-23:1 | 1:2-5:1 |
| 1 | Cinidon-ethyl | 1:384-3:1 | 1:128-1:1 | 1:48-1:6 |
| 1 | Cinmethylin | 1:34-34:1 | 1:11-12:1 | 1:4-3:1 |
| 1 | Clacyfos | 1:34-34:1 | 1:11-12:1 | 1:4-3:1 |
| 1 | Clethodim | 1:48-24:1 | 1:16-8:1 | 1:6-2:1 |

TABLE A1-continued

| Component (a) (Compound #) | Component (b) | Typical Weight Ratio | More Typical Weight Ratio | Most Typical Weight Ratio |
|---|---|---|---|---|
| 1 | Clodinafop-propargyl | 1:20-56:1 | 1:6-19:1 | 1:2-4:1 |
| 1 | Clomazone | 1:384-3:1 | 1:128-1:1 | 1:48-1:6 |
| 1 | Clomeprop | 1:171-7:1 | 1:57-3:1 | 1:21-1:3 |
| 1 | Clopyralid | 1:192-6:1 | 1:64-2:1 | 1:24-1:3 |
| 1 | Cloransulam-methyl | 1:12-96:1 | 1:4-32:1 | 1:1-6:1 |
| 1 | Cumyluron | 1:384-3:1 | 1:128-1:1 | 1:48-1:6 |
| 1 | Cyanazine | 1:384-3:1 | 1:128-1:1 | 1:48-1:6 |
| 1 | Cyclopyrimorate | 1:17-68:1 | 1:5-23:1 | 1:2-5:1 |
| 1 | Cyclosulfamuron | 1:17-68:1 | 1:5-23:1 | 1:2-5:1 |
| 1 | Cycloxydim | 1:96-12:1 | 1:32-4:1 | 1:12-1:2 |
| 1 | Cyhalofop | 1:25-45:1 | 1:8-15:1 | 1:3-3:1 |
| 1 | Daimuron | 1:192-6:1 | 1:64-2:1 | 1:24-1:3 |
| 1 | Desmedipham | 1:322-4:1 | 1:107-2:1 | 1:40-1:5 |
| 1 | Dicamba | 1:192-6:1 | 1:64-2:1 | 1:24-1:3 |
| 1 | Dichlobenil | 1:1371-1:2 | 1:457-1:4 | 1:171-1:20 |
| 1 | Dichlorprop | 1:925-2:1 | 1:308-1:3 | 1:115-1:13 |
| 1 | Diclofop-methyl | 1:384-3:1 | 1:128-1:1 | 1:48-1:6 |
| 1 | Diclosulam | 1:10-112:1 | 1:3-38:1 | 1:1-7:1 |
| 1 | Difenzoquat | 1:288-4:1 | 1:96-2:1 | 1:36-1:4 |
| 1 | Diflufenican | 1:857-2:1 | 1:285-1:3 | 1:107-1:12 |
| 1 | Diflufenzopyr | 1:12-96:1 | 1:4-32:1 | 1:1-6:1 |
| 1 | Dimethachlor | 1:768-2:1 | 1:256-1:2 | 1:96-1:11 |
| 1 | Dimethametryn | 1:192-6:1 | 1:64-2:1 | 1:24-1:3 |
| 1 | Dimethenamid-P | 1:384-3:1 | 1:128-1:1 | 1:48-1:6 |
| 1 | Dithiopyr | 1:192-6:1 | 1:64-2:1 | 1:24-1:3 |
| 1 | Diuron | 1:384-3:1 | 1:128-1:1 | 1:48-1:6 |
| 1 | EPTC | 1:768-2:1 | 1:256-1:2 | 1:96-1:11 |
| 1 | Esprocarb | 1:1371-1:2 | 1:457-1:4 | 1:171-1:20 |
| 1 | Ethalfluralin | 1:384-3:1 | 1:128-1:1 | 1:48-1:6 |
| 1 | Ethametsulfuron-methyl | 1:17-68:1 | 1:5-23:1 | 1:2-5:1 |
| 1 | Ethoxyfen | 1:8-135:1 | 1:2-45:1 | 1:1-9:1 |
| 1 | Ethoxysulfuron | 1:20-56:1 | 1:6-19:1 | 1:2-4:1 |
| 1 | Etobenzanid | 1:257-5:1 | 1:85-2:1 | 1:32-1:4 |
| 1 | Fenoxaprop-ethyl | 1:120-10:1 | 1:40-4:1 | 1:15-1:2 |
| 1 | Fenoxasulfone | 1:85-14:1 | 1:28-5:1 | 1:10-1:2 |
| 1 | Fenquinotrione | 1:17-68:1 | 1:5-23:1 | 1:2-5:1 |
| 1 | Fentrazamide | 1:17-68:1 | 1:5-23:1 | 1:2-5:1 |
| 1 | Flazasulfuron | 1:17-68:1 | 1:5-23:1 | 1:2-5:1 |
| 1 | Florasulam | 1:2-420:1 | 1:1-140:1 | 2:1-27:1 |
| 1 | Fluazifop-butyl | 1:192-6:1 | 1:64-2:1 | 1:24-1:3 |
| 1 | Flucarbazone | 1:8-135:1 | 1:2-45:1 | 1:1-9:1 |
| 1 | Flucetosulfuron | 1:8-135:1 | 1:2-45:1 | 1:1-9:1 |
| 1 | Flufenacet | 1:257-5:1 | 1:85-2:1 | 1:32-1:4 |
| 1 | Flumetsulam | 1:24-48:1 | 1:8-16:1 | 1:3-3:1 |
| 1 | Flumiclorac-pentyl | 1:10-112:1 | 1:3-38:1 | 1:1-7:1 |
| 1 | Flumioxazin | 1:25-45:1 | 1:8-15:1 | 1:3-3:1 |
| 1 | Fluometuron | 1:384-3:1 | 1:128-1:1 | 1:48-1:6 |
| 1 | Flupyrsulfuron-methyl | 1:3-336:1 | 1:1-112:1 | 2:1-21:1 |
| 1 | Fluridone | 1:384-3:1 | 1:128-1:1 | 1:48-1:6 |
| 1 | Fluroxypyr | 1:96-12:1 | 1:32-4:1 | 1:12-1:2 |
| 1 | Flurtamone | 1:857-2:1 | 1:285-1:3 | 1:107-1:12 |
| 1 | Fluthiacet-methyl | 1:48-42:1 | 1:16-14:1 | 1:3-3:1 |
| 1 | Fomesafen | 1:96-12:1 | 1:32-4:1 | 1:12-1:2 |
| 1 | Foramsulfuron | 1:13-84:1 | 1:4-28:1 | 1:1-6:1 |
| 1 | Glufosinate | 1:288-4:1 | 1:96-2:1 | 1:36-1:4 |
| 1 | Glyphosate | 1:288-4:1 | 1:96-2:1 | 1:36-1:4 |
| 1 | Halosulfuron-methyl | 1:17-68:1 | 1:5-23:1 | 1:2-5:1 |
| 1 | Halauxifen | 1:20-56:1 | 1:6-19:1 | 1:2-4:1 |
| 1 | Halauxifen methyl | 1:20-56:1 | 1:6-19:1 | 1:2-4:1 |
| 1 | Haloxyfop-methyl | 1:34-34:1 | 1:11-12:1 | 1:4-3:1 |
| 1 | Hexazinone | 1:192-6:1 | 1:64-2:1 | 1:24-1:3 |
| 1 | Hydantocidin | 1:1100-16:1 | 1:385-8:1 | 1:144-4:1 |
| 1 | Imazamox | 1:13-84:1 | 1:4-28:1 | 1:1-6:1 |
| 1 | Imazapic | 1:20-56:1 | 1:6-19:1 | 1:2-4:1 |
| 1 | Imazapyr | 1:85-14:1 | 1:28-5:1 | 1:10-1:2 |
| 1 | Imazaquin | 1:34-34:1 | 1:11-12:1 | 1:4-3:1 |
| 1 | Imazethabenz-methyl | 1:171-7:1 | 1:57-3:1 | 1:21-1:3 |
| 1 | Imazethapyr | 1:24-48:1 | 1:8-16:1 | 1:3-3:1 |
| 1 | Imazosulfuron | 1:27-42:1 | 1:9-14:1 | 1:3-3:1 |
| 1 | Indanofan | 1:342-4:1 | 1:114-2:1 | 1:42-1:5 |
| 1 | Indaziflam | 1:25-45:1 | 1:8-15:1 | 1:3-3:1 |
| 1 | Iodosulfuron-methyl | 1:3-336:1 | 1:1-112:1 | 2:1-21:1 |
| 1 | Ioxynil | 1:192-6:1 | 1:64-2:1 | 1:24-1:3 |
| 1 | Ipfencarbazone | 1:85-14:1 | 1:28-5:1 | 1:10-1:2 |
| 1 | Isoproturon | 1:384-3:1 | 1:128-1:1 | 1:48-1:6 |
| 1 | Isoxaben | 1:288-4:1 | 1:96-2:1 | 1:36-1:4 |
| 1 | Isoxaflutole | 1:60-20:1 | 1:20-7:1 | 1:7-2:1 |

TABLE A1-continued

| Component (a) (Compound #) | Component (b) | Typical Weight Ratio | More Typical Weight Ratio | Most Typical Weight Ratio |
|---|---|---|---|---|
| 1 | Lactofen | 1:42-27:1 | 1:14-9:1 | 1:5-2:1 |
| 1 | Lenacil | 1:384-3:1 | 1:128-1:1 | 1:48-1:6 |
| 1 | Linuron | 1:384-3:1 | 1:128-1:1 | 1:48-1:6 |
| 1 | MCPA | 1:192-6:1 | 1:64-2:1 | 1:24-1:3 |
| 1 | MCPB | 1:288-4:1 | 1:96-2:1 | 1:36-1:4 |
| 1 | Mecoprop | 1:768-2:1 | 1:256-1:2 | 1:96-1:11 |
| 1 | Mefenacet | 1:384-3:1 | 1:128-1:1 | 1:48-1:6 |
| 1 | Mefluidide | 1:192-6:1 | 1:64-2:1 | 1:24-1:3 |
| 1 | Mesosulfuron-methyl | 1:5-224:1 | 1:1-75:1 | 1:1-14:1 |
| 1 | Mesotrione | 1:42-27:1 | 1:14-9:1 | 1:5-2:1 |
| 1 | Metamifop | 1:42-27:1 | 1:14-9:1 | 1:5-2:1 |
| 1 | Metazachlor | 1:384-3:1 | 1:128-1:1 | 1:48-1:6 |
| 1 | Metazosulfuron | 1:25-45:1 | 1:8-15:1 | 1:3-3:1 |
| 1 | Methabenzthiazuron | 1:768-2:1 | 1:256-1:2 | 1:96-1:11 |
| 1 | Metolachlor | 1:768-2:1 | 1:256-1:2 | 1:96-1:11 |
| 1 | Metosulam | 1:8-135:1 | 1:2-45:1 | 1:1-9:1 |
| 1 | Metribuzin | 1:192-6:1 | 1:64-2:1 | 1:24-1:3 |
| 1 | Metsulfuron-methyl | 1:2-560:1 | 1:1-187:1 | 3:1-35:1 |
| 1 | Molinate | 1:1028-2:1 | 1:342-1:3 | 1:128-1:15 |
| 1 | Napropamide | 1:384-3:1 | 1:128-1:1 | 1:48-1:6 |
| 1 | Napropamide-M | 1:192-6:1 | 1:64-2:1 | 1:24-1:3 |
| 1 | Naptalam | 1:192-6:1 | 1:64-2:1 | 1:24-1:3 |
| 1 | Nicosulfuron | 1:12-96:1 | 1:4-32:1 | 1:1-6:1 |
| 1 | Norflurazon | 1:1152-1:1 | 1:384-1:3 | 1:144-1:16 |
| 1 | Orbencarb | 1:1371-1:2 | 1:457-1:4 | 1:171-1:20 |
| 1 | Orthosulfamuron | 1:20-56:1 | 1:6-19:1 | 1:2-4:1 |
| 1 | Oryzalin | 1:514-3:1 | 1:171-1:2 | 1:64-1:8 |
| 1 | Oxadiargyl | 1:384-3:1 | 1:128-1:1 | 1:48-1:6 |
| 1 | Oxadiazon | 1:548-3:1 | 1:182-1:2 | 1:68-1:8 |
| 1 | Oxasulfuron | 1:27-42:1 | 1:9-14:1 | 1:3-3:1 |
| 1 | Oxaziclomefone | 1:42-27:1 | 1:14-9:1 | 1:5-2:1 |
| 1 | Oxyfluorfen | 1:384-3:1 | 1:128-1:1 | 1:48-1:6 |
| 1 | Paraquat | 1:192-6:1 | 1:64-2:1 | 1:24-1:3 |
| 1 | Pendimethalin | 1:384-3:1 | 1:128-1:1 | 1:48-1:6 |
| 1 | Penoxsulam | 1:10-112:1 | 1:3-38:1 | 1:1-7:1 |
| 1 | Penthoxamid | 1:384-3:1 | 1:128-1:1 | 1:48-1:6 |
| 1 | Pentoxazone | 1:102-12:1 | 1:34-4:1 | 1:12-1:2 |
| 1 | Phenmedipham | 1:102-12:1 | 1:34-4:1 | 1:12-1:2 |
| 1 | Picloram | 1:96-12:1 | 1:32-4:1 | 1:12-1:2 |
| 1 | Picolinafen | 1:34-34:1 | 1:11-12:1 | 1:4-3:1 |
| 1 | Pinoxaden | 1:25-45:1 | 1:8-15:1 | 1:3-3:1 |
| 1 | Pretilachlor | 1:192-6:1 | 1:64-2:1 | 1:24-1:3 |
| 1 | Primisulfuron-methyl | 1:8-135:1 | 1:2-45:1 | 1:1-9:1 |
| 1 | Prodiamine | 1:384-3:1 | 1:128-1:1 | 1:48-1:6 |
| 1 | Profoxydim | 1:42-27:1 | 1:14-9:1 | 1:5-2:1 |
| 1 | Prometryn | 1:384-3:1 | 1:128-1:1 | 1:48-1:6 |
| 1 | Propachlor | 1:1152-1:1 | 1:384-1:3 | 1:144-1:16 |
| 1 | Propanil | 1:384-3:1 | 1:128-1:1 | 1:48-1:6 |
| 1 | Propaquizafop | 1:48-24:1 | 1:16-8:1 | 1:6-2:1 |
| 1 | Propoxycarbazone | 1:17-68:1 | 1:5-23:1 | 1:2-5:1 |
| 1 | Propyrisulfuron | 1:17-68:1 | 1:5-23:1 | 1:2-5:1 |
| 1 | Propyzamide | 1:384-3:1 | 1:128-1:1 | 1:48-1:6 |
| 1 | Prosulfocarb | 1:1200-1:2 | 1:400-1:4 | 1:150-1:17 |
| 1 | Prosulfuron | 1:6-168:1 | 1:2-56:1 | 1:1-11:1 |
| 1 | Pyraclonil | 1:42-27:1 | 1:14-9:1 | 1:5-2:1 |
| 1 | Pyraflufen-ethyl | 1:5-224:1 | 1:1-75:1 | 1:1-14:1 |
| 1 | Pyrasulfotole | 1:13-84:1 | 1:4-28:1 | 1:1-6:1 |
| 1 | Pyrazolynate | 1:857-2:1 | 1:285-1:3 | 1:107-1:12 |
| 1 | Pyrazosulfuron-ethyl | 1:10-112:1 | 1:3-38:1 | 1:1-7:1 |
| 1 | Pyrazoxyfen | 1:5-224:1 | 1:1-75:1 | 1:1-14:1 |
| 1 | Pyribenzoxim | 1:10-112:1 | 1:3-38:1 | 1:1-7:1 |
| 1 | Pyributicarb | 1:384-3:1 | 1:128-1:1 | 1:48-1:6 |
| 1 | Pyridate | 1:288-4:1 | 1:96-2:1 | 1:36-1:4 |
| 1 | Pyriftalid | 1:10-112:1 | 1:3-38:1 | 1:1-7:1 |
| 1 | Pyriminobac-methyl | 1:20-56:1 | 1:6-19:1 | 1:2-4:1 |
| 1 | Pyrimisulfan | 1:17-68:1 | 1:5-23:1 | 1:2-5:1 |
| 1 | Pyrithiobac | 1:24-48:1 | 1:8-16:1 | 1:3-3:1 |
| 1 | Pyroxasulfone | 1:85-14:1 | 1:28-5:1 | 1:10-1:2 |
| 1 | Pyroxsulam | 1:5-224:1 | 1:1-75:1 | 1:1-14:1 |
| 1 | Quinclorac | 1:192-6:1 | 1:64-2:1 | 1:24-1:3 |
| 1 | Quizalofop-ethyl | 1:42-27:1 | 1:14-9:1 | 1:5-2:1 |
| 1 | Rimsulfuron | 1:13-84:1 | 1:4-28:1 | 1:1-6:1 |
| 1 | Saflufenacil | 1:25-45:1 | 1:8-15:1 | 1:3-3:1 |
| 1 | Sethoxydim | 1:96-12:1 | 1:32-4:1 | 1:12-1:2 |
| 1 | Simazine | 1:384-3:1 | 1:128-1:1 | 1:48-1:6 |
| 1 | Sulcotrione | 1:120-10:1 | 1:40-4:1 | 1:15-1:2 |
| 1 | Sulfentrazone | 1:147-8:1 | 1:49-3:1 | 1:18-1:3 |

TABLE A1-continued

| Component (a) (Compound #) | Component (b) | Typical Weight Ratio | More Typical Weight Ratio | Most Typical Weight Ratio |
|---|---|---|---|---|
| 1 | Sulfometuron-methyl | 1:34-34:1 | 1:11-12:1 | 1:4-3:1 |
| 1 | Sulfosulfuron | 1:8-135:1 | 1:2-45:1 | 1:1-9:1 |
| 1 | Tebuthiuron | 1:384-3:1 | 1:128-1:1 | 1:48-1:6 |
| 1 | Tefuryltrione | 1:42-27:1 | 1:14-9:1 | 1:5-2:1 |
| 1 | Tembotrione | 1:31-37:1 | 1:10-13:1 | 1:3-3:1 |
| 1 | Tepraloxydim | 1:25-45:1 | 1:8-15:1 | 1:3-3:1 |
| 1 | Terbacil | 1:288-4:1 | 1:96-2:1 | 1:36-1:4 |
| 1 | Terbuthylazine | 1:857-2:1 | 1:285-1:3 | 1:107-1:12 |
| 1 | Terbutryn | 1:192-6:1 | 1:64-2:1 | 1:24-1:3 |
| 1 | Thenylchlor | 1:85-14:1 | 1:28-5:1 | 1:10-1:2 |
| 1 | Thiazopyr | 1:384-3:1 | 1:128-1:1 | 1:48-1:6 |
| 1 | Thiencarbazone | 1:3-336:1 | 1:1-112:1 | 2:1-21:1 |
| 1 | Thifensulfuron-methyl | 1:5-224:1 | 1:1-75:1 | 1:1-14:1 |
| 1 | Tiafenacil | 1:17-68:1 | 1:5-23:1 | 1:2-5:1 |
| 1 | Thiobencarb | 1:768-2:1 | 1:256-1:2 | 1:96-1:11 |
| 1 | Tolpyralate | 1:31-37:1 | 1:10-13:1 | 1:3-3:1 |
| 1 | Topramezone | 1:6-168:1 | 1:2-56:1 | 1:1-11:1 |
| 1 | Tralkoxydim | 1:68-17:1 | 1:22-6:1 | 1:8-2:1 |
| 1 | Triafamone | 1:2-420:1 | 1:1-140:1 | 2:1-27:1 |
| 1 | Triallate | 1:768-2:1 | 1:256-1:2 | 1:96-1:11 |
| 1 | Triasulfuron | 1:5-224:1 | 1:1-75:1 | 1:1-14:1 |
| 1 | Triaziflam | 1:171-7:1 | 1:57-3:1 | 1:21-1:3 |
| 1 | Tribenuron-methyl | 1:3-336:1 | 1:1-112:1 | 2:1-21:1 |
| 1 | Triclopyr | 1:192-6:1 | 1:64-2:1 | 1:24-1:3 |
| 1 | Trifloxysulfuron | 1:2-420:1 | 1:1-140:1 | 2:1-27:1 |
| 1 | Trifludimoxazin | 1:25-45:1 | 1:8-15:1 | 1:3-3:1 |
| 1 | Trifluralin | 1:288-4:1 | 1:96-2:1 | 1:36-1:4 |
| 1 | Triflusulfuron-methyl | 1:17-68:1 | 1:5-23:1 | 1:2-5:1 |
| 1 | Tritosulfuron | 1:13-84:1 | 1:4-28:1 | 1:1-6:1 |

Table A2 is constructed the same as Table A1 above except that entries below the "Component (a)" column heading are replaced with the respective Component (a) Column Entry shown below. Compound 2 in the Component (a) column is identified in Index Table A. Thus, for example, in Table A2 the entries below the "Component (a)" column heading all recite "Compound 2" (i.e. Compound 2 identified in Index Table A), and the first line below the column headings in Table A2 specifically discloses a mixture of Compound 2 with 2,4-D. Tables A3 through A7 are constructed similarly.

| Table Number | Component (a) Column Entries |
|---|---|
| A2 | Compound 2 |
| A3 | Compound 3 |
| A4 | Compound 4 |
| A5 | Compound 5 |
| A6 | Compound 6 |
| A7 | Compound 7 |
| A8 | Compound 8 |
| A9 | Compound 9 |
| A10 | Compound 10 |
| A11 | Compound 11 |
| A12 | Compound 12 |
| A13 | Compound 13 |
| A14 | Compound 14 |
| A15 | Compound 15 |
| A16 | Compound 16 |
| A17 | Compound 17 |
| A18 | Compound 18 |
| A19 | Compound 19 |
| A20 | Compound 20 |
| A21 | Compound 21 |
| A22 | Compound 22 |
| A23 | Compound 23 |
| A24 | Compound 24 |
| A25 | Compound 25 |
| A26 | Compound 26 |
| A27 | Compound 27 |
| A28 | Compound 28 |
| A29 | Compound 29 |
| A30 | Compound 30 |
| A31 | Compound 31 |
| A32 | Compound 32 |
| A33 | Compound 33 |
| A34 | Compound 34 |
| A35 | Compound 35 |
| A36 | Compound 36 |
| A37 | Compound 37 |
| A38 | Compound 38 |
| A39 | Compound 39 |
| A40 | Compound 40 |
| A41 | Compound 41 |
| A42 | Compound 42 |
| A43 | Compound 43 |
| A44 | Compound 44 |
| A45 | Compound 45 |
| A46 | Compound 46 |
| A47 | Compound 47 |

Preferred for better control of undesired vegetation (e.g., lower use rate such as from synergism, broader spectrum of weeds controlled, or enhanced crop safety) or for preventing the development of resistant weeds are mixtures of a compound of this disclosure with a herbicide selected from the group consisting of chlorimuron-ethyl, nicosulfuron, mesotrione, thifensulfuron-methyl, flupyrsulfuron-methyl, tribenuron, pyroxasulfone, pinoxaden, tembotrione, pyroxsulam, metolachlor and S-metolachlor.

The following Tests demonstrate the control efficacy of the compounds of this disclosure against specific weeds. The weed control afforded by the compounds is not limited, however, to these species. See Index Table A for compound descriptions. The following abbreviations are used in the Index Table which follows: Me is methyl, Et is ethyl, Pr is propyl, i-Pr is isopropyl, Ph is phenyl, SMe is methylthio, SOMe is methylsulfinyl, SO₂Me is methylsulfonyl, —CN is cyano and TMS is trimethylsilyl. (R) or (S) denotes the absolute chirality of the asymmetric carbon center. The abbreviation "Cmpd. No." stands for "Compound Number". The abbreviation "Ex." stands for "Example" and is followed by a number indicating in which example the compound is prepared. Mass spectra are reported with an estimated precision within ±0.5 Da as the molecular weight of the highest isotopic abundance parent ion (M+1) formed by addition of H⁺ (molecular weight of 1) to the molecule or (M−1) formed by the loss of H+ (molecular weight of 1) from the molecule, observed by using atmospheric pressure chemical ionization (AP+).

INDEX TABLE A*

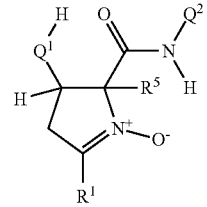

$R^1 = CH_3$, unless otherwise noted;

| Cmpd. No. | $Q^1$ | $Q^2$ | $R^5$ | m.p. (° C.) | M − 1 | M + 1 |
|---|---|---|---|---|---|---|
| 1 | Ph(4-CF₃) | Ph(2,3-di-F) | CH₃ | | | 413 |
| 2 (Ex. 2) | Ph(4-CF₃) | Ph(2,3-di-F) | H | *** | | 399 |
| 3 | Ph(3-Cl) | Ph(2,3-di-F) | H | | 363 | 365 |
| 4 | 1,3-benzodioxol-5-yl | Ph(2,3-di-F) | H | | 373 | 375 |
| 5 (Ex. 1) | Ph(4-Cl) | Ph(2,3-di-F) | H | *** | 363 | 365.3 |
| 6 | Ph(4-Me) | Ph(2,3-di-F) | H | | | 345 |
| 7 | Ph(3-CF₃) | Ph(2,3-di-F) | H | | | 400 |
| 8 | Ph(3-F) | Ph(2,3-di-F) | H | | 348 | 349 |
| 9 | Ph(4-F) | Ph(2,3-di-F) | H | | 347 | 349 |
| 10 | Ph(3,4-di-F) | Ph(2,3-di-F) | H | | | 367 |
| 11 | Ph(2-Me) | Ph(2,3-di-F) | H | | | 345 |
| 12 | Ph(3-i-Pr) | Ph(2,3-di-F) | H | | | 373 |
| 13 | Ph(3-OCF₂CF₂H) | Ph(2,3-di-F) | H | | | 448 |
| 14 | Ph(2-Cl,6-F) | Ph(2,3-di-F) | H | | | 383 |
| 15 | Ph(3-Me) | Ph(2,3-di-F) | H | | | 345 |
| 16 | Ph | Ph(2,3-di-F) | H | | 330 | 332 |
| 17 | Ph(3,4-di-F) | Ph | H | | 329 | 331 |
| 18 | Ph(2-CN) | Ph(2,3-di-F) | H | | | 456 |
| 19 | Ph(3-Br) | Ph(2,3-di-F) | H | | | 409 |
| 20 | Ph(4-Br) | Ph(2,3-di-F) | H | | | 409 |
| 21 | Ph(2-F) | Ph(2,3-di-F) | H | | 348 | 350 |
| 22 | Ph(4-CN) | Ph(2,3-di-F) | H | | 355 | 357 |
| 23 | Ph(3-CN) | Ph(2,3-di-F) | H | | 355 | 357 |
| 24 | Ph(3,4-di-Me) | Ph(2,3-di-F) | H | | 357 | 359 |
| 25 | 1,3-benzodioxol-5-yl(2,2-di-F) | Ph(2,3-di-F) | H | | 409 | 411 |
| 26 (Ex. 3) | Ph(4-CF₃) | Ph(2-F) | H | *** | | 379 |
| 27 | Ph(4-CF₃) | Ph(2-Me,3-F) | H | | | 3934 |
| 28 | Ph(4-CF₃) | Ph(2-F,3-CN) | H | | 404 | 406 |
| 29 | Ph(4-CF₃) | Ph(2-SMe) | H | | 407 | 409 |
| 30** | Ph(4-CF₃) | Ph(2,3-di-F) | H | 113-117 | | |
| 31 | Ph(4-CF₃) | Ph(2-Cl,3-F) | H | | 413 | 415 |
| 32 | Ph(4-CF₃) | Ph(2-CN) | H | | 387 | 389 |
| 33 | Ph(4-CF₃) | Ph(2-CF₃) | H | | 429 | 431 |
| 34 | Ph(4-CF₃) | Ph(2-CN,3-F) | H | | 404 | 406 |
| 35 ($R^1$ = CF₃) | Ph | Ph(2,3-di-F) | H | | | 385 |
| 36 | Ph(4-CF₃) | pyridin-4-yl(3-CF₃) | H | | 430 | 432 |
| 37 | Ph(4-CF₃) | pyridin-3-yl(2,6-di-F) | H | | 398 | 400 |
| 38 | Ph(4-CF₃) | Ph(2,3,4-tri-F) | H | | 415 | 417 |
| 39** | Ph(3,4-di-F) | Ph(2,3-di-F) | H | | | 367 |
| 40** | Ph(4-Cl) | Ph(2,3-di-F) | H | | | 365 |
| 41 | Ph(4-CF₃) | pyridin-3-yl(2-F) | H | | 380 | 382 |
| 42** | Ph(4-Me) | Ph(2,3-di-F) | H | | | 345 |
| 43 | Ph(4-CF₃) | Ph(2-SO₂Me) | H | | 440 | 442 |
| 44 | Ph(4-CF₃) | Ph(2-SOMe) | H | | 424 | 426 |
| 45** | Ph(3-CF₃) | Ph(2,3-di-F) | H | | | 399 |
| 46 | Ph(4-CF₃) | Ph(2,4-di-F) | H | | 397 | 399 |
| 47 | Ph(4-CF₃) | pyridin-2-yl(6-F) | H | | 380 | 382 |
| 48 | 3-[(5-fluoro-2-pyridinyl)oxy]-4-fluorophenyl | Ph(2,3-di-F) | H | | | 460 |

INDEX TABLE A*-continued

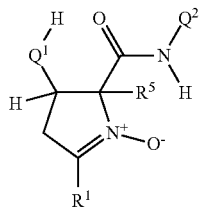

$R^1 = CH_3$, unless otherwise noted;

| Cmpd. No. | $Q^1$ | $Q^2$ | $R^5$ | m.p. (° C.) | M − 1 | M + 1 |
|---|---|---|---|---|---|---|
| 49 | pyridin-2-yl(6-Me) | Ph(2,3-di-F) | H | | | 346 |
| 50 | 3-[(6-chloro-3-pyridinyl)oxy]-5-fluorophenyl | Ph(2,3-di-F) | H | | | 476 |
| 51 | 3-[(6-chloro-3-pyridinyl)oxy]-4-fluorophenyl | Ph(2,3-di-F) | H | | | 476 |
| 52 | 4-fluoro-3-[(5-fluoro-2-pyrimidinyl)oxy]phenyl | Ph(2,3-di-F) | H | | | 461 |
| 53 | 6-methoxy-3-pyridazinyl | Ph(2,3-di-F) | H | | | 363 |
| 54** | Ph(3-OCF$_2$CF$_2$H,4-F) | Ph(2,3-di-F) | H | | | 465.4 |
| 55** | Ph(3-O-i-Pr) | Ph(2,3-di-F) | H | 102–106 | | |
| 56 | 3-[(5-chloro-2-pyridinyl)oxy]phenyl | Ph(2,3-di-F) | H | | | 458.5 |
| 57 | pyridin-4-yl(2-OCH$_3$,6-Me) | Ph(2,3-di-F) | H | | 374.4 | |
| 58 | 3-[(4-fluoro-phenyl)oxy]phenyl | Ph(2,3-di-F) | H | | 439.5 | |
| 59 | pyrimidin-2-yl(4,6-OMe) | Ph(2,3-di-F) | H | | | 393 |
| 60 | pyridin-3-yl(6-CF$_3$) | Ph(2,3-di-F) | H | | 398.3 | 400.3 |
| 61 | Ph(3-F,4-CF$_3$) | Ph(2,3-di-F) | H | | | 417.3 |
| 62 | Ph(3-CF$_3$,4-Me) | Ph(2,3-di-F) | H | | | 413.4 |
| 63 | Ph(3-Cl,4-F) | Ph(2,3-di-F) | H | | | 383.3 |
| 64 | Ph(3-CF$_3$,4-F) | Ph(2,3-di-F) | H | | | 417 |
| 65 | pyridin-2-yl(6-Br) | Ph(2,3-di-F) | H | | | 410 |
| 66 | pyridin-2-yl(5-Br) | Ph(2,3-di-F) | H | | | 410 |
| 67 | pyridin-2-yl(6-OCH$_3$) | Ph(2,3-di-F) | H | | | 362 |
| 68 | 2-[(5-fluoro-2-pyrimidinyl)oxy]-4-fluorophenyl | Ph(2,3-di-F) | H | | | 461 |
| 69** | Ph(3-O-t-Bu) | Ph(2,3-di-F) | H | 53–57 | | |
| 70** | 3-[(3,5-difluoro-pyridin-2-yl)oxy]phenyl | Ph(2,3-di-F) | H | 112–116 | | |
| 71 | Ph(3-Br,4-Me) | Ph(2,3-di-F) | H | | | 423.2 |
| 72 | Ph(3-Cl,4-Me) | Ph(2,3-di-F) | H | | | 379.63 |
| 73 | Ph(3-Br,4-CF$_3$) | Ph(2,3-di-F) | H | | | 477.3 |
| 74 | Ph(3-CF$_3$,4-OMe) | Ph(2,3-di-F) | H | | 427.4 | 429.3 |
| 75 | pyridin-2-yl(4-CF$_3$,6-Cl) | Ph(2,3-di-F) | H | | | 434.4 |
| 76 | pyrimidin-6-yl(2,4-OCH$_3$) | Ph(2,3-di-F) | H | | | 393 |
| 77 | Ph(2,3-di-Me) | Ph(2,3-di-F) | H | | | 359.3 |
| 78 | Ph(2-Me,3-F) | Ph(2,3-di-F) | H | | | 363.3 |
| 79 | Ph(2,5-di-Me) | Ph(2,3-di-F) | H | | | 359.3 |
| 80 | Ph(4-CH$_2$CFH$_2$) | Ph(2,3-di-F) | H | | | 363.3 |
| 81 | Ph(2-Me,5-F) | Ph(2,3-di-F) | H | | | 363.3 |
| 82 | Ph(3,5-di-F,4-CH$_2$CFH$_2$) | Ph(2,3-di-F) | H | | | 399.3 |
| 83 | pyridin-4-yl(2-Me,6-OCHF$_2$) | Ph(2,3-di-F) | H | | 410.4 | |
| 84** | 3-[(5-fluoro-2-pyridinyl)oxy]phenyl | Ph(2,3-di-F) | H | | | 442.4 |
| 85 | 3-[(5-fluoro-2-pyrimidinyl)oxy]-4,5-difluorophenyl | Ph(2,3-di-F) | H | | | 479.4 |
| 86 | 1-[(4-chlorophenyl)methyl]-1,2-dihydro-6-methyl-2-oxo-4-pyridinyl | Ph(2,3-di-F) | H | | | 486.3 |
| 87 | Ph(3-Me,4-CF$_3$) | Ph(2,3-di-F) | H | | | 413.5 |
| 88 | pyridin-2-yl(5-CF$_3$) | Ph(2,3-di-F) | H | | | 400 |
| 89 | pyridin-2-yl(6-Cl) | Ph(2,3-di-F) | H | | | 366 |
| 90 | pyridin-2-yl(6-CF$_3$) | Ph(2,3-di-F) | H | | | 400 |

INDEX TABLE A*-continued

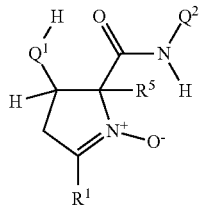

$R^1 = CH_3$, unless otherwise noted;

| Cmpd. No. | $Q^1$ | $Q^2$ | $R^5$ | m.p. (° C.) | M − 1 | M + 1 |
|---|---|---|---|---|---|---|
| 91 | Ph(3-OCH$_3$,5-Me) | Ph(2,3-di-F) | H | | 373.3 | |
| 92 | Ph(3-CF$_3$,5-Me) | Ph(2,3-di-F) | H | | 411.3 | |
| 93 | Ph(4-CF$_2$H) | Ph(2,3-di-F) | H | | | 381.2 |
| 94 | Ph(3-Cl,5-Me) | Ph(2,3-di-F) | H | | | 379.2 |
| 95 | Ph(3,4,5-tri-F) | Ph(2,3-di-F) | H | | | 385 |
| 96 | Ph(3,5-di-OCH$_3$) | Ph(2,3-di-F) | H | | | 391 |
| 97 | Ph | Ph(2,3-di-F) | H | | | 331 |
| 98 | Ph(2-Me,5-CF$_3$) | Ph(2,3-di-F) | H | | | 413 |
| 99 | Ph(2-F,3-Cl) | Ph(2,3-di-F) | H | | | 383 |
| 100 | Ph(3-OCH$_3$,4-CF$_3$) | Ph(2,3-di-F) | H | | 427.3 | |
| 101 | Ph(2-F,4-CF$_3$) | Ph(2,3-di-F) | H | | 415.3 | |
| 102 | Ph(3-Cl,4-CF$_3$) | Ph(2,3-di-F) | H | | | 433.3 |
| 103 | Ph(3-F,5-Me) | Ph(2,3-di-F) | H | | | 363 |
| 104 | Ph(3-CF$_3$,4-Cl) | Ph(2,3-di-F) | H | | | 433 |
| 105 | 3-(1,3-dioxolan-2yl)phenyl | Ph(2,3-di-F) | H | | | 403.4 |
| 106 | Ph(2-Me,3-CF$_3$) | Ph(2,3-di-F) | H | | | 413.3 |
| 107 | Ph(3-F,4-Cl) | Ph(2,3-di-F) | H | | | 383.3 |
| 108 | Ph(3-CH$_2$F,5-Me) | Ph(2,3-di-F) | H | | | 377.3 |
| 109 | Ph(3,5-di-CH$_2$CH$_3$) | Ph(2,3-di-F) | H | | | 387 |
| 110 | Ph(3,5-di-CF$_3$) | Ph(2,3-di-F) | H | | | 467 |
| 111 | Ph(3,5-di-Me,4-F) | Ph(2,3-di-F) | H | | | 377 |
| 112 | Ph(3,5-di-Me) | Ph(2,3-di-F) | H | | | 359 |
| 113 | Ph(3-F,4-OCF$_3$) | Ph(2,3-di-F) | H | | | 433 |
| 114 | Ph(3,5-F,4-CF$_3$) | Ph(2,3-di-F) | H | | | 435 |
| 115 | 3-[(5-chloro-2-pyrimidinyl)oxy]phenyl | Ph(2,3-di-F) | H | | 457.4 | |
| 116 | Ph(3-OEt,5-OMe) | Ph(2,3-di-F) | H | | | 405.4 |
| 117 | Ph(2-Me,3-Cl) | Ph(2,3-di-F) | H | | | 379 |
| 118 | 2,3-dihydro-1H-inden-4-yl | Ph(2,3-di-F) | H | | | 371 |
| 119 | 1-[(4-chlorophenyl)methyl]-1,2-dihydro-2-oxo-5-pyridinyl | Ph(2,3-di-F) | H | | 470.3 | |
| 120 ($R^1$ = CH$_2$CH$_3$) | Ph(4-CF$_3$) | Ph(2,3-di-F) | H | | 411.3 | |
| 121** | 3-[(5-fluoro-2-pyrimidinyl)oxy]phenyl | Ph(2,3-di-F) | H | 91-95 | | |
| 122 ($R^1$ = i-Pr) | Ph(4-CF$_3$) | Ph(2,3-di-F) | H | | 425.5 | |

*All compounds are reported as mixtures of enantiomers, unless otherwise indicated.
**Indicates the compound is prepared enantio-enriched at the 2 and 3 positions.

***See Synthesis Example for $^1$H NMR data.

Biological Examples

Test A

Seeds of plant species selected from barnyardgrass (*Echinochloa crus-galli*), kochia (*Kochia scoparia*), ragweed (common ragweed, *Ambrosia elatior*), ryegrass, Italian (Italian ryegrass, *Lolium multiflorum*), foxtail, giant (giant foxtail, *Setaria faberii*), foxtail, green (green foxtail, *Setaria viridis*), and pigweed (*Amaranthus retroflexus*) were planted into a blend of loam soil and sand and treated preemergence with a directed soil spray using test chemicals formulated in a non-phytotoxic solvent mixture which included a surfactant.

At the same time, plants selected from these weed species and also wheat (*Triticum aestivum*), corn (*Zea mays*), blackgrass (*Alopecurus myosuroides*), and galium (catchweed bedstraw, *Galium aparine*) were planted in pots containing the same blend of loam soil and sand and treated with postemergence applications of test chemicals formulated in the same manner. Plants ranged in height from 2 to 10 cm and were in the one- to two-leaf stage for the postemergence treatment. Treated plants and untreated controls were maintained in a greenhouse for approximately 10 days, after which time all treated plants were compared to untreated controls and visually evaluated for injury. Plant response ratings, summarized in Table A, are based on a 0 to 100 scale where 0 is no effect and 100 is complete control. A dash (-) response means no test result.

TABLE A

| 500 g ai/ha | Compounds | | | | | | | | | | | | | | |
|---|---|---|---|---|---|---|---|---|---|---|---|---|---|---|---|
| | 1 | 2 | 3 | 4 | 5 | 6 | 7 | 8 | 10 | 11 | 12 | 13 | 14 | 15 | |
| | Postemergence | | | | | | | | | | | | | | |
| Barnyardgrass | 90 | 90 | 90 | 90 | 90 | 90 | 90 | 90 | 90 | 90 | 90 | 90 | 0 | 90 | |
| Blackgrass | 70 | 90 | 80 | 20 | 50 | 80 | 80 | 30 | 30 | 0 | 50 | 90 | 0 | 30 | |
| Corn | 70 | 80 | 90 | 60 | 50 | 80 | 90 | 0 | 50 | 0 | 90 | 80 | 0 | 90 | |
| Foxtail, Giant | 80 | 90 | 90 | 90 | 70 | 90 | 90 | 90 | 90 | 90 | 90 | 90 | 0 | 90 | |
| Foxtail, Green | — | — | — | — | — | — | — | — | — | — | — | — | — | — | |
| Galium | 80 | 70 | 70 | 60 | 80 | 70 | 70 | 60 | 60 | 20 | 70 | 70 | 0 | 30 | |
| Kochia | 70 | 80 | 60 | 50 | 70 | 70 | 40 | 40 | 20 | 0 | 30 | 40 | 0 | 30 | |
| Pigweed | 60 | 80 | 20 | 20 | 70 | 50 | 50 | 20 | 20 | 0 | 20 | 40 | 0 | 40 | |
| Ragweed | 30 | 60 | 50 | 50 | 70 | 60 | 40 | 0 | 20 | 0 | 40 | 50 | 0 | 50 | |
| Ryegrass, Italian | 20 | 70 | 70 | 40 | 30 | 60 | 60 | 50 | 0 | 0 | 50 | 60 | 0 | 50 | |
| Wheat | 70 | 70 | 80 | 60 | 80 | 80 | 80 | 50 | 70 | 20 | 70 | 80 | 0 | 50 | |

| 500 g ai/ha | Compounds | | | | | | | | | | | | | |
|---|---|---|---|---|---|---|---|---|---|---|---|---|---|---|
| | 16 | 17 | 18 | 19 | 20 | 21 | 22 | 23 | 24 | 25 | 26 | 27 | 28 | 29 |
| | Postemergence | | | | | | | | | | | | | |
| Barnyardgrass | 90 | 0 | 0 | 90 | 50 | 50 | 60 | 80 | 90 | 90 | 90 | 90 | 90 | 30 |
| Blackgrass | 0 | 0 | 0 | 60 | 30 | 20 | 30 | 0 | 60 | 40 | 60 | 50 | 40 | 30 |
| Corn | 0 | 20 | 0 | 80 | 0 | 20 | 0 | 0 | 90 | 80 | 0 | 50 | 0 | 0 |
| Foxtail, Giant | — | — | — | — | — | — | — | — | — | — | — | — | — | — |
| Foxtail, Green | 80 | 20 | 0 | 60 | 60 | 20 | 50 | 80 | 90 | 90 | 90 | 90 | 90 | 50 |
| Galium | 30 | 0 | 0 | 30 | 40 | 0 | — | — | — | — | 80 | 70 | 70 | 60 |
| Kochia | 20 | 0 | 0 | 30 | 30 | 0 | 30 | 20 | 70 | 60 | 10 | 10 | 20 | 0 |
| Pigweed | 20 | 0 | 0 | 20 | 40 | 0 | 20 | 0 | 60 | 70 | 80 | 80 | 70 | 30 |
| Ragweed | 20 | 0 | 0 | 20 | 30 | 0 | 0 | 0 | 50 | 50 | 60 | 50 | 70 | 60 |
| Ryegrass, Italian | 0 | 0 | 0 | 40 | 30 | 0 | 0 | 20 | 80 | 50 | 20 | 20 | 20 | 0 |
| Wheat | 0 | 0 | 0 | 70 | 30 | 0 | 0 | 50 | 90 | 90 | 10 | 40 | 0 | 0 |

| 500 g ai/ha | Compounds | | | | | | | | | | | | | |
|---|---|---|---|---|---|---|---|---|---|---|---|---|---|---|
| | 31 | 32 | 33 | 34 | 35 | 36 | 37 | 38 | 41 | 43 | 44 | 46 | 47 | 49 |
| | Postemergence | | | | | | | | | | | | | |
| Barnyardgrass | 90 | 40 | 40 | 70 | 0 | 0 | 70 | 60 | 90 | 60 | 0 | 90 | 90 | 0 |
| Blackgrass | 80 | 20 | 0 | 80 | 0 | 20 | 90 | 70 | 50 | 30 | 20 | 70 | 0 | 0 |
| Corn | 10 | 50 | 30 | 0 | 0 | 0 | 50 | 70 | 0 | 0 | 0 | 40 | 20 | 0 |
| Foxtail, Giant | — | — | — | — | — | — | — | — | — | — | — | — | — | 0 |
| Foxtail, Green | 90 | 50 | 70 | 80 | 0 | 20 | 90 | 90 | 80 | 60 | 30 | 90 | 90 | — |
| Galium | — | 80 | 70 | — | — | — | — | — | 70 | — | — | — | 30 | 0 |
| Kochia | 10 | 20 | 0 | 30 | 0 | 0 | 70 | 0 | 20 | 0 | 10 | 40 | 0 | 0 |
| Pigweed | 30 | 20 | 20 | 70 | 0 | 0 | 70 | 30 | 70 | 0 | 20 | 30 | 20 | 0 |
| Ragweed | 20 | 20 | 40 | 50 | 0 | 0 | 60 | 20 | 40 | 0 | 0 | 30 | 40 | 20 |
| Ryegrass, Italian | 20 | 0 | 0 | 30 | 0 | 20 | 40 | 20 | 70 | 20 | 0 | 40 | 50 | 30 |
| Wheat | 40 | 0 | 0 | 50 | 0 | 0 | 60 | 60 | 30 | 0 | 0 | 20 | 0 | 0 |

| 500 g ai/ha | Compounds | | | | | | | | | | | | | |
|---|---|---|---|---|---|---|---|---|---|---|---|---|---|---|
| | 50 | 52 | 56 | 57 | 58 | 60 | 61 | 62 | 63 | 64 | 65 | 66 | 67 | 68 |
| | Postemergence | | | | | | | | | | | | | |
| Barnyardgrass | 50 | 70 | 60 | 80 | 30 | 90 | 90 | 80 | 90 | 90 | 0 | 0 | 0 | 40 |
| Blackgrass | 70 | 70 | 80 | 90 | 70 | 70 | 90 | 70 | 90 | 80 | 0 | 0 | 0 | 70 |
| Corn | 40 | 70 | 40 | 90 | 40 | 60 | 90 | 80 | 90 | 90 | 0 | 0 | 0 | 90 |
| Foxtail, Giant | 50 | 90 | 40 | 90 | 70 | 90 | 90 | 80 | 90 | 90 | 20 | 0 | 10 | 90 |
| Foxtail, Green | — | — | — | — | — | — | — | — | — | — | — | — | — | — |
| Galium | 30 | 70 | 50 | 40 | 50 | 60 | 60 | 50 | 70 | 70 | 30 | 0 | 0 | 40 |
| Kochia | 50 | 20 | 20 | 30 | 20 | 10 | 30 | 20 | 30 | 30 | 0 | 0 | 0 | 30 |
| Pigweed | 60 | 0 | 30 | 0 | 30 | 10 | 50 | 10 | 20 | 50 | 0 | 0 | 0 | 30 |
| Ragweed | 40 | 30 | 20 | 0 | 0 | 40 | 50 | 50 | 20 | 40 | 0 | 0 | 0 | 0 |
| Ryegrass, Italian | 20 | 60 | 80 | 90 | 50 | 40 | 80 | 80 | 90 | 80 | 0 | 0 | 0 | 90 |
| Wheat | 0 | 70 | 40 | 90 | 20 | 70 | 90 | 50 | 80 | 90 | 10 | 0 | 0 | 80 |

| 500 g ai/ha | Compounds | | | | | | | | | | | | | |
|---|---|---|---|---|---|---|---|---|---|---|---|---|---|---|
| | 71 | 72 | 73 | 74 | 77 | 78 | 79 | 80 | 81 | 82 | 83 | 84 | 85 | 86 |
| | Postemergence | | | | | | | | | | | | | |
| Barnyardgrass | 90 | 90 | 70 | 90 | 90 | 80 | 80 | 80 | 80 | 80 | 90 | 90 | 80 | 0 |
| Blackgrass | 70 | 70 | 80 | 70 | 80 | 70 | 70 | 70 | 50 | 70 | 80 | 90 | 80 | 0 |

TABLE A-continued

| | | | | | | | | | | | | | | |
|---|---|---|---|---|---|---|---|---|---|---|---|---|---|---|
| Corn | 90 | 70 | 70 | 80 | 60 | 50 | 70 | 60 | 20 | 50 | 90 | 40 | 90 | 10 |
| Foxtail, Giant | 60 | 80 | 70 | 80 | 90 | 90 | 90 | 90 | 80 | 90 | 90 | 70 | 80 | 0 |
| Foxtail, Green | — | — | — | — | — | — | — | — | — | — | — | — | — | — |
| *Galium* | 50 | 50 | 50 | 50 | 70 | 60 | 30 | 70 | 30 | 70 | 70 | 40 | 30 | 0 |
| *Kochia* | 50 | 40 | 20 | 10 | 20 | 50 | 0 | 70 | 0 | 40 | 50 | 20 | 0 | 0 |
| Pigweed | 10 | 30 | 70 | 40 | 20 | 20 | 0 | 60 | 0 | 30 | 80 | 40 | 0 | 0 |
| Ragweed | 50 | 50 | 20 | 20 | 60 | 60 | 30 | 70 | 0 | 60 | 70 | 30 | 0 | 0 |
| Ryegrass, Italian | 80 | 70 | 60 | 50 | 70 | 50 | 50 | 20 | 20 | 50 | 80 | 90 | 60 | 0 |
| Wheat | 70 | 80 | 60 | 60 | 70 | 60 | 70 | 80 | 30 | 70 | 80 | 50 | 90 | 0 |

| | Compounds | | | | | | | | | | | | | |
|---|---|---|---|---|---|---|---|---|---|---|---|---|---|---|
| 500 g ai/ha | 87 | 88 | 89 | 90 | 91 | 92 | 93 | 94 | 95 | 96 | 97 | 98 | 99 | 100 |
| | Postemergence | | | | | | | | | | | | | |
| Barnyardgrass | 90 | 50 | 30 | 80 | 90 | 90 | 90 | 90 | 80 | 90 | 90 | 90 | 90 | 90 |
| Blackgrass | 90 | 30 | 0 | 50 | 80 | 70 | 70 | 90 | 70 | 90 | 70 | 70 | 70 | 70 |
| Corn | 80 | 0 | 0 | 0 | 70 | 80 | 90 | 80 | 50 | 70 | 0 | 80 | 40 | 70 |
| Foxtail, Giant | 90 | 10 | 0 | 90 | 90 | 90 | 90 | 90 | 90 | 90 | 90 | 90 | 90 | 90 |
| Foxtail, Green | — | — | — | — | — | — | — | — | — | — | — | — | — | — |
| *Galium* | 70 | 50 | 0 | 20 | 30 | 60 | 70 | 60 | 50 | 20 | 50 | 40 | 50 | 80 |
| *Kochia* | 70 | 30 | 0 | 0 | 30 | 70 | 80 | 30 | 50 | 0 | 50 | 0 | 50 | 70 |
| Pigweed | 50 | 0 | 0 | 0 | 30 | 60 | 80 | 70 | 20 | 0 | 0 | 30 | 40 | 40 |
| Ragweed | 30 | 10 | 0 | 0 | 30 | 70 | 70 | 70 | 20 | 30 | 20 | 30 | 30 | 70 |
| Ryegrass, Italian | 90 | 0 | 0 | 0 | 50 | 70 | 70 | 90 | 70 | 60 | 50 | 70 | 70 | 70 |
| Wheat | 80 | 0 | 0 | 0 | 50 | 80 | 80 | 80 | 60 | 10 | 30 | 70 | 50 | 50 |

| | Compounds | | | | | | | | | | | | | |
|---|---|---|---|---|---|---|---|---|---|---|---|---|---|---|
| 500 g ai/ha | 101 | 102 | 103 | 104 | 105 | 106 | 107 | 108 | 109 | 110 | 111 | 112 | 113 | 114 |
| | Postemergence | | | | | | | | | | | | | |
| Barnyardgrass | 90 | 80 | 90 | 80 | 80 | 90 | 90 | 80 | 80 | 90 | 90 | 90 | 80 | 90 |
| Blackgrass | 80 | 80 | 70 | 70 | 60 | 70 | 70 | 90 | 90 | 90 | 80 | 80 | 80 | 80 |
| Corn | 70 | 40 | 60 | 60 | 40 | 90 | 80 | 90 | 90 | 90 | 90 | 90 | 80 | 80 |
| Foxtail, Giant | 90 | 80 | 90 | 80 | 30 | 90 | 90 | 90 | 90 | 90 | 90 | 90 | 90 | 90 |
| Foxtail, Green | — | — | — | — | — | — | — | — | — | — | — | — | — | — |
| *Galium* | 80 | 70 | 50 | 70 | 40 | 70 | 70 | 70 | 20 | 70 | 70 | 70 | 70 | 70 |
| *Kochia* | 60 | 40 | 30 | 70 | 0 | 30 | 20 | 20 | 0 | 50 | 0 | 20 | 40 | 70 |
| Pigweed | 60 | 70 | 50 | 70 | 0 | 20 | 30 | 20 | 0 | 20 | 20 | 0 | 20 | 70 |
| Ragweed | 60 | 50 | 40 | 70 | 40 | 70 | 60 | 50 | 0 | 70 | 70 | 60 | 50 | 70 |
| Ryegrass, Italian | 50 | 50 | 70 | 70 | 40 | 70 | 70 | 70 | 80 | 80 | 80 | 90 | 50 | 70 |
| Wheat | 60 | 40 | 70 | 50 | 30 | 70 | 60 | 70 | 80 | 80 | 70 | 70 | 50 | 60 |

| | Compounds | | | | | | |
|---|---|---|---|---|---|---|---|
| 500 g ai/ha | 115 | 116 | 117 | 118 | 119 | 120 | 122 |
| | Postemergence | | | | | | |
| Barnyardgrass | 60 | 80 | 80 | 80 | 0 | 70 | 0 |
| Blackgrass | 80 | 80 | 70 | 70 | 0 | 20 | 0 |
| Corn | 60 | 60 | 70 | 80 | 0 | 0 | 0 |
| Foxtail, Giant | 70 | 90 | 90 | 90 | 0 | 80 | 0 |
| Foxtail, Green | — | — | — | — | — | — | — |
| *Galium* | 70 | 20 | 70 | 50 | 0 | 50 | 0 |
| *Kochia* | 20 | 20 | 60 | 60 | 0 | 30 | 0 |
| Pigweed | 20 | 0 | 70 | 30 | 0 | 20 | 0 |
| Ragweed | 20 | 0 | 60 | 70 | 0 | 40 | 0 |
| Ryegrass, Italian | 60 | 80 | 60 | 90 | 20 | 0 | 0 |
| Wheat | 50 | 70 | 80 | 80 | 0 | 0 | 0 |

| | Compounds | | | | | | | | | | | | | |
|---|---|---|---|---|---|---|---|---|---|---|---|---|---|---|
| 125 g ai/ha | 1 | 2 | 3 | 4 | 5 | 6 | 7 | 8 | 9 | 10 | 11 | 12 | 13 | 14 |
| | Postemergence | | | | | | | | | | | | | |
| Barnyardgrass | 70 | 70 | 80 | 50 | 90 | 90 | 90 | 50 | 40 | 40 | 40 | 10 | 30 | 0 |
| Blackgrass | 20 | 20 | 30 | 0 | 20 | 50 | 60 | 0 | 0 | 20 | 0 | 0 | 30 | 0 |
| Corn | 0 | 40 | 40 | 0 | 0 | 30 | 30 | 0 | 0 | 0 | 0 | 50 | 50 | 0 |
| Foxtail, Giant | 0 | 90 | 80 | 40 | 60 | 90 | 30 | 90 | 50 | 60 | 30 | 90 | 90 | 0 |
| Foxtail, Green | — | — | — | — | — | — | — | — | — | — | — | — | — | — |
| *Galium* | 80 | 70 | 60 | 30 | 50 | 50 | 60 | 20 | 30 | 50 | 0 | 50 | 40 | 0 |
| *Kochia* | 0 | 40 | 20 | 0 | 60 | 30 | 40 | 0 | 0 | 0 | 0 | 0 | 20 | 0 |
| Pigweed | 20 | 40 | 0 | 0 | 40 | 40 | 20 | 0 | 20 | 0 | 0 | 0 | 40 | 0 |

TABLE A-continued

| | | | | | | | | | | | | | | |
|---|---|---|---|---|---|---|---|---|---|---|---|---|---|---|
| Ragweed | 0 | 30 | — | 0 | 30 | 0 | 0 | 0 | 0 | 0 | 0 | 0 | 30 | 0 |
| Ryegrass, Italian | 0 | 60 | 0 | 0 | 0 | 50 | 40 | 0 | 0 | 0 | 0 | 0 | 50 | 0 |
| Wheat | 30 | 40 | 30 | 0 | 20 | 60 | 70 | 0 | 0 | 0 | 0 | 20 | 60 | 0 |

| | Compounds | | | | | | | | | | | | | |
|---|---|---|---|---|---|---|---|---|---|---|---|---|---|---|
| 125 g ai/ha | 15 | 16 | 17 | 18 | 19 | 20 | 21 | 22 | 23 | 24 | 25 | 26 | 27 | 28 |
| | Postemergence | | | | | | | | | | | | | |
| Barnyardgrass | 90 | 80 | 0 | 0 | 10 | 10 | 0 | 0 | 70 | 90 | 70 | 60 | 50 | 20 |
| Blackgrass | 0 | 0 | 0 | 0 | 20 | 0 | 0 | 0 | 0 | 20 | 20 | 20 | 20 | 0 |
| Corn | 60 | 0 | 0 | 0 | 30 | 0 | 0 | 0 | 0 | 50 | 60 | 0 | 20 | 0 |
| Foxtail, Giant | 80 | — | — | — | — | — | — | — | — | — | — | — | — | — |
| Foxtail, Green | — | 10 | 20 | 0 | 30 | 0 | 0 | 0 | 30 | 80 | 40 | 50 | 60 | 30 |
| *Galium* | 0 | 0 | 0 | 0 | 0 | 30 | 0 | — | — | — | — | 70 | 60 | 70 |
| *Kochia* | 0 | 0 | 0 | 0 | 0 | 0 | 0 | 0 | 0 | 50 | 60 | 0 | 0 | 0 |
| Pigweed | 0 | 0 | 0 | 0 | 0 | 0 | 0 | 0 | 0 | 30 | 60 | 30 | 0 | 0 |
| Ragweed | 0 | 0 | 0 | 0 | 0 | 0 | 0 | 0 | 0 | 20 | 40 | 20 | 0 | 0 |
| Ryegrass, Italian | 30 | 0 | 0 | 0 | 0 | 0 | 0 | 0 | 0 | 90 | 40 | 0 | 0 | 0 |
| Wheat | 40 | 0 | 0 | 0 | 0 | 0 | 0 | 0 | 20 | 50 | 70 | 0 | 0 | 0 |

| | Compounds | | | | | | | | | | | | | |
|---|---|---|---|---|---|---|---|---|---|---|---|---|---|---|
| 125 g ai/ha | 29 | 30 | 31 | 32 | 33 | 34 | 35 | 36 | 37 | 38 | 39 | 40 | 41 | 42 |
| | Postemergence | | | | | | | | | | | | | |
| Barnyardgrass | 10 | 70 | 30 | 20 | 0 | 30 | 0 | 0 | 40 | 90 | 60 | 90 | 30 | 90 |
| Blackgrass | 20 | 60 | 20 | 0 | 0 | 40 | 0 | 20 | 20 | 40 | 50 | 60 | 30 | 80 |
| Corn | 0 | 70 | 0 | 10 | 10 | 0 | 0 | 20 | 20 | 20 | 10 | 30 | 0 | 50 |
| Foxtail, Giant | — | — | — | — | — | — | — | — | — | — | — | — | — | — |
| Foxtail, Green | 20 | 80 | 40 | 20 | 0 | 0 | 0 | 0 | 60 | 70 | 70 | 80 | 40 | 90 |
| *Galium* | 40 | 50 | — | 70 | 70 | — | — | — | — | — | 10 | 60 | 60 | 60 |
| *Kochia* | 0 | 0 | 0 | 0 | 0 | 0 | 0 | 0 | 10 | 0 | 0 | 0 | 0 | 30 |
| Pigweed | 10 | 30 | 0 | 0 | 0 | 30 | 0 | 0 | 0 | 0 | 0 | 0 | 30 | 20 |
| Ragweed | 0 | 40 | 0 | 0 | 0 | 0 | 0 | 0 | 0 | 0 | 0 | 0 | 0 | 30 |
| Ryegrass, Italian | 0 | 50 | 20 | 0 | 0 | 0 | 0 | — | 0 | 30 | 10 | 20 | 0 | 30 |
| Wheat | 0 | 50 | 0 | 0 | 0 | 0 | 0 | 0 | 10 | 30 | 50 | 10 | 0 | 80 |

| | Compounds | | | | | | | | | | | | | |
|---|---|---|---|---|---|---|---|---|---|---|---|---|---|---|
| 125 g ai/ha | 43 | 44 | 45 | 46 | 47 | 48 | 49 | 50 | 51 | 52 | 54 | 55 | 56 | 57 |
| | Postemergence | | | | | | | | | | | | | |
| Barnyardgrass | 20 | 0 | 50 | 10 | 50 | 0 | 0 | 0 | 0 | 30 | 70 | 60 | 20 | 80 |
| Blackgrass | 0 | 0 | 60 | 20 | 0 | 70 | 0 | 40 | 70 | 30 | 70 | 80 | 70 | 80 |
| Corn | 0 | 0 | 50 | 0 | 0 | 0 | 0 | 0 | 0 | 0 | 70 | 0 | 0 | 60 |
| Foxtail, Giant | — | — | — | — | — | 0 | 0 | 10 | 0 | 0 | 70 | 80 | 40 | 40 |
| Foxtail, Green | 20 | 0 | 80 | 40 | 50 | — | — | — | — | — | — | — | — | — |
| *Galium* | — | — | 30 | — | 50 | 40 | 0 | 0 | 70 | 20 | 70 | 30 | 30 | 30 |
| *Kochia* | 0 | 0 | 0 | 0 | 0 | 0 | 0 | 0 | 20 | 0 | 50 | 0 | 10 | 0 |
| Pigweed | 0 | 0 | 20 | 0 | 0 | 30 | 0 | 0 | 0 | 0 | 60 | 0 | 0 | 0 |
| Ragweed | 0 | 0 | 0 | 0 | 0 | 30 | 20 | 0 | 60 | 0 | 30 | 0 | 0 | 0 |
| Ryegrass, Italian | 0 | 0 | 40 | 0 | 0 | 30 | 0 | 0 | 0 | 20 | 70 | 70 | 50 | 40 |
| Wheat | 0 | 0 | 60 | 0 | 0 | 0 | 0 | 0 | 10 | 10 | 50 | 30 | 20 | 20 |

| | Compounds | | | | | | | | | | | | | |
|---|---|---|---|---|---|---|---|---|---|---|---|---|---|---|
| 125 g ai/ha | 58 | 60 | 61 | 62 | 63 | 64 | 65 | 66 | 67 | 68 | 69 | 70 | 71 | 72 |
| | Postemergence | | | | | | | | | | | | | |
| Barnyardgrass | 10 | 40 | 70 | 70 | 50 | 70 | 0 | 0 | 0 | 0 | 70 | 70 | 80 | 90 |
| Blackgrass | 20 | 10 | 50 | 40 | 70 | 80 | 0 | 0 | 0 | 70 | 70 | 30 | 40 | 60 |
| Corn | 0 | 20 | 50 | 60 | 10 | 90 | 0 | 0 | 0 | 20 | 0 | 0 | 70 | 40 |
| Foxtail, Giant | 30 | 70 | 70 | 50 | 50 | 70 | 0 | 0 | 0 | 0 | 90 | 0 | 40 | 50 |
| Foxtail, Green | — | — | — | — | — | — | — | — | — | — | — | — | — | — |
| *Galium* | 30 | 20 | 50 | 40 | 30 | 40 | 0 | 0 | 0 | 30 | 40 | 30 | 30 | 50 |
| *Kochia* | 0 | 0 | 0 | 0 | 20 | 0 | 0 | 0 | 0 | 0 | 0 | 0 | 10 | 0 |
| Pigweed | 0 | 0 | 30 | 0 | 0 | 0 | 0 | 0 | 0 | 0 | 20 | 20 | 20 | 10 |
| Ragweed | 0 | 0 | 0 | 0 | 0 | 10 | 0 | 0 | 0 | 0 | 20 | 0 | 0 | 0 |
| Ryegrass, Italian | 20 | 0 | 80 | 70 | 30 | 70 | 0 | 0 | 0 | 20 | 70 | 0 | 60 | 30 |
| Wheat | 10 | 20 | 70 | 40 | 40 | 70 | 0 | 0 | 0 | 30 | 0 | 0 | 20 | 30 |

TABLE A-continued

| 125 g ai/ha | Compounds | | | | | | | | | | | | | |
|---|---|---|---|---|---|---|---|---|---|---|---|---|---|---|
| | 73 | 74 | 77 | 78 | 79 | 80 | 81 | 82 | 83 | 84 | 85 | 86 | 87 | 88 |
| | Postemergence | | | | | | | | | | | | | |
| Barnyardgrass | 30 | 80 | 80 | 70 | 70 | 70 | 80 | 70 | 80 | 40 | 40 | 0 | 80 | 0 |
| Blackgrass | 40 | 70 | 60 | 50 | 20 | 20 | 0 | 40 | 70 | 90 | 60 | 0 | 70 | 10 |
| Corn | 50 | 40 | 50 | 0 | 20 | 40 | 20 | 20 | 70 | 0 | 60 | 0 | 70 | 0 |
| Foxtail, Giant | 40 | 60 | 90 | 80 | 70 | 80 | 60 | 60 | 80 | 50 | 60 | 0 | 60 | 0 |
| Foxtail, Green | — | — | — | — | — | — | — | — | — | — | — | — | — | — |
| *Galium* | 10 | 20 | 50 | 60 | 20 | 40 | 0 | 60 | 60 | 40 | 20 | 0 | 0 | 20 |
| *Kochia* | 10 | 0 | 0 | 20 | 0 | 20 | 0 | 0 | 30 | 0 | 0 | 0 | 10 | 0 |
| Pigweed | 30 | 20 | 0 | 0 | 0 | 0 | 0 | 0 | 30 | 10 | 0 | 0 | 0 | 0 |
| Ragweed | 0 | 0 | 20 | 0 | 30 | 30 | 0 | 0 | 30 | 0 | 0 | 0 | 10 | 0 |
| Ryegrass, Italian | 0 | 0 | 40 | 10 | 0 | 20 | 0 | 20 | 60 | 20 | 0 | 0 | 70 | 0 |
| Wheat | 0 | 60 | 50 | 40 | 20 | 60 | 0 | 60 | 60 | 0 | 50 | 0 | 70 | 0 |

| 125 g ai/ha | Compounds | | | | | | | | | | | | | |
|---|---|---|---|---|---|---|---|---|---|---|---|---|---|---|
| | 89 | 90 | 91 | 92 | 93 | 94 | 95 | 96 | 97 | 98 | 99 | 100 | 101 | 102 |
| | Postemergence | | | | | | | | | | | | | |
| Barnyardgrass | 20 | 10 | 70 | 70 | 70 | 80 | 70 | 60 | 70 | 70 | 90 | 70 | 50 | 70 |
| Blackgrass | 0 | 30 | 60 | 70 | 60 | 70 | 60 | 40 | 30 | 70 | 50 | 30 | 70 | 60 |
| Corn | 0 | 0 | 20 | 70 | 60 | 70 | 0 | 10 | 0 | 60 | 0 | 30 | 20 | 40 |
| Foxtail, Giant | 0 | 20 | 70 | 70 | 80 | 80 | 80 | 40 | 60 | 80 | 60 | 60 | 80 | 70 |
| Foxtail, Green | — | — | — | — | — | — | — | — | — | — | — | — | — | — |
| *Galium* | 0 | 20 | 0 | 50 | 60 | 20 | 0 | 0 | 30 | 0 | 30 | 70 | 70 | 50 |
| *Kochia* | 0 | 0 | 0 | 30 | 0 | 20 | 30 | 0 | 0 | 0 | 0 | 20 | 30 | 30 |
| Pigweed | 0 | 0 | 0 | 20 | 50 | 20 | 0 | 0 | 0 | 0 | 0 | 0 | 0 | 30 |
| Ragweed | 0 | 0 | 0 | 0 | 0 | 20 | 0 | 0 | 0 | 30 | 0 | 20 | 30 | 20 |
| Ryegrass, Italian | 0 | 0 | 50 | 60 | 60 | 60 | 40 | 0 | 0 | 40 | 30 | 0 | 50 | 40 |
| Wheat | 0 | 0 | 20 | 70 | 60 | 40 | 10 | 0 | 10 | 60 | 0 | 20 | 10 | 20 |

| 125 g ai/ha | Compounds | | | | | | | | | | | | | |
|---|---|---|---|---|---|---|---|---|---|---|---|---|---|---|
| | 103 | 104 | 105 | 106 | 107 | 108 | 109 | 110 | 111 | 112 | 113 | 114 | 115 | 116 |
| | Postemergence | | | | | | | | | | | | | |
| Barnyardgrass | 80 | 60 | 30 | 70 | 70 | 70 | 50 | 40 | 70 | 70 | 30 | 70 | 0 | 50 |
| Blackgrass | 80 | 70 | 20 | 80 | 70 | 90 | 80 | 80 | 80 | 80 | 40 | 80 | 40 | 80 |
| Corn | 50 | 70 | 0 | 60 | 30 | 60 | 80 | 80 | 70 | 80 | 20 | 40 | 0 | 30 |
| Foxtail, Giant | 80 | 20 | 10 | 80 | 60 | 70 | 80 | 80 | 40 | 90 | 80 | 80 | 0 | 60 |
| Foxtail, Green | — | — | — | — | — | — | — | — | — | — | — | — | — | — |
| *Galium* | 0 | 30 | 30 | 40 | 70 | 50 | 20 | 50 | 50 | 50 | 50 | 70 | 40 | 0 |
| *Kochia* | 0 | 50 | 0 | 0 | 20 | 0 | 0 | 0 | 0 | 0 | 0 | 20 | 0 | 0 |
| Pigweed | 0 | 30 | 0 | 0 | 0 | 0 | 0 | 0 | 0 | 0 | 0 | 0 | 0 | 0 |
| Ragweed | 40 | 20 | 0 | 30 | 30 | 30 | 0 | 0 | 30 | 0 | 50 | 30 | 0 | 0 |
| Ryegrass, Italian | 50 | 20 | 0 | 70 | 10 | 40 | 70 | 70 | 40 | 40 | 0 | 60 | 0 | 0 |
| Wheat | 20 | 10 | 0 | 40 | 10 | 30 | 20 | 50 | 50 | 40 | 0 | 40 | 10 | 20 |

| 125 g ai/ha | Compounds | | | | | |
|---|---|---|---|---|---|---|
| | 117 | 118 | 119 | 120 | 121 | 122 |
| | Postemergence | | | | | |
| Barnyardgrass | 60 | 60 | 0 | 20 | 60 | 0 |
| Blackgrass | 60 | 50 | 0 | 0 | 60 | 0 |
| Corn | 30 | 70 | 0 | 0 | 30 | 0 |
| Foxtail, Giant | 80 | 50 | 0 | 0 | 30 | 0 |
| Foxtail, Green | — | — | — | — | — | — |
| *Galium* | 70 | 50 | 0 | 20 | 60 | 0 |
| *Kochia* | 0 | 50 | 0 | 0 | 0 | 0 |
| Pigweed | 0 | 0 | 0 | 10 | 20 | 0 |
| Ragweed | 0 | 0 | 0 | 0 | 0 | 0 |
| Ryegrass, Italian | 30 | 50 | 10 | 0 | 30 | 0 |
| Wheat | 20 | 40 | 0 | 0 | 40 | 0 |

| 31 g ai/ha | Compounds | | | | | | | | | | | |
|---|---|---|---|---|---|---|---|---|---|---|---|---|
| | 9 | 30 | 39 | 40 | 42 | 45 | 48 | 51 | 54 | 55 | 69 | 70 | 121 |
| | Postemergence | | | | | | | | | | | | |
| Barnyardgrass | 10 | 30 | 0 | 80 | 50 | 10 | 0 | 0 | 30 | 20 | 30 | 20 | 0 |
| Blackgrass | 0 | 30 | 0 | 0 | 80 | 20 | 30 | 0 | 60 | 0 | 10 | 0 | 0 |

TABLE A-continued

| | | | | | | | | | | | | | | |
|---|---|---|---|---|---|---|---|---|---|---|---|---|---|---|
| Corn | 0 | 0 | 0 | 20 | 20 | 40 | 0 | 0 | 40 | 0 | 0 | 0 | | 0 |
| Foxtail, Giant | 20 | — | — | — | — | — | 0 | 0 | 30 | 10 | 20 | 0 | | 0 |
| Foxtail, Green | — | 30 | 10 | 40 | 50 | 30 | — | — | — | — | — | — | | — |
| *Galium* | 0 | 50 | 0 | 10 | 40 | 20 | 20 | 60 | 40 | 0 | 20 | 0 | | 30 |
| *Kochia* | 0 | 0 | 0 | 0 | 0 | 0 | 0 | 0 | 0 | 0 | 0 | 0 | | 0 |
| Pigweed | 0 | 20 | 0 | 0 | 0 | 0 | 0 | 0 | 20 | 0 | 0 | 0 | | 0 |
| Ragweed | 0 | 0 | 0 | 0 | 0 | 0 | 0 | 0 | 0 | 0 | 0 | 0 | | 0 |
| Ryegrass, Italian | 0 | 20 | 0 | 0 | 0 | 10 | 30 | 0 | 0 | 50 | 30 | 0 | | 0 |
| Wheat | 0 | 40 | 0 | 0 | 20 | 30 | 0 | 0 | 0 | 0 | 0 | 0 | | 0 |

| | Compounds | | | | | | | | | | | | | |
|---|---|---|---|---|---|---|---|---|---|---|---|---|---|---|
| 500 g ai/ha | 1 | 2 | 3 | 4 | 5 | 6 | 7 | 8 | 10 | 11 | 12 | 13 | 14 | 15 |
| | Preemergence | | | | | | | | | | | | | |
| Barnyardgrass | 100 | 100 | 100 | 100 | 100 | 100 | 100 | 90 | 90 | 100 | 100 | 100 | 0 | 100 |
| Foxtail, Giant | 100 | 100 | 100 | 100 | 100 | 100 | 100 | 90 | 90 | 100 | 100 | 100 | 0 | 100 |
| Foxtail, Green | — | — | — | — | — | — | — | — | — | — | — | — | — | — |
| *Kochia* | 90 | 80 | 90 | 80 | 60 | 70 | 80 | 50 | 60 | 0 | 50 | 40 | 0 | 30 |
| Pigweed | 80 | 90 | 70 | 90 | 90 | 90 | 100 | 40 | 60 | 0 | 30 | 70 | 0 | 0 |
| Ragweed | 30 | 90 | 70 | 100 | 90 | 100 | 100 | 80 | 90 | 30 | 90 | 30 | 0 | 90 |
| Ryegrass, Italian | 60 | 50 | 50 | 20 | 80 | 90 | 90 | 40 | 60 | 0 | 90 | 40 | 0 | 50 |

| | Compounds | | | | | | | | | | | | | |
|---|---|---|---|---|---|---|---|---|---|---|---|---|---|---|
| 500 g ai/ha | 16 | 17 | 18 | 19 | 20 | 21 | 22 | 23 | 24 | 25 | 26 | 27 | 28 | 29 |
| | Preemergence | | | | | | | | | | | | | |
| Barnyardgrass | 100 | 20 | 0 | 90 | 90 | 90 | 80 | 90 | 90 | 90 | 100 | 100 | 100 | 80 |
| Foxtail, Giant | — | — | — | — | — | — | — | — | — | — | — | — | — | — |
| Foxtail, Green | 100 | 50 | 90 | 90 | 90 | 90 | 70 | 90 | 90 | 90 | 100 | 100 | 100 | 100 |
| *Kochia* | 30 | 0 | 0 | 60 | 50 | 40 | 20 | 50 | 90 | 80 | 90 | 80 | 70 | 20 |
| Pigweed | 70 | 0 | 0 | 60 | 80 | 0 | 20 | 0 | 50 | 90 | 90 | 90 | 100 | 90 |
| Ragweed | 20 | 0 | 0 | 50 | 60 | 0 | 30 | 80 | 80 | 100 | 90 | 100 | 100 | 100 |
| Ryegrass, Italian | 0 | 0 | 0 | 40 | 20 | 0 | 0 | 0 | 70 | 50 | 70 | 30 | 20 | 20 |

| | Compounds | | | | | | | | | | | | | |
|---|---|---|---|---|---|---|---|---|---|---|---|---|---|---|
| 500 g ai/ha | 31 | 32 | 33 | 34 | 35 | 36 | 37 | 38 | 41 | 43 | 44 | 46 | 47 | 49 |
| | Preemergence | | | | | | | | | | | | | |
| Barnyardgrass | 100 | 100 | 90 | 100 | 0 | 60 | 100 | 100 | 100 | 100 | 70 | 100 | 100 | 20 |
| Foxtail, Giant | — | — | — | — | — | — | — | — | — | — | — | — | — | 40 |
| Foxtail, Green | 100 | 100 | 100 | 100 | 0 | 100 | 100 | 100 | 100 | 100 | 100 | 100 | 100 | — |
| *Kochia* | 80 | 70 | 70 | 90 | 0 | 90 | 90 | 90 | 90 | 80 | 0 | 90 | 90 | 0 |
| Pigweed | 60 | 80 | 50 | 90 | 0 | 60 | 100 | 80 | 90 | 90 | 90 | 90 | 100 | 0 |
| Ragweed | 90 | 100 | 80 | 100 | 0 | 80 | 100 | 90 | 100 | 100 | 80 | 90 | 100 | 0 |
| Ryegrass, Italian | 20 | 10 | 20 | 0 | 0 | 60 | 0 | 50 | 70 | 0 | 0 | 0 | 20 | 20 |

| | Compounds | | | | | | | | | | | | | |
|---|---|---|---|---|---|---|---|---|---|---|---|---|---|---|
| 500 g ai/ha | 50 | 52 | 56 | 57 | 58 | 60 | 61 | 62 | 63 | 64 | 65 | 66 | 67 | 68 |
| | Preemergence | | | | | | | | | | | | | |
| Barnyardgrass | 90 | 100 | 90 | 100 | 90 | 100 | 90 | 90 | 90 | 90 | 90 | 20 | 70 | 100 |
| Foxtail, Giant | 90 | 100 | 90 | 100 | 90 | 100 | 90 | 90 | 90 | 90 | 90 | 70 | 60 | 100 |
| Foxtail, Green | — | — | — | — | — | — | — | — | — | — | — | — | — | — |
| *Kochia* | 70 | 20 | 0 | 60 | 0 | 80 | 80 | 60 | 40 | 80 | 0 | 0 | 0 | 30 |
| Pigweed | 40 | 70 | 0 | 20 | 0 | 80 | 90 | 70 | 60 | 80 | 0 | 0 | 0 | 0 |
| Ragweed | 0 | 60 | 0 | 30 | 90 | 90 | 80 | 60 | 80 | 70 | 0 | 0 | 0 | 70 |
| Ryegrass, Italian | 80 | 90 | 70 | 90 | 80 | 70 | 90 | 90 | 80 | 90 | 100 | 0 | 0 | 90 |

| | Compounds | | | | | | | | | | | | | |
|---|---|---|---|---|---|---|---|---|---|---|---|---|---|---|
| 500 g ai/ha | 71 | 72 | 73 | 74 | 77 | 78 | 79 | 80 | 81 | 82 | 83 | 84 | 85 | 86 |
| | Preemergence | | | | | | | | | | | | | |
| Barnyardgrass | 90 | 90 | 90 | 90 | 90 | 90 | 90 | 90 | 90 | 90 | 90 | 90 | 100 | 0 |
| Foxtail, Giant | 90 | 90 | 90 | 90 | 90 | 90 | 90 | 90 | 90 | 90 | 90 | 90 | 100 | 0 |
| Foxtail, Green | — | — | — | — | — | — | — | — | — | — | — | — | — | — |
| *Kochia* | 80 | 80 | 60 | 90 | 70 | 60 | 20 | 70 | 50 | 80 | 50 | 50 | 10 | 0 |
| Pigweed | 40 | 30 | 70 | 60 | 70 | 80 | 0 | 80 | 20 | 80 | 90 | 30 | 0 | 0 |
| Ragweed | 60 | 90 | 80 | 40 | 80 | 70 | 0 | 80 | 0 | 60 | 90 | 20 | 0 | 0 |
| Ryegrass, Italian | 90 | 90 | 90 | 90 | 90 | 70 | 50 | 80 | 10 | 80 | 90 | 80 | 90 | 0 |

TABLE A-continued

| 500 g ai/ha | Compounds | | | | | | | | | | | | | |
|---|---|---|---|---|---|---|---|---|---|---|---|---|---|---|
| | 87 | 88 | 89 | 90 | 91 | 92 | 93 | 94 | 95 | 96 | 97 | 98 | 99 | 100 |
| Preemergence | | | | | | | | | | | | | | |
| Barnyardgrass | 90 | 90 | 40 | 90 | 90 | 90 | 90 | 90 | 90 | 100 | 100 | 90 | 90 | 90 |
| Foxtail, Giant | 90 | 90 | 30 | 90 | 90 | 90 | 90 | 90 | 100 | 90 | 90 | 100 | 90 | 90 |
| Foxtail, Green | — | — | — | — | — | — | — | — | — | — | — | — | — | — |
| *Kochia* | 80 | 70 | 0 | 60 | 60 | 50 | 80 | 60 | 70 | 40 | 60 | 80 | 70 | 80 |
| Pigweed | 100 | 60 | 0 | 0 | 60 | 80 | 90 | 80 | 80 | 10 | 60 | 70 | 60 | 60 |
| Ragweed | 70 | 80 | 0 | 0 | 70 | 70 | 90 | 90 | 80 | 0 | 90 | 80 | 80 | 80 |
| Ryegrass, Italian | 90 | 0 | 0 | 0 | 90 | 90 | 90 | 80 | 90 | 0 | 90 | 100 | 70 | 90 |

| 500 g ai/ha | Compounds | | | | | | | | | | | | | |
|---|---|---|---|---|---|---|---|---|---|---|---|---|---|---|
| | 101 | 102 | 103 | 104 | 105 | 106 | 107 | 108 | 109 | 110 | 111 | 112 | 113 | 114 |
| Preemergence | | | | | | | | | | | | | | |
| Barnyardgrass | 90 | 90 | 90 | 90 | 90 | 90 | 90 | 100 | 100 | 90 | 90 | 100 | 90 | 90 |
| Foxtail, Giant | 90 | 90 | 100 | 90 | 90 | 100 | 90 | 100 | 90 | 90 | 90 | 100 | 90 | 90 |
| Foxtail, Green | — | — | — | — | — | — | — | — | — | — | — | — | — | — |
| *Kochia* | 90 | 80 | 80 | 70 | 60 | 70 | 90 | 90 | 50 | 20 | 90 | 90 | 90 | 80 |
| Pigweed | 90 | 90 | 70 | 80 | 0 | 60 | 80 | 70 | 0 | 60 | 60 | 70 | 60 | 80 |
| Ragweed | 90 | 80 | 90 | 60 | 0 | 40 | 50 | 70 | 30 | 80 | 90 | 80 | 70 | 90 |
| Ryegrass, Italian | 90 | 90 | 90 | 90 | 80 | 90 | 80 | 90 | 100 | 90 | 90 | 100 | 80 | 90 |

| 500 g ai/ha | Compounds | | | | | | |
|---|---|---|---|---|---|---|---|
| | 115 | 116 | 117 | 118 | 119 | 120 | 122 |
| Preemergence | | | | | | | |
| Barnyardgrass | 90 | 90 | 90 | 100 | 0 | 90 | 0 |
| Foxtail, Giant | 90 | 90 | 90 | 100 | 0 | 90 | 0 |
| Foxtail, Green | — | — | — | — | — | — | — |
| *Kochia* | 30 | 0 | 80 | 80 | 0 | 70 | 0 |
| Pigweed | 0 | 0 | 80 | 80 | 0 | 60 | 0 |
| Ragweed | 20 | 0 | 90 | 90 | — | 80 | 0 |
| Ryegrass, Italian | 80 | 80 | 90 | 100 | 0 | 70 | 0 |

| 125 g ai/ha | Compounds | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Preemergence | | | | | | | | | | | | | | |
| Barnyardgrass | 90 | 90 | 100 | 100 | 100 | 100 | 100 | 90 | 90 | 90 | 80 | 100 | 100 | 0 |
| Foxtail, Giant | 100 | 100 | 100 | 100 | 100 | 100 | 100 | 90 | 90 | 80 | 90 | 100 | 100 | 0 |
| Foxtail, Green | — | — | — | — | — | — | — | — | — | — | — | — | — | — |
| *Kochia* | 70 | 90 | 30 | 0 | 10 | 70 | 30 | 0 | 0 | 0 | 0 | 0 | 30 | 0 |
| Pigweed | 20 | 90 | 20 | 20 | 50 | 80 | 20 | 20 | 30 | 50 | 0 | 0 | 60 | 0 |
| Ragweed | 0 | 40 | 30 | 0 | 50 | 40 | 20 | 0 | 90 | 0 | 40 | 0 | 0 | 0 |
| Ryegrass, Italian | 0 | 30 | 20 | 0 | 10 | 80 | 40 | 0 | 0 | 0 | 0 | 0 | 0 | 0 |

| 125 g ai/ha | Compounds | | | | | | | | | | | | | |
|---|---|---|---|---|---|---|---|---|---|---|---|---|---|---|
| | 15 | 16 | 17 | 18 | 19 | 20 | 21 | 22 | 23 | 24 | 25 | 26 | 27 | 28 |
| Preemergence | | | | | | | | | | | | | | |
| Barnyardgrass | 100 | 100 | 0 | 0 | 70 | 60 | 10 | 20 | 60 | 90 | 90 | 80 | 90 | 80 |
| Foxtail, Giant | 100 | — | — | — | — | — | — | — | — | — | — | — | — | — |
| Foxtail, Green | — | 100 | 0 | 40 | 50 | 60 | 20 | 40 | 80 | 90 | 90 | 100 | 100 | 90 |
| *Kochia* | 0 | 0 | 0 | 0 | 0 | 0 | 0 | 0 | 20 | 40 | 50 | 50 | 20 | 0 |
| Pigweed | 0 | 0 | 0 | 0 | 20 | 60 | 0 | 0 | 0 | 20 | 80 | 70 | 20 | 90 |
| Ragweed | 0 | 0 | 0 | 0 | 20 | 20 | 0 | 70 | 50 | 60 | 50 | 80 | 30 | 80 |
| Ryegrass, Italian | 0 | 0 | 0 | 0 | 0 | 0 | 0 | 0 | 40 | 80 | 20 | 20 | 20 |  |

| 125 g ai/ha | Compounds | | | | | | | | | | | | | |
|---|---|---|---|---|---|---|---|---|---|---|---|---|---|---|
| | 29 | 30 | 31 | 32 | 33 | 34 | 35 | 36 | 37 | 38 | 39 | 40 | 41 | 42 |
| Preemergence | | | | | | | | | | | | | | |
| Barnyardgrass | 0 | 100 | 50 | 0 | 90 | 80 | 0 | 70 | 90 | 90 | 100 | 100 | 90 | 100 |
| Foxtail, Giant | — | — | — | — | — | — | — | — | — | — | — | — | — | — |
| Foxtail, Green | 20 | 100 | 90 | 10 | 50 | 40 | 0 | 0 | 90 | 100 | 100 | 100 | 80 | 100 |
| *Kochia* | 0 | 80 | 0 | 0 | 0 | 0 | 0 | 0 | 70 | 0 | 30 | 80 | 0 | 90 |

TABLE A-continued

| | | | | | | | | | | | | | | |
|---|---|---|---|---|---|---|---|---|---|---|---|---|---|---|
| Pigweed | 10 | 90 | 0 | 0 | 0 | 0 | 0 | 0 | 80 | 30 | 30 | 80 | 90 | 80 |
| Ragweed | 20 | 90 | 0 | 70 | 70 | 50 | 0 | 0 | 90 | 30 | 100 | 80 | 80 | 70 |
| Ryegrass, Italian | 0 | 90 | 0 | 10 | 0 | 0 | 0 | 10 | 0 | 30 | 10 | 10 | 10 | 80 |

| | Compounds | | | | | | | | | | | | |
|---|---|---|---|---|---|---|---|---|---|---|---|---|---|
| 125 g ai/ha | 43 | 44 | 45 | 46 | 47 | 48 | 49 | 50 | 51 | 52 | 54 | 55 | 56 | 57 |
| | Preemergence | | | | | | | | | | | | |
| Barnyardgrass | 20 | 0 | 100 | 70 | 80 | 90 | 10 | 50 | 40 | 90 | 90 | 90 | 10 | 90 |
| Foxtail, Giant | — | — | — | — | — | 90 | 0 | 90 | 30 | 80 | 90 | 90 | 60 | 90 |
| Foxtail, Green | 80 | 0 | 100 | 90 | 90 | — | — | — | — | — | — | — | — | — |
| *Kochia* | 0 | 0 | 20 | 0 | 40 | 0 | 0 | 30 | 0 | 0 | 50 | 0 | 0 | 60 |
| Pigweed | 40 | 20 | 0 | 50 | 80 | 0 | 0 | 0 | 0 | 0 | 70 | 0 | 0 | 0 |
| Ragweed | 0 | 0 | 80 | 0 | 90 | 0 | 0 | 0 | 0 | 0 | 50 | 0 | 0 | 0 |
| Ryegrass, Italian | 0 | 0 | 80 | 0 | 0 | 20 | 0 | 0 | 0 | 80 | 80 | 80 | 60 | 20 |

| | Compounds | | | | | | | | | | | | |
|---|---|---|---|---|---|---|---|---|---|---|---|---|---|
| 125 g ai/ha | 58 | 60 | 61 | 62 | 63 | 64 | 65 | 66 | 67 | 68 | 69 | 70 | 71 | 72 |
| | Preemergence | | | | | | | | | | | | |
| Barnyardgrass | 10 | 90 | 90 | 90 | 80 | 90 | 0 | 0 | 0 | 20 | 90 | 80 | 90 | 80 |
| Foxtail, Giant | 40 | 90 | 90 | 90 | 90 | 90 | 0 | 10 | 0 | 50 | 100 | 90 | 80 | 90 |
| Foxtail, Green | — | — | — | — | — | — | — | — | — | — | — | — | — | — |
| *Kochia* | 0 | 10 | 30 | 0 | 0 | 20 | 0 | 0 | 0 | 0 | 0 | 0 | 10 | 20 |
| Pigweed | 0 | 50 | 80 | 10 | 10 | 50 | 0 | 0 | 0 | 0 | 0 | 0 | 0 | 30 |
| Ragweed | 0 | 0 | 50 | 0 | 0 | 0 | 0 | 0 | 0 | 0 | 0 | 0 | 0 | 20 |
| Ryegrass, Italian | 10 | 10 | 80 | 90 | 20 | 90 | 0 | 0 | 0 | 20 | 80 | 0 | 30 | 30 |

| | Compounds | | | | | | | | | | | | |
|---|---|---|---|---|---|---|---|---|---|---|---|---|---|
| 125 g ai/ha | 73 | 74 | 77 | 78 | 79 | 80 | 81 | 82 | 83 | 84 | 85 | 86 | 87 | 88 |
| | Preemergence | | | | | | | | | | | | |
| Barnyardgrass | 90 | 90 | 90 | 90 | 90 | 90 | 90 | 90 | 90 | 10 | 80 | 0 | 90 | 20 |
| Foxtail, Giant | 80 | 90 | 90 | 90 | 80 | 90 | 60 | 90 | 90 | 30 | 80 | 0 | 90 | 20 |
| Foxtail, Green | — | — | — | — | — | — | — | — | — | — | — | — | — | — |
| *Kochia* | 20 | 30 | 10 | 10 | 0 | 30 | 0 | 0 | 0 | 0 | 0 | 0 | 10 | 10 |
| Pigweed | 40 | 0 | 20 | 0 | 0 | 50 | 0 | 60 | 60 | 0 | 50 | 0 | 100 | 0 |
| Ragweed | 50 | 40 | 30 | 20 | 0 | 40 | 0 | 50 | 10 | 0 | 0 | 0 | 0 | 0 |
| Ryegrass, Italian | 50 | 90 | 10 | 30 | 30 | 0 | 0 | 40 | 70 | 0 | 60 | 0 | 90 | 0 |

| | Compounds | | | | | | | | | | | | |
|---|---|---|---|---|---|---|---|---|---|---|---|---|---|
| 125 g ai/ha | 89 | 90 | 91 | 92 | 93 | 94 | 95 | 96 | 97 | 98 | 99 | 100 | 101 | 102 |
| | Preemergence | | | | | | | | | | | | |
| Barnyardgrass | 0 | 90 | 90 | 90 | 90 | 90 | 90 | 90 | 90 | 90 | 90 | 90 | 90 | 80 |
| Foxtail, Giant | 0 | 50 | 90 | 90 | 90 | 90 | 90 | 90 | 90 | 90 | 90 | 90 | 90 | 90 |
| Foxtail, Green | — | — | — | — | — | — | — | — | — | — | — | — | — | — |
| *Kochia* | 0 | 0 | 0 | 0 | 30 | 10 | 0 | 0 | 50 | 10 | 10 | 40 | 30 | 10 |
| Pigweed | 0 | 0 | 0 | 30 | 80 | 20 | 20 | 0 | 0 | 0 | 0 | 0 | 70 | 60 |
| Ragweed | 0 | 0 | 20 | 0 | 70 | 30 | 20 | 0 | 40 | 20 | 10 | 0 | 10 | 50 |
| Ryegrass, Italian | 0 | 0 | 80 | 80 | 70 | 60 | 30 | 0 | 20 | 90 | 50 | 0 | 40 | 70 |

| | Compounds | | | | | | | | | | | | |
|---|---|---|---|---|---|---|---|---|---|---|---|---|---|
| 125 g ai/ha | 103 | 104 | 105 | 106 | 107 | 108 | 109 | 110 | 111 | 112 | 113 | 114 | 115 | 116 |
| | Preemergence | | | | | | | | | | | | |
| Barnyardgrass | 90 | 80 | 30 | 90 | 90 | 90 | 90 | 90 | 90 | 90 | 90 | 90 | 90 | 80 |
| Foxtail, Giant | 90 | 90 | 60 | 90 | 90 | 90 | 90 | 90 | 90 | 90 | 90 | 90 | 20 | 90 |
| Foxtail, Green | — | — | — | — | — | — | — | — | — | — | — | — | — | — |
| *Kochia* | 10 | 30 | 0 | 0 | 0 | 20 | 0 | 0 | 0 | 50 | 10 | 20 | 0 | 0 |
| Pigweed | 30 | 10 | 0 | 0 | 0 | 0 | 0 | 0 | 20 | 0 | 30 | 50 | 0 | 0 |
| Ragweed | 60 | 20 | 0 | 0 | 0 | 0 | 0 | 50 | 0 | 40 | 0 | 80 | 0 | 0 |
| Ryegrass, Italian | 90 | 80 | 0 | 90 | 30 | 70 | 90 | 70 | 20 | 80 | 0 | 90 | 20 | 0 |

TABLE A-continued

| 125 g ai/ha | Compounds | | | | | |
|---|---|---|---|---|---|---|
| | 117 | 118 | 119 | 120 | 121 | 122 |
| Preemergence | | | | | | |
| Barnyardgrass | 90 | 90 | 0 | 80 | 80 | 0 |
| Foxtail, Giant | 90 | 90 | 0 | 70 | 80 | 0 |
| Foxtail, Green | — | — | — | — | — | — |
| *Kochia* | 10 | 20 | 0 | 0 | 0 | 0 |
| Pigweed | 60 | 40 | 0 | 30 | 0 | 0 |
| Ragweed | 30 | 70 | 0 | — | 0 | 0 |
| Ryegrass, Italian | 60 | 90 | 0 | 0 | 80 | 0 |

| 31 g ai/ha | Compounds | | | | | | | | | | | | |
|---|---|---|---|---|---|---|---|---|---|---|---|---|---|
| | 9 | 30 | 39 | 40 | 42 | 45 | 48 | 51 | 54 | 55 | 69 | 70 | 121 |
| Preemergence | | | | | | | | | | | | | |
| Barnyardgrass | 30 | 100 | 100 | 100 | 100 | 40 | 0 | 0 | 80 | 90 | 90 | 40 | 0 |
| Foxtail, Giant | 70 | — | — | — | — | — | 0 | 0 | 90 | 70 | 90 | 20 | 0 |
| Foxtail, Green | — | 100 | 100 | 100 | 100 | 90 | — | — | — | — | — | — | — |
| *Kochia* | 0 | 0 | 0 | 0 | 0 | 0 | 0 | 0 | 0 | 0 | 0 | 0 | 0 |
| Pigweed | 0 | 0 | 0 | 0 | 0 | 0 | 0 | 0 | 0 | 0 | 0 | 0 | 0 |
| Ragweed | 0 | 30 | 0 | 20 | 0 | 0 | 0 | 0 | 0 | 0 | 0 | 0 | 0 |
| Ryegrass, Italian | 0 | 0 | 20 | 0 | 0 | 10 | 0 | 0 | 60 | 0 | 20 | 0 | 0 |

Test B

Plant species in the flooded paddy test selected from rice (*Oryza sativa*), sedge, umbrella (small-flower umbrella sedge, *Cyperus difformis*), ducksalad (*Heteranthera limosa*), and barnyardgrass (*Echinochloa crus-galli*) were grown to the 2-leaf stage for testing. At time of treatment, test pots were flooded to 3 cm above the soil surface, treated by application of test compounds directly to the paddy water, and then maintained at that water depth for the duration of the test. Treated plants and controls were maintained in a greenhouse for 13 to 15 days, after which time all species were compared to controls and visually evaluated. Plant response ratings, summarized in Table B, are based on a scale of 0 to 100 where 0 is no effect and 100 is complete control. A dash (-) response means no test result.

TABLE B

| 250 g ai/ha | Compounds | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Flood | | | | | | | | | | | | | | |
| Barnyardgrass | 70 | 70 | 80 | 60 | 65 | 85 | 80 | 85 | 85 | 85 | 90 | 70 | 60 | 40 |
| Ducksalad | 70 | 90 | 100 | 40 | 100 | 100 | 85 | 100 | 100 | 100 | 100 | 80 | 30 | 20 |
| Rice | 50 | 0 | 0 | 10 | 0 | 0 | 10 | 0 | 0 | 0 | 15 | 0 | 20 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | | |
|---|---|---|---|---|---|---|---|---|---|---|---|---|---|---|
| | 15 | 16 | 17 | 18 | 19 | 20 | 21 | 22 | 23 | 24 | 25 | 26 | 27 | 28 |
| Flood | | | | | | | | | | | | | | |
| Barnyardgrass | 85 | 85 | 0 | 0 | 85 | 95 | 40 | 0 | 50 | 70 | 75 | 60 | 60 | 30 |
| Ducksalad | 95 | 100 | 40 | 0 | 95 | 100 | 80 | 40 | 60 | 85 | 90 | 100 | 75 | 0 |
| Rice | 15 | 0 | 0 | 0 | 15 | 0 | 0 | 30 | 0 | 0 | 0 | 0 | 20 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | | |
|---|---|---|---|---|---|---|---|---|---|---|---|---|---|---|
| | 29 | 30 | 31 | 32 | 33 | 34 | 35 | 36 | 37 | 38 | 39 | 40 | 41 | 42 |
| Flood | | | | | | | | | | | | | | |
| Barnyardgrass | 0 | 85 | 0 | 0 | 20 | 35 | 0 | 30 | 45 | 60 | 90 | 80 | 20 | 90 |
| Ducksalad | 0 | 100 | 0 | 0 | 0 | 50 | 0 | 0 | 100 | 65 | 100 | 95 | 80 | 100 |
| Rice | 0 | 50 | 0 | 0 | 0 | 0 | 0 | 0 | 0 | 0 | 10 | 25 | 0 | 30 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | | |
|---|---|---|---|---|---|---|---|---|---|---|---|---|---|---|
| | 43 | 44 | 45 | 46 | 47 | 48 | 49 | 50 | 51 | 52 | 54 | 55 | 56 | 57 |

TABLE B-continued

| | Flood | | | | | | | | | | | | | |
|---|---|---|---|---|---|---|---|---|---|---|---|---|---|---|
| Barnyardgrass | 0 | 0 | 75 | 40 | 40 | 20 | 0 | 0 | 0 | 0 | 35 | 70 | 25 | 55 |
| Ducksalad | 0 | 0 | 95 | 100 | 75 | 70 | 0 | 0 | 0 | 0 | 80 | 100 | 40 | 0 |
| Rice | 0 | 0 | 0 | 20 | 0 | 10 | 0 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 250 g ai/ha | 58 | 60 | 61 | 62 | 63 | 64 | 65 | 66 | 67 | 68 | 69 | 70 | 71 | 72 |

| | Flood | | | | | | | | | | | | | |
|---|---|---|---|---|---|---|---|---|---|---|---|---|---|---|
| Barnyardgrass | 0 | 40 | 65 | 55 | 65 | 60 | 15 | 35 | 15 | 0 | 90 | 0 | 0 | 40 |
| Ducksalad | 0 | 0 | 74 | 0 | 30 | 70 | 60 | 75 | 65 | 0 | 95 | 0 | 0 | 15 |
| Rice | 0 | 0 | 0 | 0 | 0 | 0 | 10 | 15 | 15 | 0 | 0 | 0 | 0 | 0 |
| Sedge, Umbrella | 0 | 0 | 0 | 0 | 0 | 0 | 15 | 0 | 0 | 0 | 0 | 0 | 0 | 0 |

| | Compounds | | | | | | | | | | | | | |
|---|---|---|---|---|---|---|---|---|---|---|---|---|---|---|
| 250 g ai/ha | 73 | 74 | 77 | 78 | 79 | 80 | 81 | 82 | 83 | 84 | 85 | 86 | 87 | 88 |

| | Flood | | | | | | | | | | | | | |
|---|---|---|---|---|---|---|---|---|---|---|---|---|---|---|
| Barnyardgrass | 0 | 45 | 75 | 75 | 60 | 65 | 25 | 60 | 80 | 0 | 0 | 0 | 50 | 15 |
| Ducksalad | 0 | 20 | 100 | 100 | 100 | 80 | 100 | 25 | 75 | 0 | 0 | 0 | 85 | 100 |
| Rice | 0 | 0 | 0 | 0 | 0 | 0 | 0 | 0 | 0 | 0 | 0 | 0 | 0 | 15 |
| Sedge, Umbrella | 0 | 0 | 0 | 15 | 0 | 0 | 0 | 20 | 15 | 0 | 0 | 0 | 60 | 0 |

| | Compounds | | | | | | | | | | | | | |
|---|---|---|---|---|---|---|---|---|---|---|---|---|---|---|
| 250 g ai/ha | 89 | 90 | 91 | 92 | 93 | 94 | 95 | 96 | 97 | 98 | 99 | 100 | 101 | 102 |

| | Flood | | | | | | | | | | | | | |
|---|---|---|---|---|---|---|---|---|---|---|---|---|---|---|
| Barnyardgrass | 0 | 15 | 65 | 70 | 70 | 60 | 80 | 0 | 70 | 55 | 60 | 0 | 50 | 0 |
| Ducksalad | 30 | 90 | 55 | 25 | 100 | 100 | 100 | 0 | 100 | 100 | 85 | 0 | 90 | 0 |
| Rice | 0 | 0 | 0 | 0 | 15 | 0 | 0 | 0 | 0 | 0 | 0 | 0 | 0 | 0 |
| Sedge, Umbrella | 0 | 0 | 0 | 25 | 0 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 250 g ai/ha | 103 | 104 | 105 | 106 | 107 | 108 | 109 | 110 | 111 | 112 | 113 | 114 | 115 | 116 |

| | Flood | | | | | | | | | | | | | |
|---|---|---|---|---|---|---|---|---|---|---|---|---|---|---|
| Barnyardgrass | 65 | 40 | 0 | 60 | 40 | 0 | 0 | 0 | 0 | 70 | 0 | 40 | 0 | 0 |
| Ducksalad | 80 | 40 | 0 | 70 | 70 | 0 | 0 | 0 | 0 | 45 | 0 | 60 | 0 | 0 |
| Rice | 0 | 0 | 0 | 0 | 0 | 0 | 0 | 0 | 0 | 0 | 0 | 30 | 0 | 0 |
| Sedge, Umbrella | 0 | 0 | 0 | 0 | 0 | 0 | 0 | 0 | 0 | 0 | 0 | 0 | 0 | 0 |

| | Compounds | | | | | |
|---|---|---|---|---|---|---|
| 250 g ai/ha | 117 | 118 | 119 | 120 | 121 | 122 |

| | Flood | | | | | |
|---|---|---|---|---|---|---|
| Barnyardgrass | 0 | 95 | 0 | 15 | 40 | 0 |
| Ducksalad | 0 | 90 | 0 | 70 | 85 | 0 |
| Rice | 0 | 15 | 0 | 0 | 0 | 0 |
| Sedge, Umbrella | 0 | 0 | 0 | 0 | 35 | 0 |

What is claimed is:

1. A compound selected from Formula 1, N-oxides and salts thereof,

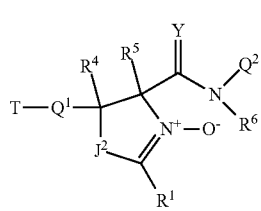

wherein $Q^1$ is a phenyl ring or a naphthalenyl ring system, each ring or ring system optionally substituted with up to 4 substituents independently selected from $R^7$; or a 4- to 7-membered heterocyclic ring; or an 8- to 10-membered bicyclic ring system, each ring or ring system containing ring members selected from carbon atoms and 1 to 5 heteroatoms independently selected from up to 2 O, up to 2 S and up to 5 N atoms, wherein up to 3 carbon ring members are independently selected from C(=O) and C(=S), and the sulfur atom ring members are independently selected from S(=O)$_u$(=NR$^8$)$_v$, each ring or ring system optionally substituted with up to 5 substituents independently selected from $R^7$ on carbon atom ring members and selected from $R^9$ on nitrogen atom ring members; or $Q^1$ is $C_2$-$C_{10}$ alkenylene, $C_2$-$C_{10}$ alkynylene, $C_2$-$C_{10}$ haloalkenylene, $C_2$-$C_{10}$ haloalkynylene, $C_4$-$C_{10}$ cycloalkenylene, $C_4$-$C_{10}$ halocycloalkenylene, $C_2$-$C_8$ alkylenecarbonyl or $C_2$-$C_8$ alkoxyalkylene;

T is H; or

T is $J^1$-A-, wherein the free bond projecting to the right next to A indicates the connecting point of $J^1$-A- to $Q^1$; or T is $R^{17}ON{=}CR^{17a}{-}$, $(R^{18})_2C{=}NO{-}$, $(R^{19})_2NN{=}CR^{17a}{-}$, $(R^{18})_2C{=}NNR^{21}$, $R^{20}N{=}CR^{17a}{-}$, $(R^{18})_2C{=}N{-}$, $R^{17}ON{=}CR^{17a}C(R^{22})_2{-}$ or $(R^{18})_2C{=}NOC(R^{23})_2{-}$, wherein the free bond projecting to the right indicates the connecting point to $Q^1$;

T is $R^7$, provided T is bonded to a carbon ring member of $Q^1$; or

T is $R^9$, provided T is bonded to a nitrogen ring member of $Q^1$;

A is a saturated, partially unsaturated or fully unsaturated chain containing 1 to 3 atoms selected from up to 3 carbon, up to 1 O, up to 1 S and up to 2 N atoms, the chain optionally substituted with up to 2 substituents independently selected from $R^{15}$ on carbon atoms and $R^{16}$ on nitrogen atoms;

$Q^2$ is a phenyl ring or a naphthalenyl ring system, each ring or ring system optionally substituted with up to 5 substituents independently selected from $R^{10}$; or a 4- to 7-membered heterocyclic ring or an 8- to 10-membered bicyclic ring system, each ring or ring system containing ring members selected from carbon atoms and 1 to 4 heteroatoms independently selected from up to 2 O, up to 2 S and up to 5 N atoms, wherein up to 3 carbon ring members are independently selected from $C({=}O)$ and $C({=}S)$, and the sulfur atom ring members are independently selected from $S({=}O)_u({=}NR^8)_v$, each ring or ring system optionally substituted with up to 5 substituents independently selected from $R^{10}$ on carbon atom ring members and selected from $R^{11}$ on nitrogen atom ring members; or $Q^2$ is $C_2$-$C_{10}$ alkenyl, $C_2$-$C_{10}$ alkynyl, $C_2$-$C_{10}$ haloalkenyl, $C_2$-$C_{10}$ haloalkynyl, $C_4$-$C_{10}$ cycloalkenyl, $C_4$-$C_{10}$ halocycloalkenyl, $C_2$-$C_8$ alkylcarbonyl or $C_2$-$C_8$ alkoxyalkyl;

$J^1$ is a phenyl ring or a naphthalenyl ring system, each ring or ring system optionally substituted with up to 5 substituents independently selected from $R^{7a}$; or a 4- to 6-membered heterocyclic ring or an 8- to 10-membered bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from $C({=}O)$ and $C({=}S)$, and the sulfur atom ring members are independently selected from $S({=}O)_u({=}NR^8)_v$, each ring or ring system optionally substituted with up to 5 substituents independently selected from $R^{7a}$ on carbon atom ring members and selected from $R^9$ on nitrogen atom ring members; or $J^1$ is $C_4$-$C_{10}$ cycloalkylalkoxy, $C_4$-$C_{10}$ cycloalkylalkyl, $C_2$-$C_8$ alkenyloxy, $C_2$-$C_8$ haloalkenyloxy, $C_2$-$C_8$ alkoxyalkoxy, $C_2$-$C_8$ alkylthioalkyl, $C_2$-$C_8$ alkylsulfinylalkyl, $C_2$-$C_8$ alkylsulfonylalkyl, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_2$-$C_8$ alkynyl, $C_2$-$C_8$ haloalkynyl, $C_2$-$C_8$ alkoxyalkyl, $C_2$-$C_8$ haloalkoxyalkyl, $C_3$-$C_8$ haloalkoxyalkoxy, $C_2$-$C_8$ haloalkoxyhaloalkyl, $C_1$-$C_8$ haloalkyl, $C_3$-$C_8$ halocycloalkyl, $C_2$-$C_8$ alkylcarbonyloxy or $C_2$-$C_8$ haloalkylcarbonyloxy;

$J^2$ is $({-}CR^2R^3{-})_z$;

Y is O, S or $NR^{12}$;

$R^1$ is H, hydroxy, amino, cyano, formyl, $C_3$-$C_8$ alkylcarbonylalkyl, $-C(C_1$-$C_4$ alkyl$){=}N{-}O(C_1$-$C_4$ alkyl), $-C(O)NH_2$, $C_1$-$C_6$ alkyl, $C_1$-$C_6$ haloalkyl, $C_2$-$C_6$ alkenyl, $C_3$-$C_6$ alkynyl, $C_2$-$C_6$ cyanoalkyl, $C_3$-$C_6$ cycloalkyl, $C_3$-$C_8$ cycloalkenyl, $C_4$-$C_8$ cycloalkylalkyl, $C_2$-$C_8$ alkoxyalkyl, $C_3$-$C_8$ alkoxyalkoxyalkyl, $C_2$-$C_8$ haloalkoxyalkyl, $C_2$-$C_8$ haloalkenylalkyl, $C_2$-$C_8$ alkylthioalkyl, $C_2$-$C_8$ alkylsulfinylalkyl, $C_2$-$C_8$ alkylsulfonylalkyl, $C_5$-$C_{10}$ cycloalkylcarbonylalkyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl; or $-CPh{=}N{-}O(C_1$-$C_4$ alkyl), each optionally substituted on ring members with up to 5 substituents independently selected from $R^{13}$; or $G^1$; or $W^1G^1$;

each $R^2$ and $R^3$, bonded to the same carbon atom, is independently H, halogen, hydroxy, $C_1$-$C_4$ alkyl, $C_1$-$C_4$ haloalkyl or $C_1$-$C_4$ alkoxy; or $R^2$ and $R^3$, together with the carbon atom to which they are both bonded, form a $C_3$-$C_7$ cycloalkyl ring;

each $R^2$ and $R^3$ bonded to the same carbon atom is defined independent of any $R^2$ and $R^3$ bonded to a different carbon atom;

$R^4$ and $R^5$ are each independently H, halogen, hydroxy, $C_1$-$C_4$ alkoxy, $C_1$-$C_4$ haloalkyl or $C_1$-$C_4$ alkyl;

$R^6$ is H, hydroxy, amino, $C_1$-$C_6$ alkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl or $C_3$-$C_{10}$ trialkylsilyl or $G^1$; or $R^6$ and $Q^2$ are taken together with the nitrogen atom to which they are both bonded to form an 8- to 10-membered bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from $C({=}O)$ and $C({=}S)$, and the sulfur atom ring members are independently selected from $S({=}O)_u({=}NR^8)_v$, each ring or ring system optionally substituted with up to 5 substituents independently selected from $R^7$ on carbon atom ring members and selected from $R^{11}$ on nitrogen atom ring members;

each $R^7$ is independently halogen, hydroxy, cyano, nitro, amino, $C_1$-$C_8$ alkyl, $C_1$-$C_8$ cyanoalkyl, $C_1$-$C_8$ cyanoalkoxy, $C_1$-$C_8$ haloalkyl, $C_1$-$C_8$ nitroalkyl, $C_2$-$C_8$ alkenyl, $C_2$-$C_8$ haloalkenyl, $C_2$-$C_8$ nitroalkenyl, $C_2$-$C_8$ alkynyl, $C_2$-$C_8$ haloalkynyl, $C_2$-$C_8$ alkoxyalkyl, $C_3$-$C_8$ alkoxyalkoxyalkyl, $C_2$-$C_8$ haloalkoxyalkyl, $C_2$-$C_8$ haloalkoxyhaloalkoxy, $C_3$-$C_6$ cycloalkyl, cyclopropylmethyl, 1-methylcyclopropyl, 2-methylcyclopropyl, $C_4$-$C_{10}$ cycloalkylalkyl, $C_4$-$C_{10}$ halocycloalkylalkyl, $C_5$-$C_{12}$ alkylcycloalkylalkyl, $C_5$-$C_{12}$ cycloalkylalkenyl, $C_5$-$C_{12}$ cycloalkylalkynyl, $C_3$-$C_8$ cycloalkyl, $C_3$-$C_8$ halocycloalkyl, $C_4$-$C_{10}$ alkylcycloalkyl, $C_6$-$C_{12}$ cycloalkylcycloalkyl, $C_3$-$C_8$ cycloalkenyl, $C_3$-$C_8$ halocycloalkenyl, $C_2$-$C_8$ haloalkoxyalkoxy, $C_2$-$C_8$ alkoxyalkoxy, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_8$ alkylamino, $C_2$-$C_8$ dialkylamino, $C_2$-$C_8$ halodialkylamino, $C_2$-$C_8$ alkylaminoalkyl, $C_2$-$C_8$ haloalkylaminoalkyl, $C_4$-$C_{10}$ cycloalkylaminoalkyl, $C_3$-$C_{10}$ dialkylaminoalkyl, —CHO, $C_2$-$C_8$ alkylcarbonyl, $C_2$-$C_8$ haloalkylcarbonyl, $C_4$-$C_{10}$ cycloalkylcarbonyl, —C(=O)OH, $C_2$-$C_8$ alkoxycarbonyl, $C_2$-$C_8$ haloalkoxycarbonyl, $C_4$-$C_{10}$ cycloalkoxycarbonyl, $C_5$-$C_{12}$ cycloalkylalkoxycarbonyl, —C(=O)NH$_2$, $C_2$-$C_8$ alkylaminocarbonyl, $C_4$-$C_{10}$ cycloalkylaminocarbonyl, $C_3$-$C_{10}$ dialkylaminocarbonyl, $C_1$-$C_8$ alkoxy, $C_1$-$C_8$ haloalkoxy, $C_2$-$C_8$ alkoxyalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_3$-$C_8$ cycloalkylsulfonyl, formylamino, $C_2$-$C_8$ alkylcarbonylamino, $C_2$-$C_8$ haloalkylcarbonylamino, $C_3$-$C_8$ cycloalkylamino, $C_2$-$C_8$ alkoxycarbonylamino, $C_1$-$C_6$ alkylsulfonylamino, $C_1$-$C_6$ haloalkylsulfonylamino, —SF$_5$, —SCN, SO$_2$NH$_2$, $C_3$-$C_{12}$ trialkylsilyl, $C_4$-$C_{12}$ trialkylsilylalkyl, $C_4$-$C_{12}$ trialkylsilylalkoxy or $C_1$-$C_6$ haloalkylamino; or $G^2$; or each $R^7$ is independently $R^{26}S(=O)=N-$, $R^{26}S(=O)_2NR^{25}-C(=O)-$,
$R^{26}(R^{25}N=)_qS(=O)_p-$, wherein the free bond projecting to the right indicates the connecting point to $Q^1$; or two adjacent $R^7$, are taken together with the carbon atoms to which they are bonded to form a $C_3$-$C_7$ cycloalkyl ring;

each $R^{7a}$ is independently halogen, hydroxy, cyano, nitro, $C_1$-$C_8$ alkyl, $C_2$-$C_4$ alkoxyalkyl, $C_3$-$C_8$ alkoxyalkoxyalkyl, $C_1$-$C_4$ cyanoalkyl, $C_1$-$C_4$ cyanoalkoxy, $C_1$-$C_8$ haloalkyl, $C_1$-$C_8$ nitroalkyl, $C_2$-$C_8$ alkenyl, $C_2$-$C_8$ haloalkenyl, $C_2$-$C_8$ nitroalkenyl, $C_2$-$C_8$ alkynyl, $C_2$-$C_8$ haloalkynyl, $C_4$-$C_{10}$ cycloalkylalkyl, $C_4$-$C_{10}$ halocycloalkylalkyl, $C_5$-$C_{12}$ alkylcycloalkylalkyl, $C_5$-$C_{12}$ cycloalkylalkenyl, $C_5$-$C_{12}$ cycloalkylalkynyl, $C_3$-$C_8$ cycloalkyl, $C_3$-$C_8$ halocycloalkyl, $C_4$-$C_{10}$ alkylcycloalkyl, $C_6$-$C_{12}$ cycloalkylcycloalkyl, $C_3$-$C_8$ cycloalkenyl, $C_3$-$C_8$ halocycloalkenyl, $C_2$-$C_8$ alkoxyalkyl, $C_2$-$C_8$ haloalkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_2$-$C_8$ haloalkylaminoalkyl, $C_4$-$C_{10}$ cycloalkylaminoalkyl, $C_3$-$C_{10}$ dialkylaminoalkyl, —CHO, $C_2$-$C_8$ alkylcarbonyl, $C_2$-$C_8$ haloalkylcarbonyl, $C_4$-$C_{10}$ cycloalkylcarbonyl, —C(=O)OH, $C_2$-$C_8$ alkoxycarbonyl, $C_2$-$C_8$ haloalkoxycarbonyl, $C_4$-$C_{10}$ cycloalkoxycarbonyl, $C_5$-$C_{12}$ cycloalkylalkoxycarbonyl, —C(=O)NH$_2$, $C_2$-$C_8$ alkylaminocarbonyl, $C_4$-$C_{10}$ cycloalkylaminocarbonyl, $C_3$-$C_{10}$ dialkylaminocarbonyl, $C_1$-$C_8$ alkoxy, $C_1$-$C_8$ haloalkoxy, $C_2$-$C_8$ alkoxyalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_3$-$C_8$ cycloalkylsulfonyl, amino, $C_1$-$C_6$ alkylamino, $C_1$-$C_6$ haloalkylamino, $C_3$-$C_8$ cycloalkylamino, $C_2$-$C_8$ dialkylamino, $C_2$-$C_8$ halodialkylamino, formylamino, $C_2$-$C_8$ alkylcarbonylamino, $C_2$-$C_8$ haloalkylcarbonylamino, $C_1$-$C_6$ alkylsulfonylamino, $C_1$-$C_6$ haloalkylsulfonylamino, —SF$_5$, —SCN, $C_3$-$C_{12}$ trialkylsilyl, $C_4$-$C_{12}$ trialkylsilylalkyl, $C_4$-$C_{12}$ trialkylsilylalkoxy; or two adjacent $R^{7a}$, are taken together with the carbon atoms to which they are bonded to form a $C_3$-$C_7$ cycloalkyl ring;

each $R^8$ is independently H, cyano, $C_2$-$C_3$ alkylcarbonyl or $C_2$-$C_3$ haloalkylcarbonyl;

each $R^9$ and $R^{11}$ are independently cyano, $C_1$-$C_3$ alkyl, $C_2$-$C_3$ alkenyl, $C_2$-$C_3$ alkynyl, $C_3$-$C_6$ cycloalkyl, $C_2$-$C_3$ alkoxyalkyl, $C_1$-$C_3$ alkoxy, $C_2$-$C_3$ alkylcarbonyl, $C_2$-$C_3$ alkoxycarbonyl, $C_2$-$C_3$ alkylaminoalkyl or $C_3$-$C_4$ dialkylaminoalkyl;

each $R^{10}$ is independently halogen, hydroxy, cyano, nitro, amino, $C_1$-$C_8$ alkyl, $C_1$-$C_8$ cyanoalkyl, $C_1$-$C_8$ cyanoalkoxy, $C_1$-$C_8$ haloalkyl, $C_1$-$C_8$ nitroalkyl, $C_2$-$C_8$ alkenyl, $C_2$-$C_8$ haloalkenyl, $C_2$-$C_8$ nitroalkenyl, $C_2$-$C_8$ alkynyl, $C_2$-$C_8$ haloalkynyl, $C_2$-$C_8$ alkoxyalkyl, $C_3$-$C_8$ alkoxyalkoxyalkyl, $C_2$-$C_8$ haloalkoxyalkyl, $C_2$-$C_8$ haloalkoxyhaloalkoxy, $C_3$-$C_6$ cycloalkyl, cyclopropylmethyl, 1-methylcyclopropyl, 2-methylcyclopropyl, $C_4$-$C_{10}$ cycloalkylalkyl, $C_4$-$C_{10}$ halocycloalkylalkyl, $C_5$-$C_{12}$ alkylcycloalkylalkyl, $C_5$-$C_{12}$ cycloalkylalkenyl, $C_5$-$C_{12}$ cycloalkylalkynyl, $C_3$-$C_8$ cycloalkyl, $C_3$-$C_8$ halocycloalkyl, $C_4$-$C_{10}$ alkylcycloalkyl, $C_6$-$C_{12}$ cycloalkylcycloalkyl, $C_3$-$C_8$ cycloalkenyl, $C_3$-$C_8$ halocycloalkenyl, $C_2$-$C_8$ haloalkoxyalkoxy, $C_2$-$C_8$ alkoxyalkoxy, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_8$ alkylamino, $C_2$-$C_8$ dialkylamino, $C_2$-$C_8$ halodialkylamino, $C_2$-$C_8$ alkylaminoalkyl, $C_2$-$C_8$ haloalkylaminoalkyl, $C_4$-$C_{10}$ cycloalkylaminoalkyl, $C_3$-$C_{10}$ dialkylaminoalkyl, —CHO, $C_2$-$C_8$ alkylcarbonyl, $C_2$-$C_8$ haloalkylcarbonyl, $C_4$-$C_{10}$ cycloalkylcarbonyl, —C(=O)OH, $C_2$-$C_8$ alkoxycarbonyl, $C_2$-$C_8$ haloalkoxycarbonyl, $C_4$-$C_{10}$ cycloalkoxycarbonyl, $C_5$-$C_{12}$ cycloalkylalkoxycarbonyl, —C(=O)NH$_2$, C$_2$-C$_8$ alkylaminocarbonyl, C$_4$-C$_{10}$ cycloalkylaminocarbonyl, C$_3$-C$_{10}$ dialkylaminocarbonyl, C$_1$-C$_8$ alkoxy, C$_1$-C$_8$ haloalkoxy, C$_2$-C$_8$ alkoxyalkoxy, C$_2$-C$_8$ alkenyloxy, C$_2$-C$_8$ haloalkenyloxy, C$_3$-C$_8$ alkynyloxy, C$_3$-C$_8$ haloalkynyloxy, C$_3$-C$_8$ cycloalkoxy, C$_3$-C$_8$ halocycloalkoxy, C$_4$-C$_{10}$ cycloalkylalkoxy, C$_3$-C$_{10}$ alkylcarbonylalkoxy, C$_2$-C$_8$ alkylcarbonyloxy, C$_2$-C$_8$ haloalkylcarbonyloxy, C$_4$-C$_{10}$ cycloalkylcarbonyloxy, C$_1$-C$_8$ alkylsulfonyloxy, C$_1$-C$_8$ haloalkylsulfonyloxy, C$_1$-C$_8$ alkylthio, C$_1$-C$_8$ haloalkylthio, C$_3$-C$_8$ cycloalkylthio, C$_1$-C$_8$ alkylsulfinyl, C$_1$-C$_8$ haloalkylsulfinyl, C$_1$-C$_8$ alkylsulfonyl, C$_1$-C$_8$ haloalkylsulfonyl, C$_3$-C$_8$ cycloalkylsulfonyl, formylamino, C$_2$-C$_8$ alkylcarbonylamino, C$_2$-C$_8$ haloalkylcarbonylamino, C$_3$-C$_8$ cycloalkylamino, C$_2$-C$_8$ alkoxycarbonylamino, C$_1$-C$_6$ alkylsulfonylamino, C$_1$-C$_6$ haloalkylsulfonylamino, —SF$_5$, —SCN, SO$_2$NH$_2$, C$_3$-C$_{12}$ trialkylsilyl, C$_4$-C$_{12}$ trialkylsilylalkyl, C$_4$-C$_{12}$ trialkylsilylalkoxy, C$_1$-C$_6$ haloalkylamino, C$_1$-C$_8$ hydroxyalkyl or G$^2$; or each R$^{10}$ is independently R$^{17}$ON=CR$^{17a}$—, (R$^{18}$)$_2$C=NO—, (R$^{19}$)$_2$NN=CR$^{17a}$—, (R$^{18}$)$_2$C=NNR$^{21}$—, R$^{20}$N=CR$^{17a}$—, (R$^{18}$)$_2$C=N—, R$^{17}$ON=CR$^{17a}$C(R$^{22}$)$_2$—, (R$^{18}$)$_2$C=NOC(R$^{23}$)$_2$—, R$^{26}$S(=O)=N—, R$^{26}$S(=O)$_2$NR$^{25}$—C(=O)— or R$^{26}$(R$^{25}$N=)$_q$S(=O)$_p$—, wherein the free bond projecting to the right of any such substituent indicates the connecting point to Q$^2$; or two adjacent R$^{10}$, are taken together with the carbon atoms to which they are bonded form a C$_3$-C$_7$ cycloalkyl ring;

each R$^{12}$ is independently H, cyano, hydroxy, CHO, C$_1$-C$_4$ alkyl, C$_1$-C$_4$ haloalkyl, C$_1$-C$_4$ alkoxy, C$_1$-C$_4$ haloalkoxy, C$_2$-C$_6$ alkylcarbonyl, C$_2$-C$_6$ haloalkylcarbonyl, —(C=O)CH$_3$ or —(C=O)CF$_3$;

each G$^1$ is independently phenyl, phenylmethyl (i.e. benzyl), pyridinylmethyl, phenylcarbonyl (i.e. benzoyl), phenylcarbonylalkyl, phenoxy, phenylethynyl, phenylsulfonyl or a 5- or 6-membered heterocyclic ring, each optionally substituted on ring members with up to 5 substituents independently selected from R$^{13}$;

each G$^2$ is independently phenyl, phenylmethyl (i.e. benzyl), pyridinylmethyl, phenylcarbonyl (i.e. benzoyl), phenylcarbonylalkyl, phenoxy, phenylethynyl, phenylsulfonyl or a 5- or 6-membered heterocyclic ring, each optionally substituted on ring members with up to 5 substituents independently selected from R$^{13}$;

W$^1$ is C$_1$-C$_3$ alkylene, C$_2$-C$_4$ alkenylene, C$_2$-C$_4$ alkynylene, —(C$_1$-C$_2$ alkylene)C(=O)—, —C(=O)(C$_1$-C$_2$ alkylene)-, —CH$_2$O—, —CH$_2$NH—, —OCH$_2$—, —NCH$_2$—, —N—, —O—, —S—, —SO— or —SO$_2$— wherein the free bond projecting to the left indicates the connecting point of W$^1$ to N and the free bond projecting to the right indicates the connecting point of W$^1$ to G$^1$;

each R$^{13}$ is independently halogen, cyano, hydroxy, amino, nitro, —CHO, —C(=O)OH, —C(=O)NH$_2$, —SO$_2$NH$_2$, C$_1$-C$_6$ alkyl, C$_1$-C$_6$ haloalkyl, C$_2$-C$_6$ alkenyl, C$_2$-C$_6$ alkynyl, C$_2$-C$_8$ alkylcarbonyl, C$_2$-C$_8$ haloalkylcarbonyl, C$_2$-C$_8$ alkoxycarbonyl, C$_4$-C$_{10}$ cycloalkoxycarbonyl, C$_5$-C$_{12}$ cycloalkylalkoxycarbonyl, C$_2$-C$_8$ alkylaminocarbonyl, C$_3$-C$_{10}$ dialkylaminocarbonyl, C$_1$-C$_6$ alkoxy, C$_1$-C$_6$ haloalkoxy, C$_2$-C$_8$ alkylcarbonyloxy, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl, C$_1$-C$_6$ haloalkylsulfonyl, C$_1$-C$_6$ alkylaminosulfonyl, C$_2$-C$_8$ dialkylaminosulfonyl, C$_3$-C$_{10}$ trialkylsilyl, C$_1$-C$_6$ alkylamino, C$_2$-C$_8$ dialkylamino, C$_2$-C$_8$ alkylcarbonylamino, C$_1$-C$_6$ alkylsulfonylamino, phenyl, pyridinyl or thienyl;

each R$^{15}$ is independently halogen, cyano, hydroxy, C$_1$-C$_4$ alkyl, C$_1$-C$_4$ haloalkyl, C$_1$-C$_4$ alkoxy, C$_1$-C$_4$ haloalkoxy, C$_2$-C$_4$ alkoxyalkyl, C$_2$-C$_4$ alkylcarbonyl, C$_2$-C$_4$ alkoxycarbonyl or C$_3$-C$_6$ cycloalkyl;

each R$^{16}$ is independently H, cyano, C$_1$-C$_4$ alkyl, C$_1$-C$_4$ haloalkyl, C$_1$-C$_4$ alkoxy, C$_2$-C$_4$ alkylcarbonyl, C$_2$-C$_4$ alkoxycarbonyl or C$_3$-C$_6$ cycloalkyl;

each R$^{17}$ is independently H, C$_1$-C$_6$ alkyl, C$_3$-C$_8$ cycloalkyl, C$_4$-C$_8$ cycloalkylalkyl, C$_1$-C$_6$ haloalkyl, C$_2$-C$_6$ alkenyl, C$_3$-C$_6$ alkynyl, C$_2$-C$_8$ alkoxyalkyl, C$_2$-C$_8$ haloalkoxyalkyl, C$_2$-C$_8$ alkylthioalkyl, C$_2$-C$_8$ alkylsulfinylalkyl, C$_2$-C$_8$ alkylsulfonylalkyl, C$_2$-C$_8$ alkylcarbonyl, C$_2$-C$_8$ haloalkylcarbonyl, C$_4$-C$_{10}$ cycloalkylcarbonyl, C$_2$-C$_8$ alkoxycarbonyl, C$_2$-C$_8$ haloalkoxycarbonyl, C$_4$-C$_{10}$ cycloalkoxycarbonyl, C$_2$-C$_8$ alkylaminocarbonyl, C$_3$-C$_{10}$ dialkylaminocarbonyl, C$_4$-C$_{10}$ cycloalkylaminocarbonyl, C$_1$-C$_6$ alkylsulfinyl, C$_1$-C$_6$ haloalkylsulfinyl, C$_3$-C$_8$ cycloalkylsulfinyl, C$_1$-C$_6$ alkylsulfonyl, C$_1$-C$_6$ haloalkylsulfonyl, C$_3$-C$_8$ cycloalkylsulfonyl, C$_1$-C$_6$ alkylaminosulfonyl, C$_2$-C$_8$ dialkylaminosulfonyl, C$_3$-C$_{10}$ trialkylsilyl or G$^1$;

each R$^{17a}$ is independently H, C$_1$-C$_6$ alkyl, C$_3$-C$_8$ cycloalkyl, C$_4$-C$_8$ cycloalkylalkyl, C$_1$-C$_6$ haloalkyl, C$_2$-C$_6$ alkenyl, C$_3$-C$_6$ alkynyl, C$_2$-C$_8$ alkoxyalkyl, C$_2$-C$_8$ haloalkoxyalkyl, C$_2$-C$_8$ alkylthioalkyl, C$_2$-C$_8$ alkylsulfinylalkyl, C$_2$-C$_8$ alkylsulfonylalkyl, C$_1$-C$_6$ alkoxy, C$_1$-C$_6$ alkylthio, C$_1$-C$_6$ haloalkylthio, C$_3$-C$_8$ cycloalkylthio, C$_3$-C$_{10}$ trialkylsilyl or G$^1$;

each R$^{18}$ is independently H, hydroxy, C$_1$-C$_6$ alkyl, C$_3$-C$_8$ cycloalkyl, C$_4$-C$_8$ cycloalkylalkyl, C$_1$-C$_6$ haloalkyl, C$_2$-C$_6$ alkenyl, C$_3$-C$_6$ alkynyl, C$_2$-C$_8$ alkoxyalkyl, C$_2$-C$_8$ haloalkoxyalkyl, C$_2$-C$_8$ alkylthioalkyl, C$_2$-C$_8$ alkylsulfinylalkyl, C$_2$-C$_8$ alkylsulfonylalkyl, C$_2$-C$_8$ alkylcarbonyl, C$_2$-C$_8$ haloalkylcarbonyl, C$_4$-C$_{10}$ cycloalkylcarbonyl, C$_2$-C$_8$ alkoxycarbonyl, C$_2$-C$_8$ haloalkoxycarbonyl, C$_4$-C$_{10}$ cycloalkoxycarbonyl, C$_2$-C$_8$ alkylaminocarbonyl, C$_3$-C$_{10}$ dialkylaminocarbonyl, C$_4$-C$_{10}$ cycloalkylaminocarbonyl, C$_1$-C$_6$ alkoxy, C$_1$-C$_6$ alkylthio, C$_1$-C$_6$ haloalkylthio, C$_3$-C$_8$ cycloalkylthio, C$_1$-C$_6$ alkylsulfinyl, C$_1$-C$_6$ haloalkylsulfinyl, C$_3$-C$_8$ cycloalkylsulfinyl, C$_1$-C$_6$ alkylsulfonyl, C$_1$-C$_6$ haloalkylsulfonyl, C$_3$-C$_8$ cycloalkylsulfonyl, C$_1$-C$_6$ alkylaminosulfonyl, C$_2$-C$_8$ dialkylaminosulfonyl, C$_3$-C$_{10}$ trialkylsilyl or G$^1$;

each R$^{19}$ is independently H, C$_1$-C$_6$ alkyl, C$_3$-C$_8$ cycloalkyl, C$_4$-C$_8$ cycloalkylalkyl, C$_1$-C$_6$ haloalkyl, C$_2$-C$_6$ alkenyl, C$_3$-C$_6$ alkynyl, C$_2$-C$_8$ alkoxyalkyl, C$_2$-C$_8$ haloalkoxyalkyl, C$_2$-C$_8$ alkylthioalkyl, C$_2$-C$_8$ alkylsulfinylalkyl, C$_2$-C$_8$ alkylsulfonylalkyl, C$_2$-C$_8$ alkylcarbonyl, C$_2$-C$_8$ haloalkylcarbonyl, C$_4$-C$_{10}$ cycloalkylcarbonyl, C$_2$-C$_8$ alkoxycarbonyl, C$_2$-C$_8$ haloalkoxycarbonyl, C$_4$-C$_{10}$ cycloalkoxycarbonyl, C$_2$-C$_8$ alkylaminocarbonyl, C$_3$-C$_{10}$ dialkylaminocarbonyl, C$_4$-C$_{10}$ cycloalkylaminocarbonyl, C$_1$-C$_6$ alkoxy, C$_1$-C$_6$ alkylsulfinyl, C$_1$-C$_6$ haloalkylsulfinyl, C$_3$-C$_8$ cycloalkylsulfinyl, C$_1$-C$_6$ alkylsulfonyl, C$_1$-C$_6$ haloalkylsulfonyl, C$_3$-C$_8$ cycloalkylsulfonyl, C$_1$-C$_6$ alkylaminosulfonyl, $C_2$-$C_8$ dialkylaminosulfonyl, $C_3$-$C_{10}$ trialkylsilyl or $G^1$;

each $R^{20}$ is independently H, hydroxy, amino, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$;

each $R^{21}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_6$ alkoxy, $C_3$-$C_{10}$ trialkylsilyl or $G^1$;

each $R^{22}$ is independently H, halogen, cyano, hydroxy, $C_1$-$C_4$ alkyl, $C_3$-$C_8$ cycloalkyl, $C_4$-$C_8$ cycloalkylalkyl, $C_1$-$C_4$ haloalkyl, $C_1$-$C_4$ alkoxy, $C_1$-$C_4$ haloalkoxy, $C_2$-$C_4$ alkoxyalkyl, $C_2$-$C_4$ alkylcarbonyl, $C_2$-$C_4$ alkoxycarbonyl or $C_3$-$C_6$ cycloalkyl;

each $R^{23}$ is independently H, $C_1$-$C_4$ alkyl, $C_3$-$C_8$ cycloalkyl, $C_4$-$C_8$ cycloalkylalkyl, $C_1$-$C_4$ haloalkyl, $C_1$-$C_4$ alkoxy, $C_1$-$C_4$ haloalkoxy, $C_2$-$C_4$ alkoxyalkyl, $C_2$-$C_4$ alkylcarbonyl, $C_2$-$C_4$ alkoxycarbonyl or $C_3$-$C_6$ cycloalkyl;

each $R^{25}$ is independently H, cyano, $C_2$-$C_3$ alkylcarbonyl or $C_2$-$C_3$ haloalkylcarbonyl;

each $R^{26}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_6$ alkoxy, $C_3$-$C_{10}$ trialkylsilyl or $G^1$;

each u and v are independently 0, 1 or 2 in each instance of $S(=O)_u(=NR^8)_v$, provided that the sum of u and v is 0, 1 or 2;

each p and q are independently 0, 1 or 2 in each instance of $R^{26}(R^{25}N=)_q S(=O)_p-$, provided that the sum of p and q is 0, 1 or 2; and z is 1, 2 or 3.

2. The compound of claim 1 wherein each $R^7$ and $R^{10}$ is independently halogen, cyano, nitro, $C_1$-$C_4$ alkyl, $C_1$-$C_4$ haloalkyl, $C_2$-$C_4$ alkenyl, $C_2$-$C_4$ haloalkenyl $C_2$-$C_4$ alkynyl, $C_2$-$C_4$ haloalkynyl, $C_1$-$C_4$ nitroalkyl, $C_2$-$C_4$ nitroalkenyl, $C_2$-$C_4$ alkoxyalkyl, $C_2$-$C_4$ haloalkoxyalkyl, $C_3$-$C_4$ cycloalkyl, $C_3$-$C_4$ halocycloalkyl, cyclopropylmethyl, methylcyclopropyl, $C_1$-$C_4$ alkoxy, $C_1$-$C_4$ haloalkoxy, $C_2$-$C_4$ alkenyloxy, $C_2$-$C_4$ haloalkenyloxy, $C_3$-$C_4$ alkynyloxy, $C_3$-$C_4$ haloalkynyloxy, $C_3$-$C_4$ cycloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, hydroxy, formyl, $C_2$-$C_4$ alkylcarbonyl, $C_2$-$C_4$ alkylcarbonyloxy, $C_1$-$C_4$ alkylsulfonyloxy, $C_1$-$C_4$ haloalkylsulfonyloxy, amino, $C_1$-$C_4$ alkylamino, $C_2$-$C_4$ dialkylamino, formylamino, $C_2$-$C_4$ alkylcarbonylamino, —$SF_5$, —SCN, $C_3$-$C_4$ trialkylsilyl, trimethylsilylmethyl or trimethylsilylmethoxy; and each $R^9$ and $R^{11}$ is $C_1$-$C_2$ alkyl.

3. The compound of claim 2 wherein

Y is O;

$R^1$ is $CH_3$; and

T, $R^2$, $R^3$, $R^4$, $R^5$ and $R^6$ are each H.

4. The compound of claim 3 wherein $Q^1$ is a phenyl ring optionally substituted with 1 to 3 substituents or a benzodioxolane ring substituted with 1 to 3 substituents independently selected from $R^7$; and $Q^2$ is a phenyl, pyridinyl or thiophenyl ring substituted with 1 to 3 substituents independently selected from $R^{10}$.

5. The compound of claim 4 wherein each $R^7$ is independently halogen, cyano, $C_1$-$C_2$ alkyl, $C_1$-$C_3$ haloalkyl or $C_1$-$C_3$ haloalkoxy; and each $R^{10}$ is independently halogen, cyano, $C_1$-$C_2$ alkyl, $C_1$-$C_3$ haloalkyl, $C_1$-$C_3$ alkylthio, $C_1$-$C_3$ alkylsulfinyl or $C_1$-$C_3$ alkylsulfonyl.

6. The compound of claim 5 wherein $Q^1$ is a phenyl ring having at least one substituent selected from $R^7$ at the meta (3-) or the para (4-) position or substituted with at least two substituents independently selected from $R^7$ wherein one substituent is at the-meta position and at least one other substituent is at a para position; and $Q^2$ is a phenyl, 2-pyridinyl, 3-pyridinyl or 3-thiophene ring substituted with 1 to 2 substituents independently selected from $R^{10}$.

7. The compound of claim 6 wherein each $R^7$ is independently F, $CH_3$ or $CF_3$; and each $R^{10}$ is F.

8. The compound of claim 1 selected from the group consisting of a compound of Formula 1 wherein $Q^1$ is Ph(4-$CF_3$), $Q^2$ if Ph(2,3-di-F), $R^1$ is $CH_3$, $J^2$ is $CH_2CH_2$ and T, $R^4$, $R^5$ and $R^6$ are H; a compound of Formula 1 wherein $Q^1$ is Ph(4-$CH_3$), $Q^2$ if Ph(2,3-di-F), $R^1$ is $CH_3$, $J^2$ is $CH_2CH_2$ and T, $R^4$, $R^5$ and $R^6$ are H, and a compound of Formula 1 wherein $Q^1$ is Ph(4-Cl), $Q^2$ is Ph(2,3-di-F), $R^1$ is $CH_3$, $J^2$ is $CH_2CH_2$ and T, $R^4$, $R^5$ and $R^6$ are H.

9. The compound of claim 1 selected from the group consisting of rel-(2S,3R)-3-(4-chlorophenyl)-N-(2,3-difluorophenyl)-3,4-dihydro-5-methyl-2H-pyrrole-2-carboxamide 1-oxide;

rel-(2S,3R)—N-(2,3-difluorophenyl)-3,4-dihydro-5-methyl-3-[4-(trifluoromethyl)phenyl]-2H-pyrrole-2-carboxamide 1-oxide;

rel-(2S,3R)—N-(2-fluorophenyl)-3,4-dihydro-5-methyl-3-[4-(trifluoromethyl)phenyl]-2H-pyrrole-2-carboxamide 1-oxide;

rel-(2S,3R)—N-(2,3-Difluorophenyl)-3,4-dihydro-5-methyl-3-(4-methylphenyl)-2H-pyrrole-2-carboxamide 1-oxide;

rel-(2S,3R)-3-(2,2-Difluoro-1,3-benzodioxol-5-yl)-N-(2,3-difluorophenyl)-3,4-dihydro-5-methyl-2H-pyrrole-2-carboxamide 1-oxide;

rel-(2S,3R)-3-(4-Difluoromethyl)phenyl)-N-(2,3-difluorophenyl) 3,4-dihydro-5-methyl-2H-pyrrole-2-carboxamide 1-oxide;

(2S,3R)—N-(2,3-Difluorophenyl)-3-[4-fluoro-3-(1,1,2,2-tetrafluoroethoxy)phenyl]-3,4-dihydro-5-methyl-2H-pyrrole-2-carboxamide 1-oxide;

rel-(2S,3R)—N-(2,6-Difluoro-3-pyridinyl)-3,4-dihydro-5-methyl-3-[4-(trifluoromethyl)phenyl]-2H-pyrrole-2-carboxamide 1-oxide;

rel-(2S,3R)—N-(2,3-Difluorophenyl)-3-[3-fluoro-4-(trifluoromethyl)phenyl]-3,4-dihydro-5-methyl-2H-pyrrole-2-carboxamide 1-oxide;

(2S,3R)-3-(4-chlorophenyl)-N-(2,3-difluorophenyl)-3,4-dihydro-5-methyl-2H-pyrrole-2-carboxamide 1-oxide;

(2S,3R)—N-(2,3-difluorophenyl)-3,4-dihydro-5-methyl-3-[4-(trifluoromethyl)phenyl]-2H-pyrrole-2-carboxamide 1-oxide; and (2S,3R)—N-(2,3-Difluorophenyl)-3,4-dihydro-5-methyl-3-(4-methylphenyl)-2H-pyrrole-2-carboxamide 1-oxide.

10. A herbicidal composition comprising a compound, N-oxide or salt of claim 1; and a surfactant, solid diluent or liquid diluent.

11. The herbicidal composition of claim 10 further comprising an additional active ingredient selected from the group consisting of other herbicides and herbicide safeners.

12. A herbicidal mixture comprising (a) a compound of claim 1; and (b) an additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvyl-shikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, hydantocidin, metam, methyldymron, oleic acid, oxaziclomefone, pelargonic acid and pyributicarb, (b16) herbicide safeners, and salts of compounds of (b1) through (b16).

13. A method for controlling the growth of undesired vegetation comprising contacting the vegetation or its environment with a herbicidally effective amount of a compound of claim 1.

* * * * *